US007691843B2

(12) United States Patent
Raju et al.

(10) Patent No.: US 7,691,843 B2
(45) Date of Patent: Apr. 6, 2010

(54) N-HYDROXYAMIDE DERIVATIVES POSSESSING ANTIBACTERIAL ACTIVITY

(75) Inventors: Bore G. Raju, Fremont, CA (US); Hardwin O'Dowd, Hayward, CA (US); Hongwu Gao, Union City, CA (US); Dinesh V. Patel, Fremont, CA (US); Jaoquim Trias, Millbrae, CA (US)

(73) Assignee: Pfizer Inc., New York, NY (US)

( * ) Notice: Subject to any disclaimer, the term of this patent is extended or adjusted under 35 U.S.C. 154(b) by 1584 days.

(21) Appl. No.: 10/617,616

(22) Filed: Jul. 11, 2003

(65) Prior Publication Data

US 2008/0058304 A1 Mar. 6, 2008

Related U.S. Application Data

(60) Provisional application No. 60/394,862, filed on Jul. 11, 2002.

(51) Int. Cl.
*A61K 31/397* (2006.01)
*C07D 205/00* (2006.01)

(52) U.S. Cl. .................... 514/210.17; 548/950
(58) Field of Classification Search ............... None
See application file for complete search history.

(56) References Cited

U.S. PATENT DOCUMENTS

| 5,925,659 A | 7/1999 | Patchett et al. |
| 5,990,963 A | 11/1999 | Mishima et al. |
| 6,020,347 A | 2/2000 | DeLaszlo et al. |
| 6,114,361 A | 9/2000 | Robinson et al. |
| 6,191,171 B1 | 2/2001 | DeLaszlo et al. |
| 6,340,678 B1 | 1/2002 | Matsuhisa et al. |
| 6,353,099 B1 | 3/2002 | DeLaszlo et al. |
| 6,407,065 B1 | 6/2002 | Wattanasin et al. |
| 6,420,418 B1 | 7/2002 | Hagmann et al. |
| 6,432,923 B1 | 8/2002 | Wattanasin et al. |
| 6,458,822 B2 | 10/2002 | Robinson et al. |
| 6,465,513 B1 | 10/2002 | Grant et al. |
| 6,492,421 B1 | 12/2002 | Thorsett et al. |
| 6,627,634 B2 | 9/2003 | Himmelsbach et al. |
| 2002/0010199 A1 | 1/2002 | Hagmann et al. |
| 2002/0019419 A1 | 2/2002 | De Laszlo et al. |
| 2002/0065391 A1 | 5/2002 | Stilz et al. |
| 2002/0143043 A1 | 10/2002 | Wehner et al. |
| 2003/0045555 A1 | 3/2003 | Rivera et al. |

FOREIGN PATENT DOCUMENTS

| EP | 0 463 596 | 1/1992 |
| EP | 0 520 336 | 12/1992 |
| EP | 0 976 722 | 2/2000 |
| EP | 1 048 652 | 11/2000 |
| WO | WO 96/10999 | 4/1996 |
| WO | WO 96/15148 | 5/1996 |
| WO | WO 96/29309 | 9/1996 |
| WO | WO 96/38471 | 12/1996 |
| WO | WO 97/18837 | 5/1997 |
| WO | WO 97/41102 | 11/1997 |
| WO | WO 97/42179 | 11/1997 |
| WO | WO 98/16512 | 4/1998 |
| WO | WO 98/31661 | 7/1998 |
| WO | WO 98/39303 | 9/1998 |
| WO | WO 98/39325 | 9/1998 |
| WO | WO 99/11258 | 3/1999 |
| WO | WO 99/25685 | 5/1999 |
| WO | WO 99/26923 | 6/1999 |
| WO | WO 99/33805 | 7/1999 |
| WO | WO 99/52926 | 10/1999 |
| WO | WO 99/63937 | 12/1999 |
| WO | WO 99/67230 | 12/1999 |
| WO | WO 00/21920 | 4/2000 |
| WO | WO 00/39081 | 7/2000 |
| WO | WO 00/43371 | 7/2000 |
| WO | WO 00/50396 | 8/2000 |
| WO | WO 00/59878 | 10/2000 |
| WO | WO 00/59880 | 10/2000 |
| WO | WO 00/60355 | 10/2000 |
| WO | WO 01/00616 | 1/2001 |
| WO | WO 01/06984 | 2/2001 |
| WO | WO 01/07044 | 2/2001 |
| WO | WO 01/07048 | 2/2001 |
| WO | WO 01/07052 | 2/2001 |
| WO | WO 01/12183 | 2/2001 |
| WO | WO 01/14328 | 3/2001 |
| WO | WO 01/15733 | 3/2001 |

(Continued)

OTHER PUBLICATIONS

Archard et al., caplus an 2001:661381.*
Berger, M. A., "Biological Activity of Cycloserine and Some of its Analogs and Homologs", Chemical Abstract Service, Accession No. 1962:48518.
Belgodere, Elena et al., "Imidazole Derivatives with Potential Biological Activity", Arzneimittel-Forschung, 1980, vol. 30 (7), pp. 1051-1056.
Anderson, M.S. et al. (1993) "UDP-*N*-acetylglucosamine Acyltransferase of *Escherichia coli*," *J. Biol. Chem.* 268(26):19858-19865.
Archibald, S.C. et al. (2000). "Discovery and Evaluation of Potent, Tyrosine-based α4β1 Integrin Antagonists," *Bioorganic & Medicinal Chemistry Letters* 10:997-999.
Astles, P.C. et al. (2001). "Diamine Containing VLA-4 Antagonists," *Bioorganic & Medicinal Chemistry* 9:2195-2202.
Azzolina, B.A. et al. (2001) "The Cell Wall and Cell Division Gene Cluster in the *Mra* Operon of *Pseudomonas aeruginosa*: Cloning, Production, and Purification of Active Enzymes," *Protein Expression and Purification* 21(3): 393-400.

(Continued)

*Primary Examiner*—Golam M. M. Shameem
*Assistant Examiner*—Sun Jae Y Loewe
(74) *Attorney, Agent, or Firm*—Gregg C. Benson; Michael Dixon; Jason Tebbutt

(57) ABSTRACT

Novel N-hydroxyamide derivatives are disclosed. These N-hydroxyamide derivatives inhibit UPD-3-O—(R-3-hydroxymyristoyl)-N-acetylglucosamine deacetylase, an enzyme present in gram negative bacteria and are therefore useful as antimicrobials and antibiotics. Methods of synthesis and of use of the compounds are also disclosed.

23 Claims, No Drawings

FOREIGN PATENT DOCUMENTS

| | | |
|---|---|---|
| WO | WO 0123376 | 4/2001 |
| WO | WO 0130781 | 5/2001 |
| WO | WO 01/70708 | 9/2001 |
| WO | WO 0177104 | 10/2001 |
| WO | WO 0192253 | 12/2001 |
| WO | WO 0202522 | 1/2002 |
| WO | WO 0208202 | 1/2002 |
| WO | WO 0208206 | 1/2002 |
| WO | WO 0208222 | 1/2002 |
| WO | WO 02/064558 | 8/2002 |
| WO | WO 03/004460 | 1/2003 |
| WO | WO 03/007949 | 1/2003 |
| WO | WO 03/008380 | 1/2003 |
| WO | WO 03/011288 | 2/2003 |
| WO | 2004062601 | 7/2004 |
| WO | WO 2007069020 | 6/2007 |

OTHER PUBLICATIONS

Batt, D.G. (2000). "Disubstituted Indazoles as Potent Antagonists of the Integrin $\alpha_v\beta_3$," *J. Med. Chem.* 43:41-58.

Belvisi, L. et al. (2001). "Potent Integrin Antagonists from a Small Library of RGD-Including Cyclic Pseudopeptides," *Organic Letters* 3(7):1001-1004.

Bianchi, E. et al. (2000). "Integrin LFA-1 Interacts with the Transcriptional Co-Activator JAB1 to Modulate AP-1 Activity," *Nature* 404:617-621.

Blythin, D.J. et al. (1994). "Synthesis of Racemic *cis*- and *trans*-3-Phenylazetidine-2-Carboxylic Acids as Conformationally Restricted Analogs of Phenylalanine," *J. Org. Chem.* 59:6098-6100.

Boer, J. et al. (2001). "Design and Synthesis of Potent and Selective $\alpha4\beta7$ Integrin Antagonists," *J. Med. Chem.* 44(16):2586-2592.

Chang, L.L. et al. (2002). "The Discovery of Small Molecule Carbamates as Potent Dual $\alpha_4\beta_1/\alpha_4\beta_7$ Integrin Antagonists," *Bioorganic & Medicinal Chemistry Letters* 12:159-163.

Chen, L. et al. (2000). "*N*-Acyl Phenylalanine Analogues as Potent Small Molecule VLA-4 Antagonists," *Bioorganic & Medicinal Chemistry Letters* 10:725-727.

Chen, L. et al. (2000). "*N*-Benzylpyroglutamyl-L-phenylalanine Derivatives as VCAM/VLA-4 Antagonists," *Bioorganic & Medicinal Chemistry Letters* 10:729-733.

Chen, L. et al. (2002). "Focused Library Approach for Identification of New *N*-Acylphenylalanines as VCAM/VLA-4 Antagonists," *Bioorganic & Medicinal Chemistry Letters* 12:1679-1682.

Chen, L. et al. (2002). "*N*-Acyl-L-phenylalanine Derivatives as Potent VLA-4 Antagonists that Mimic a Cyclic Peptide Conformation," *Bioorganic & Medicinal Chemistry Letters* 12:137-140.

Chen, M-H. et al. (1999). "Carbohydroxamido-Oxazolidines: Antibacterial Agents That Target Lipid A Biosynthesis," *Bioorg. & Med. Chem. Letts.* 9(3):313-318.

Clements, J.M. et al. (2002). "Antibacterial Activities and Characterization of Novel Inhibitors of LpxC," *Antimicrobial Agents and Chemotherapy.* 46(6):1793-1799.

Cromwell, N.H. et al. (1979). "The Azetidines. Recent Synthetic Developments." *Chemical Reviews* 79(4): 331-358.

de Laszlo, S.E. et al. (2002). "Identification of Unique VLA-4 Antagonists from a Combinatorial Library," *Bioorganic & Medicinal Chemistry Letters* 12:685-688.

Doherty, G.A. et al. (2002). "*N*-Aryl 2,6-Dimethozybiphenylalanine Analogues as VLA-4 Antagonists," *Bioorganic & Medicinal Chemistry Letters* 12:729-731.

Doherty, G.A. et al. (2002). "Substituted Tetrahydrofuroyl-1-phenylalanine Derivatives as Potent and Specific VLA-4 Antagonists," *Bioorganic & Medicinal Chemistry Letters* 12:1501-1505.

Dubree, N.J.P. et al. (2002). "Selective $\alpha4\beta7$ Integrin Antagonists and Their Potential as Antiinflammatory Agents," *J. Med. Chem.* 45(16):3451-3457.

Duggan, M.E. et al. (2000). "Nonpeptide $\alpha_v\beta_3$ Antagonists. 1. Transformation of a Potent, Integrin-Selective $\alpha_{IIb}\beta_3$ Antagonist into a Potent $\alpha_v\beta_3$ Antagonist," *J. Med. Chem.* 43:3736-3745.

Fotouhi, N. et al. (2000). "Cyclic Thioether Peptide Mimetics as VCAM-VLA-4 Antagonists," *Bioorganic & Medicinal Chemistry Letters* 10:1167-1169.

Fotouhi, N. et al. (2000). "The Design and Synthesis of Potent Cyclic Peptide VCAM-VLA-4 Antagonists Incorporating an Achiral Asp-Pro Mimetic," *Bioorganic & Medicinal Chemistry Letters* 10:1171-1173.

Gadek, T.R. et al. (2002). "Generation of an LFA-1 Antagonist by the Transfer of the ICAM-1 Immunoregulatory Epitope to a Small Molecule," *Science* 295:1086-1089.

Goodman, S.L. et al. (2002). "Nanomolar Small Molecule Inhibitors for $\alpha v\beta6$, $\alpha v\beta5$, and $\alpha v\beta3$. Integrins," *J. Med. Chem.* 45(5):1045-1051.

Hagmann, W.K. et al. (2001). "The Discovery of Sulfonylated Dipeptides as Potent VLA-4 Antagonists," *Bioorganic & Medicinal Chemistry Letters* 11:2709-2713.

Huth, J.R. et al. (2000). "NMR and Mutagenesis Evidence for an I Domain Allosteric Site That Regulates Lymphocyte Function-Associated Antigen 1 Ligand Binding," *PNAS* 97(10):5231-5236.

Hyland, S.A. et al. (1997). "Cloning, Expression, and Purification of UDP-3-O-Acyl-GlcNAc Deacetylase from *Pseudomonas aeruginosa*: A Metalloamidase of the Lipid A Biosynthesis Pathway," *J. Bacteriology* 179(6): 2029-2037.

Inagawa, T. et al. (2001). "Defective Plasmid Partition in *ftsH* Mutants of *Escherichia coli*," *Mol. Genet. Genomics* 265(5):755-762.

Jackman, J.E. (1999). "Metal Ion Requirement and Inhibition of the UDP-3-*O*-acyl-GlcNAc Deacetylases of *Escherichia coli* and *Aquifex aeolicus*," *Dissertation Department of Biochemistry, Duke University* 203 pages.

Jackman, J.E. et al. (1999). "UDP-3-*O*-(*R*-3-Hydroxymyristoyl)-*N*-acetylgucosamine Deacetylase of *Escherichia coli* Is a Zinc Metalloenzyme," *Biochemistry* 38(6):1902-1911.

Jackman, J.E. et al. (2000). "Antibacterial Agents that Target Lipid A Biosynthesis in Gram-Negative Bacteria: Inhibition of Diverse UDP-3-*O*-(*R*-3-hydroxymyristoyl)-*N*-acetylglucosamine Deacetylases by Substrate Analogs Containing ZincBinding Motifs," *J. Biol. Chem.* 275(15):11002-11009.

Jackman, J.E. et al. (2001). "Site-Directed mutagenesis of the Bacterial Metalloamidase UDP-3-*O*-acyl)-*N*-acetylglucosamine Deacetylase (LpxC). Identification of the Zinc Binding Site," *Biochemistry* 40: 514-523.

Kamenecka, T.M. et al. (2002). "*N*-Aryl-prolyl-dipeptides as Potent Antagonists of VLA-4," *Bioorganic & Medicinal Chemistry Letters* 12:2205-2208.

Kelly, T.A. et al. (1999). "Cutting Edge: A Small Molecule Antagonist of LFA-1-Mediated Cell Adhesion," *The Journal of Immunology* 163:5173-5177.

Kline, T. et al. (2001). "Potent, Novel in Vitro Inhibitors of the *Pseudomonas aeruginosa* Deacetylast LpxC," *J. Med. Chem.* 45(14):3112-3129.

Kloser, A. et al. (1998) "Modulations in Lipid A and Phospholipid Biosynthesis Pathways Influence Outer Membrane Protein Assembly in *Escherichia coli* K-12," *Mol. Microbiol.* 27(5):1003-1008.

Kloser, A.W. et al. (1996). "*asmB*, a Suppressor Locus for Assembly-Defective OmpF Mutants of *Escherichia coli*, Is Allelic to *envA* (*IpxC*)," *J. Bacteriol.* 178(17):5138-5143.

Kobayashi, T. et al. (2002). "Convenient Synthesis of 3,3,3-Trifluoropropenyl Compounds from Aromatic Aldehydes by Means of the TBAF-Mediated Horner Reaction," *J. Org. Chem.* 67(9):3156-3159.

Kopka, I.E. et al. (2002). "Substituted 3-Amino Biaryl Propionic Acids as Potent VLA-4 Antagonists," *Bioorganic & Medicinal Chemistry Letters* 12:2415-2418.

Kopka, I.E. et al. (2002). "Substituted *N*-(3,5-Dichlorobenzenesulfonyl)-L-prolyl-phenylalanine Analogues as Potent VLA-4 Antagonists," *Bioorganic & Medicinal Chemistry Letters* 12:637-640.

Lee, K-H. et al. (2002). "T Cell Receptor Signaling Precedes Immunological Synpase Formation," *Science* 295:1539-1542.

Li, B. et al. (2002). "*N*-(Arylacetyl)-biphenylalanines as Potent VLA-4 Antagonists," *Bioorganic & Medicinal Chemistry Letters* 12:2141-2144.

Li, X. et al. (2002). "Synthesis of a Carbohydrate-Derived Hydroxamic Acid Inhibitor of the Bacterial Enzyme (LpxC) Involved in Lipid A Biosynthesis," *Org. Lett.* 5(4):539-541.

Lin, K-C. et al. (1998). "Very Late Antigen 4 (VLA4) Antagonists as Anti-Inflammatory Agents," *Current Opinion in Chemical Biology* 2:453-457.

Lin, K-C. et al. (1999). "Selective, Tight-Binding Inhibitors of Integrin $\alpha 4\beta 1$ That Inhibit Allergic Airway Responses," *J. Med. Chem.* 42:920-934.

Lin, L.S. et al. (2002). "The Discovery of Acylated β-Amino Acids as Potent and Orally Bioavailable VLA-4 Antagonists," *Bioorganic & Medicinal Chemistry Letters* 12:611-614.

Link, J.T. et al. (2001). "Discovery and SAR of Diarylsulfide Cyclopropylamide LFA-1/ICAM-1 Interaction Antagonist," *Bioorganic & Medicinal Chemistry Letters* 11:973-976.

Liu, G. et al. (2000). "Discovery of Novel p-Arylthio Cinnamides as Antagonists of Leukocyte Function-Associated Antigen-1/Intracellular Adhesion Molecule-1 Interaction. 1. Identification of an Additional Binding Pocket Based on an Anilino Diaryl Sulfide Lead," *J. Med. Chem.* 43:4025-4040.

Liu, G. et al. (2001). "Novel p-Arylthio Cinnamides as Antagonists of Leukocyte Function-Associated Antigen-1/Intracellular Adhesion Molecule-1 Interaction. 2. Mechanism of Inhibition and Structure-Based Improvement of Pharmaceutical Properties," *J. Med. Chem.* 44:1202-1210.

Lu, T.T. et al. (2002). "Integrin-Mediated Long-Term B Cell Retention in the Splenic Marginal Zone," *Science* 297:409-412.

Mousa, S.A. (2002). "Vitronectin Receptors in Vascular Disorders," *Current Opinion in Investigational Drugs* 3(8):1191-1195.

Müller, G. et al. (2001). "Discovery and Evaluation of Piperidinyl Carboxylic Acid Derivatives as Potent $\alpha_4\beta_1$ Integrin Antagonists," *Bioorganic & Medicinal Chemistry Letters* 11:3019-3021.

Ogura, T. et al. (1999). "Balanced Biosynthesis of Major Membrane Components Through Regulated Degradation of the Committed Enzyme of Lipid A Biosynthesis by the AAA Protease FtsH (HflB) in *Escherichia coli*," *Mol. Microbiol.* 31(3):833-844.

Ohta, N. et al. (1999). "The Organellar Genomes of *Cyanidioschyzon merolae*," In *Enigmatic Microorganisms and Life in Extreme Environments*, Seckbach, J. ed., Kluwer Academic Publishers: The Netherlands 1:141-149.

Onishi, H.R. et al. (1996). "Antibacterial Agents That Inhibit Lipid A Biosynthesis," *Science* 274:980-982.

Pei, Z. et al. (2001). "Discovery of Potent Antagonists of Leukocyte Function-Associated Antigen-1/Intercellular Adhesion Molecule-1 Interaction. 3. Amide (C-Ring) Structure-Activity Relationship and Improvement of Overall Properties of Arylthio Cinnamides," *J. Med. Chem.* 44:2913-2920.

Pepinsky, R.B. et al. (2002). "Comparative Assessment of the Ligand and Metal Ion Binding Properties of Integrins $\alpha 9\beta 1$ and $\alpha 4\beta 1$," *Biochemistry* 41:7125-7141.

Pirrung, M.C. et al. (2002). "Inhibition of the Antibacterial Target UDP-(3-O-acyl)-N-acetrylglucosamine Deacetylase (LpxC): Isoxazoline Zinc Amidase Inhibitors Bearing Diverse Metal Binding Groups," *J. Med. Chem.* 45(19):4359-4370.

Pirrung, M.C. et al. (2003). "High-Throughput Catch-and-Release Synthesis of Oxazoline Hydroxamates. Structure-Activity of *Escherichia coli* LpxC: In Vitro Enzyme Inhibition and Antibacterial Properties," *J. Am. Chem. Soc.* 125: 1575-1586.

Pitts, W.J. et al. (2000). "Isoxazolines as Potent Antagonists of the Integrin $\alpha_v\beta_3$," *J. Med. Chem.* 43:27-40.

Porter, J.R et al. (2002). "N-(Pyrimidin-4-yl) and N-(Pyridin-2-yl) Phenylalanine Derivatives as VLA-4 Integrin Antagonists," *Bioorganic & Medicinal Chemistry Letters* 12:1595-1598.

Porter, J.R. et al. (2002). "Squaric Acid Derivatives as VLA-4 Integrin Antagonists," *Bioorganic & Medicinal Chemistry Letters* 12:1051-1054.

Porter, J.R. et al. (2003). "Dehydrophenylalanine Derivatives as VLA-4 Integrin Antagonists," *Bioorganic & Medicinal Chemistry Letters* 13:805-808.

Price, N.P. et al. (1994). "Biosynthesis of a Structurally Novel Lipid A in *Rhizobium leguminosarum*: Identification and Characterization of Six Metabolic Steps Leading From UDP-GlcNAc to 3-Deoxy-D-manno-2-Octulosonic Acid$_2$-Lipid IV$_a$," *J. Bacteriol.* 176(15):4646-4655.

Qiu, X-L. et al. (2000). "Practical Synthesis of Boc-Protected cis-4-Trifluoromethyl and cis-4-Difluoromethyl-L- prolines," *J. Org. Chem.* 67:7162-7164.

Raetz, C.R.H. (1998). "Enzymes of Lipid A Biosynthesis: Targets for the Design of New Antibiotics," In *Endotoxins and Sepsis: Molecular Mechanisms of Pathogenesis, Host Resistances, and Therapy* J. Levin et al. eds., Wiley-Liss: New York, NY pp. 1-14.

Raetz. C.R.H. (1996). "Bacterial Lipopolysaccharides: A Remarkable Family of Bioactive Macroamphiphiles" Chapter 69 In *Escherichia coli and Salmonella: Cellular and Molecular Biology* Second Edition, Neidhardt, F.C. ed., ASM Press: Materials Park, OH vol. I, pp. 1035-1063.

Rodebaugh, R.M. et al. (1971)."2-Carboazetidine Derivatives (1)," *J. Heterocycl. Chem.* 8:19-24.

Scozzafava, A. et al. (2002). "Carbonic Anhydrase Activators: High Affinity Isozymes I, II, and IV Activators, Incorporating a β-Alanyl-Histidine Scaffold," *J. Med. Chem.* 45(2):284-291.

Sekikawa, I. et al. (1983). "Synthesis of Isonipecotinoyl Analogues of Aminopterin and Folic Acid," *J. Heterocyclic Chem.* 20:807-809.

Sidduri, A. et al. (2002). "N-Aroyl-L-Phenylalanine Derivatives as VCAM/VLA-4 Antagonists," *Bioorganic & Medicinal Chemistry Letters* 12:2479-2482.

Sidduri, A. et al. (2002). "N-Cycloalkanoyl-L-Phenylalanine Derivatives as VCAM/VLA-4 Antagonists," *Bioorganic & Medicinal Chemistry Letters* 12:2475-2478.

Singh, J. et al. (2002). "Identification of Potent and Novel $\alpha 4\beta 1$ Antagonists Using in Silico Screening," *J. Med. Chem.* 45:2988-2993.

Su, T. et al. (1997). "Fibrinogen Receptor (GPIIb-IIIa) Antagonists Derived from 5,6-Bicyclic Templates. Amidinoindoles, Amidinoindazoles, and Amidinobenzofurans Containing the N-α-Sulfonamide Carboxylic Acid Function as Potent Platelet Aggregation Inhibitors," *J. Med. Chem.* 40:4308-4318.

Sutherland, P.J. et al. (1998) "*Dictyostelium discoideum* Fatty-acyl Amidase II Has Deacylase Activity on *Rhizobium* Nodulation Factors," *J. Biol. Chem.* 273(8):4459-4464.

Tilley, J. et al. (2000). "Carbacyclic Peptide Mimetics as VCAM-VLA-4 Antagonists," *Bioorganic & Medicinal Chemistry Letters* 10:1163-1165.

Tilley, J.W. et al. (2001). "Imide and Lactam Derivatives of N-Benzylpyroglutamyl-L-phenylalanine as VCAM/VLA-4 Antagonists," *Bioorganic & Medicinal Chemistry Letters* 11:1-4.

Tumey, L.N. et al. (2001). "Parallel Synthesis of Lipid A Biosynthesis Inhibitors," *Abstracts of Papers, Part 2: 222nd ACS National Meeting*: Chicago, IL, Aug. 26-30, 2001. Abstract No. 623, one page.

Vaara, M. (1996). "Lipid A: Target for Antibacterial Drugs," *Science* 274: 939-940.

van der Merwe, P.A. et al. (2002). "The Immunological Synapse—a Multitasking System," *Science* 295:1479-1480.

Wang et al. (2001). "A Fluorescence-Based Homogeneous Assay for Measuring Activity of UDP-3-O-(R-3-Hydroxymyristoyl)-N-acetylglucosamine Deacetylase." *Analytical Biochem.* 290: 338-346.

Wattanasin, S. et al. (2001). "Design and Synthesis of Potent and Selective Inhibitors of Integrin VLA-4," *Bioorganic & Medicinal Chemistry Letters* 11:2955-2958.

Wehner, V. et al. (2002). "Aromatic β-Amino Acids as Asp-Phg Mimics in LDV Derived VLA-4 Antagonists," *Synthesis* 14:2023-2036.

Wei, Y. et al. (2001). "Global Impact of *sdi*A Amplification Revealed by Comprehensive Gene Expression Profiling of *Escherichia coli*," *J. Bacteriol.* 183(7): 2265-2272.

Weitz-Schmidt, G. et al. (2001). "Statins Selectively Inhibit Leukocyte Function Antigen-1 by Binding to a Novel Regulatory Integrin Site," *Nature Medicine* 7(6):687-692.

Welsenbach, K. et al. (2002). "Small Molecule Inhibitors Induce Conformational Changes in the I Domain and the I-like Domain of Lymphocyte Function-Associated Antigen-1," *The Journal of Biological Chemistry* 277(12): 10590-10598.

Winn, M. et al. (2001). "Discovery of Novel p-Arylthio Cinnamides as Antagonists of Leukocyte Function-Associated Antigen-1/

Intercelular Adhesion Molecule-1 Interaction. 4. Structure-Activity Relationship of Substituents on the Benzene Ring of the Cinnamide," *J. Med. Chem.* 44:4393-4403.

Yang, G.X. et al. (2002). "*N*-Tetrahydrofuroyl-(L)-Phenylalanine Derivatives as Potent VLA-4 Antagonists," *Bioorganic & Medicinal Chemistry Letters* 12:1497-1500.

Young, K. et al. (1995). "The *envA* Permeability/Cell Division Gene of *Escherichia coli* Encodes the Second Enzyme of Lipid A Biosynthesis. UDP-3-*O*-(*R*-3-hydroxymyristoyl)-*N*-acetylglucosamine deacetylase," *J. Biol. Chem.* 270(51):30384-30391.

Zimmerman, C.N. (1999). "Peptide and Peptidomimetic Inhibitors of VLA-4," *Expert Opinion on Therapeutic Patents* 9(2):129-133.

Bocan, T. M. A. (Feb. 4, 2000). Database Hcaplus, Acession No. 2000:84604. WO 2000/004892 A2 dated Feb. 2000. Feb. 3, 2000. See Abstract.

International Search Report mailed on Jul. 21, 2004 for PCT patent application No. PCT/US03/21838 filed on Jul. 11, 2003, 5 pages.

Feuston, B.P. et al. (2002) "Binding Model for Nonpeptide Antagonists of $\alpha_v\beta_3$ Integrin," Journal of Medicinal Chemistry. 45(26):5640-5648.

Sorensen, P.G. et al (1996) Regulation of UDP-3-*O*-[*R*-3-hydroxymyristoyl]-*N*-acetylglucosamine Deacetylase in *Escherichia coli*, Journal of Biological Chemistry, 271(42):25898-25905.

\* cited by examiner

N-HYDROXYAMIDE DERIVATIVES POSSESSING ANTIBACTERIAL ACTIVITY

This application claims the benefit of U.S. Provisional Application 60/394,862, filed Jul. 11, 2002, which is hereby incorporated by reference in its entirety.

BACKGROUND OF THE INVENTION

1. Field of the Invention

This invention relates to N-hydroxyamide derivatives which inhibit UDP-3-O—(R-3-hydroxymyristoyl)-N-acetylglucosamine deacetylase (LpxC) and as a result, have gram negative antibacterial activity.

2. State of the Art

Lipid A is the hydrophobic anchor of lipopolysaccharide (LPS) and forms the major lipid component of the outer monolayer of the outer membrane of gram-negative bacteria. Lipid A is required for bacterial growth and inhibition of its biosynthesis is lethal to the bacteria. Furthermore, blocking Lipid A biosynthesis increases the sensitivity of bacteria to other antibiotics.

One of the key enzymes of bacterial lipid A biosynthesis is LpxC. LpxC catalyzes the removal of the N-acetyl group of UDP-3-O—(R-3-hydroxymyristoyl)-N-acetylglucosamine. The LpxC enzyme is essential in gram negative bacteria for the biosynthesis of Lipid A, and it is notably absent from mammalian genomes. Since LpxC is essential for Lipid A biosynthesis and inhibition of Lipid A biosynthesis is lethal to bacteria, inhibitors of LpxC have utility as antibiotics. In addition, the absence of LpxC from mammalian genomes reduces potential toxicity of LpxC inhibitors in mammals. Accordingly, LpxC is an attractive target for antibacterial drug discovery.

By way of example, U.S. Pat. No. 5,925,659 teaches that certain heterocyclic hydroxamate compounds, in particular oxazoline compounds, have the ability to inhibit LpxC.

Accordingly, compounds, which possess LpxC inhibitory activity, are desired as potential antibacterial agents.

SUMMARY OF THE INVENTION

The present invention provides N-hydroxyamide derivatives which inhibit LpxC and thereby possess gram negative antibacterial activity.

In one of its composition aspects, this invention is directed to a compound of Formula I, II or III:

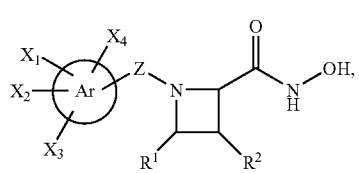

I

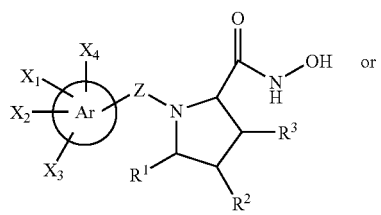

II

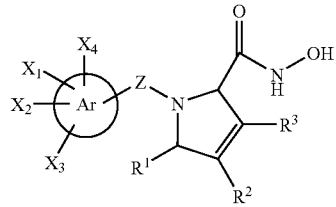

III wherein

Ar is an aryl or heteroaryl ring;

$X_1$, $X_2$, $X_3$, and $X_4$ are independently selected from the group consisting of hydrogen, alkyl, haloalkyl, alkylthio, alkylsulfinyl, alkylsulfonyl, hydroxyalkyl, alkoxy, alkoxyalkyl, haloalkoxy, alkenyl, alkenoxy, alkenoxyalkyl, alkynyl, alkynyloxy, nitro, halo, hydroxy, cycloalkyl, cycloalkylalkyl, arylalkoxy, arylalkoxyalkyl, haloalkylthio, haloalkylsulfinyl, haloalkylsulfonyl, haloarylalkyl, haloarylalkynyl, alkylsilylalkynyl, aryl, alkynyloxy, anaminocarbonylalkyl, carboxylate, carboxyl, carboxamide, heterocycle, and substituted heterocycle;

$R^1$ and $R^3$ are independently selected from the group consisting of hydrogen, alkyl, haloalkyl, hydroxyalkyl, alkenyl, alkynyl, cycloalkyl, aryl, substituted aryl, heteroaryl, substituted heteroaryl, halo, hydroxy, alkoxy, and —O—$R^4$ where $R^4$ is a substituted or unsubstituted aryl; with the proviso that $R^3$ in formula III is not hydroxyl;

$R^2$ is selected from the group consisting of hydrogen, alkyl, haloalkyl, hydroxyalkyl, alkenyl, alkynyl, cycloalkyl, aryl, substituted aryl, heteroaryl, substituted heteroaryl, halo, hydroxy, alkoxy, and —O—$R^4$ where $R^4$ is a substituted or unsubstituted aryl; with the proviso that $R^2$ in formula III is not hydroxyl;

Z is —$CH_2$— or C(O);

and pharmaceutically acceptable salts thereof, any and all tautomers of Formula I, II or III, as well as prodrugs thereof; and provided that the compounds of Formula I, II and III have a minimum inhibition concentration of 128 μg/ml or less against at least one of the organisms selected from the group consisting of *Acinetobacter baumannii, Acinetobact Acinetobacter baumannii Aeromonas hydrophila er haemolyticus, Actinobacillus actinomycetemcomitans, Aeromonas hydrophila, Bacteroides fragilis, Bacteroides theataioatamicron, Bacteroides distasonis, Bacteroides ovatus, Bacteroides vulgatus, Bordetella pertussis, Brucella melitensis, Burkholderia cepacia, Burkholderia pseudomallei, Burkholderia mallei Fusobacterium, Prevotella corporis, Prevotella intermedia, Prevotella endodontalis, Porphyromonas asaccharolytica, Campylobacter jejuni, Campylobacter fetus, Citrobacter freundii, Citrobacter koseri, Edwarsiella tarda, Eikenella corrodens, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscleromatis, Klebsiella ozaenae, Legionella penumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens, Salmonella typhi, Sal-* monella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydia pneumoniae, Chlamydia trachomatis, Ricketsia prowazekii, Coxiella burnetii, Ehrlichia chafeensis, and Bartonella hensenae.

In a preferred embodiment, this invention provides compounds of Formula IV, V or VI:

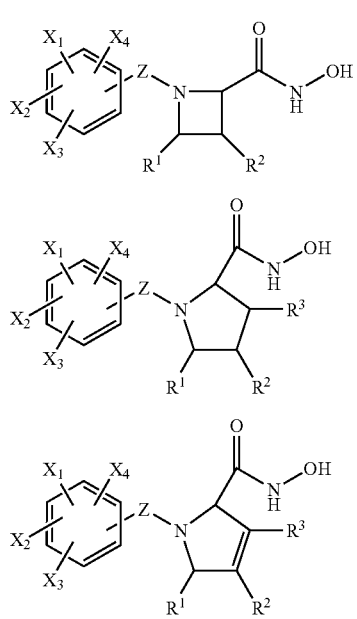

wherein:

$X_1$, $X_2$, $X_3$, and $X_4$ are independently selected from the group consisting of hydrogen, alkyl, haloalkyl, alkylthio, alkylsulfinyl, alkylsulfonyl, hydroxyalkyl, alkoxy, alkoxyalkyl, haloalkoxy, alkenyl, alkenoxy, alkenoxyalkyl, alkynyl, alkynyloxy, nitro, halo, hydroxy, cycloalkyl, cycloalkylalkyl, arylalkoxy, arylalkoxyalkyl, haloalkylthio, haloalkylsulfinyl, haloalkylsulfonyl, haloarylalkyl, haloarylalkynyl, alkylsilylalkynyl, aryl, alkynyloxy, anaminocarbonylalkyl, carboxylate, carboxyl, carboxamide, heterocycle, and substituted heterocycle;

$R^1$ and $R^3$ are independently selected from the group consisting of hydrogen, alkyl, haloalkyl, hydroxyalkyl, alkenyl, alkynyl, cycloalkyl, aryl, substituted aryl, heteroaryl, substituted heteroaryl, halo, hydroxy, alkoxy, and —O—$R^4$ where $R^4$ is a substituted or unsubstituted aryl; with the proviso that in Formula VI, $R^3$ is not hydroxyl $R^2$ is selected from the group consisting of hydrogen, alkyl, haloalkyl, hydroxyalkyl, alkenyl, alkynyl, cycloalkyl, aryl, substituted aryl, heteroaryl, substituted heteroaryl, halo, hydroxy, alkoxy, and —O—$R^4$ where $R^4$ is a substituted or unsubstituted aryl; with the proviso that in Formula VII, $R^2$ is not hydroxyl;

Z is —$CH_2$— or C(O);

and pharmaceutically acceptable salts thereof, any and all tautomers of Formula I, II or III, as well as prodrugs thereof; and provided that the compounds of Formula IV, V and VI have a minimum inhibition concentration of 128 μg/ml or less against at least one of the organisms selected from the group consisting of Acinetobacter baumannii, Acinetobacter haemolyticus, Actinobacillus actinomycetemcomitans, Aeronmonas hydrophila, Bacteroides fragilis, Bacteroides theataioatamicron, Bacteroides distasonis, Bacteroides ovatus, Bacteroides vulgatus, Bordetella pertussis, Brucella melitensis, Burkholderia cepacia, Burkholderia pseudomallei, Burkholderia mallei Fusobacterium, Prevotella corporis, Prevotella intermedia, Prevotella endodontalis, Porphyromonas asaccharolytica, Campylobacter jejuni, Campylobacterfetus, Citrobacter freundii, Citrobacter koseri, Edwarsiella tarda, Eikenella corrodens, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscleromatis, Klebsiella ozaenae, Legionella penumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonasfluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydia pneumoniae, Chlamydia trachomatis, Ricketsia prowazekii, Coxiella burnetii, Ehrlichia chafeensis, and Bartonella hensenae.

Preferably $X_1$, $X_2$, $X_3$, and $X_4$ are independently selected from the group consisting of hydrogen, alkyl, alkoxy, alkenyl, alkenyloxy, alkynyl, alkynyloxy, nitro, hydroxyalkyl, haloalkyl, haloalkoxy, halo, hydroxyl, arylalkoxy, alkoxyalkyl, cycloalkylalkyl, aminocarboxyalkyl, alkylthio, haloalkylthio, alkylsulfinyl, haloalkylsulfinyl, alkylsilanylalkynyl and haloarylalkynyl.

Preferably, Ar is phenyl or 2,5-dihydro-benzo[b]oxepine.

Particularly preferred $(X_1—)(X_2—)(X_3—)(X_4—)$—Ar— groups include the following:

3,4-dimethoxy-5-propylphenyl;
9-methoxy-2,5-dihydro-benzo[b]oxepine;
3-allyl-4-allyloxy-5-methoxyphenyl;
3,4,5-triethoxyphenyl;
3,4,5-trimethoxyphenyl;
3,5-dimethyl-4-nitrophenyl;
3,5-dimethoxy-4-methylphenyl;
3-(3-hydroxypropyl)-4,5-dimethoxyphenyl;
3-trifluoromethoxyphenyl;
3,5-dibromo-4-methylphenyl;
3-methoxy-4-methylphenyl;
3,5-dimethylphenyl;
4-hydroxy-3-methoxy-5-propylphenyl;
3-(3-allyloxypropyl)-4,5-dimethoxyphenyl;
3-(3-benzyloxypropyl)-4,5-dimethoxyphenyl;
3,4-dimethoxy-5-(3-propoxypropyl)phenyl;
3-cyclopropylmethyl-4,5-dimethoxyphenyl;
3-hexyl-4,5-dimethoxyphenyl;
3,4-dimethoxy-5-pentylphenyl;
3-allyl-4-hydroxy-5-methoxyphenyl;
4-methoxy-3-trifluoromethoxyphenyl;
3-propylphenyl;
3-allylphenyl;
4-allyloxy-3-trifluoromethoxyphenyl;
3-trifluoromethylphenyl;

3,4-dimethoxy-5-(3-methoxypropyl)phenyl;
3-(3-ethoxypropyl)-4,5-dimethoxyphenyl;
3-allyl-4,5-dimethoxyphenyl;
3-butyl-4,5-dimethoxyphenyl;
3,4-dimethoxy-5-(3,3,3-trifluoropropyl)phenyl;
3-dimethylcarbamoylmethyl-4,5-dimethoxyphenyl;
3,5-dibromo-4-methoxyphenyl;
3-iodo-4,5-dimethoxyphenyl;
3-(3-fluoropropyl)-4,5-dimethoxyphenyl;
3-trifluoromethylthiophenyl;
4-trifluoromethylthiophenyl;
3-trifluoromethylsulfinylphenyl;
3-(1-fluoropropyl)-4,5-dimethoxyphenyl;
3-ethynyl-4,5-dimethoxyphenyl;
4-methylthio-3-trifluoromethoxyphenyl;
4-methoxy-3-propylphenyl;
3-(2,2,2-trifluoroethylthio)phenyl;
3-pentafluoroethylthiophenyl;
3,5-diallyl-4-methoxyphenyl;
3-trifluoromethoxy-4-methoxy-5-propylphenyl;
3-bromo-4,5-dimethoxyphenyl;
3,4-dimethoxy-5-prop-1-ynylphenyl;
3,4-dimethoxy-5-(2,2,2-trifluoroethoxy)phenyl;
4-methoxy-3,5-dipropylphenyl;
3-methoxy-5-propylphenyl;
4-methoxy-3-trifluoromethylthiophenyl;
3-(1,2,2,2-tetrafluoro-1-trifluoromethyl)ethylthiophenyl;
3,5-bis-trifluoromethylthiophenyl;
3-methoxy-5-trifluoromethylthiophenyl;
4-methoxy-3-propyl-5-trifluoromethylthiophenyl;
3,4-dimethoxy-5-trifluoromethylthiophenyl;
4-alloxy-3-trifluoromethylthiophenyl;
4-n-propoxy-3-trifluoromethylthiophenyl;
4-n-but-3-enyloxy-3-trifluoromethylthiophenyl;
4-n-butoxy-3-trifluoromethylthiophenyl;
4-(3-methylbut-2-enyloxy-3-trifluoromethylthiophenyl;
4-(3-fluorophenethyl)-3-trifluoromethylthiophenyl;
4-n-pentyl-3-trifluoromethylthiophenyl;
3-trifluoromethylthio-4-(trimethylsilanylethynyl)phenyl;
4-ethynyl-3-trifluoromethylthiophenyl;
4-allyl-3-trifluoromethylthiophenyl;
4-n-propyl-3-trifluoromethylthiophenyl;
3-trifluoromethylthio-4-vinylphenyl;
4-ethyl-3-trifluoromethylthiophenyl;
4-propargyloxy-3-trifluoromethylthiophenyl;
3-trifluoromethoxy-4-trifluoromethylthiophenyl;
4-ethoxy-3-trifluoromethylthiophenyl;
4-(2,2,2-trifluoroeth-1-yloxy)-3-trifluoromethylthiophenyl;
3,4-dimethoxy-5-phenylphenyl;
3-trifluoromethoxy-4-vinylphenyl;
4-benzyloxy-3-trifluoromethylthiophenyl;
3-(3-fluorophenylethynyl)-4,5-dimethoxyphenyl; and
4-ethyl-3-trifluoromethoxyphenyl.

Preferred $R^2$ groups include hydrogen, alkyl, alkoxy, haloalkyl, hydroxyl, aryl, substituted aryl, and alkynyl.

Particularly preferred $R^2$ groups include α-ethyl, α-fluoro, α-hydroxy, β-methoxy, β-fluoro, β-trifluoromethyl, α-naphth-2-yloxy, α-(4-biphenyloxy), β-(4-biphenyloxy), and ethynyl.

N-hydroxyamide derivatives within the scope of this invention include those set forth in Table I, II and III as follows:

TABLE I

| $(X_1-)(X_2-)(X_3-)(X_4-)$-Ar- | A | $R^2$ |
|---|---|---|
| 3,4-dimethoxy-5-propylphenyl | —C(O)— | H |
| 9-methoxy-2,5-dihydro-benzo[b]oxepine | —C(O)— | H |
| 3-allyl-4-allyloxy-5-methoxyphenyl | —C(O)— | H |
| 3,4,5-triethoxyphenyl | —C(O)— | H |
| 3,4,5-trimethoxyphenyl | —C(O)— | H |
| 3,4-dimethoxy-5-propylphenyl | —CH$_2$— | H |
| 3,5-dimethyl-4-nitrophenyl | —C(O)— | H |
| 3,5-dimethoxy-4-methylphenyl | —C(O)— | H |
| 3-(3-hydroxypropyl)-4,5-dimethoxyphenyl | —C(O)— | H |
| 3-trifluoromethoxyphenyl | —C(O)— | H |
| 3,5-dibromo-4-methylphenyl | —C(O)— | H |
| 3-methoxy-4-methylphenyl | —C(O)— | H |
| 3,5-dimethylphenyl | —C(O)— | H |
| 4-hydroxy-3-methoxy-5-propylphenyl | —C(O)— | H |
| 3-(3-allyloxypropyl)-4,5-dimethoxyphenyl | —C(O)— | H |
| 3-(3-benzyloxypropyl)-4,5-dimethoxyphenyl | —C(O)— | H |
| 3,4-dimethoxy-5-(3-propoxypropyl)phenyl | —C(O)— | H |
| 3-cyclopropylmethyl-4,5-dimethoxyphenyl | —C(O)— | H |
| 3-hexyl-4,5-dimethoxyphenyl | —C(O)— | H |
| 3,4-dimethoxy-5-pentylphenyl | —C(O)— | H |
| 3-allyl-4-hydroxy-5-methoxyphenyl | —C(O)— | H |
| 4-methoxy-3-trifluoromethoxyphenyl | —C(O)— | H |
| 3-propylphenyl | —C(O)— | H |
| 3-allylphenyl | —C(O)— | H |
| 4-allyloxy-3-trifluoromethoxyphenyl | —C(O)— | H |
| 3-trifluoromethylphenyl | —C(O)— | H |
| 3,4-dimethoxy-5-(3-methoxypropyl)phenyl | —C(O)— | H |
| 3-(3-ethoxypropyl)-4,5-dimethoxyphenyl | —C(O)— | H |
| 3-allyl-4,5-dimethoxyphenyl | —C(O)— | H |
| 3-butyl-4,5-dimethoxyphenyl | —C(O)— | H |
| 3,4-dimethoxy-5-(3,3,3-trifluoropropyl)phenyl | —C(O)— | H |
| 3-dimethylcarbamoylmethyl-4,5-dimethoxyphenyl | —C(O)— | H |
| 3,5-dibromo-4-methoxyphenyl | —C(O)— | H |
| 3-iodo-4,5-dimethoxyphenyl | —C(O)— | H |
| 3-(3-fluoropropyl)-4,5-dimethoxyphenyl | —C(O)— | H |
| 3-trifluoromethylthiophenyl | —C(O)— | H |
| 4-trifluoromethylthiophenyl | —C(O)— | H |
| 3-trifluoromethanesulfinylphenyl | —C(O)— | H |
| 3-(1-fluoropropyl)-4,5-dimethoxyphenyl | —C(O)— | H |
| 3-ethynyl-4,5-dimethoxyphenyl | —C(O)— | H |
| 4-methylthio-3-trifluoromethoxyphenyl | —C(O)— | H |
| 4-methoxy-3-propylphenyl | —C(O)— | H |
| 3-(2,2,2-trifluoroethylthio)phenyl | —C(O)— | H |
| 3-pentafluoroethylthiophenyl | —C(O)— | H |
| 3,5-diallyl-4-methoxyphenyl | —C(O)— | H |
| 3-trifluoromethoxy-4-methoxy-5-propylphenyl | —C(O)— | H |
| 3-bromo-4,5-dimethoxyphenyl | —C(O)— | H |
| 3,4-dimethoxy-5-prop-1-ynylphenyl | —C(O)— | H |
| 3,4-dimethoxy-5-(2,2,2-trifluoroethoxy)phenyl | —C(O)— | H |
| 4-methoxy-3,5-dipropylphenyl | —C(O)— | H |
| 3-methoxy-5-propylphenyl | —C(O)— | H |
| 4-methoxy-3-trifluoromethylthiophenyl | —C(O)— | H |
| 3-(1,2,2,2-tetrafluoro-1-trifluoromethyl)ethylthiophenyl | —C(O)— | H |
| 3,5-bis-trifluoromethylthiophenyl | —C(O)— | H |
| 3-methoxy-5-trifluoromethylthiophenyl | —C(O)— | H |
| 4-methoxy-3-propyl-5-trifluoromethylthiophenyl | —C(O)— | H |
| 3,4-dimethoxy-5-trifluoromethylthiophenyl | —C(O)— | H |
| 4-alloxy-3-trifluoromethylthiophenyl | —C(O)— | H |
| 4-n-propoxy-3-trifluoromethylthiophenyl | —C(O)— | H |
| 4-n-but-3-enyloxy-3-trifluoromethylthiophenyl | —C(O)— | H |
| 4-n-butoxy-3-trifluoromethylthiophenyl | —C(O)— | H |
| 4-(3-methylbut-2-enyloxy-3-trifluoromethylthiophenyl | —C(O)— | H |
| 4-(3-fluorophenethyl)-3-trifluoromethylthiophenyl | —C(O)— | H |
| 4-n-pentyl-3-trifluoromethylthiophenyl | —C(O)— | H |
| 3-trifluoromethylthio-4-(trimethylsilanylethynyl)phenyl | | |

TABLE I-continued

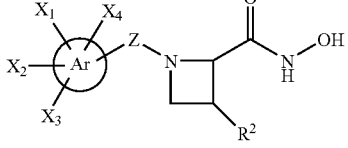

| (X₁—)(X₂—)(X₃—)(X₄—)-Ar- | A | R² |
|---|---|---|
| 4-ethynyl-3-trifluoromethylthiophenyl | —C(O)— | H |
| 4-allyl-3-trifluoromethylthiophenyl | —C(O)— | H |
| 4-n-propyl-3-trifluoromethylthiophenyl | —C(O)— | H |
| 4-methoxy-3-trifluoromethylthiophenyl | —CH₂— | H |
| 3,4-dimethoxy-5-trifluoromethylthiophenyl | —CH₂— | H |
| 3-trifluoromethylthiophenyl | —CH₂— | H |
| 3-trifluoromethylthio-4-vinylphenyl | —C(O)— | H |
| 4-ethyl-3-trifluoromethylthiophenyl | —C(O)— | H |
| 4-propargyloxy-3-trifluoromethylthiophenyl | —C(O)— | H |
| 3-trifluoromethoxy-4-trifluoromethylthiophenyl | —C(O)— | H |
| 4-ethoxy-3-trifluoromethylthiophenyl | —C(O)— | H |
| 4-(2,2,2-trifluoroeth-1-yloxy)-3-trifluoromethylthiophenyl | —C(O)— | H |
| 3,4-dimethoxy-5-n-propylphenyl | —C(O)— | ethyl |
| 3,4-dimethoxy-5-phenylphenyl | —C(O)— | H |
| 3-trifluoromethoxy-4-vinylphenyl | —C(O)— | H |
| 4-benzyloxy-3-trifluoromethylphenyl | —C(O)— | H |
| 3-(3-fluorophenylethynyl)-4,5-dimethoxyphenyl | —C(O)— | H |
| 4-ethyl-3-trifluoromethoxyphenyl | —C(O)— | H |

TABLE II

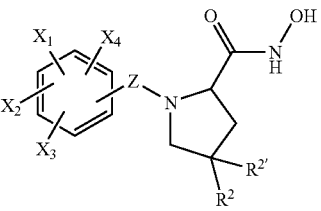

| (X₁—)(X₂—)(X₃—)(X₄—)-φ- | Z | R²/R²'* |
|---|---|---|
| 3,4-dimethoxy-5-propylphenyl | —C(O)— | H |
| 3,4-dimethoxy-5-trifluoromethylthiophenyl | —C(O)— | α-fluoro |
| 3,4-dimethoxy-5-trifluoromethylthiophenyl | —C(O)— | α-hydroxy |
| 3,4-dimethoxy-5-trifluoromethylthiophenyl | —C(O)— | β-methoxy |
| 3,4-dimethoxy-5-trifluoromethylthiophenyl | —C(O)— | β-fluoro |
| 3-trifluoromethylthiophenyl | —C(O)— | H |
| 3-methoxy-5-trifluoromethylthiophenyl | —C(O)— | H |
| 4-methoxy-3-trifluoromethylthiophenyl | —C(O)— | H |
| 4-methoxy-3-propyl-5-trifluoromethylthiophenyl | —C(O)— | H |
| 3,4-dimethoxy-5-trifluoromethylthiophenyl | —C(O)— | H |
| 3,4-dimethoxy-5-trifluoromethylthiophenyl | —C(O)— | β-trifluoromethyl |
| 3,4-dimethoxy-5-trifluoromethylthiophenyl | —C(O)— | α-naphth-2-yl |
| 3,4-dimethoxy-5-trifluoromethylthiophenyl | —C(O)— | α-(4-biphenyl) |
| 3,4-dimethoxy-5-trifluoromethylthiophenyl | —C(O)— | β-(4-biphenyl) |
| 3,4-dimethoxy-5-trifluoromethylthiophenyl | —C(O)— | fluoro/fluoro |

φ = phenyl
*Unless otherwise indicated R²' is hydrogen.

TABLE III

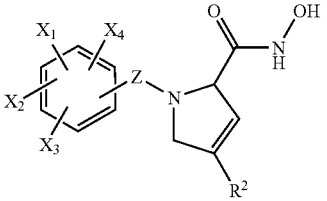

| (X₁—)(X₂—)(X₃—)(X₄—)-φ- | Z | R² |
|---|---|---|
| 3,4-dimethoxy-5-trifluoromethylthiophenyl | —C(O)— | H |
| 3,4-dimethoxy-5-trifluoromethylthiophenyl | —C(O)— | Ethynyl |
| 3,4-dimethoxy-5-trifluoromethylthiophenyl | —C(O)— | trifluoromethyl |

φ = phenyl

Specific compounds within the scope of this invention include the following compounds:

1-(3,4-dimethoxy-5-propylbenzoyl)pyrrolidine-2R-carboxylic acid hydroxyamide;

1-(3,4-dimethoxy-5-propylbenzoyl)azetidine-2R-carboxylic acid hydroxyamide;

1-(9-methoxy-2,5-dihydro-benzo[b]oxepine-7-carbonyl)azetidine-2R-carboxylic acid hydroxyamide;

1-(3-allyl-4-allyloxy-5-methoxybenzoyl)azetidine-2R-carboxylic acid hydroxyamide;

1-(3,4,5-triethoxybenzoyl)azetidine-2R-carboxylic acid hydroxyamide;

1-(3,4,5-trimethoxybenzoyl)azetidine-2R-carboxylic acid hydroxyamide;

1-(3,4-dimethoxy-5-propylbenzyl)azetidine-2R-carboxylic acid hydroxyamide;

1-(3,5-dimethyl-4-nitrobenzoyl)azetidine-2R-carboxylic acid hydroxyamide;

1-(3,5-dimethoxy-4-methylbenzoyl)azetidine-2R-carboxylic acid hydroxyamide;

1-[3-(3-hydroxypropyl)-4,5-dimethoxybenzoyl]azetidine-2R-carboxylic acid hydroxyamide;

1-(3-trifluoromethoxybenzoyl)azetidine-2R-carboxylic acid hydroxyamide;

1-(3,5-dibromo-4-methylbenzoyl)azetidine-2R-carboxylic acid hydroxyamide;

1-(3-methoxy-4-methylbenzoyl)azetidine-2R-carboxylic acid hydroxyamide;

1-(3,5-dimethylbenzoyl)azetidine-2R-carboxylic acid hydroxyamide;

1-(4-hydroxy-3-methoxy-5-propylbenzoyl)azetidine-2R-carboxylic acid hydroxyamide;

1-[3-(3-allyloxy-propyl)-4,5-dimethoxybenzoyl]azetidine-2R-carboxylic acid hydroxyamide;

1-[3-(3-benzyloxy-propyl)-4,5-dimethoxybenzoyl]azetidine-2R-carboxylic acid hydroxyamide;

1-[3,4-dimethoxy-5-(3-propoxypropyl)benzoyl]azetidine-2R-carboxylic acid hydroxyamide;

1-(3-cyclopropylmethyl-4,5-dimethoxybenzoyl)azetidine-2R-carboxylic acid hydroxyamide;

1-(3-hexyl-4,5-dimethoxybenzoyl)azetidine-2R-carboxylic acid hydroxyamide;

1-(3,4-dimethoxy-5-pentylbenzoyl)azetidine-2R-carboxylic acid hydroxyamide;

1-(3-allyl-4-hydroxy-5-methoxybenzoyl)azetidine-2R-carboxylic acid hydroxyamide;

1-(4-methoxy-3-trifluoromethoxybenzoyl)azetidine-2R-carboxylic acid hydroxyamide;

1-(3-propylbenzoyl)azetidine-2R-carboxylic acid hydroxyamide;

1-(3-allylbenzoyl)azetidine-2R-carboxylic acid hydroxyamide;

1-(4-allyloxy-3-trifluoromethoxybenzoyl)azetidine-2R-carboxylic acid hydroxyamide;

1-(3-trifluoromethylbenzoyl)azetidine-2R-carboxylic acid hydroxyamide;

1-[3,4-dimethoxy-5-(3-methoxypropyl)benzoyl]azetidine-2R-carboxylic acid hydroxyamide;

1-[3-(3-ethoxypropyl)-4,5-dimethoxybenzoyl]azetidine-2R-carboxylic acid hydroxyamide;

1-(3-allyl-4,5-dimethoxybenzoyl)azetidine-2R-carboxylic acid hydroxyamide;

1-(3-butyl-4,5-dimethoxybenzoyl)azetidine-2R-carboxylic acid hydroxyamide;

1-[3,4-dimethoxy-5-(3,3,3-trifluoropropyl)benzoyl]azetidine-2R-carboxylic acid hydroxyamide;

1-(3-dimethylcarbamoylmethyl-4,5-dimethoxybenzoyl)azetidine-2R-carboxylic acid hydroxyamide;

1-(3,5-dibromo-4-methoxybenzoyl)azetidine-2R-carboxylic acid hydroxyamide;

1-(3-iodo-4,5-dimethoxybenzoyl)azetidine-2R-carboxylic acid hydroxyamide;

1-[3-(3-fluoropropyl)-4,5-dimethoxybenzoyl]azetidine-2R-carboxylic acid hydroxyamide;

1-(3-trifluoromethylthiobenzoyl)azetidine-2R-carboxylic acid hydroxyamide;

1-(4-trifluoromethylthiobenzoyl)azetidine-2R-carboxylic acid hydroxyamide;

1-(3-trifluoromethanesulfinylbenzoyl)azetidine-2R-carboxylic acid hydroxyamide;

1-[3-(1-fluoropropyl)-4,5-dimethoxybenzoyl]azetidine-2R-carboxylic acid hydroxyamide;

1-(3-ethynyl-4,5-dimethoxybenzoyl)azetidine-2R-carboxylic acid hydroxyamide;

1-(4-methylthio-3-trifluoromethoxybenzoyl)azetidine-2R-carboxylic acid hydroxyamide;

1-(4-methoxy-3-propylbenzoyl)azetidine-2R-carboxylic acid hydroxyamide;

1-[3-(2,2,2-trifluoroethylthio)benzoyl]azetidine-2R-carboxylic acid hydroxyamide;

1-(3-pentafluoroethylthiobenzoyl)azetidine-2R-carboxylic acid hydroxyamide;

1-(3,5-diallyl-4-methoxybenzoyl)azetidine-2R-carboxylic acid hydroxyamide;

1-(3-trifluoromethoxy-4-methoxy-5-propylbenzoyl)azetidine-2R-carboxylic acid hydroxyamide;

1-(3-bromo-4,5-dimethoxybenzoyl)azetidine-2R-carboxylic acid hydroxyamide;

1-(3,4-dimethoxy-5-prop-1-ynylbenzoyl)azetidine-2R-carboxylic acid hydroxyamide;

1-[3,4-dimethoxy-5-(2,2,2-trifluoroethoxy)benzoyl]azetidine-2R-carboxylic acid hydroxyamide;

1-(4-methoxy-3,5-dipropylbenzoyl)azetidine-2R-carboxylic acid hydroxyamide;

1-(3-methoxy-5-propylbenzoyl)azetidine-2R-carboxylic acid hydroxyamide;

1-(4-methoxy-3-trifluoromethylthiobenzoyl)azetidine-2R-carboxylic acid hydroxyamide;

1-[3-(1,2,2,2-tetrafluoro-1-trifluoromethylethylthio)benzoyl]azetidine-2R-carboxylic acid hydroxyamide;

1-(3,5-bis-trifluoromethylthiobenzoyl)azetidine-2R-carboxylic acid hydroxyamide;

1-(3-methoxy-5-trifluoromethylthiobenzoyl)azetidine-2R-carboxylic acid hydroxyamide;

1-(4-methoxy-3-propyl-5-trifluoromethylthiobenzoyl)azetidine-2R-carboxylic acid hydroxyamide;

1-(3,4-dimethoxy-5-trifluoromethylthiobenzoyl)azetidine-2R-carboxylic acid hydroxyamide;

1-(3,4-dimethoxy-5-trifluoromethylthiobenzoyl)4S-fluoropyrrolidine-2R-carboxylic acid hydroxyamide 1-(3,4-dimethoxy-5-trifluoromethylthiobenzoyl)4S-hydroxypyrrolidine-2R-carboxylic acid hydroxyamide 1-(3,4-dimethoxy-5-trifluoromethylthiobenzoyl)4R-methoxypyrrolidine-2R-carboxylic acid hydroxyamide 1-(3,4-dimethoxy-5-trifluoromethylthiobenzoyl)4R-fluoropyrrolidine-2R-carboxylic acid hydroxyamide 1-(3-trifluoromethylthiobenzoyl)pyrrolidine-2R-carboxylic acid hydroxyamide 1-(3-methoxy-5-trifluoromethylthiobenzoyl)pyrrolidine-2R-carboxylic acid hydroxyamide 1-(4-methoxy-3-trifluoromethylthiobenzoyl)pyrrolidine-2R-carboxylic acid hydroxyamide 1-(4-methoxy-3-propyl-5-trifluoromethylthiobenzoyl)pyrrolidine-2R-carboxylic acid hydroxyamide 1-(3,4-dimethoxy-5-trifluoromethylthiobenzoyl)-pyrrolidine-2R-carboxylic acid hydroxyamide 1-(3,4-dimethoxy-5-trifluoromethylthiobenzoyl)-4R-trifluoromethyl-pyrrolidine-2R-carboxylic acid hydroxyamide 1-(3,4-dimethoxy-5-trifluoromethylsulfanyl-benzoyl)-4-trifluoromethyl-2,5-dihydro-1H-pyrrole-2R-carboxylic acid hydroxyamide 1-(3,4-dimethoxy-5-trifluoromethylthiobenzoyl)-4-ethynyl-2,5-dihydro-1H-pyrrole-2R-carboxylic acid hydroxyamide 1-(3,4-dimethoxy-5-trifluoromethylthiobenzoyl)-2,5-dihydro-1H-pyrrole-2R-carboxylic acid hydroxyamide 1-(3,4-dimethoxy-5-trifluoromethylthiobenzoyl)-4S-(naphthalen-2-yloxy)pyrrolidine-2R-carboxylic acid hydroxyamide 4S-(biphenyl-4-yloxy)-1-(3,4-dimethoxy-5-trifluoromethylthiobenzoyl)-pyrrolidine-2R-carboxylic acid hydroxyamide 4R-(biphenyl-4-yloxy)-1-(3,4-dimethoxy-5-trifluoromethylthiobenzoyl)-pyrrolidine-2R-carboxylic acid hydroxyamide 1-(4-allyloxy-3-trifluoromethylthiobenzoyl)azetidine-2R-carboxylic acid hydroxyamide 1-(4-propoxy-3-trifluoromethylthiobenzoyl)azetidine-2R-carboxylic acid hydroxyamide 1-(4-but-3-enyloxy-3-trifluoromethylthiobenzoyl)azetidine-2R-carboxylic acid hydroxyamide 1-(4-butoxy-3-trifluoromethylthiobenzoyl)azetidine-2R-carboxylic acid hydroxyamide 1-[4-(3-methyl-but-2-enyloxy)-3-trifluoromethylthiobenzoyl]azetidine-2R-carboxylic acid hydroxyamide 1-{4-[2-(3-fluorophenyl)ethyl]-3-trifluoromethylthiobenzoyl}azetidine-2R-carboxylic acid hydroxyamide 1-(4-pentyl-3-trifluoromethylthiobenzoyl)azetidine-2R-carboxylic acid hydroxyamide 1-[3-trifluoromethylthio-4-(trimethylsilanylethynyl)benzoyl]azetidine-2R-carboxylic acid hydroxyamide 1-(4-ethynyl-3-trifluoromethylthiobenzoyl)azetidine-2R-carboxylic acid hydroxyamide 1-(4-allyl-3-trifluoromethylthiobenzoyl)azetidine-2R-carboxylic acid hydroxyamide 1-(4-propyl-3-trifluoromethylthiobenzoyl)azetidine-2R-carboxylic acid hydroxyamide 1-(4-methoxy-3-trifluoromethylthiobenzyl)azetidine-2R-carboxylic acid hydroxyamide 1-(3,4-dimethoxy-5-trifluoroethylthiobenzyl)azetidine-2R-carboxylic acid hydroxyamide 1-(3-trifluoromethylthiobenzyl)azetidine-2R-carboxylic acid hydroxyamide 1-(3-trifluoromethylthio-4-vinylbenzoyl)azetidine-2R-carboxylic acid hydroxyamide 1-(4-ethyl-3-trifluoromethylthiobenzoyl)azetidine-2R-carboxylic acid hydroxyamide 1-(4-prop-2-ynyloxy-3-trifluoromethylthiobenzoyl)azetidine-2R-carboxylic acid hydroxyamide 1-(3-trifluoromethoxy-4-trifluoromethylthiobenzoyl)azetidine-2R-carboxylic acid hydroxyamide 1-(4-ethoxy-3-trifluoromethylthiobenzoyl)azetidine-2R-carboxylic acid hydroxyamide 1-[4-(2,2,2-trifluoroethoxy)-3-trifluoromethylthiobenzoyl]-azetidine-2R-carboxylic acid hydroxyamide (±)-trans-1-(3,4-dimethoxy-5-propylbenzoyl)-3-ethylazetidine-2-carboxylic acid hydroxyamide 1-(5,6-dimethoxybiphenyl-3-carbonyl)azetidine-2R-carboxylic acid hydroxyamide 1-[3-(3-fluorophenylethynyl)-4,5-dimethoxybenzoyl]azetidine-2R-carboxylic acid hydroxyamide 1-(3-trifluoromethoxy-4-vinylbenzoyl)azetidine-2R-carboxylic acid hydroxyamide 1-(4-ethyl-3-trifluoromethoxybenzoyl)azetidine-2R-carboxylic acid hydroxyamide 1-(4-benzyloxy-3-trifluoromethylthiobenzoyl)-azetidine-2R-carboxylic acid hydroxyamide;

1-(3,4-dimethoxy-5-trifluoromethylthiobenzoyl)-4,4-difluoropyrrolidine-2R-carboxylic acid hydroxyamide;

and pharmaceutically acceptable salts thereof as well as any and all tautomers thereof.

In another aspect, this invention provides pharmaceutical compositions comprising a pharmaceutically acceptable carrier and a therapeutically effective amount of the compounds defined herein. The pharmaceutical compositions of the present invention may further comprise one or more additional antibacterial agents, one of which may be active against gram positive bacteria. One of which may also be active against gram negative bacteria.

In one of its method aspects, this invention is directed to a method for the treatment of a microbial infection in a mammal comprising administering to the mammal a therapeutically effective amount of a compound of this invention. The compound of this invention may be administered to the mammal orally, parenterally, transdermally, topically, rectally, or intranasally in a pharmaceutical composition.

In another of its method aspects, this invention is directed to a method for the treatment of a microbial infection in a mammal comprising administering to the mammal a pharmaceutical composition comprising a therapeutically effective amount of a compound of this invention. The pharmaceutical composition may further one or more additional antibacterial agents, one of which may be active against gram positive bacteria. One of which may also be active against gram negative bacteria.

The pharmaceutical composition may be administered to the mammal orally, parenterally, transdermally, topically, rectally, or intranasally.

In a preferred embodiment, the infection is a gram negative infection. In an additional embodiment, the infection may be a gram positive infection.

In yet another aspect, the present invention provides novel intermediates and processes for preparing compounds of formula I-VI.

DETAILED DESCRIPTION OF THE INVENTION

As described above, this invention relates to N-hydroxyamide derivatives which inhibit LpxC and as a result, have gram negative antibacterial activity. However, prior to describing this invention in further detail, the following terms will first be defined.

Definitions

Unless otherwise stated, the following terms used in the specification and claims have the meanings given below:

"Halo" means fluoro, chloro, bromo, or iodo.

"Nitro" means the group —$NO_2$.

"Hydroxy" means the group —OH.

"Alkyl" means a linear saturated monovalent hydrocarbon radical of one to eight carbon atoms or a branched saturated monovalent hydrocarbon radical of three to eight carbon atoms. Examples of alkyl groups include, but are not limited to, groups such as methyl, ethyl, n-propyl, isopropyl, n-butyl, isobutyl, sec-butyl, t-butyl, n-pentyl, and the like.

"Alkylene" means a linear divalent hydrocarbon group of one to eight carbon atoms or a branched divalent hydrocarbon group of three to eight carbon atoms. Examples of alkylene groups include, but are not limited to, methylene, ethylene, 2-methylpropylene, and the like.

"Alkenyl" means a linear unsaturated monovalent hydrocarbon radical of two to eight carbon atoms or a branched monovalent hydrocarbon radical of three to eight carbon atoms containing at least one double bond, (—C=C—). Examples of alkenyl groups include, but are not limited to, allyl, vinyl, 2-butenyl, and the like.

"Alkynyl" means a linear monovalent hydrocarbon radical of two to eight carbon atoms or a branched monovalent hydrocarbon radical of three to eight carbon atoms containing at least one triple bond, (—C≡C—). Examples of alkynyl groups include, but are not limited to, ethynyl, propynyl, 2-butynyl, and the like.

"Alkynylene" means a linear divalent hydrocarbon radical of two to eight carbon atoms or a branched monovalent hydrocarbon radical of three to eight carbon atoms containing at least one triple bond, (—C≡C—). Examples of alkynylene groups include, but are not limited to, ethynylene, propynylene, and the like.

"Alkylsilylalkynyl" means the group $(alkyl)_3Si$-alkynylene- where alkyl and alkynylene are as defined above.

"Haloalkyl" means an alkyl substituted with one or more, preferably one to 6, of the same or different halo atoms. Examples of haloalkyl groups include, for example, trifluoromethyl, 3-fluoropropyl, 2,2-dichloroethyl, and the like.

"Hydroxyalkyl" refers to an alkyl substituted with one or more —OH groups provided that if two hydroxy groups are present they are not both on the same carbon atom. Examples of hydroxyalkyl groups include, for example, hydroxymethyl, 2-hydroxyethyl, 2-hydroxypropyl, and the like.

"Alkylthio" refers to the group "alkyl-S-" where alkyl is as defined above and which includes, by way of example, methylthio, butylthio, and the like.

"Alkylsulfinyl" refers to the group "alkyl-S(O)—" where alkyl is as defined above and which includes, by way of example, methyl-S(O)—, butyl-S(O)—, and the like.

"Alkylsulfonyl" refers to the group "alkyl-$S(O)_2$—" where alkyl is as defined above and which includes, by way of example, methyl-$S(O)_2$—, butyl-$S(O)_2$—, and the like.

"Alkoxy" refers to the group "alkyl-O—", wherein alkyl is as defined above, and which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkoxyalkyl" refers to the group "-alkylene-O-alkyl" where alkylene and alkyl are as defined herein and which includes, by way of example, 2-propoxyethylene, 3-methoxybutylene, and the like.

"Alkenoxy" refers to the group "alkenyl-O—" where alkenyl is as defined herein and which includes, by way of example, allyloxy, vinyloxy, 2-butenyloxy, and the like.

"Alkenoxyalkyl" refers to the group "alkenyl-O-alkylene" where alkenyl and alkylene are as defined herein and which includes, by way of example, 3-allyloxy-propylene, 2-(2-propenyloxy)ethylene, and the like.

"Alkynyloxy" refers to the group "alkynyl-O—" where alkynyl is as defined herein and which includes, by way of example, propargyloxy and the like.

"Arylalkoxyalkyl" refers to the group "aryl-alkoxy-alkylene-" where aryl, alkoxy and alkylene are as defined herein.

"Haloalkoxy" refers to the group "haloalkyl-O—" where haloalkyl is as defined herein and which includes, by way of example, trifluoromethoxy, 2,2-dichloroethoxy, and the like.

"Haloalkylthio" refers to the group "haloalkyl-S—" where haloalkyl is as defined herein and which includes, by way of example, trifluoromethylthio, 2,2-difluoropropylthio, 3-chloropropylthio, and the like.

"Haloalkyl-sulfinyl" refers to the group "haloalkyl-S(O)—" where haloalkyl is as defined herein and which includes, by way of example, trifluoromethanesulfinyl, 2,2-dichloroethanesulfinyl, and the like.

"Haloalkyl-sulfonyl" refers to the group "haloalkyl-S(O)$_2$—" where haloalkyl is as defined herein and which includes, by way of example, trifluoromethanesulfinyl, 2,2-dichloroethanesulfinyl, and the like.

"Amino" refers to the group "—NR$_a$R$_b$" wherein R$_a$ and R$_b$ are independently H, alkyl, haloalkyl, alkenyl, cycloalkyl, aryl, substituted aryl, heteroaryl, or substituted heteroaryl where each of alkyl, haloalkyl, alkenyl, cycloalkyl, aryl, substituted aryl, heteroaryl, and substituted heteroaryl are as defined herein.

"Carbonyl" means the group "—C(O)—."

"Carboyxl" refers to —COOR where R is hydrogen, alkyl, aryl, heteroaryl and heterocycle or salts thereof.

"Carboxylamide" refers to —C(O)NR$_a$R$_b$" wherein R$_a$ and R$_b$ are independently H, alkyl, haloalkyl, alkenyl, cycloalkyl, aryl, substituted aryl, heteroaryl, or substituted heteroaryl where each of alkyl, haloalkyl, alkenyl, cycloalkyl, aryl, substituted aryl, heteroaryl, and substituted heteroaryl are as defined herein.

"Acyloxy" means the group —C(O)R' wherein R' is alkyl, alkenyl, alkynyl, aryl, substituted aryl, heteroaryl, or substituted heteroaryl where alkyl, alkenyl, alkynyl, aryl, substituted aryl, heteroaryl, or substituted heteroaryl are as defined herein.

"Cycloalkyl" means a cyclic saturated hydrocarbon group of 3 to 8 ring atoms, where one or two of C atoms are optionally replaced by a carbonyl group. The cycloalkyl group may be optionally substituted with one, two, or three substituents, preferably alkyl, alkenyl, halo, hydroxyl, cyano, nitro, alkoxy, haloalkyl, alkenyl, and alkenoxy as these terms are defined herein. Representative examples include, but are not limited to, cyclopropyl, cyclohexyl, cyclopentyl, and the like.

"Cycloalkylalkyl" means a group —R$_c$R$_d$ where R$_c$ is an alkylene group and R$_d$ is a cycloalkyl group, as defined above. Examples include, but are not limited to, cyclopropylmethylene, cyclohexylethylene, and the like.

"Aryl" means a monovalent monocyclic or bicyclic aromatic carbocyclic group of 6 to 14 ring atoms. Examples include, but are not limited to, phenyl, naphthyl, and anthryl. The aryl ring may be optionally fused to a 5-, 6-, or 7-membered monocyclic non-aromatic ring optionally containing 1 or 2 heteroatoms independently selected from oxygen, nitrogen, or sulfur, the remaining ring atoms being C where one or two C atoms are optionally replaced by a carbonyl. Such fused ring systems are referred to herein as "cyclic moiety containing a total of 4, 5, 6, or 7 ring atoms." Representative aryl groups with fused rings include, but are not limited to, 2,5-dihydro-benzo[b]oxepine, 2,3-dihydrobenzo[1,4]dioxane, chroman, isochroman, 2,3-dihydrobenzofuran, 1,3-dihydroisobenzofuran, benzo[1,3]dioxole, 1,2,3,4-tetrahydroisoquinoline, 1,2,3,4-tetrahydroquinoline, 2,3-dihydro-1Hindole, 2,3-dihydro1H-isoindle, benzimidazole-2-one, 2-H-benzoxazol-2-one, and the like.

"Substituted aryl" means an aryl ring substituted with one or more substituents, preferably one to three substituents selected from the group consisting of alkyl, alkenyl, alkynyl, halo, alkoxy, acyloxy, amino, hydroxyl, carboxy, cyano, nitro, and alkylthio as these terms are defined herein. The aryl ring may be optionally fused to a 5-, 6-, or 7-membered monocyclic non-aromatic ring optionally containing 1 or 2 heteroatoms independently selected from oxygen, nitrogen, or sulfur, the remaining ring atoms being C where one or two C atoms are optionally replaced by a carbonyl.

"Heteroaryl" means a monovalent monocyclic or bicyclic aromatic radical of 5 to 10 ring atoms containing one, two, or three ring heteroatoms selected from N, O, or S, the remaining ring atoms being C. Representative examples include, but are not limited to, thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, and the like.

"Substituted heteroaryl" means a heteroaryl ring substituted with one or more substituents, preferably one to three substituents selected from the group consisting of alkyl, alkenyl, alkynyl, halo, alkoxy, acyloxy, amino, hydroxyl, carboxy, cyano, nitro, and alkylthio as these terms are defined herein.

"Aryloxy" means a group "—O—Ar" where Ar is an aryl group or substituted aryl group as these terms are defined herein. Examples include, but are not limited to, benzyloxy, 4-trifluoromethyl-benzyloxy, and the like.

"Arylalkoxy" means a group "—O-alkylene-Ar" where Ar is an aryl group or substituted aryl group as defined herein and alkylene is as also defined herein. Examples include, but are not limited to, 2-(phenyl)ethoxy, 3-(phenyl)propoxy, and the like.

"Arylalkoxyalkyl" means a group "-alkylene-O-alkylene-Ar" where Ar is an aryl group or substituted aryl group as defined herein and each alkylene is independently selected from the other, wherein alkylene is as also defined herein. Examples include, but are not limited to, benzyloxy-propylene, benzyloxy-ethylene, and the like.

"Aminocarboxyalkyl" means a group "—R$_c$C(O)NR$_a$R$_b$" where R$_c$ is an alkylene group as defined herein and R$_a$ and R$_b$ are as defined above.

"Haloarylalkyl" means the group "aryl-alkylene-" having 1 to 6 halo substituents on either the aryl and/or the alkylene groups where aryl and alkylene are as defined herein.

"Haloarylalkenyl" means the group "aryl-alkenylene-" having 1 to 6 halo substituents on either the aryl and/or the alkenylene groups where aryl and alkenylene are as defined herein.

"Haloarylalkynyl" means the group "aryl-alkynylene-" having 1 to 6 halo substituents on either the aryl and/or the alkynylene groups where aryl and alkynylene are as defined herein.

"Heterocycle" or "heterocyclic" refers to a saturated or unsaturated group having a single ring or multiple condensed rings, from 1 to 10 carbon atoms and from 1 to 4 heteroatoms selected from the group consisting of nitrogen, sulfur, or oxygen within the ring, wherein, in fused ring systems one or more of the rings can be aryl or heteroaryl as defined herein. Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

Heterocycles may be optionally substituted with from one to three substituents selected from the group consisting of alkyl, alkenyl, alkynyl, halo, alkoxy, acyloxy, amino, hydroxyl, carboxy, cyano, nitro, and alkylthio as these terms are defined herein.

"Optional" or "optionally" means that the subsequently described event or circumstance may, but need not, occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound or mixture of compounds that, when administered to a mammal for treating a disease, is sufficient to effect such treatment for the disease. The "therapeutically effective amount" will vary depending on the compound, the disease and its severity and the age, weight, etc., of the mammal to be treated.

"Pro-drugs" mean any compound which releases an active parent drug according to a compound of the subject invention in vivo when such prodrug is administered to a mammalian subject. Prodrugs of a compound of the subject invention are prepared by modifying functional groups present in a compound of the subject invention in such a way that the modifications may be cleaved in vivo to release the parent compound. Prodrugs include compounds of the subject invention wherein a hydroxy, sulfhydryl or amino group in the compound is bonded to any group that may be cleaved in vivo to regenerate the free hydroxyl, amino, or sulfhydryl group, respectively. Examples of prodrugs include, but are not limited to $C_1$-$C_{10}$ esters (e.g., acetate, formate, and benzoate derivatives), carbamates (e.g., N,N-alkylaminocarbonyl) of hydroxy functional groups in compounds of the subject invention, and the like.

The term "tautomers" refers to herein as a constitutional isomer in which migration of a hydrogen atom results in two ore more structures. As an example of one potential tautomer, the N-hydroxyamide may tautomerize to form a 1,2-dihydroxyimin, e.g.,

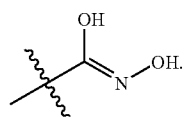

The term "mammal" refers to all mammals including humans, livestock, and companion animals.

The compounds of the present invention are generally named according to the IUPAC or CAS nomenclature system. Abbreviations which are well known to one of ordinary skill in the art may be used (e.g. "Ph" for phenyl, "Me" for methyl, "EFt" for ethyl, "h" for hour or hours and "rt" for room temperature).

General Synthetic Schemes

Compounds of this invention can be made by the methods depicted in the reaction schemes shown below.

The starting materials and reagents used in preparing these compounds are either available from commercial suppliers such as Toronto Research Chemicals (North York, ON Canada), Aldrich Chemical Co. (Milwaukee, Wis., USA), Bachem (Torrance, Calif., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

As it will be apparent to those skilled in the art, conventional protecting groups may be necessary to prevent certain functional groups from undergoing undesired reactions. Suitable protecting groups for various functional groups, as well as suitable conditions for protecting and deprotecting particular function groups are well known in the art. For example, numerous protecting groups are described in T. W. Greene and G. M. Wuts, *Protecting Groups in Organic Synthesis*, Second Edition, Wiley, New York, 1991, and references cited therein.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

The compounds of this invention will typically contain one or more chiral centers. Accordingly, if desired, such compounds can be prepared or isolated as pure stereoisomers. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

Preparation of Compounds of Formula (I)

Compounds of Formula (I) can be prepared as described in Schemes 1-5 below.

In general, a compound of Formula (I), (II), or (III) wherein Z is C(O), $R^1$ is H, $R^2$ is H and $R^3$, if present, is H, can be prepared as illustrated and described in Scheme 1 below.

Scheme 1

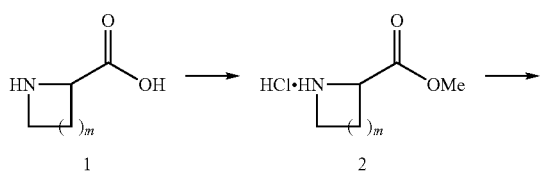

-continued

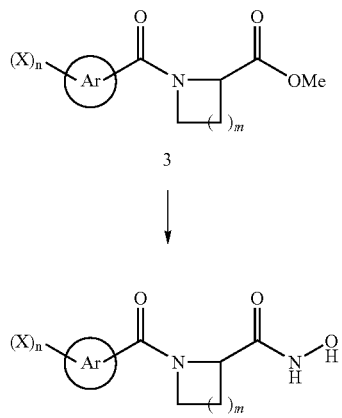

wherein $(X)_n$ Ar corresponds to $(X_1-)(X_2-)(X_3-)(X_4-)-Ar-$ as used in Formula I, II and III above.

As shown in Scheme 1, to a stirred suspension of azetidine-carboxylic acid (1) (or pyrrolidine-carboxylic acid) in methanol is added thionyl chloride or thionyl bromide. The carboxylic acids are commercially available from vendors such as Aldrich, Sigma, Toronto Research Chemicals, etc. Alternately these carboxylic acids can be prepared by methods well known in the art. The addition is typically carried out at low temperatures, e.g., 0° C., and after the addition, the reaction is allowed to warm to ambient temperatures, e.g., about 25° C. The addition provides the carboxylic acid methyl ester (2) as a salt.

The carboxylic acid methyl ester (2) is then condensed with an optionally substituted benzoic acid ($X_n-ArCO_2H$) under reactive conditions, preferably in an inert organic solvent, in the presence of a coupling reagent and an organic base to provide an amide (3). This reaction can be performed with any number of known coupling reagents, such as O-(7-azabenzotriazol-1-yl)-N,N,N',N'-tetramethyluronium hexafluorophosphate (HATU), 1-hydroxybenzotriazole hydrate (HOBT), carbodiimides, diphenylphosphoryl azide (DPPA), and the like. Suitable organic bases include diisopropylethylamine (DIEA), triethylamine (TEA), pyridine, N-methyl morpholine, and the like. Suitable inert organic solvents which can be used include, for example, N,N-dimethylformamide, acetonitrile, dichloromethane, and the like. This reaction is typically conducted using an excess of carboxylic acid methyl ester to benzoic acid at temperatures in the range of about 0° C. to about 50° C. The reaction is continued until completion, which typically occurs in from about 2 to 12 hours.

The amide (3) is then converted to the N-hydroxyamide derivative of this invention by treatment with aqueous hydroxylamine (e.g., aqueous 50% hydroxylamine) in a polar organic solvent such as dioxane and the like. The reaction is carried out at ambient temperature for about 2 to 6 hours.

Alternatively, a compound of Formula (I), (II), and (III) wherein Z is C(O), $R^1$ is H, $R^2$ is H, and $R^3$, if present, is H can be prepared as illustrated in Scheme 2 below.

Scheme 2

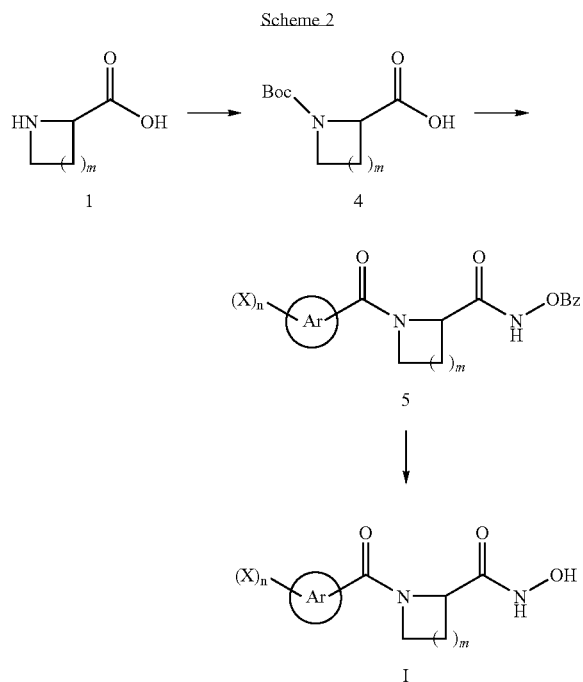

As shown in Scheme 2, to a stirred suspension of azetidine-carboxylic acid (1) (or pyrrolidine-carboxylic acid) is added a solution of di-t-butyldicarbonate (Boc$_2$O) in the presence of an organic base to provide a Boc-protected amino compound (4). The carboxylic acids are commercially available from vendors such as Aldrich, Sigma, Toranto Research Chemicals, etc. Alternately these carboxylic acids can be prepared by methods well known in the art. The addition is typically carried out in an inert organic solvent, such as dichloromethane, dioxane, tetrahydrofuran (THF), and the like, at low temperatures, e.g., 0° C. Suitable organic bases include TEA, pyridine, and the like. After the addition, the reaction mixture is continued stirring at low temperature and is then quenched with a saturated aqueous acidic solution to provide the Boc-protected compound (4).

The Boc-protected compound (4) is then condensed with O-benzyl hydroxylamine-hydrochloride under reactive conditions, preferably in an inert organic solvent, in the presence of a coupling reagent and an organic base to provide a benzyloxyamide (not shown). This reaction can be performed with any number of known coupling reagents, such as HATU, HOBT, carbodiimides, DPPA, and the like. Suitable organic bases include DIEA, TEA, pyridine, N-methyl morpholine, and the like. Suitable inert organic solvents which can be used include, for example, N,N-dimethylformamide, acetonitrile, dichloromethane, and the like. This reaction is typically conducted using an excess of O-benzyl hydroxylaminehydrochloride to Boc-protected compound (4) at temperatures in the range of about 0° C. to about 50° C. The reaction is continued until completion, which typically occurs in from about 2 to 12 hours.

The benzyloxyamide is then contacted with an acid to remove the t-butoxycarbonyl protecting group (Boc). Removal of the protecting group may be carried out with acids, such as a trifluoroacetic acid (TFA), hydrochloric acid, p-toluenesulfonic acid, and the like, in an inert organic solvent such as dichloromethane, dioxane, THF, and the like. The removal is typically conducted at low temperatures, e.g., 0° C., and then gradually allowed to warm to room temperature to provide the benzyloxyamide acid salt (not shown).

The benzyloxyamide acid salt is then condensed with an optionally substituted benzoic acid (X$_n$—ArCO$_2$H) under reactive conditions, preferably in an inert organic solvent, in the presence of a coupling reagent and an organic base to provide an amide (5). This reaction can be performed with any number of known coupling reagents, such as HATU, HOBT, carbodiimides, DPPA, and the like. Suitable organic bases include DIEA, TEA, pyridine, N-methyl morpholine, and the like. Suitable inert organic solvents which can be used include, for example, N,N-dimethylformamide, acetonitrile, dichloromethane, and the like. This reaction is typically conducted using an excess of benzyloxyamide to benzoic acid at temperatures in the range of about 0° C. to about 50° C. The reaction is continued until completion, which typically occurs in from about 2 to 12 hours.

Compound (5) is then converted to the N-hydroxyamide derivative of Formula (I) by hydrogenation to remove the benzyloxy protecting group (OBz). Deprotection is carried out in a polar organic solvent such as methanol. The hydrogenation is carried out at in the presence of a palladium (II) catalyst or palladium on carbon under hydrogen atmosphere. The hydrogenation conveniently may be carried at ambient temperatures in about 30 minutes to 2 hours.

Alternatively, a compound of Formula (I) wherein Z is —CH$_2$—, R$^1$ is H, and R$^2$ is H can be prepared as illustrated in Scheme 3 below.

Scheme 3

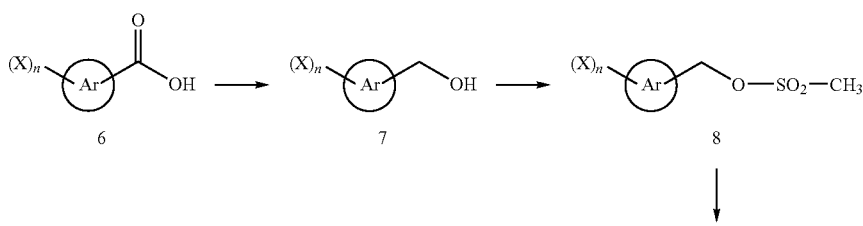

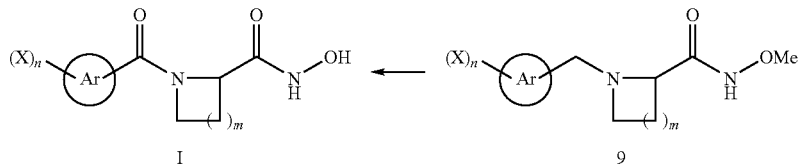

As shown in Scheme 3, to a stirred suspension of optionally substituted benzoic acid (6) in an inert organic solvent is added a reducing agent to provide an optionally substituted benzyl alcohol (7). The optionally substituted benzoic acids are commercially available from vendors such as Aldrich, Sigma, etc. Alternately, these benzoic acids can be prepared by methods well known in the art. Suitable reducing agents for reduction of the carboxylic acid to the alcohol include diisobutylaluminum hydride (DIBAH), LiAlH$_4$, and B$_2$H$_6$. The reduction is typically carried out in an inert organic solvent, such as dichloromethane, THF, diglyme, ether, and the like, at temperatures well below 0° C., e.g., −78° C., in about 30 minutes to 2 hours. The reaction mixture is quenched by the addition of an acid and allowed to gradually warm to room temperature to provide the benzyl alcohol (7).

The benzyl alcohol (7) is then contacted with methanesulfonyl chloride or p-toluenesulfonyl chloride in an inert organic solvent in the presence of an organic base to provide a methanesulfonic acid or p-toluenesulfonic acid benzyl ester (8). Suitable organic bases include triethylamine, pyridine, and the like. Suitable inert organic solvents include dichloromethane, THF, and the like. The reaction conveniently may be conducted at ambient temperature in about 30 minutes to 2 hours.

The methanesulfonic acid benzyl ester (8) is then contacted with an azetidine carboxylate hydrochloride salt (or a pyrrolidine carboxylate hydrochloride salt) under reactive conditions, preferably in an inert organic solvent, in the presence of an organic base to provide compound (9). Suitable inert organic solvents which can be used include, for example, N,N-dimethylformamide, acetonitrile, dichloromethane, N-methylpyridone, and the like. Suitable organic bases include DIEA, TEA, pyridine, and the like. The reaction conveniently may be conducted at ambient temperature for about 24 hours to 48 hours.

Compound (9) is then converted to the N-hydroxyamide derivative of Formula (I) by treatment with aqueous hydroxylamine (e.g., aqueous 50% hydroxylamine) in a polar organic solvent such as dioxane and the like. The reaction is carried out at ambient temperature for about 2 to 6 hours.

Alternatively, a compound of Formula (I) wherein Z is C(O), m is 1, and R$^1$ is H can be prepared as illustrated in Scheme 4 below.

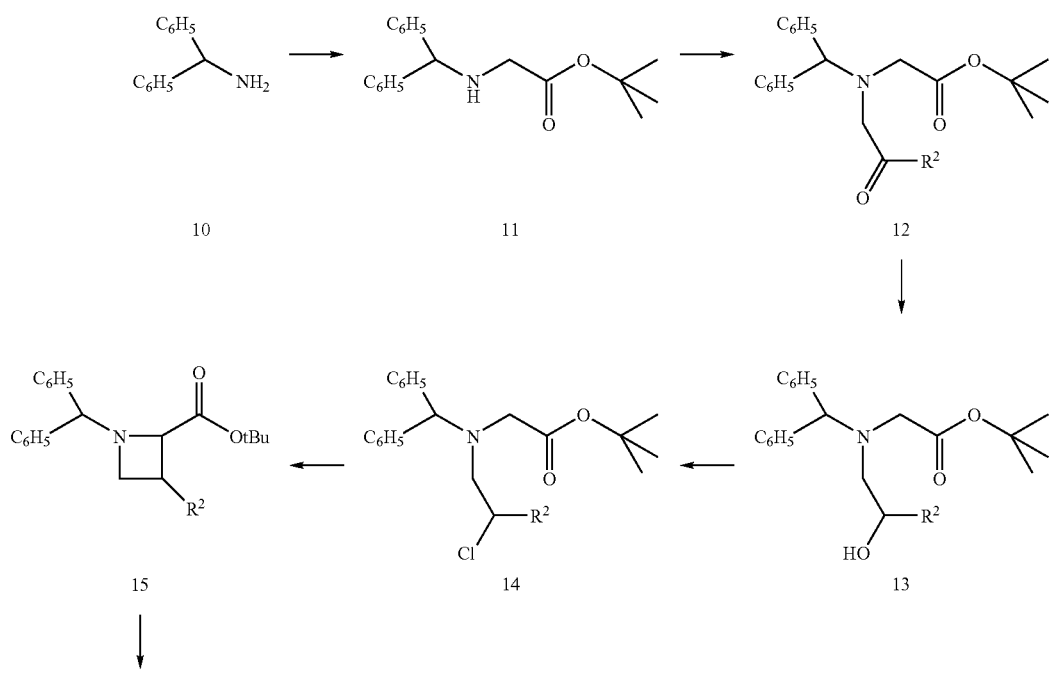

Scheme 4

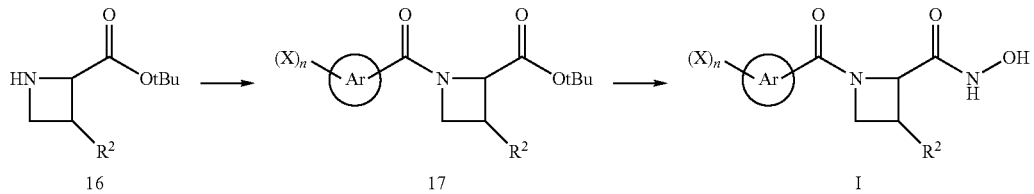

As shown in Scheme 4, benzhydrylamine or α-phenylbenzylamine (10) is alkylated with an alkylating agent in the presence of an iodide salt and a base to provide the alkylated product (11). Suitable alkylating agents include tert-butyl haloacetates such as t-butyl bromoacetate (BrCH$_2$CO$_2$tBu), t-butyl chloroacetate (ClCH$_2$CO$_2$tBu), and the like. The alkylation is conducted in an inert organic solvent such as, for example, N,N-dimethylformamide, acetonitrile, dichloromethane, and N-methylpyridone. Suitable iodide salts include potassium iodide or sodium iodide and suitable bases include potassium carbonate, cesium carbonate and the like. The reaction is typically conducted at room temperature for about 2 to about 6 hours.

The alkylated product (11) is further alkylated with a bromoacetone derivative (R$^2$COCH$_2$Br) in the presence of an organic base to provide a ketone (12). Suitable organic base such as DIEA, TEA, pyridine, N-methyl morpholine, and the like. The alkylation is conducted in an organic solvent such as, for example, acetone, N,N-dimethylformamide, and the like. The reaction is typically conducted at temperatures in the range of about −78 E to 23 EC for about 16 to about 24 hours.

To the ketone (12) is added a reducing agent to provide an alcohol (13). Suitable reducing agents for reduction of the ketone to an alcohol include sodium borohydride, LiAlH$_4$, B$_2$H$_6$, and the like. The reduction is typically carried out in an inert organic solvent, such as dichloromethane, THF, diglyme, ether, and the like, at temperatures well below 0° C., e.g., −23° C., in about 30 minutes to 2 hours. The reaction mixture is quenched by the addition of an acid and allowed to gradually warm to room temperature to provide the alcohol (13).

The alcohol (13) is then converted to the alkyl halide by contacting with thionyl halide (e.g., chloride), phosphorus trichloride, and the like in an inert organic solvent to provide the chloro compound (14) is exemplified by chloro. Suitable inert organic solvents include trichloromethane, diethylether, and the like. The reaction is typically conducted at temperatures in the range of about 0° C. to 23° C. for about 1 to about 3 hours.

The halo compound (14) is subjected to base catalyzed cyclization to give an azetidine (15), as a mixture of cis and trans isomers, as taught in Qian, X, et al., J. Org. Chem. 59 6098-6100 (1994). The base catalyzed cyclization is performed using NaHMDS in an inert organic solvent. Suitable inert organic solvents include THF, diglyme, ether, and the like, at temperatures well below 0° C., e.g., −78° C., in about 30 minutes to 2 hours. The cis and trans isomers may be separated by silica gel column chromatography.

The azetidine (15) is then hydrogenated to remove the benzhydryl protecting group to provide the free amine (16). The hydrogenation is carried out in a polar organic solvent such as methanol. The hydrogenation is carried out in the presence of a palladium (II) catalyst or palladium on carbon under hydrogen atmosphere. The hydrogenation may conveniently be carried out at ambient temperatures in about 30 minutes to 2 hours. The reduction is conducted in the presence of 1 equivalent suitable acid, such as anhydrous HCl, to provide the amine hydrochloride (16).

The amine hydrochloride (16) is then condensed with an optionally substituted benzoic acid (X$_n$—ArCO$_2$H) under reactive conditions, preferably in an inert organic solvent, in the presence of a coupling reagent and an organic base to provide an amide (17). This reaction can be performed with any number of known coupling reagents, such as HATU, HOBT, carbodiimides, DPPA, and the like. Suitable organic bases include DIEA, TEA, pyridine, N-methyl morpholine, and the like. Suitable inert organic solvents with can be used include, for example, N,N-dimethylformamide, acetonitrile, dichloromethane, and the like. This reaction is typically conducted using an excess of acid to amine at temperatures in the range of about 0 EC to about 50 EC. The reaction is continued until completion, which typically occurs in from about 2 to 12 hours.

The amide (17) is then treated with an acid in an inert organic solvent to remove the t-butyl ester protecting group and then coupled with an o-protected hydroxylamine. Suitable acids include hydrochloric acid and suitable inert organic solvents include dioxane. The acid is coupled with the o-protected hydroxylamine using a coupling reagent such as HATU in an organic base in an inert organic solvent. Suitable organic bases include DIEA, TEA, pyridine, and N-methyl morpholine, and suitable inert organic solvents include N,N-dimethylformamide, acetonitrile, dichloromethane, and the like.

The o-protected amide is then hydrogenated to remove the o-protecting group to provide a compound of formula (I). The hydrogenation is carried out in a polar organic solvent such as methanol. The reduction is carried out in the presence of a palladium (II) catalyst under hydrogen atmosphere. The reduction may conveniently be carried out at ambient temperatures in about 30 minutes to 2 hours. The reduction is quenched with a suitable acid such as hydrochloric acid.

Alternatively, a compound of Formula (I) wherein Z is C(O), m is 1, and R$^2$ is H can be prepared as illustrated in Scheme 5 below.

Scheme 5

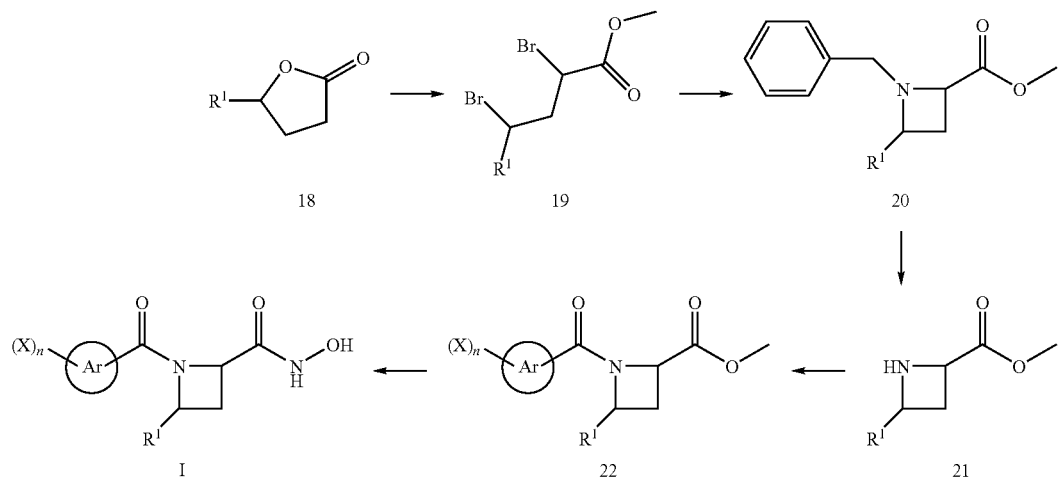

As shown in Scheme 5, the γ-lactone (18) is brominated using $Br_2$ in the presence of phosporus followed by esterification under acidic conditions to provide a dibromoester (19). The γ-lactone is commercially available from vendors such as Aldrich, Sigma, etc or may be synthesized by methods known to those skilled in the art. The reaction is conducted in a polar organic solvent such as methanol, ethanol, and the like.

The dibromoester is condensed with benzyl amine or a substituted benzyl amine as described in R. M. Rodebaugh, et al., J. Heterocycl. Chem. 8, 19 (1971) to provide an azetidine (20). This compound can be converted to the N-hydroxyamide to provide compounds of this invention wherein m=1 and Z is $CH_2$.

Alternatively, the azetidine (20) is then hydrogenated to remove the N-benzyl-protecting group to provide an unprotected azetidine hydrochloride salt (21). The hydrogenation is carried out in a polar organic solvent such as methanol. The reduction is carried out in the presence of a palladium (II) catalyst or palladium on carbon under hydrogen atmosphere. The reduction may conveniently be carried out at ambient temperatures in about 30 minutes to 2 hours. The reduction is carried out in the presence of 1 equivalent of a suitable acid such as hydrochloric acid to provide an unprotected azetidine hydrochloride salt (21).

The unprotected azetidine hydrochloride salt (21) is then condensed with an optionally substituted benzoic acid ($X_n$—$ArCO_2H$) under reactive conditions, preferably in an inert organic solvent, in the presence of a coupling reagent and an organic base to provide an amide (22). This reaction can be performed with any number of known coupling reagents, such as HATU, HOBT, carbodiimides, DPPA, and the like. Suitable organic bases include DIEA, TEA, pyridine, N-methyl morpholine, and the like. Suitable inert organic solvents which can be used include, for example, N,N-dimethylformamide, acetonitrile, dichloromethane, and the like. This reaction is typically conducted using an excess of azetidine to benzoic acid at temperatures in the range of about 0° C. to about 50° C. The reaction is continued until completion, which typically occurs in from about 2 to 12 hours.

The amide (22) is then converted to the N-hydroxyamide derivative of Formula (I) by treatment with aqueous hydroxylamine (e.g., aqueous 50% hydroxylamine) in a polar organic solvent such as dioxane and the like. The reaction is carried out at ambient temperature for about 2 to 6 hours.

Scheme 6 below illustrates numerous methods for preparing diverse proline derivatives useful as starting materials in this invention.

Such derivatives are useful for preparing compounds of Formula II and III of this invention.

Scheme 6

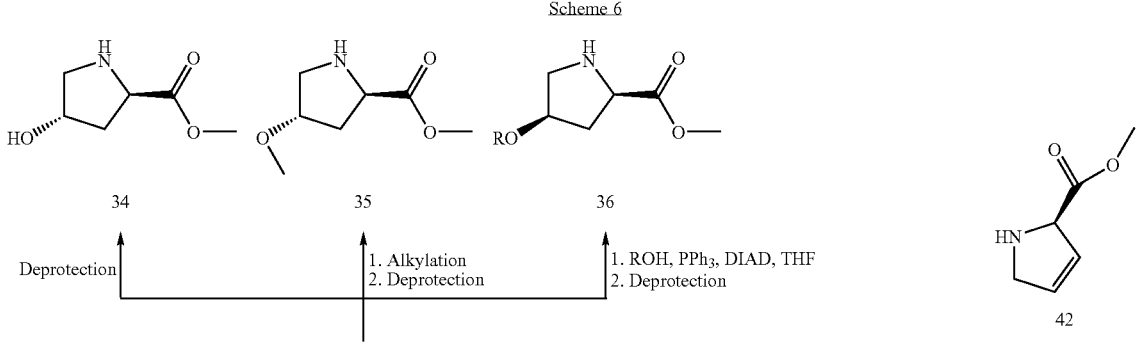

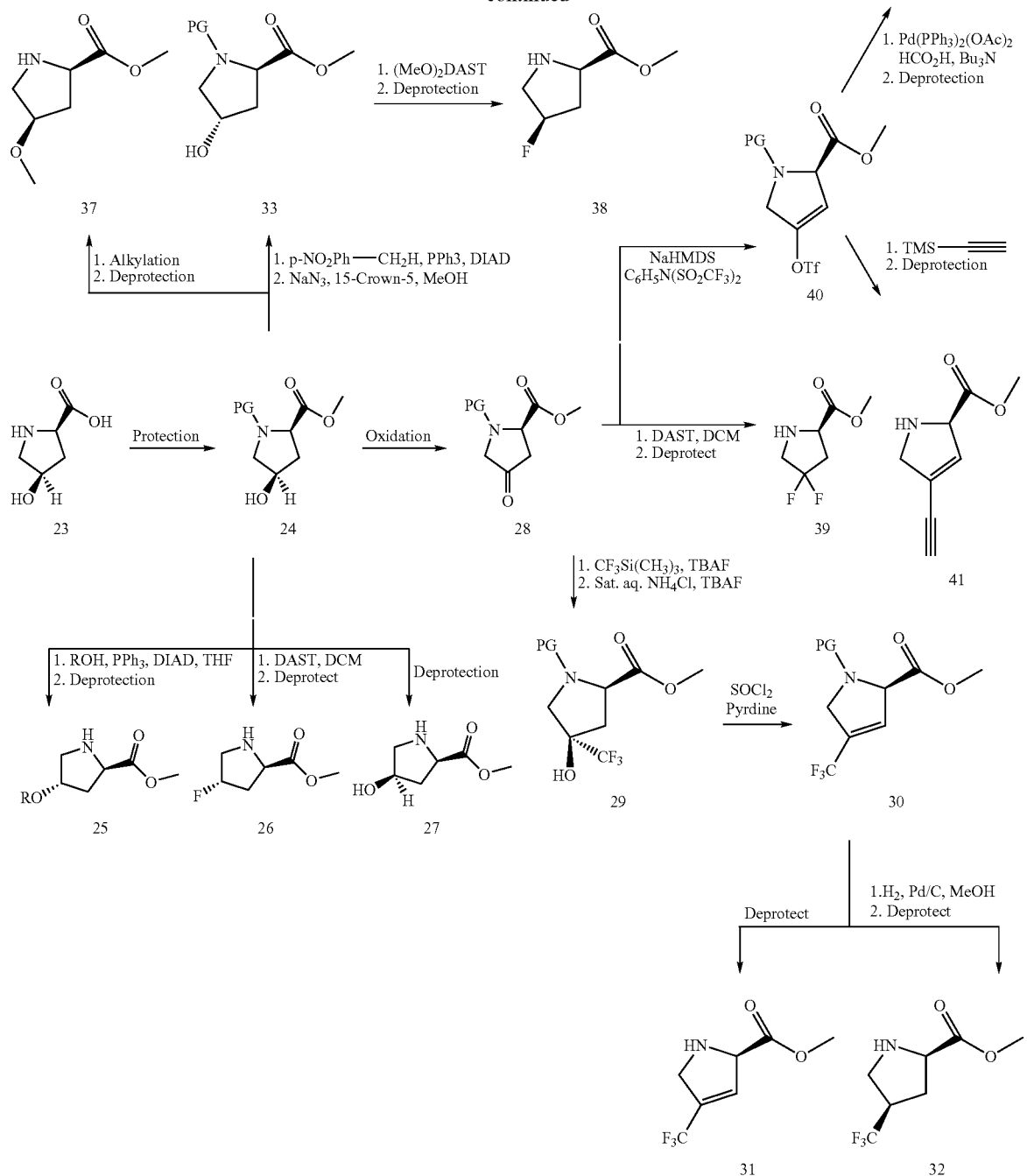

Specifically, the carboxyl and amino groups of commercially available 4-β-hydroxy-proline, compound 23, are protected by conventional means to provide for a methyl ester on the carboxyl group and a protecting group, PG, on the nitrogen and as illustrated by compound 24. Other conventional protecting groups on the carboxyl group could likewise be employed, e.g., benzyl, t-butyl, etc. Preferably, the nitrogen and carboxyl protecting groups are orthogonal to each other so that they can be differentially removed. For example, removal of the nitrogen protecting group provides for the methyl ester of 4-β-hydroxyproline, compound 27.

Conventional alkylation/arylation of the hydroxyl group of compound 24 is accomplished by treatment with a suitable alcohol, ROH, in the presence of triphenylphosphine, diisopropyl azodicarboxylate (DIAD) in a suitable inert solvent such as tetrahydrofuran (THF) using Mitsinobu conditions to provide alkoxy/aryloxy formation. Subsequent and conventional removal of the nitrogen protecting group provides for 4-α-alkoxy/aryloxy proline methyl ester, compound 25.

Compound 24 can be converted to the corresponding 4-α-fluoroproline derivative by reaction with (diethylamino)sulfur trifluoride (DAST) in a suitable solvent such as dichloromethane (DCM), chloroform, and the like. Subsequent and conventional removal of the nitrogen protecting group provides for 4-α-fluoroproline methyl ester, compound 26.

Alternatively, conventional oxidation of the hydroxyl group of compound 24 (e.g., pyridinium dichromate or dess-Martin oxidation conditions) provides for N-protected 4-oxoproline methyl ester, compound 28. In one embodiment, reaction of compound 28 with trimethylsilyltrifluoromethane (CF$_3$Si(CH$_3$)$_3$) and tetrabutylammonium fluoride (TBAF) followed by contact with a saturated aqueous solution of ammonium chloride and TBAF provides for N-protected 4-β-hydroxy-4-α-trifluoromethylproline methyl ester, compound 29 (X. Qiu, et al. *J. Org. Chem.* (2000) 67:7162-1764). Dehydration of compound 29 by contact with thionyl chloride in pyridine provides for N-protected 4-trifluoromethyl-2,5-dihydropyrrole derivative, compound 30. In one embodiment, conventional removal of the nitrogen blocking group provides for 4-trifluoromethyl-2,5-dihydropyrrole derivative, compound 31. In another embodiment, hydrogenation of the vinyl group by hydrogen and palladium/carbon in a suitable solvent such as methanol provides for a preponderance of the β-trifluoroproline methyl ester, compound 32. In this case, stereochemical control of the hydrogenation is dictated by the β-methyl ester at the β-position which favors hydrogenation from the α direction.

In another embodiment, reaction of the N-protected 4-oxoproline methyl ester, compound 28, with DAST in a suitable solvent such as dichloromethane, chloroform and the like, followed by conventional deprotection of the nitrogen provides for the 4,4-difluoroproline methyl ester, compound 39.

The N-protected 4-oxoproline methyl ester, compound 28, can be converted to the triflate, compound 40, by sodium bis(trimethylsilyl)amide (NaHMDS) and N,N—N-phenyltrifluoromethanesulfonimide. Subsequent reaction of compound 40 with trimethylsilylacetylene followed by conventional removal of the nitrogen protecting group provides for 4-ethynyl-2,5-dihydropyrrole derivative, compound 41. Alternatively, removal of the triflate group by contact with Pd(PPh$_3$)$_2$(OAc)$_2$ in formic acid and tributyl amine followed by deprotection of the nitrogen protecting group provides for 2,5-dihydropyrrole derivative, compound 42.

Compound 24 can be converted to a variety of other proline derivatives. For example, inversion of the 4-β-hydroxy substituent to the 4-hydroxy substituent in the N-protected 4-β-hydroxyproline methyl ester, compound 24, can be accomplished by reaction with p-nitrobenzoic acid, phosphine and DIAD in a suitable solvent such as tetrahydrofuran, dioxane, and the like followed by reaction with sodium azide in the presence of a suitable crown ether, e.g., commercially available 15-Crown-5, in methanol. Deprotection of the amine group provides for 4-α-hydroxyproline methyl ester, compound 34.

The N-protected 4-α-hydroxyproline methyl ester, compound 33, can be used to prepare a variety of further derivatives. For example, reaction with dimethoxyDAST followed by deprotection provides for 4-β-fluoroproline methyl ester, compound 38. Alternatively, alkylation or arylation of the hydroxyl group followed by nitrogen deprotection yields the 4-alkoxy/aryloxyproline methyl ester, compound 35. Inversion of the 4-α-hydroxy substituent to the 4-β-alkoxyproline methyl ester in compound 33 to provide for compound 36 follows the procedures outlined for conversion of compound 24 to compound 25.

Scheme 7 below illustrates conversion of various proline derivatives to their corresponding N-hydroxyamides.

Scheme 7

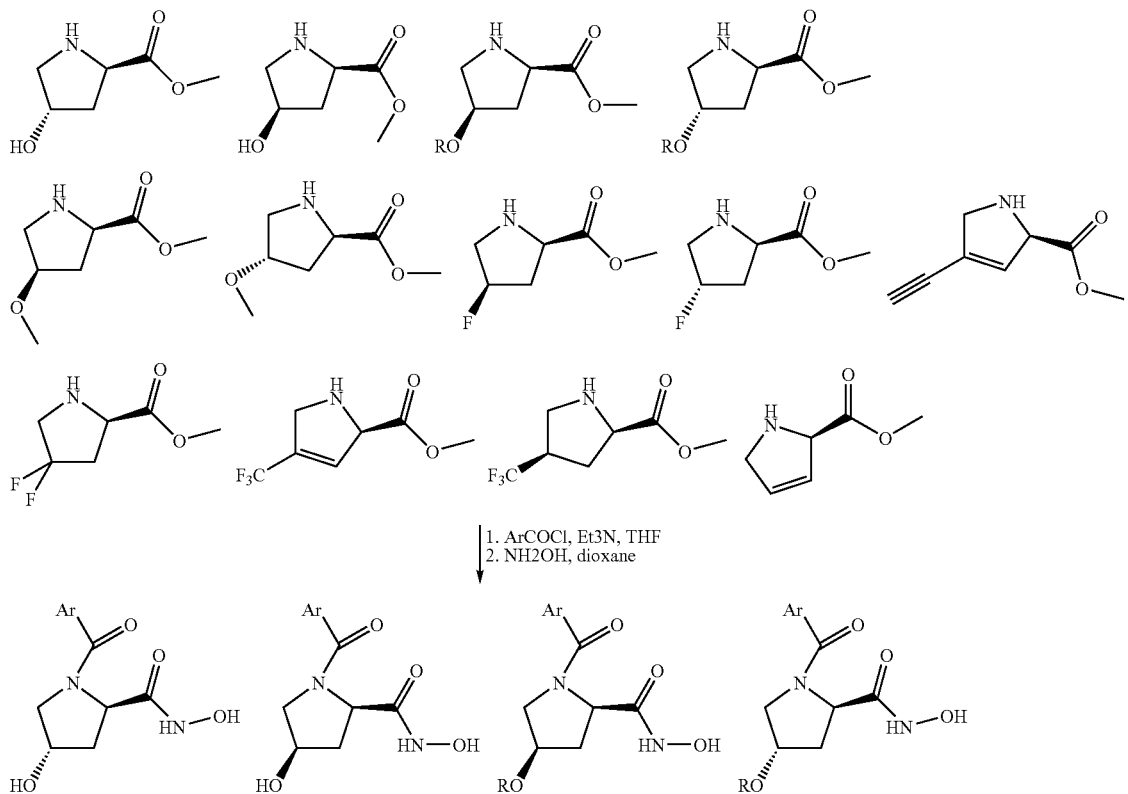

-continued

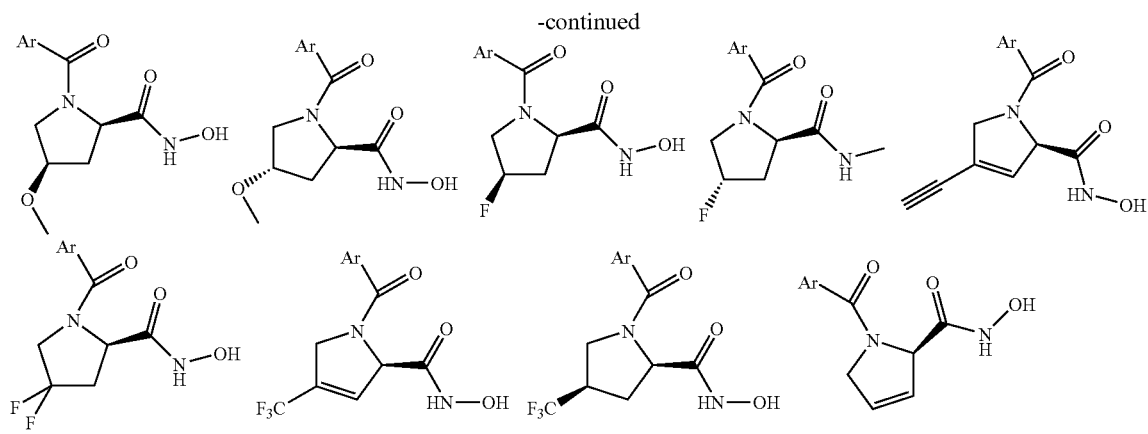

Such conversion is preferably conducted in a two step process wherein the proline methyl ester is first reacted with an aryl acid chloride in the presence of a suitable base such as triethylamine to scavenge the acid generated. The reaction is conducted in a suitable solvent such as tetrahydrofuran, dioxane, and the like. Subsequently, reaction with hydroxylamine in dioxane provides for the hydroxyamide derivative.

Pharmaceutical Formulations

When employed as pharmaceuticals, the compounds of the subject invention are usually administered in the form of pharmaceutical compositions. These compounds can be administered by a variety of routes including oral, parenteral, transdermal, topical, rectal, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of the subject invention above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The quantity of active component, that is the compound according to the subject invention, in the pharmaceutical composition and unit dosage form thereof may be varied or adjusted widely depending upon the particular application, the potency of the particular compound and the desired concentration.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the compound of the subject invention above is employed at no more than about 20 weight percent of the pharmaceutical composition, more preferably no more than about 15 weight percent, with the balance being pharmaceutically inert carrier(s).

The active compound is effective over a wide dosage range and is generally administered in a pharmaceutically or therapeutically effective amount. It will be understood, however, that the amount of the compound actually administered will be determined by a physician, in the light of the relevant circumstances, including the condition to be treated, the severity of the bacterial infection being treated, the chosen route of administration, the actual compound administered, the age, weight, and response of the individual patient, the severity of the patient's symptoms, and the like.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially or therapeutically effective amount of dosage of active component (i.e., an effective dosage) will be in the range of about 0.1 to about 100, more preferably about 1.0 to about 50 mg/kg of body weight/day.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A subcutaneous formulation may be prepared as follows:

| Ingredient | Quantity |
|---|---|
| Active Ingredient | 5.0 mg |
| Corn Oil | 1.0 mL |

FORMULATION EXAMPLE 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

An intravenous formulation may be prepared as follows:

| Ingredient | Quantity |
|---|---|
| Active Ingredient | 250 mg |
| Isotonic saline | 1000 mL |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Other suitable formulations for use in the present invention can be found in *Remington's Pharmaceutical Sciences*, Mace Publishing Company, Philadelphia, Pa., 17$^{th}$ ed. (1985).

As noted above, the compounds described herein are suitable for use in a variety of drug delivery systems described above. Additionally, in order to enhance the in vivo serum half-life of the administered compound, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

As noted above, the compounds administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 and 8. It will be understood that use of certain of the foregoing excipients, carriers, or stabilizers will result in the formation of pharmaceutical salts.

In general, the compounds of the subject invention will be administered in a therapeutically effective amount by any of the accepted modes of administration for agents that serve similar utilities. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range which includes the $IC_{50}$ (the concentration of the test compound which achieves a half-maximal inhibition of symptoms) as determined in cell culture. Such information can be used to more accurately determine useful doses in humans. Levels in plasma may be measured, for example, by high performance liquid chromatography.

Utility

The compounds of the subject invention exhibit potent activities against gram negative organisms. Accordingly, the compounds of the present invention are useful antimicrobial agents and may be effective against a number of human and veterinary pathogens, including gram negative organisms. The Gram negative organisms against which the compounds of the present invention are effective include *Acinetobacter baumannii, Acinetobacter haemolyticus, Actinobacillus actinomycetemcomitans, Aeromonas hydrophila, Bacteroides fragilis, Bacteroides theataioatamicron, Bacteroides distasonis, Bacteroides ovatus, Bacteroides vulgatus, Bordetella pertussis, Brucella melitensis, Burkholderia cepacia, Burkholderia pseudomallei, Burkholderia mallei Fusobacterium, Prevotella corporis, Prevotella intermedia, Prevotella endodontalis, Porphyromonas asaccharolytica, Campylobacter jejuni, Campylobacter fetus, Citrobacter freundii, Citrobacter koseri, Edwarsiella tarda, Eikenella corrodens, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscleromatis, Klebsiella ozaenae, Legionella penumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydia pneumoniae, Chlamydia trachomatis, Ricketsia prowazekii, Coxiella burnetii, Ehrlichia chafeensis, Bartonella hensenae*, and the like.

The compounds of the subject invention may be combined with one or more additional antibacterial agents. One or more of the additional antibacterial agents may be active against gram negative bacteria. Additionally, one or more of the additional antibacterial agents may be active against gram positive bacteria. The combination of the compounds of the subject invention and the one or may additional antibacterial agents may be used to treat a gram negative infection. Additionally, the combination of the compounds of the subject invention and the one or more additional antibacterial agents may be used to treat a gram positive infection.

The in vitro activity of compounds of the subject invention may be assessed by standard testing procedures such as the determination of minimum inhibitory concentration (MIC) by agar dilution as described in "Approved Standard. Methods for Dilution Antimicrobial Susceptibility Tests for Bacteria that Grow Aerobically," 3$^{rd}$ ed., published 1993 by the National Committee for Clinical Laboratory standards, Villanova, Pa., USA.

The amount administered to the mammalian patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 μg to about 500 μg per kilogram body weight, preferably about 100 μg to about 300 μg per kilogram body weight. Suitable dosage ranges for intranasal administration are generally about 0.1 pg to 1 mg per kilogram body weight. Effective doses can be extrapolated from dose-response curves derived from in vitro or animal model test systems.

The following synthetic and biological examples are offered to illustrate this invention and are not to be construed in any way as limiting the scope of this invention.

EXAMPLES

In the discussion above and in the examples below, the following abbreviations have the following meanings. If an abbreviation is not defined, it has its generally accepted meaning.

aq=aqueous
AcOH=acetic acid
AUC=area under the curve
$BH_3.SMe_2$=borane dimethyl sulfide complex
Bn=benzyl
bm=broad multiplet
Boc=tert-butoxycarbonyl protecting group
bd=broad doublet
bs=broad singlet
$CDCl_3$=deuterated chloroform
$CD_3OD$=deuterated methanol
CDI=1,1-carbodiimidazole
cfu=colony forming units
d=doublet
dd=doublet of doublets
dq=doublet of quartets
dt=doublet of triplets
DCC=1,3-dicyclohexylcarbodiimide
DCM=dichloromethane
DIBAH=diisobutylaluminum hydride
DIEA=diisopropylethylamine
DMF dimethylformamide
DMAP=dimethylaminopyridine
DMSO=dimethyl sulfoxide
DPPA=diphenylphosphoryl azide
dppf=bis(diphenylphosphino)ferrocene
$ED_{50}$=dose therapeutically effective in 50% of the population).
EDC=1-(3-dimethylaminopropyl)-3-ethylcarbodiimide hydrochloride
eq=equivalent
ESMS=electrospray mass spectrometry
Et=ethyl
EtOAc=ethyl acetate
$Et_3N$=triethylamine
$Et_2O$=diethyl ether
g=gram
h=hour HATU=O-(7-azabenzotriazol-1-yl)-N,N,N',N'-tetramethyluronium hexafluorophosphate
HOBT=1-hydroxybenzotriazole hydrate
HPLC=high pressure liquid chromatography
Hz=hertz
$IC_{50}$=concentration of the test compound which achieves a half-maximal inhibition of symptoms
i.p.=intraperitoneal
i.v.=intravenous
L=liter
$LD_{50}$=dose lethal to 50% of the population
LiHMDS=lithium hexamethyldisilazide
LPS=lipopolysaccharide
LpxC=UPD-3-O—(R-3-hydroxymyristoyl)-N-acetylglucosamine deacetylase
m=multiplet
M=molar
M %=mole percent
max=maximum
m-CPBA=meta-chloroperbenzoic acid
Me=methyl
MeOH=methanol
meq=milliequivalent
mg=milligram
$MgSO_4$=magnesium sulfate
MHz=megahertz
mL=milliliter
mm=millimeter
mmol=millimol
m/z=mass/charge ratio
N=normal
NMR=nuclear magnetic resonance
NaHMDS=bis-(trimethylsilyl)amide
OBz=benzyloxy protecting group
OtBu=tert-butoxy
Pd/C=palladium/carbon
pg=picogram
Ph=phenyl
Pro=L-proline
q=quartet
q.s.=bring to volume
rt=room temperature
s=singlet
sat=saturated
sec=seconds
t=triplet
TBAF=tetrabutylammonium fluoride
TEA=triethylamine
TFA=trifluoroacetic acid
THF=tetrahydrofuran
TLC=thin layer chromatography
$TMSCHN_2$=trimethylsilyldiazomethane
μL=microliter
μM=micromolar
μg=microgram
v/v=volume by volume Additionally, the term "Aldrich" indicates that the compound or reagent used in the following procedures is commercially available from Aldrich Chemical Company, Inc., 1001 West Saint Paul Avenue, Milwaukee, Wis. 53233 USA; the term "Fluka" indicates that the compound or reagent is commercially available from Fluka Chemical Corp., 980 South 2$^{nd}$ Street, Ronkonkoma N.Y. 11779 USA; the term "Lancaster" indicates that the compound or reagent is commercially available from Lancaster Synthesis, Inc., P.O. Box 100 Windham, N.H.03087 USA; the term "Sigma" indicates that the compound or reagent is commercially available from Sigma, P.O. Box 14508, St. Louis Mo. 63178 USA; the term "Chemservice" indicates that the compound or reagent is commercially available from Chemservice Inc., Westchester, Pa., USA; the term "Bachem" indicates that the compound or reagent is commercially available from Bachem Bioscience Inc., 3700 Horizon Drive, Renaissance at Gulph Mills, King of Prussia, Pa. 19406 USA; the term "Maybridge" indicates that the compound or reagent is commercially available from Maybridge Chemical Co. Trevillett, Tintagel, Cornwall PL34 OHW United Kingdom; and the term "TCI" indicates that the compound or reagent is commercially available from TCI America, 9211 North Harborgate St., Portland, Oreg., 97203, OR, USA; the term "Alfa" indicates that the compound or reagent is commercially available from Johnson Matthey Catalog Company, Inc. 30 Bond Street, Ward Hill, Mass. 01835-0747; and the term "Nova Biochem" indicates that the compound or reagent is commercially available from Nova-Biochem USA, 10933 North Torrey Pines Road, P.O. Box 12087, La Jolla Calif. 92039-2087.

In the examples below, all temperatures are in degrees Celsius (unless otherwise indicated) and the following general procedures are used to prepared the compounds as indicated.

General Procedures

Method A: To a stirred solution of amine (1.91 mmol), acid (1.91 mmol), and HATU (720 mg, 1.91 mmol) in dimethylformamide (DMF) (10 mL), diisopropylethylamine (DIEA) (1.7 mL, 9.5 mmol) was added. The reaction was stirred at room temperature for 16 h then partitioned between brine (100 mL) and diethyl ether ($Et_2O$) (100 mL). The layers were separated and the organic layer was washed with water (2×100 mL), 0.5 N HCl (100 mL), brine (50 mL), dried over magnesium sulfate ($MgSO_4$) and then concentrated in vacuo to give the desired product.

Method B: To a stirred solution of methyl ester (100-150 mg) in dioxane (3.0-5.0 mL) at room temperature was added aqueous hydroxylamine (aqueous solution, 50% by weight, 3.0 mL). The progress of the reaction was monitored by analytical high pressure liquid chromatography (HPLC). After completion of the reaction, the reaction mixture was diluted with water (5 mL) lyophilized to get crude product, which was purified by preparative HPLC to furnish the desired hydroxamate.

Method C: To a stirred suspension of potassium carbonate (1000 mmol) in anhydrous DMF (700 mL) was added phenol (91.03 g, 500 mmol) followed by an alkylating agent (600 mmol). The resulting reaction mixture was stirred at room temperature and the progress of the reaction was monitored by thin layer chromatography (TLC). After completion of the reaction, solvent was removed in vacuo and the resulting residue was suspended in ether (1000 mL). The ether layer was washed with water (5×300 mL), and brine (3×200 mL). The organic layer was dried over $MgSO_4$ and then the solvent was removed in vacuo gave the desired alkylated product.

Method D: The solution of allyloxybenzene (472.7 mmol) in N,N-diethylaniline (400 mL) was kept stirring at 200° C. under nitrogen atmosphere. The progress of the reaction was monitored by TLC. The reaction mixture was cooled to room temperature and poured on to 3 N aqueous hydrochloric acid (1.5 L). The precipitated solid was filtered, washed with water (1 L) and then dried under high vacuum to furnish 2-allylphenolic derivative.

Method E: To a stirred solution of ester (87.46 mmol) in methanol (460 mL) was added lithium hydroxide solution (459.16 mmol) in water (231 mL). After stirring 24 h at room temperature, solvent was removed in vacuo and the residue was dissolved in water (600 mL). The aqueous layer was extracted with methylene chloride or ether and the organic layer discarded. The aqueous layer was acidified with aqueous 1 N HCl at 0° C. The precipitated solid was filtered and dried under high vacuum to give the corresponding acid. If there was no precipitation of solid, the aqueous layer was extracted with organic solvent.

Method F: To a stirred solution of appropriately protected amino acid (2.32 mmol) in DMF (10 mL) O-benzyl hydroxylaminehydrochloride (2.32 mmol) and HATU (2.32 mmol) were added, followed by DIEA (11.60 mmol). The reaction mixture was stirred at room temperature for 12 h then partitioned between brine (150 mL) and EtOAc/Hexane (3:1, v/v, 200 mL). The layers were separated and the organic layer was washed with 0.5 N HCl (150 mL), saturated aqueous $NaHCO_3$ (150 mL), $H_2O$ (150 mL) and then brine (150 mL). The organic layer was dried over $MgSO_4$ and then the solvent was removed in vacuo to give the desired protected hydroxamate.

Method G: A solution of Boc-protected hydroxamate in 4.0 M hydrochloric acid in dioxane (1.87 mmol) was stirred for 30 min at 0° C. The reaction mixture was slowly warmed to room temperature while stirring for another 3 h. The dioxane was removed in vacuo to furnish the amine hydrochloride salt.

Method H: To a solution of benzyloxyamide, O-benzyl derivative, alkene, or alkyne (0.05 mmol) in methanol (10.0 mL) at room temperature 10% palladium/carbon (Pd/C) (5 mg) was added and the reaction was stirred under hydrogen atmosphere for 1 h. The reaction was filtered through a pad of celite and washed with methanol. The combined filtrate was concentrated in vacuo to get the desired product. N-hydroxyamides were purified by preparative HPLC.

Method I: To a stirred solution of hydroxy acid (Example 10, Step 1, 600 mg, 2.50 mmol) in THF (10 mL) at 0° C. NaH was added in small portions (180 mg, 7.50 mmol) and the reaction was stirred at 0° C. for 30 min. Alkyl or aryl alkyl bromide (7.50 mmol) was added and the reaction was slowly warmed to room temperature while stirring for 14 h. The reaction mixture was quenched with methanol (MeOH) (5 mL), diluted with water (50 mL), and the aqueous layer was acidified to pH 5 with 1 N aqueous HCl solution. The aqueous layer was extracted with ethyl acetate (EtOAc) (3×50 mL), the combined organic layer was dried over $MgSO_4$, and concentrated in vacuo to furnish the alkylated product.

Method J: To a suspension of Wittig salt (2.98 mmol) in THF (10 mL) at 0° C. lithium hexamethyldisilazide (LiHMDS) (1.0 M in THF, 2.98 mL, 2.98 mmol, 2.5 eq.) was added over the course of 60 sec. After stirring for 20 min at 0° C. the solution of ylide was cooled to −78° C. and treated with a solution of 3,4-dimethoxy-5-(3-oxopropyl)benzoic acid methyl ester (300 mg, 1.19 mmol) in THF (5.0 mL). After 30 min at −78° C. the solution was stirred at room temperature for 30 min. The reaction mixture was diluted with $Et_2O$ (100 mL), washed with water (100 mL), brine (100 mL), dried $MgSO_4$, and concentrated in vacuo. The crude product was purified by flash column chromatography on silica gel using 20% EtOAc in hexanes as an eluent to furnish the desired alkene.

Method K: To a stirred solution of $NaNO_3$ (221 mg, 2.6 mmol) in TFA (25 mL) at 0° C. alkoxybenzene (2.6 mmol) was added in one portion. The reaction mixture was continued stirring at 0° C. for 1 h and then at room temperature for 3 h. The reaction mixture was diluted with $H_2O$ and extracted with EtOAc (3×70 mL). The combined organic layer was washed with aqueous solution $Na_2CO_3$ (2×100 mL) and brine (200 mL). The organic layer was dried over $Na_2SO_4$ and then concentrated in vacuo to furnish the desired product.

Method L: To a stirred solution of aniline (2.11 mmol) in dioxane (5.0 mL), $H_2O$ (2.0 mL) and concentrated $H_2SO_4$ (0.3 mL) were added. The resulting solution was cooled to −5° C. using ice/salt bath and then added, dropwise, was a solution of $NaNO_2$ (0.15 g) in $H_2O$ (2.0 mL) over 20 min period. During this time the internal temperature of the reaction mixture was maintained at −5° C. After the addition was complete, the reaction mixture was stirred at −5° C. for 1 h and then was poured on to a ice cold solution of NaI (600 mg) in $H_2O$ (8.0 mL). The resulting mixture was warmed to room temperature, stirred for 30 min and then extracted with EtOAc (3×70 mL). The combined organic layer was washed with brine, dried over $Na_2SO_4$ and then concentrated in vacuo to furnish the desired iodide.

Method M: To a stirred solution of halobenzene (1.57 mmol) in THF (15.0 mL) at −78° C. was added n-BuLi (2.0 mL, 3.42 mmol, 1.6 M solution in hexane), dropwise. The resulting mixture was stirred at −78° C. and then treated with $CO_2$ gas for 30 min (bubbled at 5 mL/sec). The temperature was slowly raised to room temperature (over 40 min) with continued bubbling of $CO_2$ gas. The reaction mixture was quenched with saturated aqueous $NH_4Cl$ solution (100 mL) and then added to an aqueous solution of HCl (1.0 M, 100 mL). The aqueous layer was extracted with EtOAc (3×70 mL), the combined organic layer was washed with brine (100 mL), dried over $Na_2SO_4$, and then concentrated in vacuo to get the desired acid.

Method N: To a solution of phenol (2.25 mmol, 1 eq.) in $CH_2Cl_2$ (10 mL) at −20° C. was added $Et_3N$ (1.57 mL, 11.3 mmol, 5 eq.) followed by triflic anhydride ($Tf_2O$) (0.42 mL, 2.48 mmol, 1.1 eq.). The reaction was stirred at −20° C. for 45 min then partitioned between $H_2O$:brine (3:1, 200 mL) and $Et_2O$ (150 mL). The layers were separated and the organic layer was washed with 1.0 N HCl (2×150 mL), brine (100 mL), dried $MgSO_4$ and concentrated in vacuo to give the desired product.

Method O: To a round bottom flask containing $Pd(PPh_3)_4$ (9.5 mg, 0.008 mmol, 0.03 eq.), LiCl (35 mg, 0.82 mmol, 3 eq.) and 2,6-di-tert-butylphenol (1.5 mg, polymerization inhibitor) was added a solution of triflate (128 mg, 0.27 mmol, 1 eq.) in dioxane (4.0 mL) followed by tributylvinyltin (88 µL, 0.30 mmol, 1.1 eq.). The resulting mixture was evacuated (needle to pump) for 30 sec, purged with $N_2$ (balloon) then warmed to 100° C. After 3 h, the reaction was cooled to 23° C. then treated with KF (500 mg), $H_2O$ (5.0 mL) and MeOH (5.0 mL). After stirring for 2.5 h at 23° C. the mixture was filtered through a pad of Celite, washed with $Et_2O$ (100 mL). The resulting organic solution was partitioned between $Et_2O$ (100 mL) and $H_2O$ (100 mL). The layers were separated and the organic layer was washed with 1.0 N HCl (50 mL), brine (50 mL), dried $MgSO_4$ and concentrated in vacuo.

Method P: To a stirred solution of triflate or iodide (0.20 mmol, 1 eq.), phenylboronic acid (0.23 mmol, 1.2 eq.) and $Pd(PPh_3)_4$ (11 mg, 0.01 mmol, 0.05 eq.) in DME (2.0 mL) at 23° C. was added to aqueous $Na_2CO_3$ (2.0 M, 0.50 mL, 1.00 mmol, 5 eq.). The resulting mixture was subjected to vacuum (needle to pump) for 30 sec, then the vacuum was broken with $N_2$ (balloon). Reaction mixture was warmed to 60° C. After 2 h the reaction was cooled to 23° C. then partitioned between $H_2O$: 1.0 N HCl (1:1, 150 mL) and $Et_2O$ (150 mL). The layers were separated and the organic layer was washed with 1.0 N HCl (100 mL), brine (50 mL), dried $MgSO_4$ and concentrated in vacuo.

Method Q: The stirred solution of acid in MeOH (10 mL) at 0° C. treated with 2.0 M $TMSCHN_2$ (excess). After 30 min, TLC analysis revealed complete conversion of acid to methyl ester. Solvent was removed in vacuo to afford the desired ester.

Method R: To a stirred mixture of triflate or iodide (0.32 mmol, 1 eq.), alkyne (1.61 mmol, 5 eq.), CuI (6.1 mg, 0.032 mmol, 0.1 eq.) and $Pd(PPh_3)_2Cl_2$ (11 mg, 0.016 mmol, 0.05 eq.) in DMF (3.0 mL) at 23° C. was added $Et_3N$ (0.13 mL, 0.96 mmol, 3 eq.). The resulting mixture was warmed to 60° C. in a sealed tube under $N_2$ atmosphere (round bottom flask was used for high boiling alkyne derivatives). After 2.5 h the reaction was cooled to 23° C. then partitioned between $H_2O$ (100 mL) and $Et_2O$ (150 mL). The layers were separated and the organic layer was washed with 1.0 N HCl (100 mL), brine (50 mL), dried $MgSO_4$ and concentrated in vacuo to yield the desired product.

Method S: To a stirred solution of acid (0.99 mmol) in THF (5 mL) at 23° C. was added 4-methylmorpholine (253 µL, 2.32 mmol, 2.3 eq.) and the reaction mixture was cooled to −15° C. To this reaction mixture was added isobutylchloformate (297 µL, 2.32 mmol, 2.3 eq.) dropwise over 30 min, then the reaction mixture was stirred at −15° C. for 1 h. The reaction mixture was filtered and washed with THF (40 mL), then the filtered solid was discarded. To the filtrate was added a suspension of $NaBH_4/H_2O$ at 0° C., and the reaction mixture was stirred overnight. The reaction mixture was poured into 1.0 N HCl (100 mL) and extracted with ethyl ether (2×100 mL). The organic layer was washed with brine (2×80 mL), dried $MgSO_4$, and concentrated to yield desired product.

Method T: To a stirred solution of alcohol (0.48 mmol) in EtOAc (3 mL) at 0° C. was added triethylamine (0.2 mL), and then stirred for 15 min. Methanesulfonic anhydride (124 mg, 0.71 mmol, 1.5 eq.) was added and the reaction mixture was stirred for another 30 min. The reaction mixture was quenched by adding saturated aqueous sodium bicarbonate (5 mL) and stirred for 15 min. The resulting mixture was diluted with EtOAc (200 mL), washed with $H_2O$ (150 mL), and brine (150 mL). The organic layer was dried $MgSO_4$ and concentrated iv vacuo to yield the desired product.

Method U: To a stirred suspension of amine hydrochloride (0.34 mmol, 0.7 eq.), potassium carbonate (145 mg, 1.06 mmol, 2.2 eq.), potassium iodide (6.7 mg, 0.04 mmol, 0.1 eq.) in DMF (3 mL) was added the mesylate (0.48 mmol, 1 eq.), and the reaction mixture was stirred at 23° C. overnight. The reaction mixture was diluted with water and extracted with ether. The organic layer dried over $MgSO_4$ and concentrated in vacuo to yield the desired product.

Method V: To a stirred solution of acid (4.50 mmol) in dichloromethane (40 mL) at room temperature was added oxalyl chloride (2.0 M solution in $CH_2Cl_2$, 2.9 mL, 5.80 mmol, 1.3 eq.) and the reaction mixture was cooled to 0° C. in an ice bath. To this was added a drop of DMF and the reaction mixture slowly attained room temperature over a period of 4 h. Solvent was removed in vacuo and the residue was dried under high vacuum.

Method W: To a stirred solution of amine hydrochloride (1.58 mmol) in THF (2.5 mL) at 0° C. was added triethylamine (0.5 mL), and the reaction mixture was stirred for 30 min. A solution of acid chloride (1.58 mmol, 1 eq.) in THF (12 mL) was added dropwise, and the reaction attained room temperature overnight. This was diluted with dichloromethane (200 mL), washed with $H_2O$ (150 mL), saturated

Example 1

Preparation of 1-(3,4-dimethoxy-5-propylbenzoyl)pyrrolidine-2R-carboxylic acid hydroxyamide

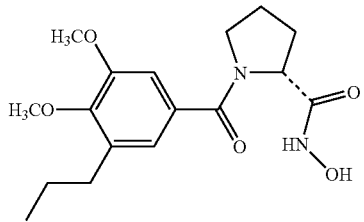

Step 1: 4-allyloxy-3-methoxybenzoic acid methyl ester was prepared from 4-hydroxy-3-methoxybenzoic acid methyl ester in 96% yield by following Method C. The reaction was conducted at room temperature for 4 h. The resulting product was used without further purification.

Step 2: 3-Allyl-4-hydroxy-5-methoxybenzoic acid methyl ester was prepared from 4-allyloxy-3-methoxybenzoic acid methyl ester in 93% yield by following Method D. The reaction was heated at 200° C. for 2 days for complete conversion of the starting material. The resulting product was used without further purification.

Step 3: 4-Hydroxy-3-methoxy-5-propylbenzoic acid methyl ester was prepared from 3-allyl-4-hydroxy-5-methoxybenzoic acid methyl ester by following Method H in 98% yield. The reaction was stirred at room temperature for 5 h. The resulting product was used without further purification.

Step 4: 3,4-Dimethoxy-5-propylbenzoic acid methyl ester was prepared from 4-hydroxy-3-methoxy-5-propylbenzoic acid methyl ester using methyl iodide as an alkylating agent in 99% yield by following Method C. The reaction was conducted at room temperature for 4 h, for complete conversion of starting material. The resulting product was used without further purification.

Step 5: 3,4-Dimethoxy-5-propylbenzoic acid was prepared from 3,4-dimethoxy-5-propylbenzoic acid methyl ester by following Method E in 94% yield. The reaction was conducted at room temperature for 24 h. The product was used without further purification.

Step 6: 2R-Benzyloxycarbamoylpyrrolidine-1-carboxylic acid tert-butyl ester was prepared from Boc-D-proline by following Method F in 84% yield. The resulting product was without further purification.

Step 7: 2R-Benzyloxycarbamoylpyrrolidine hydrochloride salt was prepared from 2R-benzyloxycarbamoylpyrrolidine-1-carboxylic acid tert-butyl ester by following Method G in 99% yield. The product was used without further purification.

Step 8: 1-(3,4-Dimethoxy-5-propylbenzoyl)pyrrolidine-2R-carboxylic acid benzyloxyamide was prepared by coupling 2R-benzyloxycarbamoylpyrrolidine hydrochloride salt with 3,4-dimethoxy-5-propylbenzoic acid according to Method A. The reaction was stirred at room temperature for 12 h and the resulting product was purified by column chromatography (75% EtOAc in hexane) to yield the desired product in 36% yield. Electrospray Mass Spectrometry (ESMS): m/z 449.5 [M+Na].

Step 9: 1-(3,4-Dimethoxy-5-propylbenzoyl)pyrrolidine-2R-carboxylic acid hydroxyamide was prepared from 1-(3,4-dimethoxy-5-propylbenzoyl)pyrrolidine-2R-carboxylic acid benzyloxyamide according to Method H. ESMS: m/z 359.4 [M+Na]. $^1$H NMR (300 MHz, CD$_3$OD): 7.01 (d, 1.8 Hz, 1H), 6.94 (d, 1.8 Hz, 1H), 4.32 (t, 7 Hz, 1H), 3.76 (s, 3H), 3.71 (s, 3H), 3.60 (m, 1H), 3.45 (m, 1H), 2.51 (t, 7 Hz, 2H), 2.2 (m, 1H), 1.92 (m, 2H), 1.8 (m, 1H), 1.51 (q, 7 Hz, 2H), 0.84 (t, 7 Hz, 3H).

Example 2

Preparation of 1-(3,4-dimethoxy-5-propylbenzoyl)azetidine-2R-carboxylic acid hydroxyamide

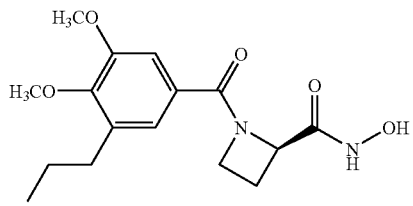

Step 1: To a stirred suspension of azetidine-2R-carboxylic acid (504 mg, 4.99 mmol) in MeOH (20 mL) at 0° C. thionyl chloride (0.90 mL) was added over the course of 1 min. After 50 min the reaction was warmed to 23° C., stirred for a further 17 h, then concentrated in vacuo to give azetidine-2R-carboxylic acid methyl ester as hydrochloride salt (hygroscopic).

Step 2: 1-(3,4-Dimethoxy-5-propylbenzoyl)azetidine-2R-carboxylic acid methyl ester was prepared from 3,4-dimethoxy-5-propylbenzoic acid (Example 1, Step 5) and azetidine-2R-carboxylic acid methyl ester hydrochloride salt by following Method A in 81% yield. The product was used without further purification. ESMS: m/z 322.4 [M+H].

Step 3: 1-(3,4-Dimethoxy-5-propylbenzoyl)azetidine-2R-carboxylic acid hydroxyamide was prepared from 1-(3,4-dimethoxy-5-propylbenzoyl)azetidine-2R-carboxylic acid methyl ester in 5 h by following Method B. ESMS: m/z 323.4 [M+H]. $^1$H NMR (300 MHz, CDCl$_3$): 7.09 (s, 1H), 7.0 (s, 1H), 5.04 (m, 1H), 4.2-4.40 (m, 2H), 3.87 (s, 3H), 3.85 (s, 3H), 2.8 (m, 1H), 2.6 (m, 2H), 2.5 (m, 1H), 1.6 (m, 2H), 0.94 (t, 7.5 Hz, 3H).

Example 3

Preparation of 1-(9-methoxy-2,5-dihydrobenzo[b]oxepine-7-carbonyl)azetidine-2R-carboxylic acid hydroxyamide

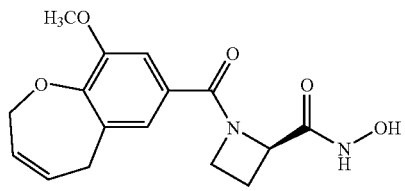

Step 1: 3-Allyl-4-allyloxy-5-methoxybenzoic acid methyl ester was prepared from 3-allyl-4-hydroxy-5-methoxybenzoic acid methyl ester (Example 1, Step 2) by following Method C in 95% yield. The reaction was conducted at 80° C. for 8 h for complete conversion of starting material to give 3-allyl-4-allyloxy-5-methoxybenzoic acid methyl ester in 95% yield. The product was used without further purification.

Step 2: 3-Allyl-4-allyloxy-5-methoxybenzoic acid was prepared from 3-allyl-4-allyloxy-5-methoxybenzoic acid methyl ester using Method E in 85% yield. The reaction was conducted at room temperature for 18 h. The product was used without further purification.

Step 3: To a stirred solution of 3-allyl-4-allyloxy-5-methoxybenzoic acid (200 mg, 0.81 mmol) in $CH_2Cl_2$ (20 mL) at room temperature was added benzylidene-bis-(tricyclohexylphosphine)dichlororuthenium (Grubb's catalyst, 35 mg, 0.04 mmol, 0.05 eq.). After stirring for 2 h the reaction was diluted with EtOAc (150 mL) then extracted with 2.0 N NaOH (100 mL). Aqueous layer was treated with brine (100 mL) then acidified to pH 5 using 1.0 N HCl. The aqueous layer was then extracted with EtOAc (2×200 mL). The organic layer was dried over $MgSO_4$ and then concentrated in vacuo to afford 9-methoxy-2,5-dihydrobenzo[b]oxepine-7-carboxylic acid (179 mg, 100%) which was used without further purification.

Step 4: 1-(9-Methoxy-2,5-dihydrobenzo[b]oxepine-7-carbonyl)azetidine-2R-carboxylic acid methyl ester was prepared by reacting 9-methoxy-2,5-dihydrobenzo[b]oxepine-7-carboxylic acid and azetidine-2R-carboxylic acid methyl ester hydrochloride salt according to Method A in 14% yield.

Step 5: 1-(9-Methoxy-2,5-dihydrobenzo[b]oxepine-7-carbonyl)azetidine-2R-carboxylic acid hydroxyamide was prepared from 1-(9-methoxy-2,5-dihydrobenzo[b]oxepine-7-carbonyl)azetidine-2R-carboxylic acid methyl ester according to Method B. The reaction was complete in 4.5 h. The crude product was purified by preparative HPLC to furnish 1-(9-methoxy-2,5-dihydrobenzo[b]oxepine-7-carbonyl)azetidine-2R-carboxylic acid hydroxyamide in 32% yield. ESMS: m/z 319.4 [M+H]. $^1$H NMR (300 MHz, $CDCl_3$): 7.12 (bs, 1H), 6.95 (bs, 1H), 5.84 (m, 1H), 5.5 (m, 1H), 5.02 (m, 1H), 4.62 (s, 2H), 4.40 (m, 1H), 4.24 (m, 1H), 3.88 (s, 3H), 3.49 (m, 2H), 2.83 (m, 1H), 2.52 (m, 1H).

Example 4

Preparation of 1-(3-allyl-4-allyloxy-5-methoxybenzoyl)azetidine-2R-carboxylic acid hydroxyamide

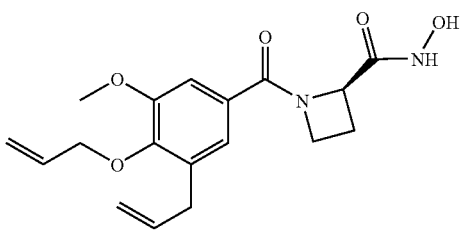

Step 1: 1-(3-Allyl-4-allyloxy-5-methoxybenzoyl)azetidine-2R-carboxylic acid methyl ester was prepared from the azetidine-2R-carboxylic acid methyl ester hydrochloride salt and 3-allyl-4-allyloxy-5-methoxybenzoic acid (Example 3, Step 2) by following Method A using dichloromethane (DCM) as a solvent in 67% yield. ESMS: m/z 346 [M+H].

Step 2: 1-(3-Allyl-4-allyloxy-5-methoxybenzoyl)azetidine-2R-carboxylic acid hydroxyamide was prepared from 1-(3-allyl-4-allyloxy-5-methoxybenzoyl)azetidine-2R-carboxylic acid methyl ester using Method B in 51% yield. The methyl ester was converted to the corresponding hydroxamate in 4 h. ESMS: m/z 345.5 [M −1]. $^1$H NMR (300 MHz, $CDCl_3$): 7.10 (s, 1H), 7.0 (s, 1H), 5.82-6.09 (m, 2H), 5.21 (m, 2H), 4.99-5.07 (m, 3H), 4.50 (d, 6.0 Hz, 2H), 4.16-4.40 (m, 2H), 3.84 (s, 3H), 3.38 (d, 6.6 Hz, 2H), 2.50 (bm, 1H), 2.49 (bm, 1H).

Example 5

Preparation of 1-(3,4,5-triethoxybenzoyl)azetidine-2R-carboxylic acid hydroxyamide

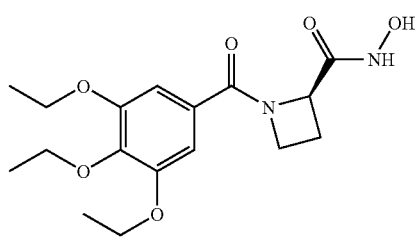

Step 1: 1-(3,4,5-Triethoxybenzoyl)azetidine-2R-carboxylic acid methyl ester was prepared by coupling azetidine-2R-carboxylic acid methyl ester hydrochloride salt with 3,4,5-triethoxybenzoic acid according to Method A in 60% yield using DCM as a solvent. This was used without further purification. ESMS: m/z 351 [M+H].

Step 2: 1-(3,4,5-Triethoxybenzoyl)azetidine-2R-carboxylic acid hydroxyamide was prepared from the 1-(3,4,5-triethoxybenzoyl)azetidine-2R-carboxylic acid methyl ester by following Method B in 70% yield. The methyl ester was converted to the corresponding hydroxamate in 4 h. ESMS: m/z 351.5 (M−H). $^1$H NMR (300 MHz, $CDCl_3$): 6.79 (s, 2H), 4.96 (m, 1H), 4.37 (m, 1H), 4.19 (m, 1H), 4.08 (m, 6H), 2.73 (m, 1H), 2.46 (m, 1H), 1.35 (m, 9H).

Example 6

Preparation of 1-(3,4,5-trimethoxybenzoyl)azetidine-2R-carboxylic acid hydroxyamide

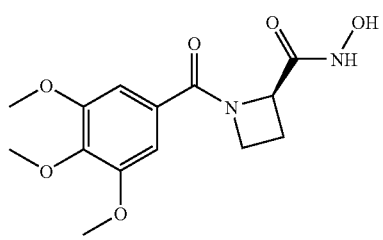

Step 1: 1-(3,4,5-Trimethoxybenzoyl)azetidine-2R-carboxylic acid methyl ester was prepared by coupling azetidine-2R-carboxylic acid methyl ester hydrochloride salt with 3,4,5-trimethoxybenzoic acid according to Method A. This product was used without further purification. ESMS: m/z 332.4 [M+Na].

Step 2: 1-(3,4,5-Trimethoxybenzoyl)azetidine-2R-carboxylic acid hydroxyamide was prepared from the 1-(3,4,5-trimethoxybenzoyl)azetidine-2R-carboxylic acid methyl ester by following Method B in 5 h. ESMS: m/z 333.4 [M+Na]. $^1$H NMR (300 MHz, DMSO-$d_6$): 10.99 (bs, 1H), 7.11 (bs, 2H), 5.0 (bs, 1H), 4.8 (bm, 1H), 4.6 (bm, 1H), 4.3 (bm, 1H), 3.99 (s, 6H), 3.89 (s, 3H), 2.26 (bm, 2H).

Example 7

Preparation of 1-(3,4-dimethoxy-5-propylbenzyl)azetidine-2R-carboxylic acid hydroxyamide

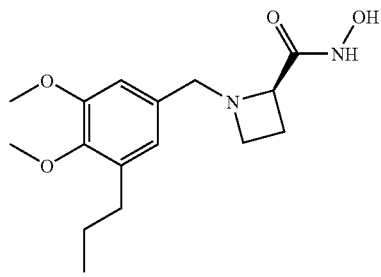

Step 1: To a stirred solution of methyl 3,4-dimethoxy-5-propylbenzoic acid methyl ester (Example 1, Step 4, 6.0 g, 25.2 mmol) in DCM (400 mL) at −78° C. was added DIBAH (1.0 M in toluene, 76 mL, 76 mmol). The reaction mixture was stirred at −78° C. for 30 min then quenched with EtOAc (50 mL). The quenched reaction was warmed to room temperature then treated with 1:1 saturated aqueous potassium tartrate/saturated aqueous sodium bicarbonate (400 mL). The biphasic mixture was stirred vigorously for 30 min then the layers separated. The aqueous layer was extracted with EtOAc (300 mL), then the combined organic layer was dried over MgSO$_4$, and concentrated to give 3,4-dimethoxy-5-propylbenzylalcohol (5.42 g, 100% yield). The product was used without further purification.

Step 2: To a stirred solution of 3,4-dimethoxy-5-propylbenzylalcohol (171 mg, 0.82 mmol) in CH$_2$Cl$_2$ (5.0 mL) at room temperature was added triethylamine (0.23 mL, 1.63 mmol) followed by methanesulfonyl chloride (95 μL, 1.22 mmol, 1.5 eq.). After 30 min the reaction mixture was diluted with hexanes (20 mL) and filtered through a pad of silica gel. The pad was then washed with 25% EtOAc in hexanes (100 mL). The combined organic filtrate was then concentrated to give methanesulfonic acid 3,4-dimethoxy-5-propylbenzyl ester (122 mg) as oil, which was used without further purification.

Step 3: To a solution of methanesulfonic acid 3,4-dimethoxy-5-propylbenzyl ester (122 mg, 0.52 mmol) in DMF (3.0 mL) at room temperature was added DIEA (0.28 mL, 1.56 mmol) followed by azetidine-2R-carboxylate hydrochloride salt (94 mg, 0.62 mmol). After 2 days, the reaction mixture was concentrated to give 1-(3,4-dimethoxy-5-propylbenzyl)azetidine-2R-carrboxylic acid methyl ester. This was used without further purification.

Step 4: 1-(3,4-Dimethoxy-5-propylbenzyl)azetidine-2R-carboxylic acid hydroxyamide was prepared from 1-(3,4-dimethoxy-5-propylbenzyl)azetidine-2R-carboxylic acid methyl ester by following Method B in 5.5 h. ESMS: m/z 309.4 [M+H]. $^1$H NMR (300 MHz, CD$_3$OD): 6.82-6.98 (m, 2H), 4.29 (s, 2H), 4.17 (m, 2H), 4.00 (m, 1H), 3.87 (s, 3H), 3.77 (s, 3H), 2.45-2.88 (m, 4H), 1.60 (m, 2H), 0.94 (t, 7.5 Hz, 3H).

Example 8

Preparation of 1-(3,5-dimethyl-4-nitrobenzoyl)azetidine-2R-carboxylic acid hydroxyamide

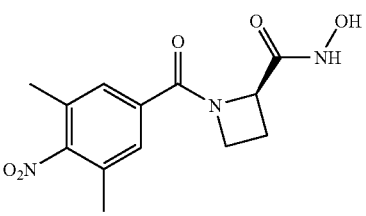

Step 1: 1-(3,5-Dimethyl-4-nitrobenzoyl)azetidine-2R-carboxylic acid methyl ester was prepared by reacting azetidine-2R-carboxylic acid methyl ester hydrochloride salt with 3,5-dimethyl-4-nitrobenzoic acid according to Method A. The product was used without further purification. ESMS: m/z 293.4 [M+H].

Step 2: 1-(3,5-Dimethyl-4-nitrobenzoyl)azetidine-2R-carboxylic acid hydroxyamide was prepared from 1-(3,5-dimethyl-4-nitrobenzoyl)azetidine-2R-carboxylic acid methyl ester by following Method B. The methyl ester was converted to the corresponding hydroxamate in 5 h. ESMS: m/z 316.4 [M+Na]. $^1$H NMR (300 MHz, CD$_3$OD): 7.55 (bs, 1H), 7.35 (bs, 2H), 7.32 (s, 1H), 4.79 (m, 1H), 4.40 (m, 1H), 4.16 (m, 1H), 2.58 (m, 1H), 2.36 (m, 1H), 2.28 (bs, 6H).

Example 9

Preparation of 1-(3,5-dimethoxy-4-methylbenzoyl)azetidine-2R-carboxylic acid hydroxyamide

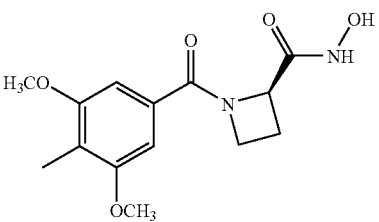

Step 1: 1-(3,5-Dimethoxy-4-methylbenzoyl)azetidine-2R-carboxylic acid methyl ester was prepared by coupling azetidine-2R-carboxylic acid methyl ester hydrochloride salt with 3,5-dimethoxy-4-methylbenzoic acid according to Method A. This product was used without further purification. ESMS: m/z 294.4 [M+H].

Step 2: 1-(3,5-Dimethoxy-4-methylbenzoyl)azetidine-2R-carboxylic acid hydroxyamide was prepared from 1-(3,5-dimethoxy-4-methylbenzoyl)azetidine-2R-carboxylic acid methyl ester by following Method B in 5 h. ESMS: m/z 317.4 [M+Na]. $^1$H NMR (300 MHz, CD$_3$OD): 6.96 (s, 1H), 6.87 (bs, 2H), 6.69 (bs, 1H), 4.79 (m, 1H), 4.50 (m, 1H), 4.17 (m, 1H), 3.82 (s, 3H), 3.81 (s, 3H), 2.30-2.7 (m, 2H), 2.03 (bs, 3H).

Example 10

Preparation of 1-[3-(3-hydroxypropyl)-4,5-dimethoxybenzoyl]azetidine-2R-carboxylic acid hydroxyamide

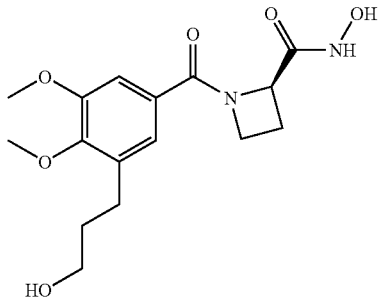

Step 1: To a solution of 3-allyl-4,5-dimethoxybenzoic acid methyl ester (Example 30, Step 1, 10.2 g, 43.2 mmol) in THF (100 mL) at 0° C. was added BH$_3$.SMe$_2$ (4.10 mL, 43.2 mmol). After 45 min the reaction mixture was warmed to 23° C. After stirring for 1.2 h the reaction was cooled to 0° C. and slowly treated with 3.0 N NaOH (39 mL) followed 10 min later by addition of H$_2$O$_2$ (30 weight %, 60 mL). Following the addition, the mixture was allowed to reach 23° C., then heated to reflux for 2 h. After cooling to room temperature, the mixture was partitioned between brine (400 mL) and EtOAc (500 mL). The aqueous layer was separated and extracted with EtOAc (400 mL). The organic layer was discarded and the aqueous was adjusted to pH 5 by addition of 1.0 N HCl then the product was extracted with EtOAc (2×500 mL). The organic layer was dried over MgSO$_4$ and then concentrated in vacuo to give 3-(3-hydroxypropyl)-4,5-dimethoxybenzoic acid (9.24 g, 89%) of the desired alcohol, which was used without further purification. ESMS: m/z 239.3 [M−H].

Step 2: 1-[3-(3-Hydroxypropyl)-4,5-dimethoxybenzoyl] azetidine-2R-carboxylic acid methyl ester was prepared by coupling azetidine-2R-carboxylic acid methyl ester hydrochloride salt with 3-(3-hydroxypropyl)-4,5-dimethoxybenzoic acid according to Method A and the crude product was used without further purification. ESMS: m/z 338.4 [M+H].

Step 3: 1-[3-(3-Hydroxypropyl)-4,5-dimethoxybenzoyl] azetidine-2R-carboxylic acid hydroxyamide was prepared from 1-[3-(3-hydroxypropyl)-4,5-dimethoxybenzoyl]azetidine-2R-carboxylic acid methyl ester according to Method B in 12 h. ESMS: m/z 339.4 [M+H]. $^1$H NMR (300 MHz, CD$_3$OD): 7.18 (s, 1H), 7.14 (s, 1H), 4.82 (bm, 1H), 4.47 (bm, 1H), 4.22 (bm, 1H), 3.86 (s, 3H), 3.82 (s, 3H), 3.55 (t, 7 Hz, 2H), 2.69 (bt, 7 Hz, 2H), 2.57 (bm, 1H), 2.37 (bm, 1H), 1.78 (m, 2H).

Example 11

Preparation of 1-(3-trifluoromethoxybenzoyl)azetidine-2R-carboxylic acid hydroxyamide

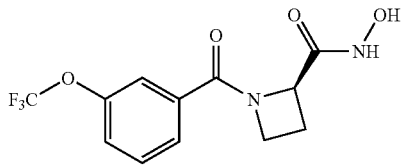

Step 1: 1-(3-Trifluoromethoxybenzoyl)azetidine-2R-carboxylic acid methyl ester was prepared by coupling azetidine-2R-carboxylic acid methyl ester hydrochloride salt with 3-trifluoromethoxybenzoic acid according to Method A and the product was used without further purification. ESMS: m/z 304.4 [M+H].

Step 2: 1-(3-Trifluoromethoxybenzoyl)azetidine-2R-carboxylic acid hydroxyamide was prepared from 1-(3-trifluoromethoxybenzoyl)azetidine-2R-carboxylic acid methyl ester according to Method B in 12 h. ESMS: m/z 327.3 [M+Na].

$^1$H NMR (300 MHz, CD$_3$OD): 7.43-7.74 (m, 4H), 4.82 (bm, 1H), 4.44 (bm, 1H), 4.22 (bm, 1H), 2.61 (bm, 1H), 2.38 (bm, 1H).

Example 12

Preparation of 1-(3,5-dibromo-4-methylbenzoyl) azetidine-2R-carboxylic acid hydroxyamide

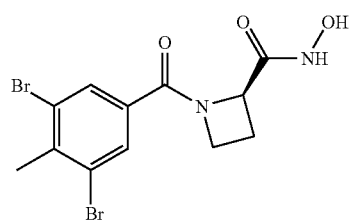

Step 1: 1-(3,5-Dibromo-4-methylbenzoyl)azetidine-2R-carboxylic acid methyl ester was prepared by coupling azetidine-2R-carboxylic acid methyl ester hydrochloride salt with 3,5-dibromo-4-methylbenzoic acid according to Method A. This product was used without further purification. ESMS: nm/z 392.2 [M+H].

Step 2: 1-(3,5-Dibromo-4-methylbenzoyl)azetidine-2R-carboxylic acid hydroxyamide was prepared from 1-(3,5-dibromo-4-methylbenzoyl)azetidine-2R-carboxylic acid methyl ester by following Method B in 5 h. ESMS: m/z 393.1 [M+H]. $^1$H NMR (300 MHz, CD$_3$OD): 7.75 (bs, 2H), 4.75 (m, 1H), 4.37 (m, 1H), 4.20 (m, 1H), 2.62 (s, 3H), 2.60 (bm, 1H), 2.33 (bm, 1H).

Example 13

Preparation of 1-(3-methoxy-4-methylbenzoyl)azetidine-2R-carboxylic acid hydroxyamide

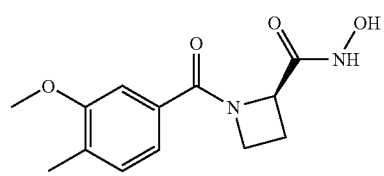

Step 1: 1-(3-Methoxy-4-methylbenzoyl)azetidine-2R-carboxylic acid methyl ester was prepared by coupling azetidine-2R-carboxylic acid methyl ester hydrochloride salt with 3-methoxy-4-methylbenzoic acid according to Method A. The product was used without further purification. ESMS: m/z 264.4 [M+H].

Step 2: 1-(3-Methoxy-4-methylbenzoyl)azetidine-2R-carboxylic acid hydroxyamide was prepared from 1-(3-methoxy-4-methylbenzoyl)azetidine-2R-carboxylic acid methyl ester by following Method B in 6.5 h. The reaction was monitored by analytical HPLC.
ESMS: m/z 265.4 [M+H]. ¹H NMR (300 MHz, CD₃OD): 7.06-7.10 (m, 3H), 4.71 (m, 1H), 4.37 (m, 1H), 4.10 (m, 1H), 3.75 (s, 3H), 2.49 (m, 1H), 2.26 (m, 1H), 2.11 (s, 3H).

Example 14

Preparation of 1-(3,5-dimethylbenzoyl)azetidine-2R-carboxylic acid hydroxyamide

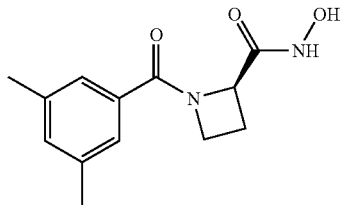

Step 1: 1-(3,5-Dimethylbenzoyl)azetidine-2R-carboxylic acid methyl ester was prepared by coupling azetidine-2R-carboxylic acid methyl ester hydrochloride salt with 3,5-dimethylbenzoic acid according to Method A. This product was used without further purification. ESMS: m/z 270.4 [M+Na].

Step 2: 1-(3,5-Dimethylbenzoyl)azetidine-2R-carboxylic acid hydroxyamide was prepared from the 1-(3,5-dimethylbenzoyl)azetidine-2R-carboxylic acid methyl ester by following Method B in 6.5 h. ESMS: m/z 271.4 [M+Na]. ¹H NMR (300 MHz, CD₃OD): 7.19 (s, 2H), 7.06 (s, 1H), 7.0 (s, 1H), 4.66 (m, 1H), 4.29 (m, 1H), 4.02 (m, 1H), 2.42 (m, 1H), 2.28 (m, 1H), 2.19 (s, 6H).

Example 15

Preparation of 1-(4-hydroxy-3-methoxy-5-propyl-benzoyl)azetidine-2R-carboxylic acid hydroxyamide

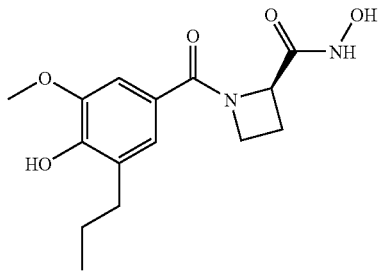

Step 1: 4-Hydroxy-3-methoxy-5-propylbenzoic acid was prepared from 4-hydroxy-3-methoxy-5-propylbenzoic acid methyl ester (Example 1, Step 3) by following Method E in quantitative yield. The reaction was conducted at room temperature for 16 h. The product was used without further purification.

Step 2: 1-(4-Hydroxy-3-methoxy-5-propylbenzoyl)azetidine-2R-carboxylic acid methyl ester was prepared by coupling azetidine-2R-carboxylic acid methyl ester hydrochloride salt with 4-hydroxy-3-methoxy-5-propylbenzoic acid according to Method A. This product was used without further purification. ESMS: m/z 330.4 [M+Na].

Step 3: 1-(4-Hydroxy-3-methoxy-5-propylbenzoyl)azetidine-2R-carboxylic acid hydroxyamide was prepared from 1-(4-hydroxy-3-methoxy-5-propylbenzoyl)azetidine-2R-carboxylic acid methyl ester by following Method B in 5 h. ESMS: 331.4 [M+Na]. ¹H NMR (300 MHz, CD₃OD): 7.08 s (bs, 1H), 7.06 s (bs, 1H), 4.77 (m, 1H), 4.47 (bs, 1H), 4.19 (bs, 1H), 3.83 (s, 3H), 2.54 (m, 3H), 2.32 (m, 1H), 1.57 (m, 2H), 0.89 (t, 13 Hz, 3H).

Example 16

Preparation of 1-[3-(3-allyloxypropyl)-4,5-dimethoxybenzoyl]azetidine-2R-carboxylic acid hydroxyamide

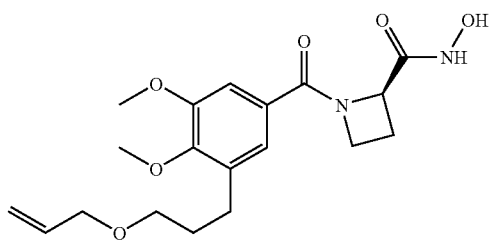

Step 1: 3-(3-Allyloxypropyl)-4,5-dimethoxybenzoic acid was prepared from 3-(3-hydroxypropyl)-4,5-dimethoxybenzoic acid (Example 10, Step 1) and allyl bromide in quantitative yield by following Method I and used without further purification.

Step 2: 1-[3-(3-Allyloxypropyl)-4,5-dimethoxybenzoyl]azetidine-2R-carboxylic acid methyl ester was prepared by coupling azetidine-2R-carboxylic acid methyl ester hydrochloride salt with 3-(3-allyloxypropyl)-4,5-dimethoxybenzoic acid according to Method A and the product was used without further purification. ESMS: m/z 378.5 [M+H].

Step 3: 1-[3-(3-Allyloxypropyl)-4,5-dimethoxybenzoyl]azetidine-2R-carboxylic acid hydroxyamide was prepared from 1-[3-(3-allyloxypropyl)-4,5-dimethoxybenzoyl]azetidine-2R-carboxylic acid methyl ester according to Method B in 6 h. MS: m/z 379.5 [M+H]. ¹H NMR (300 MHz, CD₃OD): 7.2 (bs, 1H), 7.14 (bs, 1H), 5.91 (m, 1H), 5.28 (dd, 18 Hz, 12 Hz, 2H), 4.82 (bm, 1H), 4.47 (bm, 1H), 4.22 (bm, 1H), 3.96 (m, 2H), 3.86 (s, 3H), 3.82 (s, 3H), 3.42 (t, 7 Hz, 2H), 2.70 (t, 7 Hz, 2H), 2.57 (bm, 1H), 2.37 (bm, 1H), 1.78 (m, 2H).

Example 17

Preparation of 1-[3-(3-benzyloxypropyl)-4,5-dimethoxybenzoyl]azetidine-2R-carboxylic acid hydroxyamide

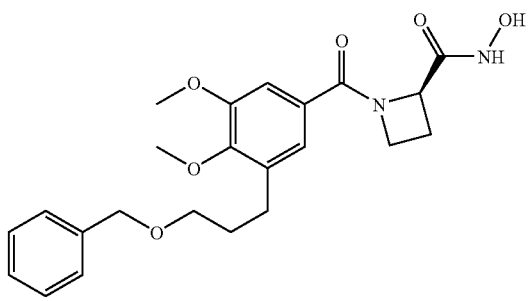

Step 1: 3-(3-Benzyloxypropyl)-4,5-dimethoxybenzoic acid was prepared from 3,4-dimethoxy-5-hydroxypropylbenzoic acid (Example 10, Step 1) and benzyl bromide in 68% yield by following Method I and used without further purification.

Step 2: 1-[3-(3-Benzyloxypropyl)-4,5-dimethoxybenzoyl]azetidine-2R-carboxylic acid methyl ester was prepared by coupling azetidine-2R-carboxylic acid methyl ester hydrochloride salt with 3-(3-benzyloxypropyl)-4,5-dimethoxybenzoic acid according to Method A and the product was used without further purification. ESMS: 428.5 [M+H].

Step 3: 1-[3-(3-Benzyloxypropyl)-4,5-dimethoxybenzoyl] azetidine-2R-carboxylic acid hydroxyamide was prepared from 1-[3-(3-benzyloxypropyl)-4,5-dimethoxybenzoyl]azetidine-2R-carboxylic acid methyl ester according to Method B in 6 h. ESMS: 429.5 [M+H]. $^1$H MR (300 MHz, CD$_3$OD): 7.25-7.33 (m, 5H), 7.18 (s, 1H), 7.11 (s, 1H), 4.79 (m, 1H), 4.48 (s, 2H), 4.45 (bm, 1H), 4.14 (bm, 1H), 3.86 (s, 3H), 3.81 (s, 3H), 3.49 (t, 7 Hz, 2H), 2.72 (t, 6.6 Hz, 2H), 2.57 (bm, 1H), 2.37 (bm, 1H), 1.78 (m, 2H).

Example 18

Preparation of 1-[3,4-dimethoxy-5-(3-propoxypropyl)benzoyl]azetidine-2R-carboxylic acid hydroxyamide

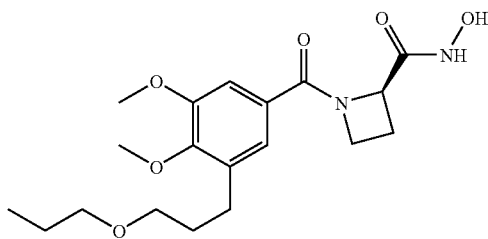

Step 1: 3,4-Dimethoxy-5-(3-propoxypropyl)benzoic acid was prepared from 3-(3-allyloxypropyl)-4,5-dimethoxybenzoic acid (Example 16, Step 1) by following Method H in 94% yield. The reaction was conducted for 16 h at room temperature. The resulting product was used without further purification.

Step 2: 1-[3,4-Dimethoxy-5-(3-propoxypropyl)benzoyl] azetidine-2R-carboxylic acid methyl ester was prepared by coupling azetidine-2R-carboxylic acid methyl ester hydrochloride salt with 3,4-dimethoxy-5-(3-propoxypropyl)benzoic acid by following Method A and this product was used without further purification. ESMS: m/z 380.5 [M+H].

Step 3: 1-[3,4-Dimethoxy-5-(3-propoxypropyl)benzoyl] azetidine-2R-carboxylic acid hydroxyamide was prepared from 1-[3,4-dimethoxy-5-(3-propoxypropyl)benzoyl]azetidine-2R-carboxylic acid methyl ester according to Method B in 6 h. ESMS: m/z 381.4 [M+H]. $^1$H NMR (300 MHz, CD$_3$OD): 7.18 (s, 1H), 7.13 (s, 1H), 4.81 (bs, 1H), 4.48 (bm, 1H), 4.21 (bm, 1H), 3.86 (s, 3H), 3.82 (s, 3H), 3.42 (m, 4H), 2.69 (bt, 2H), 2.59 (bm, 1H), 2.36 (bm, 1H), 1.82 (m, 2H) 1.58 (m, 2H), 0.92 (t, 7 Hz, 3H).

Example 19

Preparation of 1-(3-cyclopropylmethyl-4,5-dimethoxybenzoyl)azetidine-2R-carboxylic acid hydroxyamide

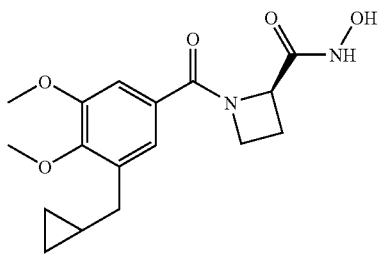

Step 1: To stirred dichloromethane (10 mL) at 0° C. was added Et$_2$Zn (1.0 M in hexane, 10.0 mL, 10 mmol, 2 eq.). The resulting solution was then treated with a solution of TFA (0.77 mL, 10 mmol) in CH$_2$Cl$_2$ (5.0 mL) added over the course of 3 min. After stirring for 20 min at 0° C. diiodomethane (0.80 mL, 10.0 mmol) in CH$_2$Cl$_2$ was added. After 20 min at 0° C., a solution of 3-allyl-4,5-dimethoxybenzoic acid methyl ester (Example 30, Step 1, 1.18 g, 5.0 mmol) in CH$_2$Cl$_2$ (5.0 mL) was added and the reaction was warmed to 23° C. After 50 min the reaction was quenched by addition of 0.1 N HCl (25 mL) and then diluted with hexanes (100 mL). The organic layer was separated, washed with saturated NaHCO$_3$ (100 mL), H$_2$O (100 mL), brine (100 mL) dried MgSO$_4$ and concentrated in vacuo. The crude product was purified by flash column chromatography on silica gel using 20% EtOAc in hexanes as an eluent to furnish 3-cyclopropylmethyl-4,5-dimethoxybenzoic acid methyl ester (0.96 g, 80% yield).

Step 2: 3-Cyclopropylmethyl-4,5-dimethoxybenzoic acid was prepared from 3-cyclopropylmethyl-4,5-dimethoxybenzoic acid methyl ester by following Method E in quantitative yield and used the without further purification.

Step 3: 1-(3-Cyclopropylmethyl-4,5-dimethoxybenzoyl) azetidine-2R-carboxylic acid methyl ester was prepared by reacting azetidine-2R-carboxylic acid methyl ester hydrochloride salt with 3-cyclopropylmethyl-4,5-dimethoxybenzoic acid by following Method A. ESMS: m/z 334.4 [M+H].

Step 4: 1-(3-Cyclopropylmethyl-4,5-dimethoxybenzoyl) azetidine-2R-carboxylic acid hydroxyamide was prepared from 1-(3-cyclopropylmethyl-4,5-dimethoxybenzoyl)azetidine-2R-carboxylic acid methyl ester by following Method B in 5 h. ESMS: m/z 335.4 [M+H]. $^1$H NMR (300 MHz, CD$_3$OD): 7.26 (s, 1H), 7.19 (s, 1H), 4.81 (bm, 1H), 4.49 (bm, 1H) 4.22 (bm, 1H), 3.86 (s, 3H), 3.81 (s, 3H), 2.53 (bm, 3H), 2.36 (bm, 1H), 0.96 (bm, 1H), 0.49 (m, 2H), 0.19 (m, 2H).

Example 20

Preparation of 1-(3-hexyl-4,5-dimethoxybenzoyl) azetidine-2R-carboxylic acid hydroxyamide

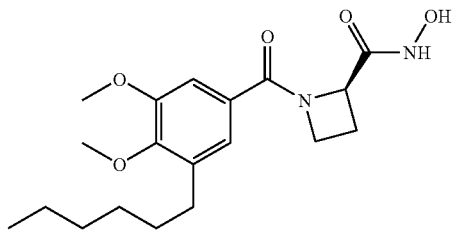

Step 1: To a stirred solution of 3-(3-hydroxypropyl)-4,5-dimethoxybenzoic acid (Example 10, Step 1, 3.53 g, 14.7 mmol) in MeOH (37 mL) at 0° C. was slowly added trimethylsilyldiazomethane (TMSCHN$_2$) (2.0 M, 37 mL, 73.5 mmol) over the course of 5 min. After stirring for 10 min the reaction mixture was concentrated. The crude product was purified by flash column chromatography on silica gel using 67% EtOAc in hexanes as an eluent to furnish 3-(3-hydroxypropyl)-4,5-dimethoxybenzoic acid methyl ester (2.76 g).

Step 2: To a solution of oxallyl chloride (1.34 mL, 15.4 mmol) in CH$_2$Cl$_2$ (30 mL) at −78° C. was added a solution of dimethyl sulfoxide (DMSO) (1.45 mL, 20.5 mmol) in CH$_2$Cl$_2$ (10 mL) via cannula over the course of 1 min. After stirring for 20 min at −78° C. a solution of 3-(3-hydroxypropyl)-4,5-dimethoxybenzoic acid methyl ester (1.30 g, 5.12 mmol) in CH$_2$Cl$_2$ (10 mL) was added via syringe. The reaction was stirred at −78° C. for 45 min then treated with triethylamine (Et$_3$N) (5.7 mL, 10 eq.). After 20 min at −78° C. the reaction was allowed to warm to room temperature. After stirring at room temperature for 30 min, the reaction mixture was diluted with 1:1 EtOAc:hexanes (250 mL), washed with H$_2$O (2×200 mL), brine (200 mL), dried over MgSO$_4$ and then concentrated under reduced pressure. The crude product was purified by flash column chromatography on silica gel using 50% EtOAc in hexanes as an eluent to furnish 3,4-dimethoxy-5-(3-oxopropyl)benzoic acid methyl ester (1.20 g, 93%).

Step 3: 3-Hex-3-enyl-4,5-dimethoxybenzoic acid methyl ester was prepared from 3,4-dimethoxy-5-(3-oxopropyl)benzoic acid methyl ester and propyltriphenylphosphonium bromide by following Method J. The crude product was purified by flash column chromatography on silica gel using 20% EtOAc in hexanes as an eluent to furnish 3-hex-3-enyl-4,5-dimethoxybenzoic acid methyl ester in 63% yield.

Step 4: 3-Hexyl-4,5-dimethoxybenzoic acid methyl ester was prepared from 3-hex-3-enyl-4,5-dimethoxybenzoic acid methyl ester by following Method H using EtOAc as a solvent. The reaction was conducted for 2.5 h under hydrogen atmosphere. The product obtained in quantitative yield was used without further purification.

Step 5: 3-Hexyl-4,5-dimethoxybenzoic acid was prepared from of 3-hexyl-4,5-dimethoxybenzoic acid methyl ester by following Method E in quantitative yield. The acid obtained was used without further purification.

Step 6: 1-(3-Hexyl-4,5-dimethoxybenzoyl)azetidine-2R-carboxylic acid methyl ester was prepared by reacting azetidine-2R-carboxylic acid methyl ester hydrochloride salt with 3-hexyl-4,5-dimethoxybenzoic acid by following Method A and the crude product was used without further purification. ESMS: m/z 364.5 [M+H].

Step 7: 1-(3-Hexyl-4,5-dimethoxybenzoyl)azetidine-2R-carboxylic acid hydroxyamide was prepared from 1-(3-hexyl-4,5-dimethoxybenzoyl)azetidine-2R-carboxylic acid methyl ester by following Method B in 5 h. ESMS: m/z 365.5 [M+H]. $^1$H NMR (300 MHz, CD$_3$OD): 7.16 (s, 1H), 7.11 (s, 1H), 4.80 (bm, 1H), 4.47 (bm, 1H) 4.19 (bm, 1H), 3.85 (s, 3H), 3.81 (s, 3H), 2.60 (bt, 3H), 2.35 (bm, 1H), 1.55 (m, 2H), 1.31 (m, 6H), 0.88 (t, 7 Hz, 3H).

Example 21

Preparation of 1-(3,4-dimethoxy-5-pentylbenzoyl) azetidine-2R-carboxylic acid hydroxyamide

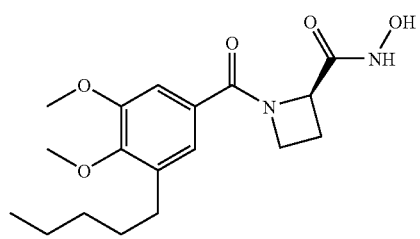

Step 1: 3,4-Dimethoxy-5-pent-3-enylbenzoic acid methyl ester was prepared from 3,4-dimethoxy-5-(3-oxopropyl)benzoic acid methyl ester (Example 20, Step 2) and ethyltriphenylphosphonium bromide by following Method J. The crude product was purified by flash column chromatography on silica gel using 20% EtOAc in hexanes as an eluent to furnish 3,4-dimethoxy-5-pent-3-enylbenzoic acid methyl ester in 37% yield.

Step 2: 3,4-Dimethoxy-5-pentylbenzoic acid methyl ester was prepared 3,4-dimethoxy-5-pent-3-enylbenzoic methyl ester by following Method H using EtOAc as a solvent. The reaction was conducted for 2.5 h under hydrogen atmosphere. The product, obtained in quantitative yield, was used without further purification.

Step 3: 3,4-Dimethoxy-5-pentylbenzoic acid was prepared from 3,4-dimethoxy-5-pentylbenzoic acid methyl ester by following Method E in 91% yield. The acid was used without further purification.

Step 4: 1-(3,4-Dimethoxy-5-pentylbenzoyl)azetidine-2R-carboxylic acid methyl ester was prepared by reacting azetidine-2R-carboxylic acid methyl ester hydrochloride with 3,4-dimethoxy-5-pentylbenzoic by following Method A and the crude product was used without further purification. ESMS: m/z 350.4 [M+H].

Step 5: 1-(3,4-Dimethoxy-5-pentylbenzoyl)azetidine-2R-carboxylic acid hydroxyamide was prepared from 1-(3,4-dimethoxy-5-pentylbenzoyl)azetidine-2R-carboxylic acid methyl ester by following Method B in 6 h. ESMS: m/z 351.5 [M+H]. $^1$H NMR (300 MHz, CD$_3$OD): 7.13 (s, 1H), 7.10 (s, 1H), 4.85 (m, 1H), 4.46 (m, 1H), 4.19 (bm, 1H) 3.84 (s, 3H), 3.79 (s, 3H), 2.60 (m, 3H), 2.34 (bm, 1H), 1.57 (m, 2H), 1.31 (m, 4H), 0.88 (t, 7 Hz, 3H).

Example 22

Preparation of 1-(3-allyl-4-hydroxy-5-methoxybenzoyl)azetidine-2R-carboxylic acid hydroxyamide

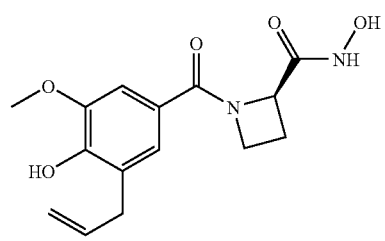

Step 1: 3-Allyl-4-hydroxy-5-methoxybenzoic acid was prepared from 3-allyl-4-hydroxy-5-methoxybenzoic acid methyl ester (Example 1, Step 2) using Method E. In this method LiOH was replaced with NaOH and the reaction was conducted at room temperature for 18 h. The product was extracted with ether. The crude product was used without further purification.

Step 2: 1-(3-Allyl-4-hydroxy-5-methoxybenzoyl)azetidine-2R-carboxylic acid methyl ester was prepared by reacting azetidine-2R-carboxylic acid methyl ester hydrochloride salt with 3-allyl-4-hydroxy-5-methoxybenzoic acid by following Method A and the crude product was used without further purification.

Step 3: 1-(3-Allyl-4-hydroxy-5-methoxybenzoyl)azetidine-2R-carboxylic acid hydroxyamide was prepared from 1-(3-Allyl-4-hydroxy-5-methoxybenzoyl)azetidine-2R-carboxylic acid methyl ester by following Method B in 6 h. ESMS: m/z 305.2 [M−H]. $^1$H NMR (300 MHz, CD$_3$OD): 7.21 (s, 1H), 7.15 (s, 1H), 7.0 (bs, 1H), 6.15 (m, 1H), 4.81-5.08 (m, 3H), 4.56 (bm, 1H), 4.35 (bm, 1H), 3.95 (s, 3H), 3.40 (d, 2H), 2.65 (bm, 1H), 2.4 (bm, 1H).

Example 23

Preparation of 1-(4-methoxy-3-trifluoromethoxybenzoyl)azetidine-2R-carboxylic acid hydroxyamide

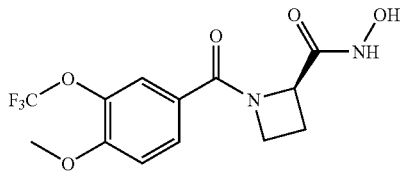

Step 1: 2-Trifluoromethoxyanisole was prepared from 2-trifluoromethoxyphenol by following Method C in 78% yield. Methyl iodide was used in this reaction as an alkylating agent and the reaction was conducted at room temperature for 17 h. The product was used without further purification.

Step 2: 4-Nitro-2-trifluoromethoxyanisole was prepared from 2-trifluoromethoxyanisole by following Method K in 73% yield. The product was used without further purification.

Step 3: To a stirred solution of 4-nitro-2-trifluoromethoxyanisole (500 mg, 2.11 mmol) in MeOH (8.0 mL) at room temperature was added aqueous HCl solution (1.0 mL, 3.0 M) followed by 10% Pd/C (80 mg). The reaction mixture was stirred under $H_2$ atmosphere for 17 h, filtered through a pad of celite and concentrated to give 4-amino-2-trifluoromethoxyanisole as a hydrochloride salt (500 mg). The product was used without further purification.

Step 4: 4-Iodo-2-trifluoromethoxyanisole was prepared from 4-amino-2-trifluoromethoxyanisole by following Method L. The crude product was purified by flash column chromatography (silica gel) to afford 4-iodo-2-trifluoromethoxyanisole in 75% yield.

Step 5: 4-Methoxy-3-trifluoromethoxybenzoic acid was prepared from 4-iodo-2-trifluoromethoxyanisole by following Method M. The resulting crude product was purified by flash column chromatography (silica gel) to give 4-methoxy-3-trifluoromethoxybenzoic acid in 59% yield.

Step 6: 1-(4-Methoxy-3-trifluoromethoxybenzoyl)azetidine-2R-carboxylic acid methyl ester was prepared by coupling azetidine-2R-carboxylic acid methyl ester hydrochloride salt with 4-methoxy-3-trifluoromethoxybenzoic acid according to Method A. This product was used without further purification. ESMS: m/z 334.4 [M+H].

Step 7: 1-(4-Methoxy-3-trifluoromethoxybenzoyl)azetidine-2R-carboxylic acid hydroxyamide was prepared from 1-(4-methoxy-3-trifluoromethoxybenzoyl)azetidine-2R-carboxylic acid methyl ester by following Method B in 5 h. ESMS: m/z 335.4 [M+H]. $^1$H NMR (300 MHz, CD$_3$OD): 7.70 (d, 8 Hz, 1H), 7.63 (s, 1H), 7.22 (d, 8 Hz, 1H), 4.81 (m, 1H), 4.47 (m, 1H), 4.25 (m, 1H), 3.92 (s, 3H), 2.59 (m, 1H), 2.36 (m, 1H).

Example 24

Preparation of 1-(3-allylbenzoyl)azetidine-2R-carboxylic acid hydroxyamide

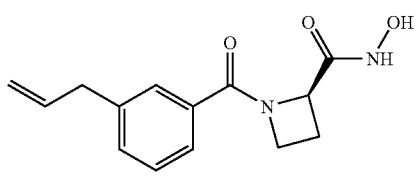

Step 1: 1-(3-Allylbenzoyl)azetidine-2R-carboxylic acid methyl ester was prepared by coupling azetidine-2R-carboxylic acid methyl ester hydrochloride salt with 3-allylbenzoic acid according to Method A using DCM as a solvent. This product was used without further purification.

Step 2: 1-(3-Allylbenzoyl)azetidine-2R-carboxylic acid hydroxyamide was prepared from 1-(3-allylbenzoyl)azetidine-2R-carboxylic acid methyl ester by following Method B in 5 h. ESMS: m/z 261.4 [M+H]. $^1$H NMR (300 MHz, CD$_3$OD): 7.43 (m, 1H), 7.28 (m, 3H), 5.84 (m, 1H), 5.02 (m, 2H), 4.73 (m, 1H), 4.36 (m, 1H), 4.10 (m, 1H), 3.35 (d, 6.3 Hz, 2H), 2.51 (m, 1H), 2.28 (m, 1H).

Example 25

Preparation of 1-(3-propylbenzoyl)azetidine-2R-carboxylic acid hydroxyamide

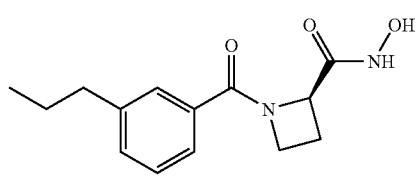

Step 1: 1-(3-Propylbenzoyl)azetidine-2R-carboxylic acid methyl ester was prepared from 1-(3-allylbenzoyl)azetidine-2R-carboxylic acid methyl ester (Example 24, Step 1) by following Method H. The reaction was conducted at room temperature for 4 h. The resulting product was used without further purification.

Step 2: 1-(3-Propylbenzoyl)azetidine-2R-carboxylic acid hydroxyamide was prepared from the 1-(3-propylbenzoyl)azetidine-2R-carboxylic acid methyl ester by following Method B in 5 h. ESMS: m/z 263.4 [M+H]. $^1$H NMR (300 MHz, CD$_3$OD): 7.40 (m, 1H), 7.26 (m, 3H), 4.72 (m, 1H), 4.35 (m, 1H), 4.09 (m, 1H), 2.54 (t, 7.5 Hz, 2H), 2.50 (m, 1H), 2.28 (m, 1H), 1.56 (m, 2H), 0.84 (t, 7.5 Hz, 3H).

Example 26

Preparation of 1-(4-allyloxy-3-trifluoromethoxybenzoyl)azetidine-2R-carboxylic acid hydroxyamide

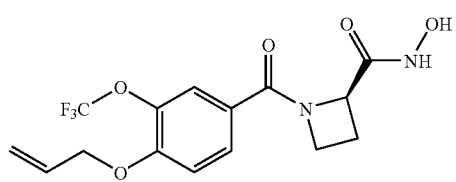

Step 1: 1-Allyloxy-2-trifluoromethoxybenzene was prepared from 2-trifluoromethoxyphenol by following Method C in quantitative yield and the product was used without further purification.

Step 2: 1-Allyloxy-4-nitro-2-trifluoromethoxybenzene was prepared from 1-allyloxy-2-trifluoromethoxybenzene according to Method K. The residue was chromatographed on silica gel to afford 1-allyloxy-4-nitro-2-trifluoromethoxybenzene in 42% yield.

Step 3: To a solution of NH₄Cl (3.3 g, 61.7 mmol) in EtOH (30.0 mL) and H₂O (15.0 mL) at 90° C., was added a solution of 1-allyloxy-4-nitro-2-trifluoromethoxybenzene (1.6 g, 6.08 mmol) in THF (5.0 mL) followed by the addition of iron (1.02 g, 17.9 mmol, 3.0 equi) in two portions with 5 minutes interval. The resulting suspension was stirred at 90° C. for two hours then filtered through a pad of celite and the celite washed with EtOAc. The filtrate was diluted with H₂O and extracted with EtOAc (3×70 mL). The combined organic layer was washed with aq. Na₂CO₃ (2×100 mL), brine (200 mL), dried over Na₂SO₄, and concentrated in vacuo to afford 4-allyloxy-3-trifluoromethoxyaniline (1.6 g). The product was used in the subsequent Step without further purification.

Step 4: 1-Allyloxy-4-iodo-2-trifluoromethoxybenzene was prepared from 4-allyloxy-3-trifluoromethoxyaniline according to Method L. The residue was chromatographed on silica gel to afford 1-allyloxy-4-iodo-2-trifluoromethoxybenzene in 78% yield.

Step 5: 4-Allyloxy-3-trifluoromethoxybenzoic acid was prepared from 1-allyloxy-4-iodo-2-trifluoromethoxybenzene by following Method M. The residue was purified by flash column chromatography on silica gel to give 4-allyloxy-3-trifluoromethoxybenzoic acid 67% yield.

Step 6: 1-(4-allyloxy-3-trifluoromethoxybenzoyl)azetidine-2R-carboxylic acid methyl ester was prepared by coupling azetidine-2R-carboxylic acid methyl ester hydrochloride salt with 4-allyloxy-3-trifluoromethoxybenzoic acid by following Method A and the crude product was used without further purification. ESMS: m/z 360.3 [M+H].

Step 7: 1-(4-allyloxy-3-trifluoromethoxybenzoyl)azetidine-2R-carboxylic acid hydroxyamide was prepared from 1-(4-allyloxy-3-trifluoromethoxybenzoyl)azetidine-2R-carboxylic acid methyl ester by following Method B in 5 h. ESMS: m/z 361.4 [M+H]. ¹H NMR (300 MHz, CD₃OD): 7.63 (m, 2H), 7.20 (d, 6 Hz, 1H), 6.05 (m, 2H), 4.87-5.45 (m, 1H), 4.81 (m, 1H), 4.68 (m, 2H), 4.46 (m, 1H), 4.23 (m, 1H), 2.57 (m, 1H), 2.35 (m, 1H).

Example 27

Preparation of 1-(3-trifluoromethylbenzoyl)azetidine-2R-carboxylic acid hydroxyamide

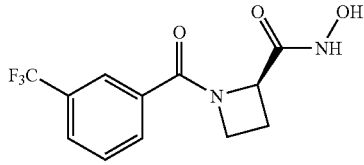

Step 1: To a stirred suspension of azetidine-2R-carboxylic acid (5 g, 49.5 mmol) in DCM (100 mL) at 0° C. was added Et₃N (8.3 mL) followed by a solution Boc₂O (12.5 mL) in DCM (10 mL) over the period of 10 min. The resulting reaction mixture was continued stirring for 3 h at 0° C. and then treated with saturated aqueous citric acid solution (25 mL). The organic layer was separated, washed with brine (50 mL), water (50 mL), brine (50 mL), dried over MgSO₄, and concentrated to give desired product (10.4 g).

Step 2: 2R-Benzyloxycarbamoylazetidine-1-carboxylic acid tert-butyl ester was prepared from Boc-protected azetidine-2R-carboxylic acid by following Method F. The residue was chromatographed (gradient, 100% hexane, 50% hexane/EtOAc, then 75% EtOAc/hexane) to provide 2R-benzyloxycarbamoylazetidine-1-carboxylic acid tert-butyl ester in quantitative yield.

Step 3: To 2R-benzyloxycarbamoylazetidine-1-carboxylic acid tert-butyl ester (1.37 g, 4.47 mmol) was added 30% TFA solution in methylene chloride (40 mL) at 0° C. and the reaction was stirred at that temperature for 30 min. The reaction mixture was slowly warmed to room temperature while stirring for another 3 h. The reaction mixture was concentrated to yield the desired product (1.76 g).

Step 4: 1-(3-Trifluoromethylbenzoyl)azetidine-2R-carboxylic acid benzyloxyamide was prepared by coupling 2R-benzyloxycarbamoylazetidine trifluoroacetic acid salt with m-trifluoromethylbenzoic acid by following Method A. The residue was chromatographed (gradient from 0 to 75% EtOAc in hexane to get 1-(3-trifluoromethylbenzoyl)azetidine-2R-carboxylic acid benzyloxyamide in quantitative yield. ESMS: m/z 379.3 [M+H].

Step 5: 1-(3-Trifluoromethylbenzoyl)azetidine-2R-carboxylic acid hydroxyamide was prepared from 1-(3-trifluoromethylbenzoyl)azetidine-2R-carboxylic acid benzyloxyamide according to Method H. This crude product was purified by preparative HPLC (H₂O/Acetonitrile in 0.1% TFA) to furnish 1-(3-trifluoromethylbenzoyl)azetidine-2R-carboxylic acid hydroxyamide. ESMS: nm/z 289.4 [M+H]. ¹H NMR (300 MHz, CD₃OD): 7.63-7.98 (m, 4H), 4.82 (bm, 1H), 4.44 (m, 1H) 4.21 (m, 1H), 2.59 (m, 1H), 2.37 (m, 1H).

Example 28

Preparation of 1-[3,4-dimethoxy-5-(3-methoxypropyl)benzoyl]azetidine-2R-carboxylic acid hydroxyamide

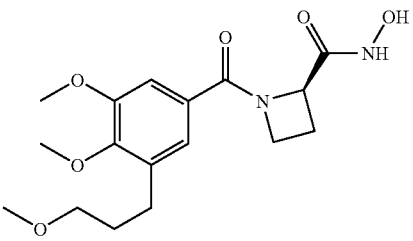

Step 1: 3,4-Dimethoxy-5-(3-methoxypropyl)benzoic acid was prepared from 3-(3-hydroxypropyl)-4,5-Dimethoxybenzoic acid (Example 10, Step 1) and methyl iodide by following Method I in 69% yield. The product was used without further purification.

Step 2: 1-[3,4-Dimethoxy-5-(3-methoxypropyl)benzoyl]azetidine-2R-carboxylic acid benzyloxyamide was prepared by coupling 2R-benzyloxycarbamoylazetidine trifluoroacetic acid salt (Example 27, Step 3) with 3,4-Dimethoxy-5-(3-methoxypropyl)benzoic acid following Method A. The residue was chromatographed (gradient from 0 to 75% EtOAc in hexane) to get 1-[3,4-dimethoxy-5-(3-methoxypropyl)benzoyl]azetidine-2R-carboxylic acid benzyloxyamide in 45% yield. ESMS: m/z 443.5 [M+H].

Step 3: 1-[3,4-Dimethoxy-5-(3-methoxypropyl)benzoyl]azetidine-2R-carboxylic acid hydroxyamide was prepared from 1-[3,4-dimethoxy-5-(3-methoxypropyl)benzoyl]azetidine-2R-carboxylic acid benzyloxyamide by following Method H. The product was purified by preparative HPLC (H₂O/Acetonitrile in 0.1% TFA) to furnish 1-[3,4-dimethoxy-5-(3-methoxypropyl)benzoyl]azetidine-2R-carboxylic acid hydroxyamide. ESMS: m/z 353.4 [M+H]. ¹H NMR (300 MHz, CD₃OD): 7.17 (s, 1H), 7.11 (s, 1H), 4.78 (bm, 1H), 4.47 (bm, 1H), 4.20 (bm, 1H), 3.85 (s, 3H), 3.81 (s, 3H), 3.38 (t, 6.3 Hz, 2H), 3.31 (s, 3H), 2.67 (t, 7.5 Hz, 2H), 2.57 (bm, 1H), 2.35 (bm, 1H), 1.81 (m, 2H).

Example 29

Preparation of 1-[3-(3-ethoxypropyl)-4,5-dimethoxybenzoyl]azetidine-2R-carboxylic acid hydroxyamide

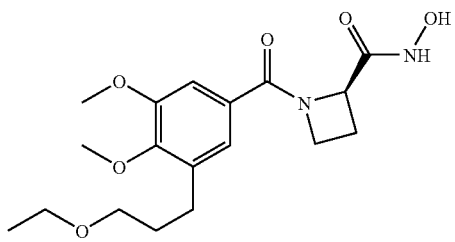

Step 1: 3-(3-Ethoxypropyl)-4,5-dimethoxybenzoic acid was prepared from 3-(3-hydroxypropyl)-4,5-Dimethoxybenzoic acid (Example 10, Step 1) and ethyl bromide by following Method I in 72% yield. The product was used without further purification.

Step 2: 1-[3-(3-Ethoxypropyl)-4,5-dimethoxybenzoyl]azetidine-2R-carboxylic acid benzyloxyamide was prepared by coupling 2R-benzyloxycarbamoylazetidine trifluoroacetic acid salt (Example 27, Step 3) with 3-(3-ethoxypropyl)-4,5-dimethoxybenzoic acid by following Method A. The residue was chromatographed (gradient from 0 to 75% EtOAc in hexane) to get 1-[3-(3-ethoxypropyl)-4,5-dimethoxybenzoyl]azetidine-2R-carboxylic acid benzyloxyamide in 22% yield. ESMS: m/z 457.5 [M+H].

Step 3: 1-[3-(3-Ethoxypropyl-4,5-dimethoxybenzoyl]azetidine-2R-carboxylic acid hydroxyamide was prepared from 1-[3-(3-ethoxypropyl-4,5-dimethoxybenzoyl]azetidine-2R-carboxylic acid benzyloxyamide by following Method H. The product was purified by preparative HPLC($H_2O$/Acetonitrile in 0.1% TFA) to furnish 1-[3-(3-ethoxypropyl-4,5-dimethoxybenzoyl]azetidine-2R-carboxylic acid hydroxyamide. ESMS: m/z 367.5 [M+H]. $^1$H NMR (300 MHz, $CD_3OD$): 7.18 (s, 1H), 7.13 (s, 1H), 4.80 (bm, 1H), 4.49 (bm, 1H), 4.22 (bm, 1H), 3.85 (s, 3H), 3.82 (s, 3H), 3.46 (m, 4H), 2.68 (t, 7.2 Hz, 2H), 2.59 (bm, 1H), 2.37 (bm, 1H), 1.82 (m, 2H), 1.17 (t, 7 Hz, 3H).

Example 30

Preparation of 1-(3-allyl-4,5-dimethoxybenzoyl) azetidine-2R-carboxylic acid hydroxyamide

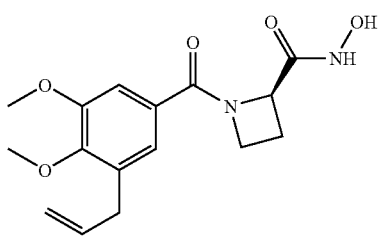

Step 1: 3-Allyl-4,5-dimethoxybenzoic acid methyl ester was prepared from 3-allyl-4-hydroxy-5-methoxybenzoic acid methyl ester (Example 1, Step 2) by following Method C using methyl iodide as alkylating agent. The reaction was conducted at room temperature for 16 h and crude product was purified by flash column chromatography (96% yield).

Step 2: 3-Allyl-4,5-dimethoxybenzoic acid was prepared from 3-allyl-4,5-dimethoxybenzoic acid methyl ester by following Method E in quantitative yield and used without further purification.

Step 3: 1-(3-Allyl-4,5-dimethoxybenzoyl)azetidine-2R-carboxylic acid methyl ester was prepared by reacting azetidine-2R-carboxylic acid methyl ester hydrochloride with 3-allyl-4,5-dimethoxybenzoic acid by following Method A and the crude product was used without further purification. ESMS: m/z 320.4 [M+H].

Step 4: 1-(3-Allyl-4,5-dimethoxybenzoyl)azetidine-2R-carboxylic acid hydroxyamide was prepared from 1-(3-allyl-4,5-dimethoxybenzoyl)azetidine-2R-carboxylic acid methyl ester by following Method B in 3 h. ESMS: m/z 321.5 [M+H]. $^1$H NMR (300 MHz, $CD_3OD$); 7.19 (s, 1H), 7.11 (s, 1H), 5.92 (m, 1H), 5.05 (m, 1H), 5.00 (m, 1H), 4.79 (bm, 1H), 4.45 (bm, 1H), 4.18 (bm, 1H), 3.86 (s, 3H), 3.80 (s, 3H), 3.37 (m, 2H), 2.54 (bm, 1H), 2.34 (bm, 1H).

Example 31

Preparation of 1-(3-butyl-4,5-dimethoxybenzoyl) azetidine-2R-carboxylic acid hydroxyamide

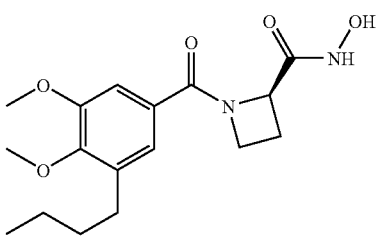

Step 1: 3-But-3-enyl-4,5-dimethoxybenzoic acid methyl ester was prepared from 3,4-dimethoxy-5-(3-oxopropyl)benzoic acid methyl ester (Example 20, Step 2) and methyltriphenylphosphonium bromide by following Method J in 29% yield.

Step 2: 3-Butyl-4,5-dimethoxybenzoic acid methyl ester was prepared from 3-but-3-enyl-4,5-dimethoxybenzoic acid methyl ester by following Method H in 93% yield.

Step 3: 3-Butyl-4,5-dimethoxybenzoic acid was prepared from 3-butyl-4,5-dimethoxybenzoic acid methyl ester by following Method E in 85% yield. The product was used without further purification. ESMS: m/z 237.1 [M−H].

Step 4: 1-(3-Butyl-4,5-dimethoxybenzoyl)azetidine-2R-carboxylic acid methyl ester was prepared by reacting azetidine-2R-carboxylic acid methyl ester hydrochloride with 3-butyl-4,5-dimethoxybenzoic acid according to Method A. ESMS: m/z 336.5 [M+H].

Step 5: 1-(3-Butyl-4,5-dimethoxybenzoyl)azetidine-2R-carboxylic acid hydroxyamide was prepared from 1-(3-butyl-4,5-dimethoxybenzoyl)azetidine-2R-carboxylic acid methyl ester by following Method B in 4 h. ESMS: m/z 337.5 [M+H]. $^1$H NMR (300 MHz, $CDCl_3$): 7.08 (bs, 1H), 7.00 (bs, 1H), 5.00 (m, 1H), 4.40 (m, 1H), 4.20 (m, 1H), 3.86 (s, 3H), 3.84 (s, 3H), 2.82-2.43 (m, 4H), 1.55 (m, 2H), 1.36 (m, 2H), 0.92 (t, 7.5 Hz, 3H).

Example 32

Preparation of 1-[3,4-dimethoxy-5-(3,3,3-trifluoropropyl)benzoyl]azetidine-2R-carboxylic acid hydroxyamide

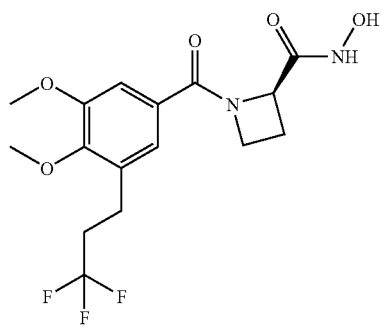

Step 1: To a stirred solution of 2,3-dimethoxybenzaldehyde (20.0 g, 120 mmol, 1 eq.) in $CHCl_3$ (170 mL) at 0° C. was added a solution of bromine (8.0 mL, 155 mmol, 1.29 eq.) in $CHCl_3$ (30 mL) over the course of 1 h. After stirring for 2 h at 0° C. the reaction was warmed to room temperature and stirred a further 20 h, then diluted with $Et_2O$ (1 L). The organic solution was washed successively with $H_2O$ (2×500 mL), saturated aqueous $NaHCO_3$ (4×500 mL), brine (2×500 mL), dried over $MgSO_4$ and then concentrated under reduced pressure. The crude product was purified by flash column chromatography on silica gel using 15% EtOAc in hexanes as an eluent to afford (21 g) of the desired bromide as a yellow solid. The product was further purified by recrystallization from hot hexanes (300 mL) to give 5-bromo-2,3-dimethoxybenzaldehyde (18 g, 61%).

Step 2: To a solution of tetrabutylammonium fluoride (TBAF) in THF (1.0 M, 100 mL, 100 mmol) was added activated 4 Å molecular sieves (powder, 80 g) and stirred for 16 h. Then the suspension was cooled to 0° C. and a solution of aldehyde (2.45 g, 10 mmol) and 2,2,2-trifluoroethyldiphenylphosphine oxide (Kobayashi, T. et al. J. Org. Chem. 2002, 67, 3156-3159; 5.50 g, 19 mmol) in THF (50 mL+50 mL flush) was added via cannula. After 90 min at 0° C. the reaction was warmed to room temperature and stirred a further 2 h, then the suspension was filtered through a pad of celite and washed with EtOAc (500 mL). The combined filtrate was washed with $H_2O$ (300 mL), brine (300 mL), dried over $MgSO_4$ and then concentrated in vacuo. The crude product was purified by flash column chromatography on silica gel using 15% EtOAc in hexanes as eluent to afford 5-bromo-1,2-dimethoxy-3-(3,3,3-trifluoropropenyl)benzene (865 mg, 28%), as a mixture of E/Z isomers.

Step 3: 3,4-Dimethoxy-5-(3,3,3-trifluoropropenyl)benzoic acid was prepared from 5-bromo-1,2-dimethoxy-3-(3,3,3-trifluoropropenyl)benzene by following Method M in 70% yield. The product was used without further purification. ESMS: m/z 275.3 [M−H].

Step 4: 3,4-Dimethoxy-5-(3,3,3-trifluoropropyl)benzoic acid was prepared from 3,4-dimethoxy-5-(3,3,3-trifluoropropenyl)benzoic acid by following Method H in 88% yield. The reaction was conducted at room temperature for 1.5 h. The product was used without further purification. ESMS: m/z 277.4 [M−H].

Step 5: 1-[3,4-Dimethoxy-5-(3,3,3-trifluoropropyl)benzoyl]azetidine-2R-carboxylic acid methyl ester was prepared by reacting azetidine-2R-carboxylic acid methyl ester hydrochloride salt with 3,4-dimethoxy-5-(3,3,3-trifluoropropyl)benzoic acid according to Method A and the crude product was used without further purification. ESMS: m/z 376.4 [M+H].

Step 6: 1-[3,4-Dimethoxy-5-(3,3,3-trifluoropyl)benzoyl]azetidine-2R-carboxylic hydroxyamide was prepared from 1-[3,4-dimethoxy-5-(3,3,3-trifluoropyl)benzoyl]azetidine-2R-carboxylic acid methyl ester by following Method B in 4.5 h. ESMS: m/z 377.4 [M+H]. $^1H$ NMR (300 MHz, $CDCl_3$): 7.15 (bs, 1H), 6.98 (bs, 1H), 5.03 (m, 1H), 4.40 (m, 1H), 4.22 (m, 1H), 3.90 (s, 3H), 3.89 (s, 3H), 2.78-3.03 (m, 3H), 2.26-2.59 (m, 3H).

Example 33

Preparation of 1-(3-dimethylcarbamoylmethyl-4,5-dimethoxybenzoyl)azetidine-2R-carboxylic acid hydroxyamide

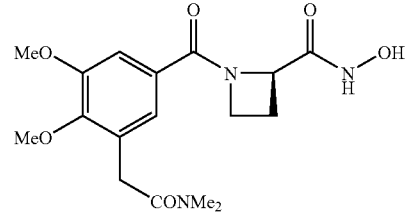

Step 1: To a stirred solution of 3-allyl-4,5-dimethoxybenzoic acid methyl ester (Example 30, Step 1, 1.0 g, 9.24 mmol) in DMF (20 mL) was added $OsO_4$ (0.54 mL, 0.042 mmol) and continued stirring for 5 min under nitrogen atmosphere. To this was added oxone (104 g, 16.9 mmol) and the reaction mixture stirred for 3 h. $Na_2SO_3$ Solution was added. The aqueous layer was extracted with EtOAc. The combined organic layer was washed with 1 N aqueous HCl, brine, dried over $Na_2SO_4$, and concentrated in vacuo. The resulting residue was chromatographed (silica gel column) using EtOAc/Hexanes/MeOH (30:65:5) to afford the acid (0.6 g, 60% yield). To a stirred solution of acid (2.54 g, 10 mmol), obtained from above, was added oxalyl chloride (3.4 mL, 10 mmo) followed by a drop of DMF and continued stirring the reaction mixture for 14 h. The solvent was removed in vacuo and the residue was dried under high vacuum. This was used without further purification.

Step 2: To a stirred solution of acyl chloride obtained from Step 1 (350 mg, 1.28 mmol) in dry THF (5.0 mL) was cooled to 0° C. under $N_2$ atmosphere then treated with N,N-dimethylamine (2.57 mL, 5.13 mmol). The reaction was allowed to warm to room temperature and was stirred for 3 h. THF was removed in vacuo and the residue was dissolved with ether. The $Et_2O$ layer was washed with saturated aqueous $NaHCO_3$ aqueous solution, dried over anhydrous $Na_2SO_4$, filtered and concentrated in vacuo to give 3-dimethylcarbamoylmethyl-4,5-dimethoxybenzoic acid methyl ester (0.31 g, 86%).

Step 3: 3-Dimethylcarbamoylmethyl-4,5-dimethoxybenzoic acid was prepared from 3-dimethylcarbamoylmethyl-4,5-dimethoxybenzoic acid methyl ester by following Method E. The product was used without further purification.

Step 4: 1-(3-Dimethylcarbamoylmethyl-4,5-dimethoxybenzoyl)azetidine-2R-carboxylic acid methyl ester was prepared by reacting azetidine-2R-carboxylic acid methyl ester hydrochloride salt with 3-dimethylcarbamoylmethyl-4,5-dimethoxybenzoic acid by following Method A and the crude product was used without further purification.

Step 5: 1-(3-Dimethylcarbamoylmethyl-4,5-dimethoxybenzoyl)azetidine-2R-carboxylic acid hydroxyamide was prepared from 1-(3-Dimethylcarbamoylmethyl-4,5-dimethoxybenzoyl)azetidine-2R-carboxylic acid methyl ester according to Method B in 1.5 h. ESMS: m/z 366.5 [M+H]. $^1$H NMR (300 MHz, CD$_3$OD): 7.14 (s, 1H), 6.99 (s, 1H), 4.69 (m, 1H), 4.34 (m, 1H), 4.09 (m, 1H), 3.74 (s, 3H), 3.68 (s, 3H), 3.61 (s, 2H), 2.98 (s, 3H), 2.83 (s, 3H), 2.45 (m, 1H), 2.20 (m, 1H).

Example 34

Preparation of 1-(3,5-dibromo-4-methoxybenzoyl)azetidine-2R-carboxylic acid hydroxyamide

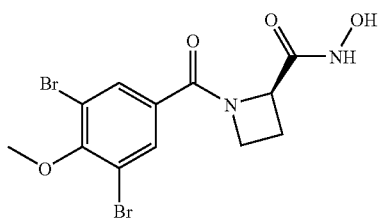

Step 1: 3,5-Dibromo-4-methoxybenzoic acid methyl ester was prepared from 3,5-dibromo-4-hydroxybenzoic acid methyl ester by following Method C using methyl iodide as an alkylating agent in quantitative yield. The product was used without further purification.

Step 2: 3,5-Dibromo-4-methoxybenzoic acid was prepared from 3,5-dibromo-4-methoxybenzoic acid methyl ester by following Method E in 99% yield. The product was used without further purification.

Step 3: 1-(3,5-dibromo-4-methoxybenzoyl)azetidine-2R-carboxylic acid methyl ester was prepared by coupling azetidine-2R-carboxylic acid methyl ester hydrochloride salt with 3,5-dibromo-4-methoxybenzoic acid by following Method A and the product was used without further purification. ESMS: m/z 408.1 [M+H].

Step 4: 1-(3,5-dibromo-4-methoxybenzoyl)azetidine-2R-carboxylic acid hydroxyamide was prepared from 1-(3,5-dibromo-4-methoxybenzoyl)azetidine-2R-carboxylic acid methyl ester by following Method B in 5 h. ESMS: m/z 407.1 [M−H]. $^1$H NMR (300 MHz, CD$_3$OD): 7.87 (m, 2H), 4.76 (m, 1H), 4.40 (m, 1H), 4.20 (m, 1H), 3.87 (s, 3H), 2.56 (m, 1H), 2.33 (m, 1H).

Example 35

Preparation of 1-(3-iodo-4,5-dimethoxybenzoyl)azetidine-2R-carboxylic acid hydroxyamide

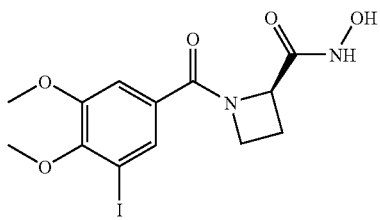

Step 1: To a stirred solution of 3-iodo-4,5-dimethoxybenzaldehyde (25.0 g, 85.6 mmol) in CH$_3$CN (800 mL) at room temperature, was added a solution of sulfamic acid (10.65 g, 109 mmol) in H$_2$O (135 mL). To this was added, dropwise, a solution of NaClO$_2$ (12.65 g, 112 mmol) in H$_2$O (135 mL) over 20 min period. After stirring for a further 30 min at room temperature, the solvent was removed in vacuo. The reaction was diluted with 1.0 M aqueous HCl (700 mL) and extracted with EtOAc (3×300 mL). The combined organic layers were washed with brine (600 mL), dried over Na$_2$SO$_4$ and concentrated in vacuo to give 3,4-dimethoxy-5-iodobenzoic acid (26 g). The product was used without further purification.

Step 2: 1-(3-Iodo-4,5-dimethoxybenzoyl)azetidine-2R-carboxylic acid methyl ester was prepared by coupling azetidine-2R-carboxylic acid methyl ester hydrochloride salt with 3-iodo-4,5-dimethoxybenzoic acid by following Method A and the crude product was used without further purification. ESMS: m/z 406.4 [M+H].

Step 3: 1-(3-Iodo-4,5-dimethoxybenzoyl)azetidine-2R-carboxylic acid hydroxyamide was prepared from 1-(3-iodo-4,5-dimethoxybenzoyl)azetidine-2R-carboxylic acid methyl ester by following Method B in 5 h. ESMS: m/z 407.3 [M+H]. $^1$H NMR (300 MHz, CD$_3$OD): 7.63 (bs, 1H), 7.29 (bs, 1H), 4.77 (m, 1H), 4.42 (m, 1H), 4.18 (m, 1H), 3.85 (s, 3H), 3.79 (s, 3H), 2.55 (m, 1H), 2.33 (m, 1H).

Example 36

Preparation of 1-[3-(3-fluoropropyl)-4,5-dimethoxybenzoyl]azetidine-2R-carboxylic acid hydroxyamide

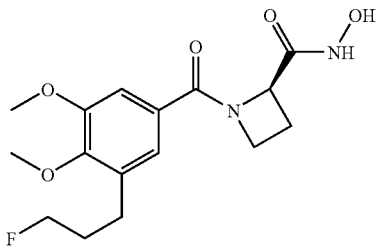

Step 1: To a stirred solution of 3-(3-hydroxypropyl-4,5-dimethoxy)benzoic acid methyl ester (Example 20, Step 1, 1.30 g, 5.12 mmol) in CH$_2$Cl$_2$ (20 mL) at 0° C. was added triethylamine (2.14 mL, 15.4 mmol) followed by methanesulfonyl chloride (0.58 mL, 7.68 mmol). After 60 min the reaction mixture was loaded directly onto a column of silica gel and chromatographed using 1:1 EtOAc:hexanes as an eluent to gave the desired mesylate (1.66 g, 98%). To a stirred solution of mesylate, from above, (435 mg, 1.31 mmol) in THF (5.0 mL) at room temperature was added TBAF (1.0 M in THF, 2.60 mL, 2.62 mmol). Following the addition, the reaction was heated to reflux for 30 min then allowed to return to room temperature. The reaction mixture was then diluted with Et$_2$O (100 mL), washed with H$_2$O (100 mL), saturated aqueous NH$_4$Cl (100 mL), brine (100 mL), dried over MgSO$_4$ and concentrated in vacuo. The crude product was purified by flash column chromatography on silica gel using 15% EtOAc in hexanes as an eluent to furnish 3-(3-fluoropropyl)-4,5-dimethoxybenzoic acid methyl ester (214 mg).

Step 2: 3-(3-Fluoropropyl)-4,5-dimethoxybenzoic acid was prepared from 3-(3-fluoropropyl)-4,5-dimethoxybenzoic acid methyl ester by following Method E and the product was used in subsequent Step without further purification.

Step 3: 1-[3-(3-Fluoropropyl)-4,5-dimethoxybenzoyl]azetidine-2R-carboxylic acid methyl ester was prepared by coupling azetidine-2R-carboxylic acid methyl ester hydrochloride with 3-(3-fluoropropyl)-4,5-dimethoxybenzoic acid by following Method A and the crude product was used without further purification. ESMS: m/z 340.5 [M+H].

Step 4: 1-[3-(3-Fluoropropyl)-4,5-dimethoxybenzoyl]azetidine-2R-carboxylic acid hydroxyamide was prepared from 1-[3-(3-fluoropropyl)-4,5-dimethoxybenzoyl]azetidine-2R-carboxylic acid methyl ester by following Method B in 3 h. ESMS: m/z 341.4 [M+H]. $^1$H NMR (300 MHz, CDCl$_3$): 7.13 (bs, 1H), 7.01 (bs, 1H), 5.02 (m, 1H), 4.18-4.55 (m, 4H), 3.88 (s, 3H), 3.87 (s, 3H), 2.71-2.87 (m, 3H), 2.53 (m, 1H), 1.88-2.05 (m, 2H).

Example 37

Preparation of 1-(3-trifluoromethylthiobenzoyl)azetidine-2R-carboxylic acid hydroxyamide

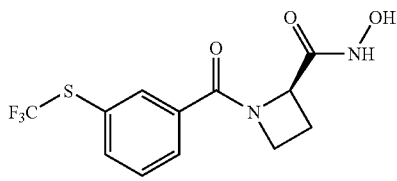

Step 1: 1-(3-Trifluoromethylthiobenzoyl)azetidine-2R-carboxylic acid methyl ester was prepared by reacting azetidine-2R-carboxylic acid methyl ester hydrochloride salt with 3-trifluoromethylthiobenzoic acid by following Method A and the crude product was used without further purification. ESMS: m/z 320.3 [M+H].

Step 2: 1-(3-Trifluoromethylthiobenzoyl)azetidine-2R-carboxylic acid hydroxyamide was prepared from 1-(3-trifluoromethylthiobenzoyl)azetidine-2R-carboxylic acid methyl ester by following Method B in 4 h. ESMS: m/z 321.3 [M+H]. $^1$H NMR (300 MHz, CDCl$_3$): 7.90 (bs, 1H), 7.75 (m, 2H), 7.47 (m, 1H), 5.03 (m, 1H), 4.45 (m, 1H), 4.18 (m, 1H), 2.75 (m, 1H), 2.55 (m, 1H).

Example 38

Preparation of 1-(4-trifluoromethylthiobenzoyl)azetidine-2R-carboxylic acid hydroxyamide

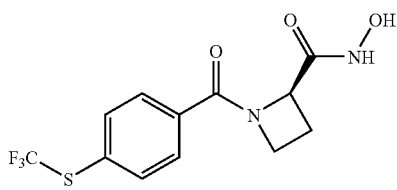

Step 1: 1-(4-Trifluoromethylthiobenzoyl)azetidine-2R-carboxylic acid methyl ester was prepared by reacting azetidine-2R-carboxylic acid methyl ester hydrochloride salt with 4-trifluoromethylthiobenzoic acid by following Method A and the crude product was used without further purification. ESMS: m/z 320.3 [M+H].

Step 2: 1-(4-Trifluoromethylthiobenzoyl)azetidine-2R-carboxylic acid hydroxyamide was prepared from 1-(4-trifluoromethylthiobenzoyl)azetidine-2R-carboxylic acid methyl ester by following Method B in 3 h. ESMS: m/z 321.2 [M+H]. $^1$H NMR (300 MHz, CDCl$_3$): 7.68 (q, 7.2 Hz, 4H), 5.08 (m, 1H), 4.45 (m, 1H), 4.27 (m, 1H), 2.85 (m, 1H), 2.55 (m, 1H).

Example 39

Preparation of 1-(3-trifluoromethanesulfinylbenzoyl)azetidine-2R-carboxylic acid hydroxyamide

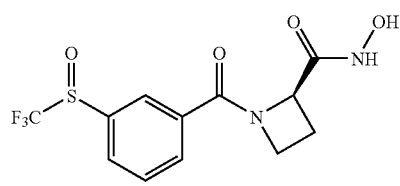

Step 1: To a stirred solution of 1-(3-trifluoromethylthiobenzoyl)azetidine-2R-carboxylic acid hydroxyamide (Example 37, Step 2, 65 mg, 0.20 mmol, 1 eq.) in CH$_2$Cl$_2$ (3.0 mL) at 23° C. was added meta-chloroperbenzoic acid (m-CPBA) (commercial 77% max, 70 mg). After 3 h, more m-CPBA (70 mg) was added. After stirring for 45 min, the solution was concentrated and the crude product was purified by preparative HPLC to furnish 1-(3-trifluoromethanesulfinylbenzoyl)azetidine-2R-carboxylic acid hydroxyamide (19 mg). ESMS: m/z 337.3 [M+H]. $^1$H NMR (300 MHz, CDCl$_3$): 8.08 (bs, 1H), 7.89 (m, 2H), 7.69 (m, 1H), 5.04 (m, 1H), 4.48 (m, 1H), 4.20 (m, 1H), 2.76 (m, 1H), 2.56 (m, 1H).

Example 40

Preparation of 1-(3-trifluoromethoxy-4-methoxy-5-propylbenzoyl)azetidine-2R-carboxylic acid hydroxyamide

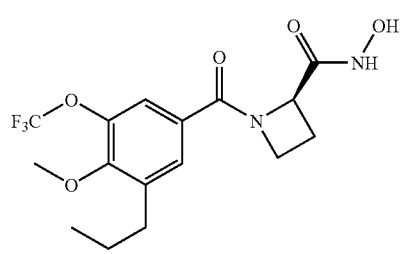

Step 1: 2-Allyl-4-nitro-6-trifluoromethoxyphenol was prepared from 1-allyloxy-4-nitro-2-trifluoromethoxybenzene (Example 26, Step 2) following Method D. The reaction was conducted for 17 h. The residue was purified by flash column chromatography on silica gel using EtOAc:hexanes (0-20%) as an eluent to give 2-allyl-4-nitro-6-trifluoromethoxyphenol in 70% yield.

Step 2: 1-Allyl-2-methoxy-5-nitro-3-trifluoromethoxybenzene was prepared from 2-allyl-4-nitro-6-trifluoromethoxyphenol and methyl iodide by following Method C. The reaction was conducted at room temperature for 17 h. The residue was purified by flash column chromatography on silica gel using EtOAc:hexanes (0-5%) as an eluent to give 1-allyl-2-methoxy-5-nitro-3-trifluoromethoxybenzene in 52% yield.

Step 3: To a stirred solution of 1-allyl-2-methoxy-5-nitro-3-trifluoromethoxybenzene (1.9 g, 6.86 mmol, 1 eq.) in MeOH (26 mL) at room temperature was added aqueous HCl solution (3.4 mL, 3.0 M) followed by 10% Pd/C (256 mg). The reaction mixture was stirred under $H_2$ atmosphere for 17 h, filtered through a pad of celite and concentrated in vacuo to give 4-methoxy-3-propyl-5-trifluoromethoxyphenylamine hydrochloride (1.6 g). The product was used without further purification.

Step 4: 5-Iodo-2-methoxy-1-propyl-3-trifluoromethoxybenzene was prepared from 4-methoxy-3-propyl-5-trifluoromethoxyaniline hydrochloride salt by following Method L. The residue was chromatographed on silica gel to afford 5-iodo-2-methoxy-1-propyl-3-trifluoromethoxybenzene 71% yield.

Step 5: 4-Methoxy-3-propyl-5-trifluoromethoxybenzoic acid was prepared from 5-iodo-2-methoxy-1-propyl-3-trifluoromethoxybenzene by following Method M. The residue was purified by flash column chromatography on silica gel to give 4-methoxy-3-propyl-5-trifluoromethoxybenzoic acid in quantitative yield.

Step 6: 1-(4-Methoxy-3-propyl-5-trifluoromethoxybenzoyl)azetidine-2R-carboxylic acid methyl ester was prepared by coupling azetidine-2R-carboxylic acid methyl ester hydrochloride with 4-methoxy-3-propyl-5-trifluoromethoxybenzoic acid by following Method A and the crude product was used without purification. ESMS: m/z 376.3 [M+H].

Step 7: 1-(4-Methoxy-3-propyl-5-trifluoromethoxybenzoyl)azetidine-2R-carboxylic acid hydroxyamide was prepared from 1-(4-methoxy-3-propyl-5-trifluoromethoxybenzoyl)azetidine-2R-carboxylic acid methyl ester by following Method B in 5 h. ESMS: m/z 377.4 [M+H]. $^1$H NMR (300 MHz, $CD_3OD$): 7.50 (s, 1H), 7.47 (s, 1H), 4.79 (m, 1H), 4.42 (m, 1H), 4.20 (m, 1H), 3.86 (s, 3H), 2.64 (t, 7.5 Hz, 2H), 2.60 (m, 1H), 2.34 (m, 1H), 1.60 (m, 2H), 0.934 (t, 7.2 Hz, 3H).

Example 41

Preparation of 1-(3-bromo-4,5-dimethoxybenzoyl)azetidine-2R-carboxylic acid hydroxyamide

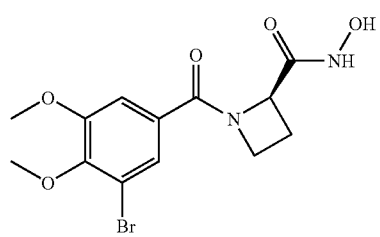

Step 1: To a stirred solution of 3-bromo-4,5-dimethoxybenzaldehyde (5.0 g, 20.5 mmol, 1 eq.) in $CH_3CN$ (192 mL) at room temperature was added a solution of sulfamic acid (2.55 g, 26.3 mmol) in H2O (32 mL) followed by a dropwise addition of a solution of $NaClO_2$ (3.03 g, 26.8 mmol, 1.3 eq.) in $H_2O$ (32 mL) over 20 min period. After stirring for 30 min at room temperature, the solvent was removed in vacuo. The residue was dissolved in 1.0 M aqueous HCl (300 mL) and extracted with EtOAc (3×100 mL). The combined organic layer was washed with brine (300 mL), dried over $Na_2SO_4$ and concentrated in vacuo to give 3-bromo-4,5-dimethoxybenzoic acid (5.0 g). The product was used without further purification.

Step 2: 1-(3-Bromo-4,5-dimethoxybenzoyl)azetidine-2R-carboxylic acid methyl ester was prepared by coupling azetidine-2R-carboxylic acid methyl ester hydrochloride salt with 3-bromo-4,5-dimethoxybenzoic acid according to Method A and used the crude product without further purification. ESMS: m/z 359.2 [M+H].

Step 3: 1-(3-Bromo-4,5-dimethoxybenzoyl)azetidine-2R-carboxylic acid hydroxyamide was prepared from 1-(3-bromo-4,5-dimethoxybenzoyl)azetidine-2R-carboxylic acid methyl ester by following Method B in 5 h. ESMS: m/z 358.2 [M−H]. $^1$H NMR (300 MHz, $CD_3OD$): 7.45 (s, 1H), 7.29 (s, 1H), 4.79 (m, 1H), 4.44 (m, 1H), 4.19 (m, 1H), 3.88 (s, 3H), 3.82 (s, 3H), 2.58 (m, 1H), 2.34 (m, 1H).

Example 42

Preparation of 1-(3-ethynyl-4,5-dimethoxybenzoyl)azetidine-2R-carboxylic acid hydroxyamide

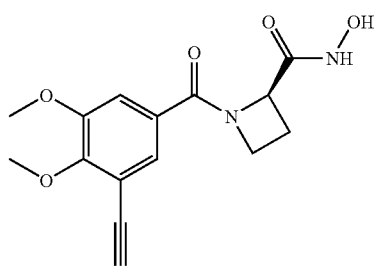

Step 1: To a stirred solution of 3-iodo-4,5-dimethoxybenzoic acid (6.16 g, 20.0 mmol) in a mixture of $Et_3N$ (40 mL) and benzene (40 mL) at room temperature, was added CuI (380 mg, 2 mmol), $Pd(PPh_3)_4$ (462 mg, 0.4 mmol) and (trimethylsilyl)acetylene (3.4 mL, 24 mmol). After stirring for 3 days at room temperature, the solvent was removed in vacuo, the residue was diluted with 1 N HCl aqueous solution (300 mL) and then extracted with EtOAc (3×100 mL). The combined organic layer was washed with brine (300 mL), dried over $Na_2SO_4$ and concentrated in vacuo to give 3,4-dimethoxy-5-(trimethylsilanylethynyl)benzoic acid (5.6 g). The product was used without further purification.

Step 2: To a stirred solution of 3,4-dimethoxy-5-(trimethylsilanylethynyl)benzoic acid (5.56 g, 20 mmol) in THF (115 mL) at 0° C. was added TBAF (1.0 M solution in THF, 30 mL, 30 mmol). The resulting solution was stirred at 0° C. for 30 min, then the reaction mixture was diluted with 1 N HCl aqueous solution (200 mL), extracted with EtOAc (3×70 mL). The combined organic layer was washed with brine (100 mL), dried over $Na_2SO_4$, concentrated in vacuo to give 3-ethynyl-4,5-dimethoxybenzoic acid (4.0 g). The product was used without further purification.

Step 3: 1-(3-Ethynyl-4,5-dimethoxybenzoyl)azetidine-2R-carboxylic acid methyl ester was prepared by coupling azetidine-2R-carboxylic acid methyl ester hydrochloride salt with 3-ethynyl-4,5-dimethoxybenzoic acid according to Method A and used the crude product without further purification.

Step 4: 1-(3-Ethynyl-4,5-dimethoxybenzoyl)azetidine-2R-carboxylic acid hydroxyamide was prepared from 1-(3-ethynyl-4,5-dimethoxybenzoyl)azetidine-2R-carboxylic acid methyl ester by following Method B in 5 h. ESMS: m/z 303.1 [M−H]. $^1$H NMR (300 MHz, $CD_3OD$): 7.32 (bs, 2H), 4.79 (m, 1H), 4.44 (m, 1H), 4.19 (m, 1H), 3.88 (s, 3H), 3.86 (s, 3H), 3.71 (s, 1H), 2.58 (m, 1H), 2.35 (m, 1H).

Example 43

Preparation of 1-(3,4-dimethoxy-5-prop-1-ynylbenzoyl)azetidine-2R-carboxylic acid hydroxyamide

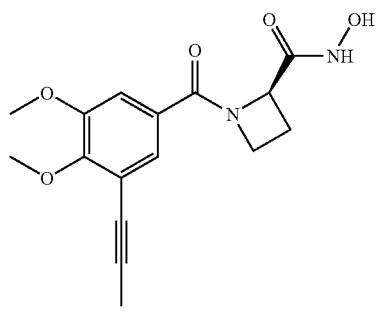

Step 1: To a stirred solution of 3-iodo-4,5-dimethoxybenzoic acid (12.32 g, 40.0 mmol) in mixture of Et₃N (80 mL) and benzene (80 mL) at room temperature was added CuI (760 mg, 4 mmol) followed by Pd(PPh₃)₄ (924 mg, 0.8 mmol, 0.02 eq.). After stirring for 2 days under propyne atmosphere (balloon) at room temperature, the solvent was removed, the residue was suspended in 1N HCl aqueous solution (300 mL) and then extracted with EtOAc (3×100 mL). The combined organic layer wash washed with brine (300 mL), dried over Na₂SO₄ and then concentrated in vacuo to give 3,4-dimethoxy-5-prop-1-ynylbenzoic acid (9.7 g). The product was used without further purification.

Step 2: 1-(3,4-Dimethoxy-5-prop-1-ynylbenzoyl)azetidine-2R-carboxylic acid methyl ester was prepared by coupling azetidine-2R-carboxylic acid methyl ester hydrochloride salt with 3,4-dimethoxy-5-prop-1-ynylbenzoic acid according to Method A and used this product without further purification.

Step 3: 1-(3,4-Dimethoxy-5-prop-1-ynylbenzoyl)azetidine-2R-carboxylic acid hydroxyamide was prepared from 1-(3,4-dimethoxy-5-prop-1-ynylbenzoyl)azetidine-2R-carboxylic acid methyl ester by following Method B in 5 h. ESMS: m/z 317.3 [M−H]. ¹H NMR (300 MHz, CD₃OD): 7.25 (bs, 2H), 7.09 (bs, 1H), 4.81 (m, 1H), 4.45 (m, 1H), 4.20 (m, 1H), 3.87 (s, 3H), 3.86 (s, 3H), 2.58 (m, 1H), 2.36 (m, 1H), 2.06 (s, 3H).

Example 44

Preparation of 1-(3-methoxy-5-propylbenzoyl)azetidine-2R-carboxylic acid hydroxyamide

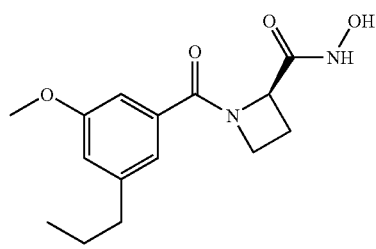

Step 1: To a stirred solution of 4-hydroxy-3-methoxy-5-propylbenzoic acid methyl ester (Example 1, Step 3, 1.5 g, 6.7 mmol) in CH₂Cl₂ (40 mL) at 0° C., was added 2,6-lutidine (0.93 mL, 8.04 mmol), followed by trifluoromethanesulfonic anhydride (1.35 mL, 8.02 mmol). The reaction mixture was continued stirring at room temperature for 2 h. To this was added 1N HCl aqueous solution (150 mL) and the resulting suspension was extracted with CH₂Cl₂ (3×50 mL). The combined organic layer was washed with brine (100 mL), dried over Na₂SO₄ and concentrated in vacuo. The resulting residue was purified by column chromatography to afford 3-methoxy-5-propyl-4-trifluoromethanesulfonyloxybenzoic acid methyl ester (2.0 g).

Step 2: To a mixture of 3-methoxy-5-propyl-4-trifluoromethanesulfonyloxybenzoic acid methyl ester (1.0 g, 2.8 mmol), Pd(OAc)₂ (31 mg, 0.138 mmol) and 1,1'-bis-(diphenylphosphino)ferrocene (155 mg, 0.28 mmol) at room temperature was added DMF (20 mL), then Et₃N (1.17 mL, 8.4 mmol) followed by formic acid (0.21 mL, 5.6 mmol). The resulting mixture was stirred at 60° C. for 2 h and cooled to room temperature. The reaction mixture was diluted with aqueous NaHCO₃ solution (150 mL) and then extracted with EtOAc (3×70 mL). The combined organic layer was washed with brine (100 mL), dried over Na₂SO₄, concentrated in vacuo, and the residue was purified by column chromatography to afford 3-methoxy-5-propylbenzoic acid methyl ester (0.56 g).

Step 3: 3-Methoxy-5-propylbenzoic acid was prepared from 3-methoxy-5-propylbenzoic acid methyl ester following Method E. The reaction was conducted at room temperature for 20 h. The product was used without further purification Step 4: 1-(3-Methoxy-5-propylbenzoyl)azetidine-2R-carboxylic acid methyl ester was prepared by coupling azetidine-2R-carboxylic acid methyl ester hydrochloride salt with 3-methoxy-5-propylbenzoic acid according to Method A and used the product without further purification.

Step 5: 1-(3-Methoxy-5-propylbenzoyl)azetidine-2R-carboxylic acid hydroxyamide was prepared from 1-(3-methoxy-5-propylbenzoyl)azetidine-2R-carboxylic acid methyl ester by following Method B in 5 h. ESMS: m/z 291.1 [M−H]. ¹H NMR (300 MHz, CD₃OD): 7.06 (s, 1H), 7.02 (s, 1H), 6.89 (bs, 2H), 4.78 (m, 1H), 4.42 (m, 1H), 4.15 (m, 1H), 3.79 (s, 3H), 2.59 (m, 3H), 2.35 (m, 1H), 1.63 (m, 2H), 0.96 (t, 3H).

Example 45

Preparation of 1-(3-methoxy-5-trifluoromethylthiobenzoyl)azetidine-2R-carboxylic acid hydroxyamide

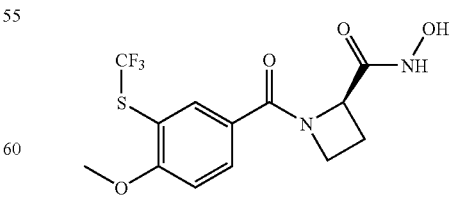

Step 1: To a stirred solution of 3-hydroxy-4-methoxybenzoic acid methyl ester (10.0 g, 54.95 mmol) in DMF (160 mL) at 0° C. was added NaH (2.32 g, 58 mmol, 60% in mineral oil) in small portions. The resulting mixture was stirred at room temperature for 30 min then cooled to 0° C. using ice bath. To this solution was added dimethylthiocarbonyl chloride (7.5 g, 60.7 mmol, 1.1 equi) in one portion. The resulting mixture was stirred at room temperature for 3 h and then at 75° C. for 1.5 h. The reaction mixture was cooled to room temperature, stirred at room temperature for 17 h, then diluted with water (1500 mL) and extracted with ethyl ether (3×300 mL). The combined organic layer was washed with brine (500 mL), dried over $Na_2SO_4$, concentrated in vacuo and the residue was purified by column chromatography to afford 3-dimethylthiocarbamoyloxy-4-methoxybenzoic acid methyl ester.

Step 2: A stirred solution of 3-dimethylthiocarbamoyloxy-4-methoxybenzoic acid methyl ester (5.6 g, 20.8 mmol) in phenyl ether (150 mL) was heated to reflux for 20 h. The reaction mixture was cooled to room temperature and was purified by silica gel column to afford 3-dimethylcarbamoylthio-4-methoxybenzoic acid methyl ester (4.13 g).

Step 3: To a stirred solution of 3-dimethylcarbamoylthio-4-methoxybenzoic acid methyl ester (530 mg, 1.97 mmol) in THF (10 mL), was added MeONa (10 mL, 0.5 M solution in MeOH). The resulting mixture was heated to reflux for 3 h and then cooled to room temperature. The reaction mixture was diluted with 1N HCl aqueous solution (100 mL), extracted with EtOAc (3×50 mL). The combined organic layer was washed with brine (100 mL), dried over $Na_2SO_4$, concentrated in vacuo to afford 3-mercapto-4-methoxybenzoic acid methyl ester (0.42 g). The product was used without further purification.

Step 4: To a stirred solution of 3-mercapto-4-methoxybenzoic acid methyl ester (0.42 g, 2.12 mmol) in DMF (5.0 mL) at 0° C. was added NaH (102 mg, 2.55 mmol, 60% in mineral oil) in small portions. The resulting mixture was stirred at room temperature for 30 min and then charged with a balloon full of $CF_3I$ gas. The reaction was stirred at room temperature for 30 min and then at 70° C. for 2 h. After cooling to room temperature, the reaction mixture was diluted with water (100 mL) and extracted with EtOAc (3×50 mL). The combined organic layer was washed with brine (100 mL), dried over $Na_2SO_4$ and concentrated in vacuo. The resulting residue was purified by column chromatography to afford 4-methoxy-3-trifluoromethylthiobenzoic acid methyl ester (0.33 g).

Step 5: 4-Methoxy-3-trifluoromethylthiobenzoic acid was prepared from 4-methoxy-3-trifluoromethylthiobenzoic acid methyl ester following Method E. The reaction was conducted at room temperature for 20 h and the resulting product was used without further purification.

Step 6: 1-(4-Methoxy-3-trifluoromethylthiobenzoyl)azetidine-2R-carboxylic acid methyl ester was prepared by coupling azetidine-2R-carboxylic acid methyl ester hydrochloride salt with 4-methoxy-3-trifluoromethylthiobenzoic acid according to Method A and used the product without further purification.

Step 7: 1-(4-Methoxy-3-trifluoromethylthiobenzoyl)azetidine-2R-carboxylic acid hydroxyamide was prepared from 1-(4-methoxy-3-trifluoromethylthiobenzoyl)azetidine-2R-carboxylic acid methyl ester by following Method B in 5 h. ESMS: m/z 349.0 [M−H]. $^1$H NMR (300 MHz, $CD_3OD$): 7.98 (s, 1H), 7.88 (bd, J=8.4 Hz, 1H), 7.20 (d, J=8.4 Hz, 1H), 4.82 (m, 1H), 4.48 (m, 1H), 4.23 (m, 1H), 3.95 (s, 3H), 2.59 (m, 1H), 2.37 (m, 1H).

Example 46

Preparation of 1-[3-(1,2,2,2-tetrafluoro-1-trifluoromethylethylthio)benzoyl]-azetidine-2R-carboxylic acid hydroxyamide

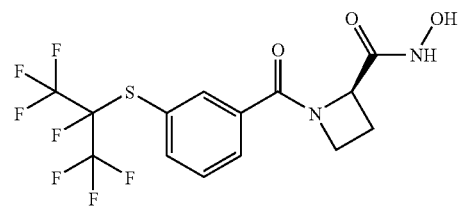

Step 1: To a stirred solution of 3-mercaptobenzoic acid methyl ester (2.32 g, 13.8 mmol) in DMF (15 mL) at 0° C. was added NaH (60% dispersion in mineral oil, 608 mg, 15.2 mmol) in small portions. After stirring for 10 min at 0° C., and a further 30 min at room temperature, perfluoroisopropyl iodide (2.16 mL, 15.2 mmol, 1.1) was added to the reaction. Following the addition, the reaction was stirred for 10 min at room temperature and then heated to 60° C. After 90 min at 60° C. the reaction was cooled to room temperature, diluted with ethyl ether (150 mL), washed with brine (2×200 mL), saturated aqueous $NaHCO_3$ (200 mL), brine (100 mL), dried over $MgSO_4$ and then concentrated in vacuo. The residue was purified by flash column chromatography on silica gel using 5% EtOAc in hexanes as an eluent to furnish 3-(1,2,2,2-tetrafluoro-1-trifluoromethylethylthio)benzoic acid methyl ester (3.13 g).

Step 2: 3-(1,2,2,2-tetrafluoro-1-trifluoromethylethylthio)benzoic acid was prepared from 3-(1,2,2,2-tetrafluoro-1-trifluoromethylethylthio)benzoic acid methyl ester by following Method E in quantitative yield and the product was used without further purification. ESMS: m/z 321.1 [M−H].

Step 3: 1-[3-(1,2,2,2-tetrafluoro-1-trifluoromethylethylthio)benzoyl]azetidine-2R-carboxylic acid methyl ester was prepared by reacting azetidine-2R-carboxylic acid methyl ester hydrochloride salt with 3-(1,2,2,2-tetrafluoro-1-trifluoromethylethylthio)benzoic acid following Method A. ESMS: m/z 420.1 [M+H].

Step 4: 1-[3-(1,2,2,2-tetrafluoro-1-trifluoromethylethylthio)benzoyl]azetidine-2R-carboxylic acid hydroxyamide was prepared from 1-[3-(1,2,2,2-tetrafluoro-1-trifluoromethylethylthio)benzoyl]azetidine-2R-carboxylic acid methyl ester by following Method B in 5 h. ESMS: m/z 421.1 [M+H]. $^1$H NMR (300 MHz, $CDCl_3$): 7.88 (bs, 1H), 7.80 (bs, 1H), 7.77 (bs, 1H), 7.50 (t, 7.5 Hz, 1H), 5.04 (m, 1H), 4.41 (m, 1H), 4.19 (m, 1H), 2.82 (m, 1H), 2.58 (m, 1H).

Example 47

Preparation of 1-(3,5-bis-trifluoromethylthiobenzoyl)azetidine-2R-carboxylic acid hydroxyamide

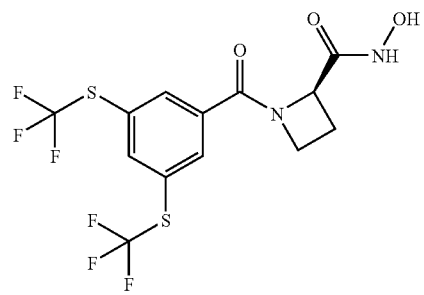

Step 1: To a stirred solution of 3,5-dihydroxybenzoic acid methyl ester (10.0 g, 59.5 mmol) in DMF (200 mL) at 0° C. was added NaH (60% dispersion in mineral oil, 5.00 g, 125 mmol, 2.1 eq.) in small portions. The reaction mixture was stirred at 0° C. for 15 min then warmed to room temperature. After 1 h, the reaction mixture was cooled to 0° C. and then added dimethylthiocarbamoyl chloride (14.7 g, 119 mmol). Following the addition, the reaction was stirred for 45 min at 0° C., then for 30 min at room temperature and then heated to 80° C. After 2 h at 80° C., the reaction mixture was cooled to room temperature and then added to 1% aqueous KOH (500 mL). The resulting mixture was extracted with ethyl ether (2×500 mL). The organic layer was washed with $H_2O$ (500 mL), brine (300 mL), dried over $MgSO_4$ and concentrated in vacuo to afford 3,5-bis-dimethylthiocarbamoyloxybenzoic acid methyl ester (13.0 g). This material was used without further purification.

Step 2: 3,5-Bis-dimethylthiocarbamoyloxybenzoic acid methyl ester (3.2 g) was heated under vacuum at 200° C. for 18 h. After cooling to room temperature, the product was purified by flash column chromatography on silica gel using 67% EtOAc in hexanes as an eluent to furnish 3,5-bis-dimethylcarbamoylthiobenzoic acid methyl ester (1.46 g).

Step 3: To a stirred solution of 3,5-bis-dimethylcarbamoylthiobenzoic acid methyl ester (445 mg, 1.30 mmol) in THF (10 mL) at room temperature was added MeONa (0.5 M in MeOH, 10.0 mL, 5.0 mmol). The reaction was refluxed for 3 h, then cooled to room temperature, and added to 1.0 N HCl aqueous solution (100 mL). The resulting mixture was extracted with EtOAc (100 mL). The organic layer was washed with brine (50 mL), dried over $MgSO_4$ and concentrated in vacuo to afford 3,5-dimercaptobenzoic acid methyl ester (220 mg). The product was used without further purification.

Step 4: To a stirred solution of 3,5-dimercaptobenzoic acid methyl ester (220 mg, 1.1 mmol) in DMF (10 mL) at room temperature was added NaH (60% dispersion in mineral oil, 132 mg, 3.3 mmol, 3 eq.) in small portions. After stirring for 40 min at room temperature, the reaction vessel was evacuated for 30 sec (needle to pump) then the vacuum was broken with trifluoromethyl iodide gas (balloon). The reaction was stirred for 20 min at room temperature then heated to 60° C. After 60 min at 60° C. the reaction was cooled to room temperature, diluted with ethyl ether (100 mL), washed with 1 N HCl aqueous solution (100 mL), brine (50 mL), dried over $MgSO_4$ and concentrated in vacuo to give 3,5-bis-trifluoromethylthiobenzoic acid methyl ester. The crude product was used without further purification.

Step 5: 3,5-Bis-trifluoromethylthiobenzoic acid was prepared from give 3,5-bis-trifluoromethylthiobenzoic acid methyl ester by following Method E and the product was without further purification.

Step 6: 1-(3,5-Bis-trifluoromethylthiobenzoyl)azetidine-2R-carboxylic acid methyl ester was prepared by reacting azetidine-2R-carboxylic acid methyl ester hydrochloride salt with 3,5-bis-trifluoromethylthiobenzoic acid following Method A.

Step 7: 1-(3,5-Bis-trifluoromethylthiobenzoyl)azetidine-2R-carboxylic acid hydroxyamide was prepared from 1-(3,5-bis-trifluoromethylthiobenzoyl)azetidine-2R-carboxylic acid methyl ester by following Method B in 5 h. ESMS: m/z 421.0 [M+H]. $^1$H NMR (300 MHz, $CDCl_3$): 8.05 (bs, 1H), 8.03 (bs, 2H), 5.03 (dd, 6.0 Hz, 9.0 Hz, 1H), 4.48 (dd, 9.0 Hz, 15 Hz, 1H), 4.19 (dd, 8.4 Hz, 15 Hz, 1H), 2.71 (m, 1H), 2.56 (m, 1H).

Example 48

Preparation of 1-(3-methoxy-5-trifluoromethylthiobenzoyl)azetidine-2R-carboxylic acid hydroxyamide

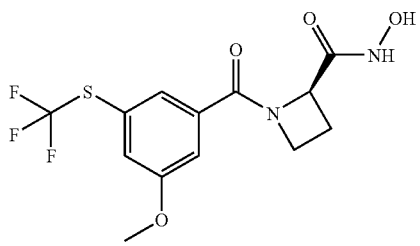

Step 1: To a stirred solution of 3,5-dihydroxybenzoic acid methyl ester (10.0 g, 59.5 mmol) in DMF (200 mL) at 0° C. was added NaH (60% dispersion in mineral oil, 2.62 g, 65.4 mmol) in small portions. The reaction mixture was stirred at 0° C. for 15 min then warmed to room temperature. After 1 h at room temperature, the reaction mixture was cooled to 0° C. and then dimethylthiocarbamoyl chloride (7.35 g, 59.5 mmol) was added. Following the addition, the reaction was stirred for 15 min at 0° C., then for 30 min at room temperature and then heated to 80° C. After 2 h at 80° C. the reaction mixture was cooled to room temperature then added to 1 N HCl aqueous solution (500 mL). The resulting mixture was extracted with ethyl ether (500 mL). The organic layer was washed with $H_2O$ (300 mL), brine (150 mL), dried over $MgSO_4$ and concentrated in vacuo. 3-Dimethylthiocarbamyloxy-5-hydroxybenzoic acid methyl ester was separated from the undesired bis-adduct by flash column chromatography using 50% EtOAc in hexanes as eluent. The material obtained (2.37 g) was contaminated with unreacted 3,5-dihydroxybenzoic acid methyl ester and was used without further purification.

Step 2: To a stirred solution of 3-dimethylthiocarbamyloxy-5-hydroxybenzoic acid methyl ester (2.37 g, impure) in DMF (30 mL) at room temperature was added $K_2CO_3$ (3.85 g, 27.9 mmol), followed by iodomethane (1.16 mL, 18.6 mmol). After stirring for 3.5 h at room temperature the reaction mixture was partitioned between ethyl ether (200 mL) and $H_2O$ (200 mL). The organic layer was washed with brine (100 mL), dried over $MgSO_4$ and concentrated in vacuo. The residue was purified by flash column chromatography on silica gel using 33% EtOAc in hexanes as an eluent to furnish 3-dimethylthiocarbamyloxy-5-methoxybenzoic acid methyl ester (1.30 g, 4.83 mmol).

Step 3: 3-Dimethylcarbamyloxy-5-methoxybenzoic acid methyl ester was heated under nitrogen atmosphere at 240° C. for 4 h. After cooling to room temperature the product was purified by flash column chromatography on silica gel using 50% EtOAc in hexanes as an eluent to furnish 3-dimethylcarbamylthio-5-methoxybenzoic acid methyl ester (77% yield).

Step 4: To a stirred solution of 3-dimethylcarbamylthio-5-methoxybenzoic acid methyl ester (500 mg, 1.86 mmol) in THF (10 mL) at room temperature was added MeONa (0.5 M in MeOH, 10.0 mL, 5.0 mmol, 2.69 eq.). The reaction was refluxed for 2 h, then cooled to room temperature and added to 1.0 N HCl aqueous solution (150 mL). The resulting mixture was extracted with EtOAc/hexanes (1:1, 150 mL). The organic layer was washed with brine (100 mL), dried over $MgSO_4$ and concentrated in vacuo to give 3-mercapto-5-methoxybenzoic acid methyl ester (0.365 g). The product was used without further purification.

Step 5: To a stirred solution of 3-mercapto-5-methoxybenzoic acid methyl ester (360 mg, 1.82 mmol) in DMF (15 mL) at 0° C. was added NaH (60% dispersion in mineral oil, 87 mg, 2.18 mmol, 1.2 eq.) in small portions. After stirring for 10 min at 0° C., then for a further 40 min at room temperature, the reaction vessel was evacuated (60 sec, needle to pump) then the vacuum was broken with trifluoromethyl iodide gas (balloon). This was stirred for 5 min at room temperature then heated to 100° C. After 2 h at 100° C. the reaction was cooled to room temperature, diluted with ethyl ether (100 mL), washed with 1 N HCl aqueous solution (100 mL), brine (50 mL), dried over $MgSO_4$ and concentrated in vacuo. The residue was purified by flash column chromatography on silica gel using 20% EtOAc in hexanes as an eluent to furnish 3-methoxy-5-trifluoromethylthiobenzoic acid methyl ester (160 mg).

Step 6: 3-Methoxy-5-trifluoromethylthiobenzoic acid was prepared from 3-methoxy-5-trifluoromethylthiobenzoic acid methyl ester in quantitative yield by following Method E and the product was used without further purification. ESMS: m/z 251.3 [M−H].

Step 7: 1-(3-Methoxy-5-trifluoromethylthiobenzoyl)azetidine-2R-carboxylic acid methyl ester was prepared by reacting azetidine-2R-carboxylic acid methyl ester hydrochloride salt with 3-methoxy-5-trifluoromethylthiobenzoic acid following Method A and the product was used without further purification.

Step 8: 1-(3-Methoxy-5-trifluoromethylthiobenzoyl)azetidine-2R-carboxylic acid hydroxyamide was prepared from the 1-(3-methoxy-5-trifluoromethylthiobenzoyl)azetidine-2R-carboxylic acid methyl ester by following Method B in 5 h. ESMS: m/z 349.0 [M−H]. $^1$H NMR (300 MHz, $CDCl_3$): 7.40 (bs, 1H), 7.27 (bs, 1H), 7.26 (bs, 1H), 5.01 (dd, 6.0 Hz, 9.0 Hz, 1H), 4.41 (dd, 9.0 Hz, 15 Hz, 1H), 4.17 (dd, 8.4 Hz, 15 Hz, 1H), 3.84 (s, 3H), 2.71 (m, 1H), 2.56 (m, 1H).

Example 49

Preparation of 1-(4-methoxy-3-propyl-5-trifluoromethylthiobenzoyl)azetidine-2R-carboxylic acid hydroxyamide

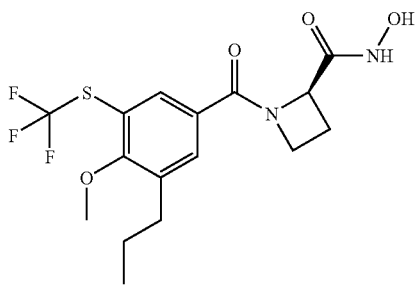

Step 1: 4-Allyloxybenzoic acid methyl ester was prepared by reacting 4-hydroxybenzoic acid methyl ester with allyl bromide following Method C in 91% yield. The reaction was conducted at room temperature for 16 h and the resulting product was used without further purification.

Step 2: 3-Allyl-4-hydroxybenzoic acid methyl ester was prepared from 4-allyloxybenzoic acid methyl ester following Method D in 90% yield. The reaction was conducted neat at 200° C. for 2 days. The resulting product was passed through a pad of silica gel and eluted with 30% hexanes in EtOAc.

Step 3: 3-Allyl-4-methoxybenzoic acid methyl ester was prepared from 3-Allyl-4-hydroxybenzoic acid methyl ester according to Method C using methyl iodide as an alkylating agent in quantative yield. This product was used without further purification.

Step 4: 4-Methoxy-3-propylbenzoic acid methyl ester was prepared from the corresponding 3-Allyl-4-methoxybenzoic acid methyl ester according to Method H. This product was used without further purification.

Step 5: To a stirred solution of $NaNO_3$ (0.82 g, 9.62 mmol) in TFA (15 mL) at 0° C. was added 4-methoxy-3-propylbenzoic acid methyl ester (2.0 g, 9.62 mmol). After 45 min the reaction was warmed to room temperature. After stirring for a further 2 days, the reaction mixture was diluted with ethyl ether (200 mL), washed with $H_2O$ (3×100 mL), saturated aqueous $NaHCO_3$ solution (2×100 mL), brine (50 mL), dried over $MgSO_4$ and concentrated in vacuo. The product was purified by flash column chromatography on silica gel using 20% EtOAc in hexanes as an eluent to afford 4-methoxy-3-nitro-5-propylbenzoic acid methyl ester (2.20 g).

Step 6: To a stirred solution of 4-methoxy-3-nitro-5-propylbenzoic acid methyl ester (2.20 g, 8.70 mmol) in MeOH (70 mL) at room temperature was added 3.0 N HCl aqueous solution (4.5 mL, 13.5 mmol) followed by Pd/C (10% by wt., 500 mg). The resulting mixture was evacuated for 60 sec (needle to pump) then the vacuum was broken with $H_2$ gas (balloon). After stirring for 4 days at room temperature, the reaction mixture was filtered through a pad of celite and washed with MeOH (150 mL). The combined filtrate was concentrated in vacuo and the residue was purified by flash column chromatography on silica gel using 25% EtOAc in hexanes as an eluent to furnish the desired product. Recrystallization from hot EtOAc gave pure 3-amino-4-methoxy-5-propylbenzoic acid methyl ester (1.47 g).

Step 7: To a stirred solution of 3-amino-4-methoxy-5-propylbenzoic acid methyl ester (1.47 g, 5.65 mmol) in dioxane (20 mL) and $H_2O$ at room temperature was added $H_2SO_4$ (concentrated, 0.80 mL). The resulting mixture was cooled to −10° C. and treated with a solution of $NaNO_2$ (400 mg) in $H_2O$ (5.6 mL) by adding dropwise over a period of 5 min. After stirring a further 30 min at −10° C., the reaction was warmed to 0° C. After a stirring a further 30 min at 0° C. the reaction mixture was poured onto an ice-cold solution of $EtOCS_2K$ (1.80 g, 2 eq.) in $H_2O$ (20 mL). The transfer was quantitated with $H_2O$ wash (10 mL). The resulting mixture was allowed to warm to room temperature and stirred for a further 30 min before extracting with EtOAc (2×100 mL). The organic layer was washed with brine (50 mL), dried over $MgSO_4$ and concentrated in vacuo. The residue was purified by flash column chromatography on silica gel using 20% EtOAc in hexanes as an eluent to furnish 2-ethoxythiocarbonylthio-4-methoxy-5-propylbenzoic acid methyl ester. ESMS: m/z 351.1 [M+Na].

Step 8: To a stirred solution of 3-ethoxythiocarbonylthio-4-methoxy-5-propylbenzoic acid methyl ester (720 mg, 2.20 mmol) in THF (13 mL) at room temperature was added MeONa (0.5 M in MeOH, 13 mL, 6.5 mmol, 3 eq.). The reaction mixture was refluxed for 75 min, then cooled to room temperature and added to 1 N HCl aqueous solution (100 mL). The resulting mixture was extracted with EtOAc/hexanes (1:1, 100 mL). The organic layer was washed with brine (50 mL), dried over $MgSO_4$ and concentrated in vacuo to give 3-mercapto-4-methoxy-5-propylbenzoic acid methyl ester (0.55 g). The product was used without further purification.

Step 9: To a stirred solution of 3-mercapto-4-methoxy-5-propylbenzoic acid methyl ester (550 mg, 2.3 mmol) in DMF (15 mL) at 0° C. was added NaH (60% dispersion in mineral oil, 110 mg, 2.75 mmol, 1.2 eq.) in small portions. After stirring for 10 min at 0° C., then for a further 35 min at room temperature, the reaction vessel was evacuated (60 sec, needle to pump) then the vacuum was broken with trifluoromethyl iodide gas (balloon). The reaction mixture was stirred for 5 min at room temperature, then heated to 70° C. After 65 min at 70° C. the reaction was cooled to room temperature, diluted with EtOAc/hexanes (100 mL), washed with 1.0 N HCl aqueous solution (100 mL), brine (50 mL), dried over $MgSO_4$ and concentrated in vacuo. The residue was purified by flash column chromatography on silica gel using 20% EtOAc in hexanes as an eluent to furnish 4-methoxy-3-propyl-5-trifluoromethylthiobenzoic acid methyl ester (60 mg).

Step 10: 4-Methoxy-3-propyl-5-trifluoromethylthiobenzoic acid was prepared from 4-methoxy-3-propyl-5-trifluoromethylthiobenzoic acid methyl ester in quantitative yield by following Method E and the product was used without further purification. ESMS: m/z 293.2 [M–H].

Step 11: 1-(4-Methoxy-3-propyl-5-trifluoromethylthiobenzoyl)azetidine-2R-carboxylic acid methyl ester was prepared by reacting azetidine-2R-carboxylic acid methyl ester hydrochloride salt with 4-methoxy-3-propyl-5-trifluoromethylthiobenzoic acid following Method A and the product was used without further purification. ESMS: m/z 392.3 [M+H].

Step 12: 1-(4-Methoxy-3-propyl-5-trifluoromethylthiobenzoyl)azetidine-2R-carboxylic acid hydroxyamide was prepared from 1-(4-methoxy-3-propyl-5-trifluoromethylthiobenzoyl)azetidine-2R-carboxylic acid methyl ester by following Method B in 5 h. ESMS: m/z 415.2 [M+Na]. $^1$H NMR (300 MHz, $CD_3OD$): 7.83 (bs, 1H), 7.72 (bs, 1H), 4.83 (m, 1H), 4.45 (m, 1H), 4.20 (m, 1H), 3.86 (s, 3H), 2.69 (t, 7.8 Hz, 2H), 2.60 (m, 1H), 2.37 (m, 1H), 1.66 (m, 2H), 0.96 (t, 7.2 Hz, 3H).

Example 50

Preparation of 1-[3-(1-fluoropropyl)-4,5-dimethoxybenzoyl)azetidine-2R-carboxylic acid hydroxyamide

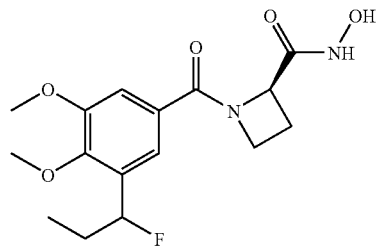

Step 1: To a stirred solution of 5-bromo-2,3-dimethoxybenzaldehyde (Example 32, Step 1, 1.50 g, 5.30 mmol) in $Et_2O$ (20 mL) at –78° C. was added EtMgBr (9.10 mL, 7.30 mmol, 1.5 eq.) and the reaction was allowed to warm to room temperature and stirred for 5 h. The reaction was quenched with saturated aqueous $NH_4Cl$, extracted with $Et_2O$, dried over $Na_2SO_4$, and concentrated in vacuo to give the crude product (96%). The product was used without further purification.

Step 2: To a stirred solution of 1-(5-bromo-2,3-dimethoxyphenyl)propan-1-ol (400 mg, 1.45 mmol) in DCM (10 mL) at –78° C. was added DAST (0.58 mL, 4.36 mmol) and stirred the reaction for 10 min at –78° C., then warmed to 0° C. for 2 h. The reaction was quenched with water and saturated aqueous $NH_4Cl$ (100 mL), extracted with EtOAc, dried over $Na_2SO_4$ and concentrated in vacuo. The crude product was purified by flash column chromatography on silica gel using 30% EtOAc in hexanes as an eluent to furnish 5-bromo-1-(1-fluoropropyl)-2,3-dimethoxybenzene (80%).

Step 3: 3-(1-Fluoropropyl)-4,5-dimethoxybenzoic acid was prepared from 5-bromo-1-(1-fluoropropyl)-2,3-dimethoxybenzene by following Method M in 1 h and the crude product was used without further purification.

Step 4: 1-[3-(1-Fluoropropyl)-4,5-dimethoxybenzoyl]azetidine-2R-carboxylic acid methyl ester was prepared by coupling azetidine-2R-carboxylic acid methyl ester hydrochloride with 3-(1-fluoropropyl)-4,5-dimethoxybenzoic acid by following Method A overnight and the crude product was used without further purification.

Step 5: 1-[3-(1-Fluoropropyl)-4,5-dimethoxybenzoyl]azetidine-2R-carboxylic acid hydroxyamide was prepared from 1-[3-(1-fluoropropyl)-4,5-dimethoxybenzoyl]azetidine-2R-carboxylic acid methyl ester by following Method B in 1 h. ESMS: m/z 341.5 [M+H]. $^1$H NMR (300 MHz, $CDCl_3$): 7.31 (s, 2H), 5.58-5.76 (m, 1H), 4.82 (m, 1H), 4.48 (m, 1H), 4.20 (m, 1H), 3.90 (s, 3H), 3.87 (s, 3H), 2.61 (m, 1H), 2.37 (m, 1H), 1.94-1.80 (m, 2H), 0.97 (t, 6.3 Hz, 3H).

Example 51

Preparation of 1-(4-methylthio-3-trifluoromethoxybenzoyl)azetidine-2R-carboxylic acid Hydroxyamide

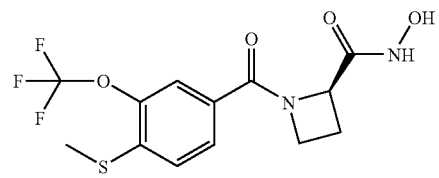

Step 1: 4-Bromo-1-methylthio-2-trifluoromethoxybenzene was prepared from 4-bromo-2-trifluoromethoxybenzenethiol and methyl iodide by following Method C. The reaction was conducted at room temperature overnight. The crude residue was chromatographed in 20% EtOAc/Hexanes to afford 4-bromo-1-methylthio-2-trifluoromethoxybenzene (85% yield).

Step 2: 4-Methylthio-3-trifluoromethoxybenzoic acid was prepared from 4-bromo-1-methylthio-2-trifluoromethoxybenzene by following Method M in 4 h. The product was used without further purification.

Step 3: 1-[4-Methylthio-3-trifluoromethoxybenzoyl)azetidine-2R-carboxylic acid methyl ester was prepared by coupling azetidine-2R-carboxylic acid methyl ester hydrochloride with 4-methylthio-3-trifluoromethoxybenzoic acid by following Method A overnight and the crude product was used without further purification.

Step 4: 1-[4-Methylthio-3-trifluoromethoxybenzoyl)azetidine-2R-carboxylic acid hydroxyamide was prepared from 1-[4-methylthio-3-trifluoromethoxybenzoyl) azetidine-2R- carboxylic acid methyl ester by following Method B in 2 h. ESMS: m/z 351.4 [M+H]. $^1$H NMR (300 MHz, CDCl$_3$): 7.56 (d, 8.1 Hz, 1H), 7.49 (s, 1H), 7.31 (d, 8.1 Hz, 1H), 4.72 (m, 1H), 4.37 (m, 1H), 4.14 (m, 1H), 2.48 (m, 1H), 2.41 (s, 3H), 2.27 (m, 1H).

Example 52

Preparation of 1-[3-(2,2,2-trifluoroethylthio)benzoyl] azetidine-2R-carboxylic acid hydroxyamide

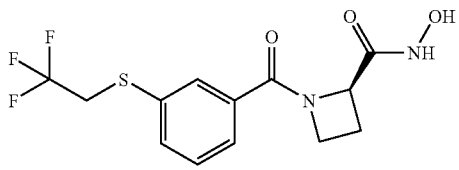

Step 1: 3-(2,2,2-Trifluoroethylthio)benzoic acid methyl ester was prepared 3-mercaptobenzoic acid methyl ester and trifluoroethyl iodide by following Method C. The reaction was conducted at room temperature overnight. The crude residue was chromatographed in 10-20% EtOAc/hexanes to afford 3-(2,2,2-trifluoroethylthio)benzoic acid methyl ester (82% yield).

Step 2: 3-(2,2,2-Trifluoroethylthio)benzoic acid was prepared from 3-(2,2,2-trifluoroethylthio)benzoic acid methyl ester by following Method E. The reaction as conducted at room temperature overnight. The product was used without further purification.

Step 3: 1-[3-(2,2,2-Trifluoroethylthio)benzoyl]azetidine-2R-carboxylic acid methyl ester was prepared by coupling azetidine-2R-carboxylic acid methyl ester hydrochloride with 3-(2,2,2-trifluoroethylthio)benzoic acid by following Method A and the crude product was used without further purification.

Step 4: 1-[3-(2,2,2-Trifluoroethylthio)benzoyl]azetidine-2R-carboxylic acid hydroxyamide was prepared from 1-[3-(2,2,2-trifluoroethylthio)benzoyl]azetidine-2R-carboxylic acid methyl ester by following Method B in 2 h. ESMS: m/z 335.1 [M+H]. $^1$H NMR (300 MHz, CDCl$_3$): 7.69 (s, 1H), 7.53 (d, 7.2 Hz, 1H), 7.47 (d, 7.8 Hz, 1H), 7.33 (t, 7.8 Hz, 1H), 4.65 (m, 1H), 4.32 (m, 1H), 4.11 (m, 1H), 3.68-3.58 (m, 2H), 2.47 (m, 1H), 2.26 (m, 1H).

Example 53

Preparation of 1-(3-pentafluoroethylthiobenzoyl) azetidine-2R-carboxylic acid aydroxyamide

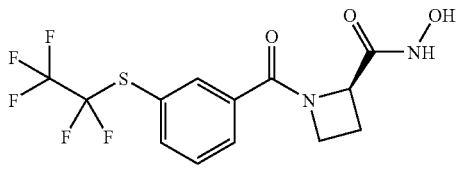

Step 1: 3-Pentafluoroethylthiobenzoic acid methyl ester was prepared from 3-mercaptobenzoic acid methyl ester and pentafluoroethyl iodide by following Method I in 5 h at room temperature and the crude product was used without further purification.

Step 2: 3-Pentafluoroethylthiobenzoic acid was prepared from 3-pentafluoroethylthiobenzoic acid methyl ester by following Method E in 2 h. The product was used without further purification.

Step 3: 1-(3-Pentafluoroethylthiobenzoyl]azetidine-2R-carboxylic acid methyl ester was prepared by coupling azetidine-2R-carboxylic acid methyl ester hydrochloride with 3-pentafluoroethylthiobenzoic acid by following Method A overnight and the crude product was used without further purification.

Step 4: 1-(3-Pentafluoroethylthiobenzoyl]azetidine-2R-carboxylic acid hydroxyamide was prepared from 1-(3-pentafluoroethylthiobenzoyl]azetidine-2R-carboxylic acid methyl ester by following Method B in 2 h. ESMS: m/z 371.1 [M+H]. $^1$H NMR (300 MHz, CDCl$_3$): 7.90 (s, 1H), 7.84-7.72 (m, 2H), 7.47 (m, 1H), 4.74 (m, 1H), 4.33 (m, 1H), 4.11 (m, 1H), 2.49 (m, 1H), 2.27 (m, 1H).

Example 54

Preparation of 1-(3,5-diallyl-4-methoxybenzoyl) azetidine-2R-carboxylic acid hydroxyamide

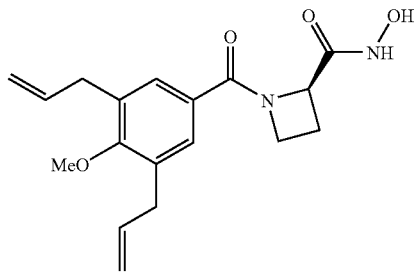

Step 1: 4-Allyloxy-3-allylbenzoic acid methyl ester was prepared by reacting 3-allyl-4-hydroxybenzoic acid methyl ester (Example 49, Step 2) with allyl bromide following Method C in 93% yield. The reaction was conducted at room temperature for 16 h and the resulting product was used without further purification.

Step 2: 3,5-Diallyl-4-hydroxybenzoic acid methyl ester was prepared from 4-allyloxy-3-allylbenzoic acid methyl ester following Method D in 90% yield. The reaction was conducted neat at 200° C. for 2 days. The resulting product was passed through a pad of silica gel and eluted with 20% hexanes in EtOAc.

Step 3: 3,5-Diallyl-4-methoxybenzoic acid methyl ester was prepared from 3,5-diallyl-4-hydroxybenzoic acid methyl ester and methyl iodide following Method C. The resulting product was used without further purification.

Step 4: 3,5-Diallyl-4-methoxybenzoic acid was prepared 3,5-diallyl-4-methoxybenzoic acid methyl ester following Method E. The resulting product was used without further purification.

Step 5: 1-(3,5-Diallyl-4-methoxybenzoyl)azetidine-2R-carboxylic acid methyl ester was prepared by coupling azetidine-2R-carboxylic acid methyl ester hydrochloride with 3,5-diallyl-4-methoxybenzoic acid by following Method A in 6 h and the crude product was used without further purification.

Step 6: 1-(3,5-Diallyl-4-methoxybenzoyl)azetidine-2R-carboxylic acid hydroxyamide was prepared from 1-(3,5-diallyl-4-methoxybenzoyl)azetidine-2R-carboxylic acid methyl ester by following Method B in 2 h. ESMS: m/z 331.2 [M+H]. $^1$H NMR (300 MHz, CDCl$_3$): 7.32 (s, 2H), 5.95-5.81

(m, 2H), 5.00-4.95 (m, 4H), 4.71 (m, 1H), 4.32 (m, 1H), 4.08 (m, 1H), 3.64 (s, 3H), 3.35 (d, 4H), 2.48 (m, 1H), 2.25 (m, 1H).

Example 55

Preparation of 1-(4-methoxy-3,5-dipropylbenzoyl) azetidine-2R-carboxylic acid hydroxyamide

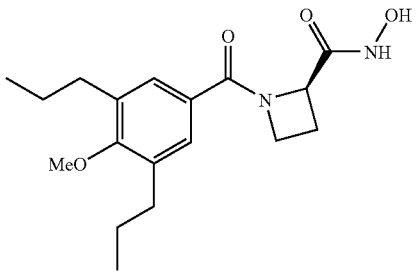

Step 1: 1-(4-Methoxy-3,5-dipropylbenzoyl)azetidine-2R-carboxylic acid methyl ester was prepared from 1-(3,5-diallyl-4-methoxybenzoyl)azetidine-2R-carboxylic acid methyl ester (Example 54, Step 5) by following Method H in 5 h. The crude product was used without further purification.

Step 2: 1-(4-Methoxy-3,5-dipropylbenzoyl)azetidine-2R-carboxylic acid hydroxyamide was prepared from 1-(4-methoxy-3,5-dipropylbenzoyl)azetidine-2R-carboxylic acid methyl ester by following Method B in 2 h. ESMS: m/z 335.2 [M+H]. $^1$H NMR (300 MHz, CDCl$_3$): 7.29 (s, 2H), 4.72 (m, 1H), 4.36 (m, 1H), 4.09 (m, 1H), 3.64 (s, 3H), 2.54 (m, 4H), 2.51 (m, 1H), 2.27 (m, 1H), 1.54 (m, 4H), 0.87 (m, 6H).

Example 56

Preparation of 1-[3,4-dimethoxy-5-(2,2,2-trifluoroethoxy)benzoyl]azetidine-2R-carboxylic acid hydroxyamide

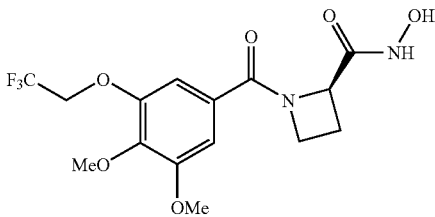

Step 1: 3,4-Dimethoxy-5-(2,2,2-trifluoroethoxy)benzoic acid methyl ester was prepared 3-hydroxy-4,5-dimethoxybenzoic acid methyl ester and methyl iodide by following Method C. The reaction was conducted at room temperature overnight. The product was used without further purification.

Step 2: 3,4-Dimethoxy-5-(2,2,2-trifluoroethoxy)benzoic acid was prepared from 3,4-dimethoxy-5-(2,2,2-trifluoroethoxy)benzoic acid methyl ester by following Method E overnight at room temperature. The product was used without further purification.

Step 3: 1-[3,4-Dimethoxy-5-(2,2,2-trifluoroethoxybenzoyl)]azetidine-2R-carboxylic acid methyl ester was prepared by coupling azetidine-2R-carboxylic acid methyl ester hydrochloride with 3,4-dimethoxy-5-(2,2,2-trifluoroethoxy) benzoic acid by following Method A in 4 h and the crude product was used without further purification.

Step 4: 1-[3,4-Dimethoxy-5-(2,2,2-trifluoroethoxybenzoyl)]azetidine-2R-carboxylic acid hydroxyamide was prepared from 1-[3,4-dimethoxy-5-(2,2,2-trifluoroethoxybenzoyl)]azetidine-2R-carboxylic acid methyl ester by following Method B in 2 h. ESMS: m/z 379.2 [M+H]. $^1$H NMR (300 MHz, CDCl$_3$): 7.00 (s, 1H), 6.93 (s, 1H), 4.72 (m, 1H), 4.51-4.46 (m, 2H), 4.39 (m, 1H), 4.12 (m, 1H), 3.78 (s, 3H), 3.73 (s, 3H), 2.49 (m, 1H), 2.27 (m, 1H).

Example 57

Preparation of 1-(4-methoxy-3-propylbenzoyl)axetidine-2R-carboxylic acid hydroxyamide

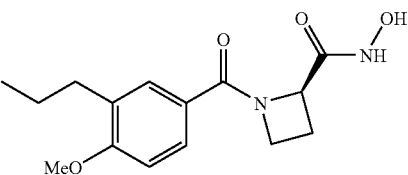

Step 1: 4-Methoxy-5-propylbenzoic acid was prepared from 4-methoxy-5-propylbenzoic acid methyl ester (Example 49, Step 4) following Method E in quantitative yield. The product was used without further purification.

Step 2: 1-(4-Methoxy-5-propylbenzoyl)azetidine-2R-carboxylic acid methyl ester was prepared by reacting azetidine-2R-carboxylic acid methyl ester hydrochloride salt with 4-methoxy-5-propylbenzoic acid according to Method A and the product was used without further purification.

Step 3: 1-(4-Methoxy-5-propylbenzoyl)azetidine-2R-carboxylic acid hydroxyamide was prepared from 1-(4-methoxy-5-propylbenzoyl)azetidine-2R-carboxylic acid methyl ester following Method B. ESMS: m/z 293.2 [M+H]. $^1$H NMR (300 MHz, CD$_3$OD): 7.53 (bd, J=7.5 Hz, 1H), 7.47 (bs, 1H), 6.96 (d, J=8.1 Hz, 1H), 4.79 (m, 1H), 4.47 (m, 1H), 4.20 (m, 1H), 3.84 (s, 3H), 2.57 (m, 3H), 2.35 (m, 1H), 1.57 (m, 2H), 0.91 (t, J=7.2 Hz, 3H).

Example 58

Preparation of 1-(3,4-dimethoxy-5-trifluoromethylthiobenzoyl)azetidine-2R-carboxylic acid hydroxyamide

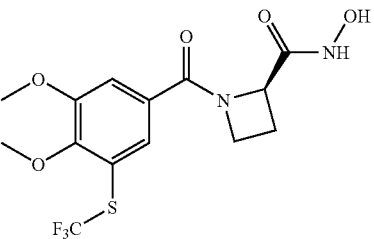

Step 1: To a stirred suspension of 60% sodium hydride in mineral oil (0.93 mg, 23.5 mmol) in DMF (27 mL) at room temperature under nitrogen atmosphere was added dropwise a solution of 3,4-dimethoxy-5-hydroxybenzoic acid methyl ester (5.0 g, 23.5 mmol) in DMF (6 mL), followed by the dropwise addition of a solution of dimethylthiocarbamoyl chloride (2.9 g, 23.5 mmol) in DMF (4 mL). The reaction mixture was stirred at room temperature under nitrogen for 44 h, then diluted with ether (600 mL), filtered through a pad of celite and the filtrate was washed with water (3×200 mL). The organic layer was dried (Na$_2$SO$_4$), filtered and evaporated in vacuo to give 3-dimethylthiocarbornyloxy-4,5-dimethoxybenzoic acid methyl ester (4.07 g).

Step 2: A stirred solution of 3-dimethylthiocarbornyloxy-4,5-dimethoxybenzoic acid methyl ester (2.0 g, 6.69 mmol) in phenyl ether (10 mL) was heated to reflux for 48 h. The reaction mixture was cooled to room temperature, mixed with silica gel and transferred to a silica gel column and eluted with 0 to 50% EtOAc in hexane to yielded 3-dimethylcarbamoylthio-4,5-dimethoxybenzoic acid methyl ester (1.04 g).

Step 3: To a stirred solution 3-dimethylcarbamoylthio-4,5-dimethoxybenzoic acid methyl ester (800 mg, 2.67 mmol) in THF (21 mL) was added MeONa (0.5 M in MeOH, 21 mL) at room temperature and the reaction was heated to reflux. After refluxing for 3 h, the reaction mixture was cooled to room temperature, poured into 1 N HCl aqueous solution (150 mL) and extracted with mixture of EtOAc:hexane (1:1, 150 mL). The organic layer was washed with brine (100 mL), dried over $MgSO_4$ and concentrated in vacuo to give 3-mercapto-4,5-dimethoxybenzoic acid methyl ester (0.581 g).

Step 4: To a solution of 3-mercapto-4,5-dimethoxybenzoic acid methyl ester (500 mg, 2.19 mmol) in DMF (15 mL) at 0° C. was added NaH (60% in mineral oil, 101 mg, 2.63 mmol) in small portions and the reaction mixture was slowly warmed to room temperature while stirring for 30 minutes. The reaction flask was charged with trifluoromethyl iodide gas in a balloon and the reaction mixture was continued stirring at room temperature for 4 h. The reaction mixture was poured into 1 N HCl aqueous solution (100 mL) and extracted with ether (100 mL). The organic layer was washed with brine (80 mL), dried over $MgSO_4$ and concentrated in vacuo. The residue was purified by flash column chromatography (gradient from 20 to 40% EtOAc in pentane) to get 3,4-dimethoxy-5-trifluoromethylthiobenzoic acid methyl ester (0.295 g).

Step 5: 3,4-Dimethoxy-5-trifluoromethylthiobenzoic acid was prepared from 3,4-dimethoxy-5-trifluoromethylthiobenzoic acid methyl ester according to Method E in 53% yield.

Step 6: 1-(3,4-Dimethoxy-5-trifluoromethylthiobenzoyl) azetidine-2R-carboxylic acid methyl ester was prepared by coupling azetidine-2R-carboxylic acid methyl ester hydrochloride salt with 3,4-Dimethoxy-5-trifluoromethylthiobenzoic acid following Method A and used the product without further purification. ESMS: m/z 380.2 [M+H].

Step 7: 1-(3,4-Dimethoxy-5-trifluoromethylthiobenzoyl) azetidine-2R-carboxylic acid hydroxyamide was prepared from 1-(3,4-Dimethoxy-5-trifluoromethylthiobenzoyl)azetidine-2R-carboxylic acid methyl ester following Method B. MS (ESNEG): 379.0 [M−H]. $^1$H NMR (300 MHz, $CD_3OD$): 7.56 (s, 1H), 7.51 (s, 1H), 4.84 (m, 1H), 4.49 (m, 1H), 4.23 (m, s, 1H), 3.94 (s, 3H), 3.92 (s, 3H), 2.60 (m, 1H), 2.38 (m, 1H).

Example 59

Preparation of 1-(3-trifluoromethoxy-4-vinylbenzoyl)azetidine-2R-carboxylic acid hydroxyamide

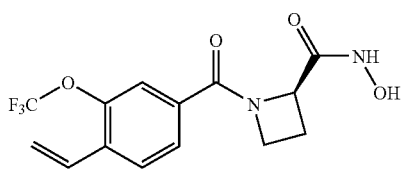

Step 1: 4-Bromo-3-trifluoromethoxyphenol was prepared from 2-trifluoromethoxyphenol according to literature procedure (T. Kline, et al. J. Med. Chem. 2002, 45, 3112-3129).

Step 2. 4-Benzyloxy-1-bromo-2-trifluoromethoxybenzene was prepared 4-bromo-2-trifluoromethoxyphenol in 90% yield by following Method C. The reaction was conducted at room temperature for 4 h using benzyl bromide as an alkylating agent. The resulting product was purified by silica gel chromatography by eluting with 0.5% EtOAc in hexanes.

Step 3: 4-Benzyloxy-3-trifluoromethoxybenzoic acid was prepared from 4-benzyloxy-1-bromo-3-trifluoromethoxybenzene by following Method M. The crude product was purified by crystallization using a mixture of EtOAc and hexanes as a solvent (19% yield of desired product from the first crop).

Step 4: 1-(4-Benzyloxy-3-trifluoromethoxybenzoyl)azetidine-2R-carboxylic acid methyl ester was prepared by coupling azetidine-2R-carboxylic acid methyl ester hydrochloride salt with 4-benzyloxy-3-trifluoromethoxybenzoic acid by following Method A in 81% yield. The crude product was purified by silica gel column chromatography using 1:1 mixture of EtOAc and hexanes. ESMS: m/z 410.2 [M+H].

Step 5: 1-(4-Hydroxy-3-trifluoromethoxybenzoyl)azetidine-2R-carboxylic acid methyl ester was prepared from 1-(4-benzyloxy-3-trifluoromethoxybenzoyl)azetidine-2R-carboxylic acid methyl ester by following Method H in 94% yield. The reaction was conducted at room temperature for 8 h using a balloon of hydrogen. ESMS: m/z 320.2 [M+H].

Step 6: 1-(4-Trifluoromethanesulfonyloxy-3-trifluoromethoxybenzoyl)azetidine-2R-carboxylic acid methyl ester was prepared from 1-(4-hydroxy-3-trifluoromethoxybenzoyl)azetidine-2R-carboxylic acid methyl ester according to Method N in 89% yield. The reaction was conducted at −78° C. for 30 min and the crude product was purified via flash column chromatography on silica gel (60% EtOAc/hexanes as an eluent) to obtain the desired product. ESMS: m/z 452.1 [M+H].

Step 7: 1-(3-Trifluoromethoxy-4-vinylbenzoyl)azetidine-2R-carboxylic acid methyl ester was prepared from 1-(4-trifluoromethanesulfonyloxy-3-trifluoromethoxybenzoyl)azetidine-2R-carboxylic acid methyl ester following Method O in 75% yield after purifying the crude product by silica gel column chromatography using 1:1 mixture of EtOAc and hexanes as an eluent. ESMS: m/z 352.2 [M+Na].

Step 8: 1-(3-Trifluoromethoxy-4-vinylbenzoyl)azetidine-2R-carboxylic acid hydroxyamide was prepared from 1-(3-trifluoromethoxy-4-vinylbenzoyl)azetidine-2R-carboxylic acid methyl ester in 2 h by following method Method B. ESMS: m/z 329.2 [M−H]. $^1$H NMR (300 MHz, $CDCl_3$): 7.40-7.64 (m, 3H), 6.92 (m, 1H), 5.83 (m, 1H), 5.44 (m, 1H), 4.98 (m, 1H), 4.39 (m, 1H), 4.16 (m, 1H), 2.74 (m, 1H), 2.50 (m, 1H).

Example 60

Preparation of 1-(4-ethyl-3-trifluoromethoxybenzoyl)azetidine-2R-carboxylic acid hydroxyamide

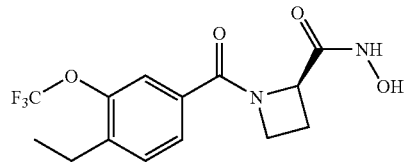

Step 1: 1-(4-Ethyl-3-trifluoromethoxybenzoyl)azetidine-2R-carboxylic acid methyl ester was prepared from 1-(3- trifluoromethoxy-4-vinylbenzoyl)azetidine-2R-carboxylic acid methyl ester (Product from Example 59 Step 7) by following Method H in 95% yield. ESMS: m/z 332.2 [M+H]

Step 2: 1-(4-Ethyl-3-trifluoromethoxybenzoyl)azetidine-2R-carboxylic acid hydroxyamide was prepared from 1-(4-ethyl-3-trifluoromethoxybenzoyl)azetidine-2R-carboxylic acid methyl ester by following Method B. ESMS: m/z 331.0 [M−H]. $^1$H NMR (300 MHz, CDCl$_3$): 7.46 (m, 2H), 7.31 (m, 1H), 4.99 (m, 1H), 4.39 (m, 1H), 4.18 (m, 1H), 2.49-2.78 (m, 4H), 1.20 (t, J=7.7 Hz, 3H).

Example 61

Preparation of 1-(4-benzyloxy-3-trifluoromethylthiobenzoyl)azetidine-2R-carboxylic acid hydroxyamide

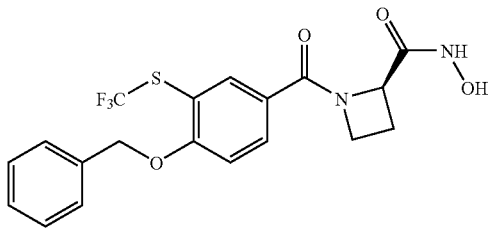

Step 1: To a stirred suspension of NaH (29 g, 0.73 mol, 2.0 eq., 60% in mineral oil) in DMF (600 mL) at 0° C. was added 2-mercaptophenol (46 g, 365 mmol, 1.0 eq.) dropwise. The resulting mixture was stirred at room temperature for 30 min and then charged with trifluoromethyl iodide (balloon). The reaction mixture was stirred at room temperature for 30 min, 70° C. for 2 h and cooled to room temperature. The reaction mixture was diluted with water (1000 mL) and extracted with EtOAc (3×350 mL). The combined organic layer was washed with brine (800 mL), dried (Na$_2$SO$_4$), and concentrated in vacuo. The crude product was purified by column chromatography using 0-30% EtOAc in hexanes as an eluent to afford 16.3 g (approximately 50% purity). This was used without further purification.

Step 2: To a stirred solution of 1-hydroxy-2-trifluoromethylthiobenzene (16 mmol, 1.0 eq.) in CH$_2$Cl$_2$ (40 mL) at −78° C. was added a solution of Br$_2$ (0.83 mL, 16 mmol, 1.0 eq.) in CH$_2$Cl$_2$ (18 mL) slowly. The resulting mixture was stirred at −78° C. for 2 h and then warmed to room temperature overnight. The reaction mixture was diluted with water (300 mL) and extracted with CH$_2$Cl$_2$ (3×150 mL). The combined organic layer was washed with brine (400 mL), dried (Na$_2$SO$_4$) and concentrated in vacuo. The crude product was purified by column chromatography using 0-10% EtOAc in hexanes as an eluent to afford 4-bromo-1-hydroxy-2-trifluoromethylthiobenzene in 93% yield as a crystalline solid.

Step 3: 1-Benzyloxy-4-bromo-2-trifluoromethylthiobenzene was prepared from 4-bromo-1-hydroxy-2-trifluoromethylthiobenzene following Method C. The reaction was conducted at 50° C. for 1 h using benzyl bromide as an alkylating agent and the resulting product was purified by column chromatography using hexanes as an eluent to afford 1-benzyloxy-4-bromo-2-trifluoromethylthiobenzene in 63% yield.

Step 4: To a mixture of 1-benzyloxy-4-bromo-2-trifluoromethylthiobenzene (5 g, 13.8 mmol, 1 eq.), KOAc (5.4 g, 55 mmol, 4.0 eq.), Pd(OAc)$_2$ (160 mg, 0.71 mmol, 0.05 eq.) and dppf (1.53 g, 2.77 mmol, 0.2 eq.) was added anhydrous DMSO (80 mL). The resulting mixture was stirred at 60° C. under CO balloon for 20 h, then cooled to room temperature, diluted with 1.0 M HCl (400 mL), and extracted with EtOAc (3×150 mL). The combined organic layer was washed with brine (400 mL), dried (Na$_2$SO$_4$), and concentrated in vacuo. The crude product was purified by column chromatography using 0-40% EtOAc in hexanes as an eluent to afford 4-benzyloxy-3-trifluoromethylthiobenzoic acid (2.1 g, 47% yield).

Step 5: 1-(4-Benzyloxy-3-trifluoromethylthiobenzoyl)azetidine-2R-carboxylic acid methyl ester was prepared by coupling azetidine-2R-carboxylic acid methyl ester hydrochloride salt with 4-benzyloxy-3-trifluoromethylthiobenzoic acid by following Method A in 75% yield. The crude product was purified by silica gel column chromatography using 2:3 mixture of EtOAc and hexanes. ESMS: m/z 426.1 [M+H].

Step 6: 1-(4-Benzyloxy-3-trifluoromethylthiobenzoyl)azetidine-2R-carboxylic acid hydroxyamide was prepared from 1-(4-benzyloxy-3-trifluoromethylthiobenzoyl)-azetidine-2R-carboxylic acid methyl ester by following Method B. ESMS: m/z 425.2 [M−H]. $^1$H NMR (300 MHz, CDCl$_3$): 7.90 (bs, 1H), 7.73 (d, J=8.24 Hz, 1H), 7.31-7.41 (m, 5H), 6.99 (d, J=8.79 Hz, 1H), 5.19 (s, 2H), 4.98 (m, 1H), 4.40 (m, 1H), 4.19 (m, 1H), 2.78 (m, 1H), 2.49 (m, 1H).

Example 62

Preparation of 1-(3-trifluoromethylthio-4-vinylbenzoyl)azetidine-2R-carboxylic Acid Hydroxyamide

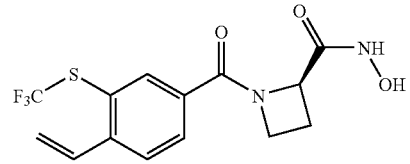

Step 1: 1-(4-Hydroxy-3-trifluoromethylthiobenzoyl)azetidine-2R-carboxylic acid methyl ester was prepared from 1-(4-benzyloxy-3-trifluoromethylthiobenzoyl)azetidine-2R-carboxylic acid methyl ester (Product from Step 5 of Example 61) by following Method H in 88% yield. The reaction was conducted at room temperature for 4 h using a balloon of hydrogen.

Step 2: 1-(4-Trifluoromethanesulfonyloxy-3-trifluoromethylthiobenzoyl)azetidine-2R-carboxylic acid methyl ester was prepared from 1-(4-hydroxy-3-trifluoromethylthiobenzoyl)azetidine-2R-carboxylic acid methyl ester according to Method N in 66% yield. The reaction was conducted at −20° C. for 45 min and the crude product was purified via flash column chromatography on silica gel (60% EtOAc/hexanes as an eluent) to obtain the desired product.

Step 3: 1-(3-Trifluoromethylthio-4-vinylbenzoyl)azetidine-2R-carboxylic acid methyl ester was prepared from 1-(4-trifluoromethanesulfonyloxy-3-trifluoromethylthiobenzoyl)azetidine-2R-carboxylic acid methyl ester following Method O in 61% yield after purifying the crude product via flash column chromatography on silica gel (60% EtOAc/ hexanes as an eluent). ESMS: m/z 346.0 [M+H].

Step 4: 1-(3-Trifluoromethylthio-4-vinylbenzoyl)azetidine-2R-carboxylic acid hydroxyamide was prepared from 1-(3-trifluoromethylthio-4-vinylbenzoyl)azetidine-2R-carboxylic acid methyl ester in 3.5 h by following method Method B. ESMS: m/z 345.1 [M−H]. $^1$H NMR (300 MHz, CD$_3$OD): 8.04 (s, 1H), 7.92-7.81 (m, 2H), 7.38 (dd, J=11.1, 17.1 Hz, 1H), 5.96 (d, J=17.7 Hz, 1H), 5.55 (d, J=11.4 Hz, 1H), 4.82 (dd, J=6.0, 10.8 Hz, 1H), 4.47 (dd, J=8.4, 14.4 Hz, 1H), 4.23 (dd, J=8.4, 14.4 Hz, 1H), 2.68-2.53 (m, 1H), 2.44-2.32 (m, 1H).

Example 63

Preparation of 1-(4-ethyl-3-trifluoromethylthiobenzoyl)azetidine-2R-carboxylic acid hydroxyamide

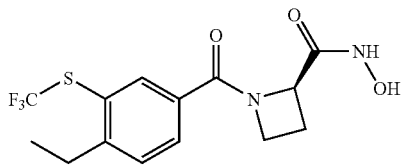

Step 1: 1-(4-Ethyl-3-trifluoromethylthiobenzoyl)azetidine-2R-carboxylic acid methyl ester was prepared from 1-(3-trifluoromethylthio-4-vinylbenzoyl)azetidine-2R-carboxylic acid methyl ester (Product from Step 3 of Example 62) by following Method H in quantitative yield. The reaction was conducted at room temperature for 2 h using a balloon of hydrogen. The resulting product was used without further purification. ESMS: m/z 348.1 [M+H].

Step 2: 1-(4-Ethyl-3-trifluoromethylthiobenzoyl)azetidine-2R-carboxylic acid hydroxyamide was prepared from 1-(4-ethyl-3-trifluoromethylthiobenzoyl)azetidine-2R-carboxylic acid methyl ester by following Method B at room temperature for 5 h. ESMS: m/z 347.2 [M−H]. $^1$H NMR (300 MHz, CD$_3$OD): 8.01 (s, 1H), 7.80 (d, J=6.6 Hz, 1H), 7.54 (d, J=7.8 Hz, 1H), 4.82 (dd, J=5.4, 8.4 Hz, 1H), 4.46 (dd, J=8.4, 14.7 Hz, 1H), 4.22 (dd, J=9.0, 15.6 Hz, 1H), 2.98 (q, J=7.5 Hz, 2H), 2.66-2.53 (m, 1H), 2.43-2.30 (m, 1H), 1.23 (t, J=7.8 Hz, 3H).

Example 64

Preparation of 1-(4-allyl-3-trifluoromethylthiobenzoyl)azetidine-2R-carboxylic acid hydroxyamide

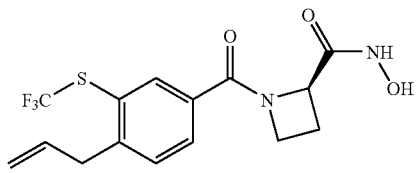

Step 1: To a solution of 1-(4-trifluoromethanesulfonyloxy-3-trifluoromethylthiobenzoyl)-azetidine-2R-carboxylic acid methyl ester (150 mg, 0.32 mmol, 1 eq.). The product from Step 2 of Example 62) and allyltributyltin (0.15 mL, 0.48 mmol, 1.5 eq.) in DMF (3.0 mL) was added Pd(PPh$_3$)$_4$ (19 mg, 0.016 mmol, 0.05 eq.) in DMF (3.0 mL) at 23° C. was added Et$_3$N (0.16 mL, 1.17 mmol, 3 eq.). The resulting mixture was warmed to 125° C. under N$_2$ atmosphere. After 2 h the reaction was cooled to 23° C. then diluted with Et$_2$O (100 mL) and treated with 10% aqueous KF (100 mL). After stirring for 3 h at 23° C. the layers were separated and the organic layer was washed with brine (50 mL), dried MgSO$_4$ and concentrated in vacuo. The crude product was purified via flash column chromatography on silica gel (50% EtOAc/hexanes as an eluent) to give 1-(4-allyl-3-trifluoromethylthiobenzoyl)azetidine-2R-carboxylic acid methyl ester (61 mg, 0.17 mmol, 53%) as a yellow oil. ESMS: m/z 360.0 [M+H].

Step 2: 1-(4-Allyl-3-trifluoromethylthiobenzoyl)azetidine-2R-carboxylic acid hydroxyamide was prepared from 1-(4-allyl-3-trifluoromethylthiobenzoyl)azetidine-2R-carboxylic acid methyl ester by following Method B at room temperature for 4 h. ESMS: m/z 361.0 [M+H]. $^1$H NMR (300 MHz, CD$_3$OD): 8.04 (s, 1H), 7.81 (d, J=6.6 Hz, 1H), 7.52 (d, J=7.8 Hz, 1H), 6.02-5.87 (m, 1H), 5.10 (dd, J=1.5, 10.2 Hz, 1H), 5.00 (dd, J=1.5, 17.1 Hz, 1H), 4.82 (dd, J=6.0, 10.8 Hz, 1H), 4.46 (dd, J=9.0, 14.7 Hz, 1H), 4.22 (dd, J=8.4, 14.7 Hz, 1H), 3.73 (d, J=10.2 Hz, 2H), 2.66-2.53 (m, 1H), 2.43-2.30 (m, 1H).

Example 65

Preparation of 1-(4-propyl-3-trifluoromethylthiobenzoyl)azetidine-2R-carboxylic acid hydroxyamide

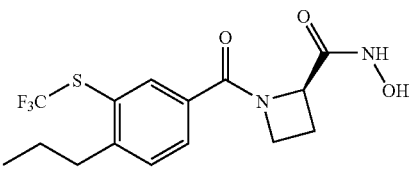

Step 1: 1-(4-Propyl-3-trifluoromethylthiobenzoyl)azetidine-2R-carboxylic acid methyl ester was prepared from 1-(4-allyl-3-trifluoromethylthiobenzoyl)azetidine-2R-carboxylic acid methyl ester (Product from Step 1 of Example 64) by following Method H in quantitative yield. The reaction was conducted at room temperature for 2 h using a balloon of hydrogen. The product was used without further purification. ESMS: m/z 362.0 [M+H]

Step 2: 1-(4-Propyl-3-trifluoromethylthiobenzoyl)azetidine-2R-carboxylic acid hydroxyamide was prepared from 1-(4-propyl-3-trifluoromethylthiobenzoyl)azetidine-2R-carboxylic acid methyl ester by following Method B at room temperature for 3.5 h. ESMS: m/z 361.0 [M−H]. $^1$H NMR (300 MHz, CD$_3$OD): 8.02 (s, 1H), 7.78 (d, J=7.8 Hz, 1H), 7.52 (d, J=7.8 Hz, 1H), 4.82 (dd, J=5.7, 9.3 Hz, 1H), 4.46 (dd, J=8.7, 14.7 Hz, 1H), 4.22 (dd, J=9.3, 15.3 Hz, 1H), 2.93 (t, J=7.5 Hz, 2H), 2.66-2.53 (m, 1H), 2.43-2.30 (m, 1H), 1.70-1.56 (m, 2H), 0.98 (t, J=6.9 Hz, 3H).

Example 66

Preparation of 1-(5,6-dimethoxybiphenyl-3-carbonyl)azetidine-2R-carboxylic acid hydroxyamide

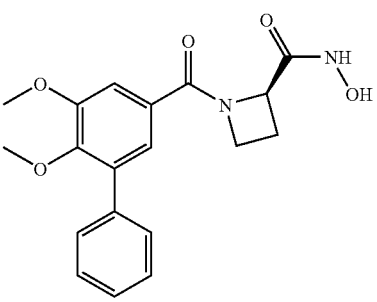

Step 1: 5,6-Dimethoxybiphenyl-3-carboxylic acid was prepared by coupling phenylboronic acid with 3-iodo-4,5-dimethoxybenzoic acid according to Method P. The crude product was purified via flash column chromatography on silica gel (5% MeOH in CH$_2$Cl$_2$ as an eluent) to give the desired acid in 88% yield. ESMS: m/z 257.3 [M−H].

Step 2: 1-(5,6-Dimethoxybiphenyl-3-carbonyl)azetidine-2R-carboxylic acid methyl ester was prepared by coupling azetidine-2R-carboxylic acid methyl ester hydrochloride salt with 5,6-dimethoxybiphenyl-3-carboxylic acid by following Method A in 75% yield. The crude product was purified by silica gel column chromatography using 2:1 mixture of EtOAc and hexanes. ESMS: m/z 356.3 [M+H].

Step 3: 1-(5,6-Dimethoxybiphenyl-3-carbonyl)azetidine-2R-carboxylic acid hydroxyamide was prepared from 1-(5,6-Dimethoxybiphenyl-3-carbonyl)azetidine-2R-carboxylic acid methyl ester following Method B in 16 h. ESMS: m/z 355.4 [M−H]. $^1$H NMR (300 MHz, CDCl$_3$): 7.39 (m, 5H), 7.24 (bs, 1H), 7.14 (bs, 1H), 4.99 (m, 1H), 4.37 (m, 1H), 4.28 (m, 1H), 3.91 (s, 3H), 3.67 (s, 3H), 2.79 (m, 1H), 2.47 (m, 1H).

Example 67

Preparation of 1-[3-trifluoromethylthio-4-(trimethylsilanylethynyl)benzoyl]azetidine-2R-carboxylic acid hydroxyamide

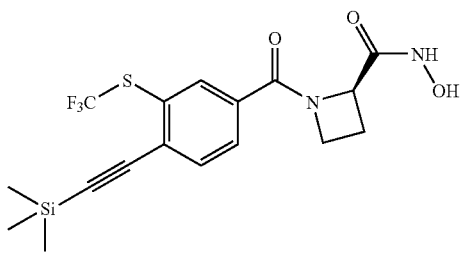

Step 1: 1-[3-Trifluoromethylthio-4-(trimethylsilanylethynyl)benzoyl]azetidine-2R-carboxylic acid methyl ester was prepared by coupling trimethylsilylacetylene with 1-(4-trifluoromethanesulfonyloxy-3-trifluoromethylthiobenzoyl)azetidine-2R-carboxylic acid methyl ester (Product from Step 2 of Example 62) according to Method R. The crude product was purified via flash column chromatography on silica gel (50% EtOAc/hexanes as an eluent) to give the desired product in 72% yield. ESMS: m/z 416.0 [M+H]

Step 2: 1-[3-Trifluoromethylthio-4-(trimethylsilanylethynyl)benzoyl]azetidine-2R-carboxylic acid hydroxyamide was prepared from 1-[3-trifluoromethylthio-4-(trimethylsilanylethynyl)benzoyl]-azetidine-2R-carboxylic acid methyl ester following Method B in 4 h. ESMS: m/z 415.0 [M−H]. $^1$H NMR (300 MHz, CD$_3$OD): 8.06 (s, 1H), 7.81 (d, J=8.1 Hz, 1H), 7.69 (d, J=8.1 Hz, 1H), 4.82 (dd, J=6.0, 9.0 Hz, 1H), 4.44 (dd, J=8.7, 14.7 Hz, 1H), 4.22 (dd, J=8.7, 15.0 Hz, 1H), 2.66-2.53 (m, 1H), 2.43-2.30 (m, 1H), 0.25 (s, 9H).

Example 68

Preparation of 1-(4-ethynyl-3-trifluoromethylthiobenzoyl)azetidine-2R-carboxylic Acid Hydroxyamide

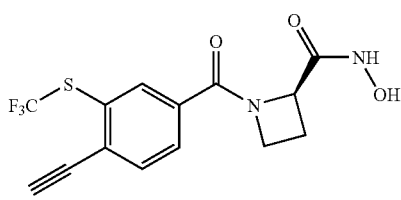

Step 1: To a stirred solution of 1-[3-trifluoromethylthio-4-(trimethylsilanylethynyl)benzoyl]-azetidine-2R-carboxylic acid methyl ester (50 mg, 0.12 mmol, 1 eq.) in MeOH (2.0 mL) at 23° C. was added K$_2$CO$_3$ (33 mg, 0.24 mmol, 2 eq.). After stirring for 45 min at 23° C. the resulting solution was partitioned between 1.0 N HCl (100 mL) and Et$_2$O (100 mL). The layers were separated and the organic layer was washed with brine (50 mL), dried MgSO$_4$ and concentrated to give 1-(4-ethynyl-3-trifluoromethylthiobenzoyl)azetidine-2R-carboxylic acid methyl ester (45 mg, 0.12 mmol, quantitative yield) as a red oil. The product was used without further purification. ESMS: m/z 344.1 [M+H].

Step 2: 1-(4-Ethynyl-3-trifluoromethylthiobenzoyl)azetidine-2R-carboxylic acid hydroxyamide was prepared from 1-(4-ethynyl-3-trifluoromethylthiobenzoyl)azetidine-2R-carboxylic acid methyl ester by following Method B in 3.5 h. ESMS: m/z 343.0 [M−H]. $^1$H NMR (300 MHz, CD$_3$OD): 8.07 (s, 1H), 7.82 (d, J=8.1 Hz, 1H), 7.74 (dd, J=2.1, 8.4 Hz, 1H), 4.82 (dd, J=5.7, 9.3 Hz, 1H), 4.45 (dd, J=8.7, 14.7 Hz, 1H), 4.22 (dd, J=9.0, 15.0 Hz, 1H), 4.12 (s, 1H), 2.69-2.53 (m, 1H), 2.43-2.30 (m, 1H).

Example 69

Preparation of 1-(4-pentyl-3-trifluoromethylthiobenzoyl)azetidine-2R-carboxylic acid hydroxyamide

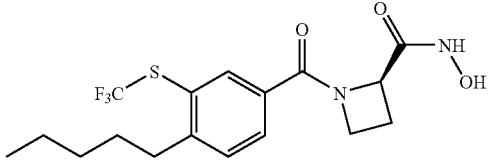

Step 1: 1-(4-Pent-1-ynyl-3-trifluoromethylthiobenzoyl)azetidine-2R-carboxylic acid methyl ester was prepared by coupling 1-pentyne with 1-(4-trifluoromethanesulfonyloxy-3-trifluoromethylthiobenzoyl)azetidine-2R-carboxylic acid methyl ester (Product from Step 2 of Example 62) according to Method R. The crude product was purified via flash column chromatography on silica gel (50% EtOAc/hexanes as an eluent) to give the desired product in 87% yield.

Step 2: 1-(4-Pentyl-3-trifluoromethylthiobenzoyl)azetidine-2R-carboxylic acid methyl ester was prepared from 1-(4-pent-1-ynyl-3-trifluoromethylthiobenzoyl)azetidine-2R-carboxylic acid methyl ester according to method Method H. The reaction was conducted at room temperature under a balloon of hydrogen for 7 h and the resulting product was used without further purification. ESMS: m/z 390.2 [M+H].

Step 3: 1-(4-Pentyl-3-trifluoromethylthiobenzoyl)azetidine-2R-carboxylic acid hydroxyamide was prepared from 1-(4-pentyl-3-trifluoromethylthiobenzoyl)azetidine-2R-carboxylic acid methyl ester according to Method B in 5 h. ESMS: m/z 389.2 [M−H]. $^1$H NMR (300 MHz, CD$_3$OD): 8.02 (s, 1H), 7.79 (d, J=7.5 Hz, 1H), 7.52 (d, J=8.1 Hz, 1H), 4.82 (dd, J=6.0, 9.3 Hz, 1H), 4.47 (dd, J=8.7, 14.7 Hz, 1H), 4.22 (dd, J=8.7, 15.0 Hz, 1H), 2.94 (t, J=7.8 Hz, 2H), 2.66-2.53 (m, 1H), 2.43-2.31 (m, 1H), 1.65-1.54 (m, 2H), 1.42-1.31 (m, 4H), 0.91 (t, J=6.9 Hz, 3H).

Example 70

Preparation of 1-{4-[2-(3-fluorophenyl)ethyl]-3-trifluoromethylthiobenzoyl}azetidine-2R-carboxylic acid hydroxyamide

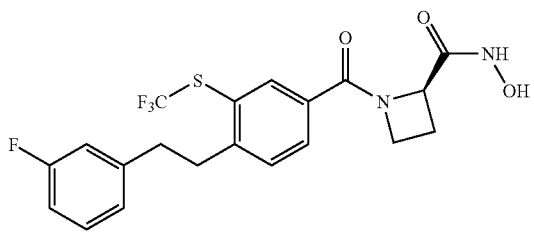

Step 1: 1-[4-(Fluorophenylethynyl)-3-trifluoromethylthiobenzoyl]azetidine-2R-carboxylic acid methyl ester was prepared by coupling 1-ethynyl-3-fluorobenzene with 1-(4-trifluoromethanesulfonyloxy-3-trifluoromethylthiobenzoyl)azetidine-2R-carboxylic acid methyl ester (Product from Step 2 of Example 62) according to Method R. The crude product was purified via flash column chromatography on silica gel (50% EtOAc/hexanes as eluent) to give 1-[4-(fluorophenylethynyl)-3-trifluoromethylthiobenzoyl]azetidine-2R-carboxylic acid methyl ester in 96% yield. ESMS: m/z 438.1 [M+H].

Step 2: 1-{4-[2-(3-Fluorophenyl)ethyl]-3-trifluoromethylthiobenzoyl}azetidine-2R-carboxylic acid methyl ester was prepared from 1-[4-(3-fluorophenylethynyl)-3-trifluoromethylthiobenzoyl]azetidine-2R-carboxylic acid methyl ester according to method Method H. The reaction was conducted at room temperature under a balloon pressure of hydrogen for 7 h and the resulting product was used without further purification. ESMS: m/z 442.2 [M+H].

Step 3: 1-{4-[2-(3-Fluorophenyl)ethyl]-3-trifluoromethylthiobenzoyl}azetidine-2R-carboxylic acid hydroxyamide was prepared from 1-{4-[2-(3-fluorophenyl)ethyl]-3-trifluoromethylthiobenzoyl}azetidine-2R-carboxylic acid methyl ester according to Method B in 5 h. ESMS: m/z 441.1 [M–H]. $^1$H NMR (300 MHz, CD$_3$OD): 8.03 (s, 1H), 7.79 (d, J=7.2 Hz, 1H), 7.51 (d, J=8.1 Hz, 1H), 7.26 (dd, J=7.5, 14.1 Hz, 1H), 6.98-6.84 (m, 3H), 4.84 (dd, J=6.3, 9.3 Hz, 1H), 4.47 (dd, J=8.4, 14.7 Hz, 1H), 4.22 (dd, J=8.4, 15.0 Hz, 1H), 3.28 (t, J=8.1 Hz, 2H), 2.93 (t, J=8.1 Hz, 2H), 2.68-2.54 (m, 1H), 2.44-2.33 (m, 1H).

Example 71

Preparation of 1-[3-(3-fluorophenylethynyl)-4,5-dimethoxybenzoyl]azetidine-2R-carboxylic acid hydroxyamide

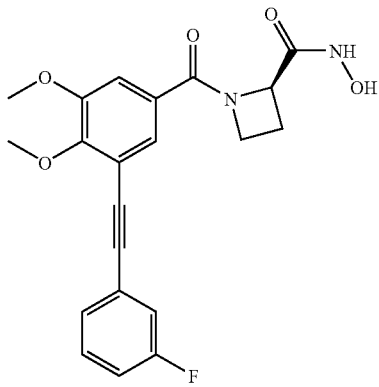

Step 1: 3-(3-Fluorophenylethynyl)-4,5-dimethoxybenzoic acid was prepared by coupling 1-ethynyl-3-fluorobenzene with 3-iodo-4,5-dimethoxybenzoic acid Method R. The crude product was purified via flash column chromatography on silica gel (5% MeOH in CH$_2$Cl$_2$ as an eluent) to give 3-(3-fluorophenylethynyl)-4,5-dimethoxybenzoic acid in 95% yield. ESMS: m/z 299.3 [M–H].

Step 2: 1-[3-(3-Fluorophenylethynyl)-4,5-dimethoxybenzoyl]azetidine-2R-carboxylic acid methyl ester was prepared by coupling azetidine-2R-carboxylic acid methyl ester hydrochloride salt with 3-(3-fluorophenylethynyl)-4,5-dimethoxybenzoic acid by following Method A in 78% yield. The crude product was purified by silica gel column chromatography using 1:2 mixture of EtOAc and hexanes. ESMS: m/z 398.3 [M+H].

Step 3: 1-[3-(3-Fluorophenylethynyl)-4,5-dimethoxybenzoyl]azetidine-2R-carboxylic acid hydroxyamide was prepared from 1-[3-(3-fluorophenylethynyl)-4,5-dimethoxybenzoyl]azetidine-2R-carboxylic acid methyl ester by following Method B in 16 h. ESM: m/z 397.4 [M–H]. $^1$H NMR (300 MHz, CDCl$_3$): 7.18-7.31 (m, 5H), 7.04 (m, 1H), 5.00 (m, 1H), 4.42 (m, 1H), 4.25 (m, 1H), 4.01 (s, 3H), 3.87 (s, 3H), 2.82 (m, 1H), 2.52 (m, 1H).

Example 72

Preparation of 1-(4-allyloxy-3-trifluoromethylthiobenzoyl)azetidine-2R-carboxylic acid hydroxyamide

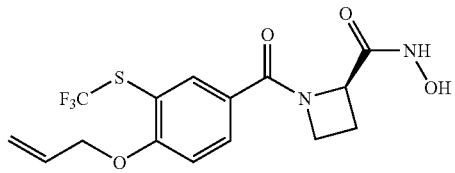

Step 1: 1-(4-Allyloxy-3-trifluoromethylthiobenzoyl)azetidine-2R-carboxylic acid methyl ester was prepared by alkylating 1-(4-hydroxy-3-trifluoromethylthiobenzoyl)azetidine-2R-carboxylic acid methyl ester (Product from Step 1 of Example 62) with allyl bromide according to Method C in 89% yield. The reaction was conducted at room temperature for 3.5 h and the resulting product was used without further purification. ESMS: m/z 376.2 [M+H].

Step 2: 1-(4-Allyloxy-3-trifluoromethylthiobenzoyl)azetidine-2R-carboxylic acid hydroxyamide was prepared from 1-(4-allyloxy-3-trifluoromethylthiobenzoyl)azetidine-2R-carboxylic acid methyl ester according to Method B in 6 h. ESMS: m/z 377.2 [M+H]. $^1$H NMR (300 MHz, CDCl$_3$): 7.87 (d, J=1.5 Hz, 1H), 7.74 (dd, J=1.5, 8.4 Hz, 1H), 6.93 (d, J=8.7 Hz, 1H), 6.09-5.95 (m, 1H), 5.47 (dd, J=1.5, 17.4 Hz, 1H), 5.33 (dd, J=0.9, 10.5 Hz, 1H), 4.99 (dd, J=6.6, 8.7 Hz, 1H), 4.64 (d, J=5.1 Hz, 2H), 4.44 (dd, J=8.7, 15.0 Hz, 1H), 4.17 (dd, J=8.7, 15.6 Hz, 1H), 2.72-2.59 (m, 1H), 2.58-2.44 (m, 1H).

Example 73

Preparation of 1-(4-propoxy-3-trifluoromethylthiobenzoyl)azetidine-2R-carboxylic acid hydroxyamide

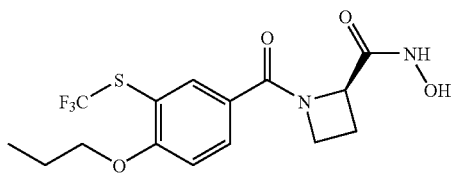

Step 1: 1-(4-Propoxy-3-trifluoromethylthiobenzoyl)azetidine-2R-carboxylic acid methyl ester was prepared from 1-(4-allyloxy-3-trifluoromethylthiobenzoyl)azetidine-2R-carboxylic acid methyl ester (Product from Step 1 of Example 72) according to Method H in 96% yield. The reaction was conducted at room temperature for 4.5 h using a balloon of hydrogen and the resulting product was used without further purification. ESMS: m/z 378.1 [M+H].

Step 2: 1-(4-Propoxy-3-trifluoromethylthiobenzoyl)azetidine-2R-carboxylic acid hydroxyamide was prepared from 1-(4-propoxy-3-trifluoromethylthiobenzoyl)azetidine-2R-carboxylic acid methyl ester according to Method B in 7.5 h. ESMS: m/z 379.2 [M+H]. $^1$H NMR (300 MHz, CDCl$_3$): 7.87 (d, J=1.8 Hz, 1H), 7.76 (dd, J=1.8, 8.7 Hz, 1H), 6.93 (d, J=8.7 Hz, 1H), 5.00 (dd, J=6.6, 9.0 Hz, 1H), 4.44 (dd, J=9.0, 15.0 Hz, 1H), 4.18 (dd, J=8.7, 15.3 Hz, 1H), 4.02 (t, J=6.3 Hz, 2H), 2.78-2.64 (m, 1H), 2.58-2.44 (m, 1H), 1.93-1.80 (m, 2H), 1.07 (t, J=7.2 Hz, 3H).

Example 74

Preparation of 1-(4-but-3-enyloxy-3-trifluoromethylthiobenzoyl)azetidine-2R-carboxylic acid hydroxyamide

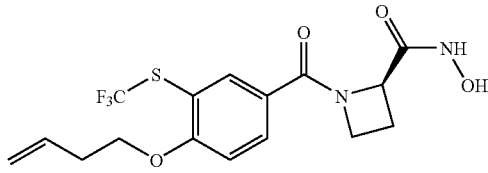

Step 1: 1-(4-But-3-enyloxy-3-trifluoromethylthiobenzoyl)azetidine-2R-carboxylic acid methyl ester was prepared by alkylating 1-(4-hydroxy-3-trifluoromethylthiobenzoyl)azetidine-2R-carboxylic acid methyl ester (Product from Step 1 of Example 62) with 4-bromobut-1-ene according to Method C in 92% yield. The reaction was conducted at room temperature for 21 h and the resulting product was used without further purification. ESMS: m/z 390.1 [M+H].

Step 2: 1-(4-But-3-enyloxy-3-trifluoromethylthiobenzoyl) azetidine-2R-carboxylic acid hydroxyamide was prepared from 1-(4-But-3-enyloxy-3-trifluoromethylthiobenzoyl)-azetidine-2R-carboxylic acid methyl ester according to Method B in 6 h. ESMS: m/z 391.1 [M+H]. $^1$H NMR (300 MHz, CDCl$_3$): 7.85 (s, 1H), 7.75 (dd, J=1.5, 8.7 Hz, 1H), 6.93 (d, J=9.0 Hz, 1H), 6.00-5.84 (m, 1H), 5.24-5.09 (m, 2H), 4.99 (dd, J=6.6, 8.7 Hz, 1H), 4.44 (dd, J=7.8, 14.1 Hz, 1H), 4.17 (dd, J=8.4, 15.3 Hz, 1H), 4.10 (t, J=6.6 Hz, 2H), 2.72-2.59 (m, 1H), 2.59 (q, J=6.6 Hz, 2H), 2.58-2.44 (m, 1H).

Example 75

Preparation of 1-(4-butoxy-3-trifluoromethylthiobenzoyl)azetidine-2R-carboxylic acid hydroxyamide

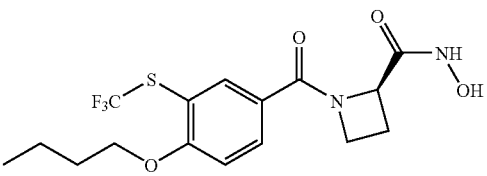

Step 1: 1-(4-Butoxy-3-trifluoromethylthiobenzoyl)azetidine-2R-carboxylic acid methyl ester was prepared from 1-(4-but-3-enyloxy-3-trifluoromethylthiobenzoyl)azetidine-2R-carboxylic acid methyl ester (product from Step 1 of Example 74) according to Method H in 88% yield. The reaction was conducted at room temperature for 4.5 h using a balloon of hydrogen and the resulting product was used without further purification. ESMS: m/z 392.3 [M+H].

Step 2: 1-(4-Butoxy-3-trifluoromethylthiobenzoyl)azetidine-2R-carboxylic acid hydroxyamide was prepared from 1-(4-butoxy-3-trifluoromethylthiobenzoyl)azetidine-2R-carboxylic acid methyl ester according to Method B in 7.5 h. ESMS: m/z 393.1 [M+H]. $^1$H NMR (300 MHz, CDCl$_3$): 7.86 (d, J=1.2 Hz, 1H), 7.75 (dd, J=1.8, 8.7 Hz, 1H), 6.93 (d, J=8.7 Hz, 1H), 5.00 (dd, J=6.3, 9.0 Hz, 1H), 4.44 (dd, J=8.7, 14.7 Hz, 1H), 4.18 (dd, J=8.7, 15.0 Hz, 1H), 4.06 (t, J=6.3 Hz, 2H), 2.76-2.64 (m, 1H), 2.58-2.44 (m, 1H), 1.87-1.76 (m, 2H), 1.59-1.46 (m, 2H), 0.98 (t, J=7.2 Hz, 3H).

Example 76

Preparation of 1-[(4-(3-methylbut-3-enyloxy)-3-trifluoromethylthiobenzoyl]azetidine-2R-carboxylic acid hydroxyamide

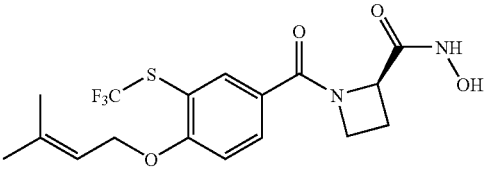

Step 1: 1-[4-(3-Methylbut-3-enyloxy)-3-trifluoromethylthiobenzoyl]azetidine-2R-carboxylic acid methyl ester was prepared by alkylating 1-(4-hydroxy-3-trifluoromethylthiobenzoyl)azetidine-2R-carboxylic acid methyl ester (Product from Step 1 of Example 62) with 1-bromo-3-methylbut-2-ene according to Method C in 92% yield. The reaction was conducted at room temperature for 5 h and the resulting product was used without further purification. ESMS: m/z 404.2 [M+H].

Step 2: 1-[(4-(3-Methylbut-3-enyloxy)-3-trifluoromethylthiobenzoyl]azetidine-2R-carboxylic acid hydroxyamide was prepared from 1-[4-(3-methylbut-3-enyloxy-3-trifluoromethylthiobenzoyl]-azetidine-2R-carboxylic acid methyl ester according to Method B in 6 h. ESMS: m/z 405.1 [M+H].

¹H NMR (300 MHz, CDCl₃): 7.85 (d, J=1.8 Hz, 1H), 7.73 (dd, J=1.8, 8.7 Hz, 1H), 6.93 (d, J=9.0 Hz, 1H), 5.43 (br t, J=6.6 Hz, 1H), 4.98 (dd, J=6.3, 8.7 Hz, 1H), 4.62 (d, J=6.6 Hz, 2H), 4.43 (dd, J=7.8, 14.4 Hz, 1H), 4.17 (dd, J=8.7, 15.6 Hz, 1H), 2.70-2.43 (m, 2H), 1.79 (s, 3H), 1.74 (s, 3H).

Example 77

Preparation of 1-(4-prop-2-ynyloxy-3-trifluoromethylthiobenzoyl)azetidine-2R-carboxylic acid hydroxyamide

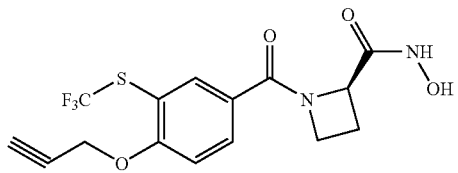

Step 1: 1-(4-Prop-2-ynyloxy-3-trifluoromethylthiobenzoyl)azetidine-2R-carboxylic acid methyl ester was prepared by alkylating 1-(4-hydroxy-3-trifluoromethylthiobenzoyl)azetidine-2R-carboxylic acid methyl ester (Product from Step 1 of Example 62) with propargyl bromide according to Method C in 83% yield. The reaction was conducted at room temperature for 5 h and the resulting product was used without further purification. ESMS: m/z 374.1 [M+H].

Step 2: 1-(4-Prop-2-ynyloxy-3-trifluoromethylthiobenzoyl)azetidine-2R-carboxylic acid hydroxyamide was prepared from 1-(4-prop-2-ynyloxy-3-trifluoromethylthiobenzoyl)-azetidine-2R-carboxylic acid methyl ester according to Method B in 6 h. ESMS: m/z 375.1 [M+H]. ¹H NMR (300 MHz, CDCl₃): 7.90 (d, J=1.8 Hz, 1H), 7.79 (d, J=8.7 Hz, 1H), 7.14 (d, J=8.7 Hz, 1H), 5.00 (dd, J=6.6, 8.7 Hz, 1H), 4.83 (d, J=2.4 Hz, 2H), 4.46 (dd, J=8.7, 15.0 Hz, 1H), 4.20 (dd, J=8.7, 15.6 Hz, 1H), 2.75-2.63 (m, 1H), 2.57 (t, J=2.4 Hz, 1H), 2.56-2.45 (m, 1H).

Example 78

Preparation of 1-(4-ethoxy-3-trifluoromethylthiobenzoyl)azetidine-2R-carboxylic acid hydroxyamide

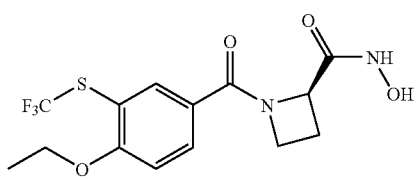

Step 1: 1-(4-Ethoxy-3-trifluoromethylthiobenzoyl)azetidine-2R-carboxylic acid methyl ester was prepared by alkylating 1-(4-hydroxy-3-trifluoromethylthiobenzoyl)azetidine-2R-carboxylic acid methyl ester (Product from Step 1 of Example 62) with ethyl iodide according to Method C in quantitative yield. The reaction was conducted at room temperature for 60 h and the resulting product was used without further purification. ESMS: m/z 364.2 [M+H].

Step 2: 1-(4-Ethoxy-3-trifluoromethylthiobenzoyl)azetidine-2R-carboxylic acid hydroxyamide was prepared from 1-(4-ethoxy-3-trifluoromethylthiobenzoyl)-azetidine-2R-carboxylic acid methyl ester according to Method B in 5 h. ESMS: m/z 387.1 [M+Na]. ¹H NMR (300 MHz, CD₃OD): 7.89 (s, 1H), 7.79-7.76 (m, 1H), 7.10 (d, J=8.4 Hz, 1H), 4.76-4.72 (m, 1H), 4.41-4.37 (m, 1H), 4.19-4.15 (m, 1H), 4.10 (dd, J=6.6 Hz, 13.5 Hz, 2H), 2.56-2.46 (m, 1H), 2.36-2.26 (m, 1H), 1.36 (t, J=6.9 Hz, 3H).

Example 79

Preparation of 1-[4-(2,2,2-trifluoroethoxy)-3-trifluoromethylthiobenzoyl]azetidine-2R-carboxylic acid hydroxyamide

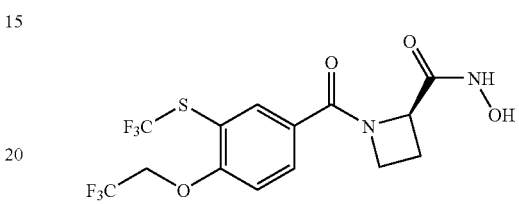

Step 1: 1-[4-(2,2,2-Trifluoroethoxy)-3-trifluoromethylthiobenzoyl]azetidine-2R-carboxylic acid methyl ester was prepared by alkylating 1-(4-hydroxy-3-trifluoromethylthiobenzoyl)azetidine-2R-carboxylic acid methyl ester (Product from Step 1 of Example 62) with 1,1,1-trifluoro-2-iodoethane according to Method C in 70% yield. The reaction was conducted at room temperature for 12 days and the resulting product was used without further purification. ESMS: m/z 418.2 [M+H].

Step 2: 1-[4-(2,2,2-Trifluoroethoxy)-3-trifluoromethylthiobenzoyl]azetidine-2R-carboxylic acid hydroxyamide was prepared from 1-[4-(2,2,2-trifluoro)-3-trifluoromethylthiobenzoyl]azetidine-2R-carboxylic acid methyl ester according to Method B in 5 h. ESMS: m/z 419.1 [M+H]. ¹H NMR (300 MHz, CD₃OD): 7.95 (s, 1H), 7.83-7.80 (m, 1H), 7.21-7.18 (m, 1H), 4.73-4.69 (m, 1H), 4.68-4.63 (m, 2H), 4.41-4.35 (m, 1H), 4.17-4.11 (m, 1H), 2.54-2.48 (m, 1H), 2.34-2.24 (m, 1H).

Example 80

Preparation of (+)-trans-1-(3,4-dimethoxy-5-propylbenzoyl)-3-ethylazetidine-2-carboxylic acid hydroxyamide

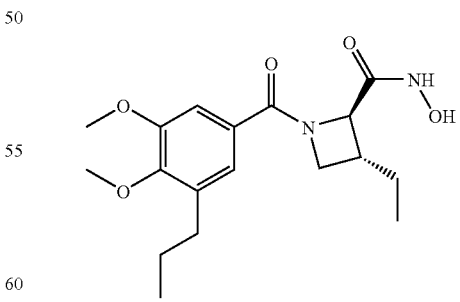

Step 1: (Benzhydrylamino)acetic acid tert-butyl ester was prepared as reported in reference D. J. Blythin et al. J. Org. Chem. 1994, 59, 6098-6100.

Step 2: To a solution of (benzhydrylamino)acetic acid tert-buyl ester (6.1 g, 20.5 mmol, 1 eq.) in dry acetone (75 mL) at −50° C. to −60° C. was added DIEA (3.58 mL, 20.5 mmol, 1 eq.) followed by a solution of 1-bromobuta-2-none (2.33 mL, 20.5 mmol, 1 eq.) in acetone (75 mL). The reaction mixture was allowed to warm to room temperature and then heated to reflux for 2 h. The reaction was cooled and then added additional 5% (by weight) of DIEA and 1-bromobuta-2-none. The resulting mixture was continued to be heated at reflux overnight. The reaction mixture was cooled to room temperature and added Et$_2$O. The precipitated solid was filtered off and washed with Et$_2$O. The combined organic layer was washed with brine, dried over MgSO$_4$, filtered, and concentrated in vacuo to afford [benzhydryl-(2-oxobutyl)amino]acetic acid tert-butyl ester in 98% yield (crude product), which was used without further purification. ESMS: m/z 368.4 [M+H].

Step 3: To a stirred solution of [benzhydryl-(2-oxobutyl)amino]acetic acid tert-butyl ester (7.4 g, 20.1 mmol, 1 eq.) in dry MeOH:THF (100 mL, 1:1) at −23° C., was added CeCl$_3$.7H$_2$O (1.43 g, 3.83 mmol, 0.19 eq.). The reaction mixture was stirred until homogeneous, then NaBH$_4$ (0.57 g, 15.1 mmol, 0.75 eq.) was added slowly (in small portions). The reaction was stirred for additional 20 min, then poured onto brine. This mixture was extracted with DCM, dried over MgSO$_4$, filtered, and concentrated in vacuo to afford [benzhydryl-(2-hydroxybutyl)amino]acetic acid tert-butyl ester in quantative yield. This was used without further purification. ESMS: m/z 370.4 [M+H].

Step 4: To a stirred solution of [benzhydryl-(2-hydroxybutyl)amino]acetic acid tert-butyl ester (7.4 g, 20 mmol, 1 eq.) in dry CHCl$_3$ (50 mL) at 0° C. was added SOCl$_2$ (3.13 mL, 43 mmol, 2.15 eq.) dropwise. After 30 min, the solvent was removed in vacuo to afford [benzhydryl-(2-chlorobutyl)amino]acetic acid tert-butyl ester (99% crude yield), which was used without further purification. ESMS: 388.3 [M+H].

Step 5: To a stirred solution of [benzhydryl-(2-chlorobutyl)amino]acetic acid tert-butyl ester (7.7 g, 19.9 mmol, 1 eq.) in dry THF (120 mL) at −78° C. was added NaHMDS (49.7 mL, 49.6 mmol, 2.5 eq.) dropwise over 45 min. The reaction was then neutralized with AcOH (0.2 mL). The solid formed was filtered off and washed with EtOAc and the filtrate was concentrated in vacuo. The residue was redissolved in EtOAc, washed with brine, dried over MgSO$_4$, filtered, concentrated in vacuo. The resulting product was chromatographed on silica gel using 50% DCM/hexanes/0.5% EtOAc mixture as eluent to afford (+)-trans-1-benzhydryl-3-ethylazetidine-2-carboxylic acid tert-butyl ester 86% yield. ESMS: m/z 352.3 [M+H].

Step 6: To a stirred solution of (+)trans-1-benzhydryl-3-ethylazetidine-2-carboxylic acid tert-butyl ester (2.85 mmol, 1 eq.) in dry MeOH (50 mL) was added 1 M acetyl chloride (3.1 mL, 3.13 mmol, 1.1 eq.) in MeOH and sonicated the mixture to obtain clear solution. To this was added palladium hydroxide on carbon (20% Pd(OH)/C, 200 mg) and the mixture was hydrogenated at 60 psi for 5 h. The catalyst was filtered off and the filtrate was concentrated in vacuo to afford (+)-trans-3-ethylazetidine-2-carboxylic acid tert-butyl ester in quantitative yield. This was used without further purification.

Step 6: (+)-trans-1-(3,4-Dimethoxy-5-propylbenzoyl)-3-ethylazetidine-2-carboxylic acid tert-butyl ester was prepared by coupling (+)-trans-3-ethylazetidine-2-carboxylic acid tert-butyl ester with 3,4-dimethoxy-5-propylbenzoic (Product from Step 3 of Example 1) by following Method A in 84% yield. The reaction was stirred at 0° C. for 1 h, and then at room temperature overnight. The product was used without further purification. ESMS: m/z 414.3 [M+Na].

Step 7: To a solution of (+)-trans-1-(3,4-dimethoxy-5-propylbenzoyl)-3-ethylazetidine-2-carboxylic acid tert-butyl ester (160 mg, 0.41 mmol, 1 eq.) in dry DCM (3.5 mL) at room temperature was added TFA (1.5 mL). The resulting reaction mixture stirred at room temperature for 2 h. The solvent was removed in vacuo and dried under high vacuum. The residue was dissolved in ether and washed with 2% NaOH solution. The aqueous layer was acidified with 1 M HCl and extracted with EtOAc. The organic layer dried over Na$_2$SO$_4$, filtered, and concentrated in vacuo to afford (+)-trans-1-(3,4-dimethoxy-5-propylbenzoyl)-3-ethylazetidine-2-carboxylic acid in 80% yield, which was used without further purification. ESMS: m/z 336.3 [M+H].

Step 8: To a solution of (+)-trans-1-(3,4-dimethoxy-5-propylbenzoyl)-3-ethylazetidine-2-carboxylic acid (110 mg, 0.33 mmol, 1 eq.) in dry DMF (2.5 mL) were added HATU (150 mg, 0.39 mmol, 1.2 eq.), DIEA (0.23 mL, 1.31 mmol, 4.0 eq.), HOBt (50 mg, 0.39 mmol, 1 eq.) and the mixture was cooled to 0° C. then the O-benzylhydroxylamine hydrochloride (63 mg, 0.39 mmol, 1.2 eq.) was added. The resulting mixture was stirred at 0° C. for 1 h, and then at room temperature overnight. The reaction was diluted with EtOAc, washed with 1M aqueous HCl solution, saturated NaHCO$_3$ solution, and brine. The organic layer was dried over MgSO$_4$, filtered and concentrated in vacuo to give (+)-trans-1-(3,4-dimethoxy-5-propylbenzoyl)-3-ethylazetidine-2-carboxylic acid benzyloxyamide in 68% yield, which was used without further purification. ESMS: m/z 441.3 [M+H].

Step 9: (+)-trans-1-(3,4-Dimethoxy-5-propylbenzoyl)-3-ethylazetidine-2-carboxylic acid hydroxyamide was prepared from (+)-trans-1-(3,4-dimethoxy-5-propylbenzoyl)-3-ethylazetidine-2-carboxylic acid benzyloxyamide by following Method H in 90% yield. The reaction was conducted at room temperature using a balloon of hydrogen for 1 h. ESMS: 351.6 [M+H]. $^1$H NMR (300 MHz, CD$_3$OD): 6.93 (s, 1H), 6.90 (s, 1H), 4.80 (m, 1H), 4.48 (m, 1H), 4.32 (m, 1H), 3.75 (s, 3H), 3.71 (s, 3H), 2.62 (m, 1H), 2.49 (t, 2H), 1.85 (m, 1H), 1.72 (m, 1H), 1.50 (m, 2H), 0.84 (t, 6H)

Example 81

Preparation of 1-(3-trifluoromethoxy-4-trifluoromethylthiobenzoyl)azetidine-2R-carboxylic acid hydroxyamide

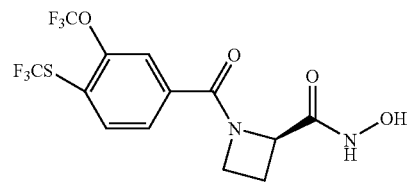

Step 1: To a stirred solution of 4-bromo-2-trifluoromethoxybenzenethiol (1.76 g, 6.44 mmol) in DMF (10 mL) at 0° C. was added NaH (60% in mineral oil, 283 mg, 7.08 mmol) in small portions and the reaction mixture was slowly warmed to 23° C. over 30 minutes. The reaction vessel was evacuated and flushed with trifluoromethyl iodide gas and finally a balloon of trifluoromethyl iodide gas was attached and continued the reaction at 23° C. till the gas is consumed. The reaction mixture was heated to 80° C. with stirring for 2 h, cooled to room temperature and stirred overnight. The reaction mixture was poured into 1.0 N HCl (100 mL) and extracted with ethyl ether. The combined organic layer was washed with brine (80 mL), dried MgSO$_4$ and concentrated in vacuo to get the crude product. This was purified by silica gel column chromatography using pentane as a eluent to afford 4-bromo-2-trifluoromethoxy-1-trifluoromethylthiobenzene (1.12 g, 51%).

Step 2: To a stirred solution of 4-bromo-2-trifluoromethoxy-1-trifluoromethylthiobenzene (500 mg, 1.47 mmol) in DMSO (10 mL) was added potassium acetate (577 mg, 5.88 mmol), followed by palladium acetate (16 mg, 0.07 mmol) and dppf (41 mg, 0.07 mmol). The reaction mixture was purged with carbon monoxide for 5 min and stirred under a balloon pressure of carbon monoxide at 60° C. for 8 h. The reaction mixture was cooled to room temperature and stirred overnight. The reaction mixture was diluted with 0.5 N HCl (100 mL) and extracted with dichloromethane (3×100 mL). The combined organic layer was washed with brine (2×200 mL), dried $MgSO_4$ and concentrated in vacuo to yield 3-trifluoromethoxy-4-trifluoromethylthiobenzoic acid (449 mg, quantitative yield).

Step 3: 1-(3-Trifluoromethoxy-4-trifluoromethylthiobenzoyl)azetidine-2R-carboxylic acid methyl ester was prepared by coupling azetidine-2R-carboxylic acid methyl ester hydrochloride salt with 3-trifluoromethoxy-4-trifluoromethylthiobenzoic acid by following Method A in 53% yield. The crude product was purified by silica gel column chromatography using 1:1 mixture of EtOAc and hexanes. ESMS: m/z 404.1 [M+H].

Step 4: 1-(3-Trifluoromethoxy-4-trifluoromethylthiobenzoyl)azetidine-2R-carboxylic acid hydroxyamide was prepared from 1-(3-trifluoromethoxy-4-trifluoromethylthiobenzoyl)azetidine-2R-carboxylic acid methyl ester in 3 h by following Method B. ESMS: m/z 403.0 [M−H]. $^1$H NMR (300 MHz, $CD_3OD$): 7.98-7.60 (m, 3H), 4.8144.82 (m, 1H), 4.57-4.40 (m, 1H), 4.35-4.20 (m, 1H), 2.70-2.52 (m, 1H), 2.48-2.34 (m, 1H).

Example 82

Preparation of 1-(4-methoxy-3-trifluoromethylthiobenzyl)azetidine-2R-carboxylic acid hydroxyamide

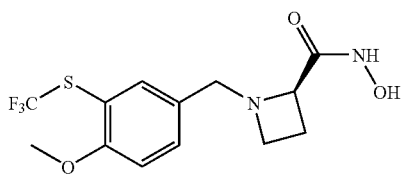

Step 1: (4-Methoxy-3-trifluoromethylthiophenyl)methanol was prepared from 4-methoxy-3-trifluoromethylthiobenzoic acid following Method S in 94% yield. The resulting product was used without further purification.

Step 2: Methanesulfonic acid 4-methoxy-3-trifluoromethylthiobenzyl ester was prepared from (4-methoxy-3-trifluoromethylthiophenyl)methanol according to Method T in quantitative yield and the resulting product was used without further purification.

Step 3: 1-(4-Methoxy-3-trifluoromethylthiobenzyl)azetidine-2R-carboxylic acid methyl ester was prepared by reacting methanesulfonic acid 4-methoxy-3-trifluoromethylthiobenzyl ester with azetidine-2R-carboxylic acid methyl ester hydrochloride salt according to Method U and the resulting product was used without further purification. ESMS: m/z 336.5 [M+H].

Step 4: 1-(4-Methoxy-3-trifluoromethylthiobenzyl)azetidine-2R-carboxylic acid hydroxyamide was prepared from 1-(4-methoxy-3-trifluoromethylthiobenzyl)azetidine-2R-carboxylic acid methyl ester following method B in 2 h. ESMS: m/z 335.2 [M−H]. $^1$H NMR (300 MHz, $CD_3OD$): 7.74 (dd, J=2.4 Hz, 8.1 Hz, 1H), 7.65-7.59 (m, 1H), 7.19 (dd, J=2.1 Hz, 8.7 Hz, 1H), 5.43 (t, J=9.6 Hz, 1H), 4.20 (s, 2H), 4.20-4.08 (m, 1H), 4.00-3.95 (m, 1H), 3.91 (s, 3H), 2.76-2.60 (m, 1H), 2.57-2.50 (m, 1H).

Example 83

Preparation of 1-(3,4-dimethoxy-5-trifluoromethylthiobenzyl)azetidine-2R-carboxylic acid hydroxyamide

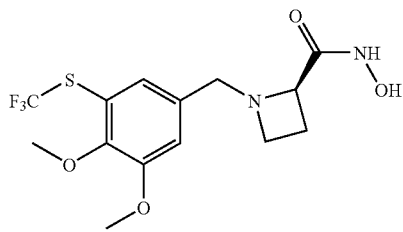

Step 1: To a stirred solution of 3,4-dimethoxy-5-trifluoromethylthiobenzoic acid methyl ester (300 mg, 1.01 mmol) in dichloromethane (21 mL) at −78° C. was added diisobutylaluminumhydride (1.0 M in hexane, 3.0 mL) slowly and the reaction mixture was stirred for 1 h. Excess diisobutylaluminumhydride was decomposed by adding EtOAc (3.0 mL) at −78° C. The reaction mixture was warmed to −15° C., and treated with saturated aqueous NaK tartrate/saturated aqueous sodium bicarbonate (25 mL, 1:1, v/v). Resulting mixture was stirred at 23° C. for 2 h then extracted with EtOAc (40 mL). The organic layer, washed with brine (2×80 mL), dried $MgSO_4$, and concentrated in vacuo to yield (3,4-dimethoxy-5-trifluoromethylthiophenyl)methanol (355 mg).

Step 2: Methanesulfonic acid 3,4-dimethoxy-5-trifluoromethylthiobenzyl ester was prepared from (3,4-dimethoxy-5-trifluoromethylthiophenyl)methanol according to Method T in 90% yield and the resulting product was used without further purification.

Step 3: 1-(3,4-dimethoxy-5-trifluoromethylthiobenzyl)azetidine-2R-carboxylic acid methyl ester was prepared by reacting methanesulfonic acid 3,4-dimethoxy-5-trifluoromethylthiobenzyl ester with azetidine-2R-carboxylic acid methyl ester hydrochloride salt according to Method U and the resulting product was used without further purification. ESMS: m/z 366.5 [M+H].

Step 4: 1-(3,4-dimethoxy-5-trifluoromethylthiobenzyl)azetidine-2R-carboxylic acid hydroxyamide was prepared from 1-(3,4-dimethoxy-5-trifluoromethylthiobenzyl)azetidine-2R-carboxylic acid methyl ester following method B in 2 h. ESMS: m/z 365.5 [M−H]. $^1$H NMR (300 MHz, $CD_3OD$): 7.31 (s, 1H), 7.28 (s, 1H), 5.47 (t, J=9.3 Hz, 1H), 4.35 (s, 2H), 4.19-4.10 (m, 1H), 4.05-3.95 (m, 1H), 3.92 (s, 3H), 3.87 (s, 3H), 2.76-2.60 (m, 1H), 2.57-2.50 (m, 1H).

Example 84

Preparation of 1-(3-trifluoromethylthiobenzyl)azetidine-2R-carboxylic acid hydroxyamide

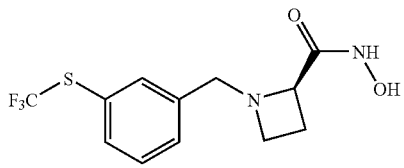

Step 1: (3-trifluoromethylthiophenyl)methanol was prepared from 3-trifluoromethylthiobenzoic acid following Method S in 78% yield. The resulting product was used without further purification.

Step 2: Methanesulfonic acid 3-trifluoromethylthiobenzyl ester was prepared from (3-trifluoromethylthiophenyl)methanol according to Method T in 91% yield and the resulting product was used without further purification.

Step 3: 1-(3-Trifluoromethylthiobenzyl)azetidine-2R-carboxylic acid methyl ester was prepared by reacting methanesulfonic acid 3-trifluoromethylthiobenzyl ester with azetidine-2R-carboxylic acid methyl ester hydrochloride salt according to Method U and the resulting product was used without further purification. ESMS: m/z 306.5 [M+H].

Step 4: 1-(3-Trifluoromethylthiobenzyl)azetidine-2R-carboxylic acid hydroxyamide was prepared from 1-(3-trifluoromethylthiobenzyl)azetidine-2R-carboxylic acid methyl ester following method B in 2 h. ESMS: m/z 307.5 [M+H]. $^1$H NMR (300 MHz, CD$_3$OD): 8.06-7.76 (m, 4H), 4.91-4.88 (m, 1H) 4.35 (s, 2H), 4.17-4.03 (m, 1H), 3.92-3.87 (m, 1H), 2.59-2.52 (m, 1H), 2.49-2.39 (m, 1H).

Example 85

Preparation of 1-(3-trifluoromethylthiobenzoyl)pyrrolidine-2R-carboxylic acid hydroxyamide

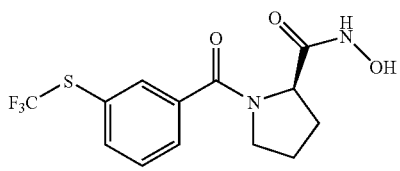

Step 1: 3-Trifluoromethylthiobenzoyl chloride was prepared from 3-trifluoromethylthiobenzoic acid according to Method V and the resulting product was used without further purification.

Stet 2: 1-(3-Trifluoromethylthiobenzoyl)pyrrolidine-2R-carboxylic acid methyl ester was prepared by reacting pyrrolidine-2R-carboxylic acid methyl ester with 3-trifluoromethylthiobenzoyl chloride according to Method W. The product was used without further purification. ESMS: m/z 334.5 [M+H].

Step 3: 1-(3-Trifluoromethylthiobenzoyl)pyrrolidine-2R-carboxylic acid hydroxyamide was prepared from 1-(3-trifluoromethylthiobenzoyl)pyrrolidine-2R-carboxylic acid methyl ester following Method B. The reaction was conducted for 4 days at room temperature. ESMS: m/z 333.5 [M−H]. $^1$H NMR (300 MHz, CD$_3$OD): 7.95 (s, 1H), 7.82-7.72 (m, 2H), 7.58 (t, J=8.1 Hz, 1H), 4.48 (dd, J=6.0 Hz, 8.1 Hz, 1H), 3.67-3.59 (m, 1H), 3.51-3.44 (m, 1H), 2.32-2.24 (m, 1H), 2.08-1.85 (m, 3H).

Example 86

Preparation of 1-(3-methoxy-5-trifluoromethylthiobenzoyl)pyrrolidine-2R-carboxylic acid hydroxyamide

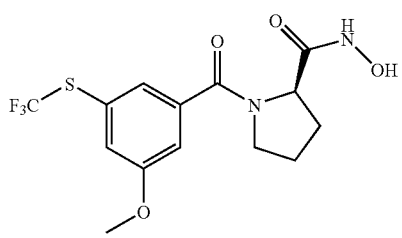

Step 1: 3-Methoxy-5-trifluoromethylthiobenzoyl chloride was prepared from 3-methoxy-5-trifluoromethylthiobenzoic acid (Product from Step 6 of Example 48) according to Method V and the resulting product was used without further purification.

Step 2: 1-(3-Methoxy-5-trifluoromethylthiobenzoyl)pyrrolidine-2R-carboxylic acid methyl ester was prepared by reacting pyrrolidine-2R-carboxylic acid methyl ester with 3-methoxy-5-trifluoromethylthiobenzoyl chloride according to Method W. The product was used without further purification. ESMS: m/z 364.5 [M+H].

Step 3: 1-(3-Methoxy-5-trifluoromethylthiobenzoyl)pyrrolidine-2R-carboxylic acid hydroxyamide was prepared from 1-(3-methoxy-5-trifluoromethylthiobenzoyl)-pyrrolidine-2R-carboxylic acid methyl ester following Method B. The reaction was conducted for 4 days at room temperature. ESMS: 363.5 [M−H]. $^1$H NMR (300 MHz, CD$_3$OD): 7.48 (s, 1H), 7.33 (s, 2H), 4.41 (t, J=7.2 Hz, 1H), 3.86 (s, 3H), 3.72-3.58 (m, 1H), 3.58-3.40 (m, 1H), 2.38-2.20 (m, 1H), 2.10-1.80 (m, 3H).

Example 87

Preparation of 1-(4-methoxy-3-trifluoromethylthiobenzoyl)pyrrolidine-2R-carboxylic acid hydroxyamide

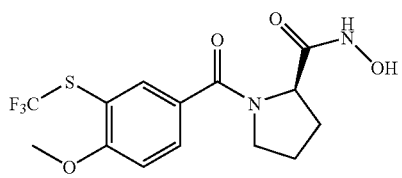

Step 1: 4-Methoxy-3-trifluoromethylthiobenzoyl chloride was prepared from 4-methoxy-3-trifluoromethylthiobenzoic acid (Product from Step 5 of Example 45) according to Method V and the resulting product was used without further purification.

Stet 2: 1-(4-Methoxy-3-trifluoromethylthiobenzoyl)pyrrolidine-2R-carboxylic acid methyl ester was prepared by reacting pyrrolidine-2R-carboxylic acid methyl ester with 4-methoxy-3-trifluoromethylthiobenzoyl chloride according to Method W. The product was used without further purification. ESMS: m/z 364.5 [M+H].

Step 3: 1-(4-Methoxy-3-trifluoromethylthiobenzoyl)pyrrolidine-2R-carboxylic acid hydroxyamide was prepared from 1-(4-methoxy-3-trifluoromethylthiobenzoyl)-pyrrolidine-2R-carboxylic acid methyl ester following Method B. The reaction was conducted for 4 days at room temperature. ESMS: 363.5 [M–H]. $^1$H NMR (300 MHz, CD$_3$OD): 7.93 (s, 1H), 7.81 (dd, J=2.4 Hz, 8.7 Hz, 1H), 7.20 (d, J=8.4 Hz, 1H) 4.43 (t, J=14.4 Hz, 1H), 3.95 (s, 3H), 3.71-3.66 (m, 1H), 3.59-3.51 (m, 1H), 2.31-2.25 (m, 1H), 2.08-1.84 (m, 3H).

Example 88

Preparation of 1-(3,4-dimethoxy-5-trifluoromethylthiobenzoyl)pyrrolidine-2R-carboxylic acid hydroxyamide

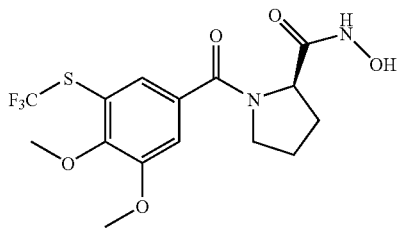

Step 1: 3,4-Dimethoxy-5-trifluoromethylthiobenzoyl chloride was prepared from 3,4-dimethoxy-5-trifluoromethylthiobenzoic acid (Product from Step 5 of Example 58) according to Method V and the resulting product was used without further purification.

Step 2: 1-(3,4-Dimethoxy-5-trifluoromethylthiobenzoyl)pyrrolidine-2R-carboxylic acid methyl ester was prepared by reacting pyrrolidine-2R-carboxylic acid methyl ester with 3,4-dimethoxy-5-trifluoromethylthiobenzoyl chloride according to Method W. The product was used without further purification. ESMS: m/z 394.5 [M+H].

Step 3: 1-(3,4-dimethoxy-5-trifluoromethylthiobenzoyl)pyrrolidine-2R-carboxylic acid hydroxyamide was prepared from 1-(3,4-dimethoxy-5-trifluoromethylthiobenzoyl)-pyrrolidine-2R-carboxylic acid methyl ester following Method B. The reaction was conducted for 4 days at room temperature. ESMS: m/z 393.5 [M–H]. $^1$H NMR (300 MHz, CD$_3$OD): 7.49 (s, 1H), 7.46 (d, J=1.8 Hz, 1H), 4.47 (t, J=7.8 Hz, 1H), 3.94 (s, 3H), 3.92 (s, 3H), 3.71-3.68 (m, 1H), 3.65-3.51 (m, 1H), 2.34-2.25 (m, 1H), 2.10-1.86 (m, 3H).

Example 89

Preparation of 1-(4-methoxy-3-propyl-5-trifluoromethylthiobenzoyl)pyrrolidine-2R-carboxylic acid hydroxyamide

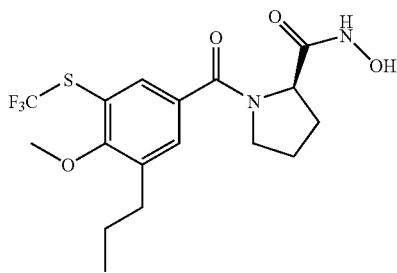

Step 1: 4-methoxy-3-propyl-5-trifluoromethylthiobenzoyl chloride was prepared from 4-methoxy-3-propyl-5-trifluoromethylthiobenzoic acid (Product from Step 10 of Example 49) according to Method V and the resulting product was used without further purification.

Step 2: 1-(4-methoxy-3-propyl-5-trifluoromethylthiobenzoyl)pyrrolidine-2R-carboxylic acid methyl ester was prepared by reacting pyrrolidine-2R-carboxylic acid methyl ester with 4-methoxy-3-propyl-5-trifluoromethylthiobenzoyl chloride according to Method W. The product was used without further purification. ESMS: m/z 406.5 [M+H].

Step 3: 1-(4-methoxy-3-propyl-5-trifluoromethylthiobenzoyl)pyrrolidine-2R-carboxylic acid hydroxyamide was prepared from 1-(4-methoxy-3-propyl-5-trifluoromethylthiobenzoyl)pyrrolidine-2R-carboxylic acid methyl ester following Method B. The reaction was conducted for 4 days at room temperature. ESMS: m/z 405.5 [M–H]. $^1$H NMR (300 MHz, CD$_3$OD): 7.78 (s, 1H), 7.67 (s, 1H), 4.45-4.40 (t, J=7.8 Hz, 1H), 3.88 (s, 3H), 3.77-3.63 (m, 1H), 3.58-3.44 (m, 1H), 2.72 (t, J=7.8 Hz, 2H), 2.35-2.22 (m, 1H), 2.12-1.85 (m, 3H), 1.72-1.64 (m, 2H), 0.98 (t, J=7.5 Hz, 3H).

Example 90

Preparation of 1-(3,4-dimethoxy-5-trifluoromethylthiobenzoyl)-4S-fluoropyrrolidine-2R-carboxylic acid hydroxyamide

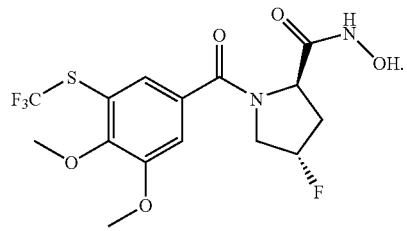

Step 1: To a stirred solution of 4R-hydroxypyrrolidine-2R-carboxylic acid (10.0 g, 76.3 mmol, 1 eq.) in MeOH (300 mL) at 0° C. was added SOCl$_2$ (10.0 mL, excess) over the course of 1.5 min. The reaction was allowed to warm to 23° C. After 16 h the reaction mixture was concentrated in vacuo to give 4R-hydroxypyrrolidine-2R-carboxylic acid methyl ester hydrochloride salt as a white solid (15.9 g, 100% yield).

Step 2: To a stirred suspension of 4R-hydroxypyrrolidine-2R-carboxylic acid methyl ester hydrochloride salt (15.9 g, 76.3 mmol, 1 eq.) in CH$_2$Cl$_2$ (200 mL) at 23° C. was added Et$_3$N (21.3 mL, 153 mmol, 2 eq.) followed by Boc$_2$O (21.1 mL, 91.6 mmol, 1.2 eq.). The resulting mixture was stirred for 5 h, then treated with silica gel (20 g). The volatiles were removed in vacuo to give a free-flowing powder, which was dry-loaded onto a pre-packed silica gel column. The product was purified via flash column chromatography (100% EtOAc as an eluent) to give 4R-hydroxypyrrolidine-1,2R-dicarboxylic acid 1-tert-butyl ester 2-methyl ester (14.4 g, 58.9 mmol, 77% yield).

Step 3: To a stirred solution of 4R-hydroxypyrrolidine-1,2R-dicarboxylic acid 1-tert-butyl ester 2-methyl ester (1.62 g, 6.59 mmol, 1 eq.) in CH$_2$Cl$_2$ (30 mL) at −78° C. was added DAST solution (1.0 M in CH$_2$Cl$_2$, 7.91 mL, 7.91 mmol, 1.2 eq.). The resulting solution was stirred at −78° C. for 30 min, followed by room temperature for 60 min, then quenched with saturated aqueous NaHCO$_3$ (15 mL). The resulting mixture was partitioned between H$_2$O (100 mL) and Et$_2$O (150 mL). The layers were separated, the organic layer washed with brine (100 mL), dried MgSO$_4$ and concentrated in vacuo.

The product was purified via flash column chromatography on silica gel (40% EtOAc/hexanes as an eluent) to give 4S-fluoropyrrolidine-1,2R-dicarboxylic acid 1-tert-butyl ester 2-methyl ester (248 mg, 1.00 mmol, 15% yield). ESMS: 270.5 [M+Na].

Step 4: 4S-fluoropyrrolidine-1,2R-dicarboxylic acid 1-tert-butyl ester 2-methyl ester (240 mg, 0.97 mmol, 1 eq.) was treated with anhydrous 4.0 M HCl in dioxane (20 mL, excess). The resulting mixture was stirred vigorously at 23° C. for 4 h, then concentrated to give the desired of 4S-fluoropyrrolidine-2R-carboxylic acid methyl ester hydrochloride salt. This was used without further purification.

Step 5: 1-(3,4-Dimethoxy-5-trifluoromethylthiobenzoyl)-4S-fluoropyrrolidine-2R-carboxylic acid methyl ester was prepared by reacting of 4S-fluoropyrrolidine-2R-carboxylic acid methyl ester hydrochloride salt with 3,4-dimethoxy-5-trifluoromethylthiobenzoyl chloride (Product from Step 1 of Example 88) according to Method W in 14 h. The product was purified by silica gel column chromatography (80% EtOAc/hexanes as an eluent) to give 1-(3,4-dimethoxy-5-trifluoromethylthiobenzoyl)4S-fluoropyrrolidine-2R-carboxylic acid methyl ester in 58% yield. ESMS: m/z 412.5 [M+H].

Step 6: 1-(3,4-dimethoxy-5-trifluoromethylthiobenzoyl)4S-fluoropyrrolidine-2R-carboxylic acid hydroxyamide was prepared from 1-(3,4-dimethoxy-5-trifluoromethylthiobenzoyl)4S-fluoropyrrolidine-2R-carboxylic acid methyl ester following Method B in 24 h. ESMS: m/z 411.5 [M−H]. $^1$H NMR (300 MHz, CDCl$_3$): 7.35 (s, 1H), 7.29 (s, 1H), 5.34 (br s, 1H), 5.27 (br s, 1H), 4.88 (t, J=6.9 Hz, 1H), 3.95 (s, 3H), 3.91 (s, 3H), 3.90-3.75 (m, 1H), 2.85-2.43 (m, 2H).

Example 91

Preparation of 1-(3,4-dimethoxy-5-trifluoromethylthiobenzoyl)4R-fluoropyrrolidine-2R-carboxylic acid hydroxyamide

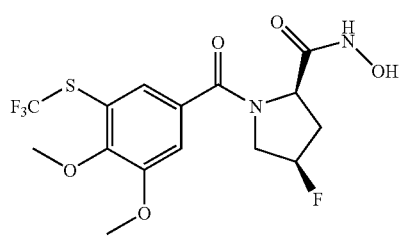

Step 1: To a stirred solution of 4R-hydroxypyrrolidine-1,2R-dicarboxylic acid 1-tert-butyl ester 2-methyl ester (2.23 g, 9.11 mmol, 1 eq.; Product from Step 2 of Example 90), 4-nitrobenzoic acid (3.05 g, 18.2 mmol, 2 eq.) and PPh$_3$ (4.78 g, 18.2 mmol, 2 eq.) in THF (100 mL) at 0° C. was added DIAD (3.59 mL, 18.2 mmol, 2 eq.). The reaction bath was slowly allowed to warm to 23° C. After 24 h the reaction mixture was partitioned between H$_2$O (100 mL) and EtOAc (200 mL). The layers were separated, the organic layer was washed with saturated aqueous NaHCO$_3$ (200 mL), brine (200 mL), dried MgSO$_4$ and concentrated in vacuo. The product was purified via flash column chromatography on silica gel (33% EtOAc/hexanes as an eluent) to give 4S-(4-nitrobenzoyloxy)pyrrolidine-1,2R-dicarboxylic acid 1-tert-butyl ester 2-methyl ester (6.46 g) which was contaminated with hydrazine biscarbamate. This was used without further purification.

Step 2: 4S-(4-Nitrobenzoyloxy)pyrrolidine-1,2R-dicarboxylic acid 1-tert-butyl ester 2-methyl ester was dissolved in MeOH (200 mL) and treated with NaN$_3$ (2.17 g, 33 mmol, 3.7 eq.) followed by 15-crown-5 (4.0 mL, 20 mmol, 2.1 eq.). The resulting solution was warmed to 40° C. for 2.5 h, then concentrated. The residue was partitioned between H$_2$O (150 mL) and EtOAc (200 mL). The layers were separated, the organic layer washed with H$_2$O (150 mL), brine (100 mL), dried MgSO$_4$ and concentrated concentrated in vacuo. The product was purified via flash column chromatography on silica gel (50-100% EtOAc/hexanes as eluent) to give 4S-hydroxypyrrolidine-1,2R-dicarboxylic acid 1-tert-butyl ester 2-methyl ester (1.40 g, 5.71 mmol, 63% yield).

Step 3: To a stirred solution of 4S-hydroxypyrrolidine-1,2R-dicarboxylic acid 1-tert-butyl ester 2-methyl ester (716 mg, 2.92 mmol, 1 eq.) in CH$_2$Cl$_2$ (15 mL) at −78° C. was added aqueous (MeO)$_2$DAST (2.15 mL, 11.7 mmol, 4 eq.) over the course of 2 min. After 2 h the reaction mixture was warmed to 0° C., and after a further 2 h warmed to 23° C. After 1.5 h at 23° C. the reaction was quenched with NaHCO$_3$. The mixture was then filtered through a pad of Celite and concentrated in vacuo. The product was purified via flash column chromatography on silica gel (40% EtOAc/hexanes as eluent) to give 4R-fluoropyrrolidine-1,2R-dicarboxylic acid 1-tert-butyl ester 2-methyl ester (255 mg, 1.03 mmol, 35% yield).

Step 4: To 4R-fluoropyrrolidine-1,2R-dicarboxylic acid 1-tert-butyl ester 2-methyl ester (255 mg, 1.03 mmol, 1 eq.) was added anhydrous 4.0 M HCl in dioxane (20 mL) at 23° C. After 2.5 h the reaction mixture was concentrated to give the 4R-fluoropyrrolidine-2R-carboxylic acid methyl ester hydrochloride salt. The product was used without further purification.

Step 5: 1-(3,4-Dimethoxy-5-trifluoromethylthiobenzoyl)-4R-fluoropyrrolidine-2R-carboxylic acid methyl ester was prepared by reacting 4R-fluoropyrrolidine-2R-carboxylic acid methyl ester hydrochloride salt with 3,4-dimethoxy-5-trifluoromethylthiobenzoyl chloride according (Product from Step 1 of Example 88) to Method W in 13 h. The product was purified by silica gel column chromatography (EtOAc as an eluent) to give 1-(3,4-dimethoxy-5-trifluoromethylthiobenzoyl)4R-fluoropyrrolidine-2R-carboxylic acid methyl ester in 91% yield. ESMS: m/z 412.5 [M+H].

Step 6: To a stirred suspension of HCl.H$_2$N—OBn (38 mg, 0.24 mmol, 2 eq.) in toluene (3.0 mL) at 0° C. was added trimethylaluminum (2.0 M in hexane, 0.12 mL, 0.24 mmol, 2 eq.). After 15 min at 0° C. and a further 30 min at 23° C., the reaction was treated with a solution of 1-(3,4-dimethoxy-5-trifluoromethylthiobenzoyl)-4R-fluoropyrrolidine-2R-carboxylic acid methyl ester (50 mg, 0.12 mmol, 1 eq.) in toluene (1.0 mL+1.0 mL flush, added via cannula). The resulting mixture was warmed to 50° C. for 45 min then cooled to 23° C. This was partitioned between 1.0 N HCl (80 mL) and Et$_2$O (100 mL). The layers were separated, the organic layer was washed with 1.0 N HCl (80 mL), brine (50 mL), dried MgSO$_4$ and concentrated in vacuo to give 1-(3,4-dimethoxy-5-trifluoromethylthiobenzoyl)-4R-fluoropyrrolidine-2R-carboxylic acid benzyloxyamide (58 mg). This was used without further purification.

Step 7: 1-(3,4-Dimethoxy-5-trifluoromethylthiobenzoyl) 4R-fluoropyrrolidine-2R-carboxylic acid benzyloxyamide was dissolved in EtOH (6.0 mL) then treated with Pd/BaSO$_4$ (5 wt. %, 50 mg). Following evacuation the reaction vessel was purged with H$_2$ (balloon). The reaction mixture was stirred at 23° C. for 3 h, then filtered through a pad of Celite, washing with MeOH (50 mL). The resulting solution was concentrated and the crude product was purified by preparative HPLC to furnish 1-(3,4-dimethoxy-5-trifluoromethylthiobenzoyl)-4R-fluoropyrrolidine-2R-carboxylic acid hydroxyamide (11 mg). ESMS: m/z 411.5 [M−H]. ¹H NMR (300 MHz, CD₃OD): 7.60-7.30 (m, 2H), 5.40-5.10 (m, 1H), 4.81-4.74 (m, 1H), 3.93 (s, 3H), 3.91 (s, 3H), 3.90-3.70 (m, 2H), 2.63-2.32 (m, 2H).

Example 92

Preparation of 1-(3,4-dimethoxy-5-trifluoromethylthiobenzoyl)-4R-methoxypyrrolidine-2R-carboxylic acid hydroxyamide

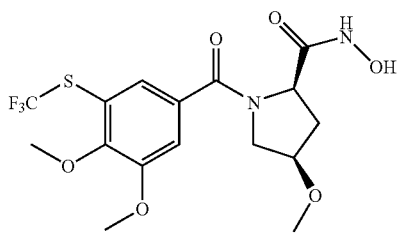

Step 1: To a stirred solution of 4R-hydroxypyrrolidine-2R-carboxylic acid (5.02 g, 38.3 mmol, 1 eq.) and NaHCO₃ (8.05 g, 95.8 mmol, 2.5 eq.) in H₂O (85 mL) at 23° C. was added a solution of Cbz-Cl (6.28 mL, 44.0 mmol, 1.15 eq.) in toluene (20 mL) over 15 min period. After 24 h the layers were separated and the aqueous layer was extracted with Et₂O (2×100 mL) and discarded the combined organic layer. The aqueous layer was then acidified to pH 2 with concentrated HCl, and the product was extracted with EtOAc (2×100 mL). The organic layer was dried and concentrated in vacuo to give 4R-hydroxypyrrolidine-1,2R-dicarboxylic acid 1-benzyl ester 2-methyl ester (9.97 g, 100%).

Step 2: To a solution of 4R-hydroxypyrrolidine-1,2R-dicarboxylic acid 1-benzyl ester 2-methyl ester (4.64 g, 18.1 mmol, 1 eq.) in acetone (35 mL) at 23° C. was added Ag₂O (14.0 g, 59.2 mmol, 3.27 eq.) followed by iodomethane (3.90 mL, 62.7 mmol, 3.46 eq.). The resulting mixture was stirred for 24 h, then filtered through Celite and concentrated in vacuo. The residue obtained was re-subjected to the same reaction conditions three times before the final purification. The product was purified via flash column chromatography on silica gel (60-70% EtOAc/hexanes as an eluent) to give 4R-methoxyoxypyrrolidine-1,2R-dicarboxylic acid 1-benzyl ester 2-methyl ester (4.31 g, 15.2 mmol, 84%). ESMS: m/z 316.5 [M+Na].

Step 3: To a stirred 4R-methoxyoxypyrrolidine-1,2R-dicarboxylic acid 1-benzyl ester 2-methyl ester (1.14 g, 4.01 mmol, 1 eq.) in MeOH (20 mL) was added Pd/C (10 wt. %, 167 mg). Following evacuation the reaction vessel was purged with H₂ (balloon), then 1.0 N HCl (6.0 mL, 6.0 mmol, 1.5 eq.) added. The resulting mixture was stirred vigorously at 23° C. for 2 h, then filtered through Celite, washing with MeOH (150 mL). The resulting solution was concentrated to give the desired 4R-methoxyoxypyrrolidine-2R-carboxylic acid methyl ester hydrochloride salt. This was used without further purification.

Step 4: 1-(3,4-Dimethoxy-5-trifluoromethylthiobenzoyl)-4R-methoxypyrrolidine-2R-carboxylic acid methyl ester was prepared by reacting 4R-methoxypyrrolidine-2R-carboxylic acid methyl ester hydrochloride salt with 3,4-dimethoxy-5-trifluoromethylthiobenzoyl chloride (Product from Step 1 of Example 88) according to Method W in 15 h. The product was purified by silica gel column chromatography (EtOAc/hexanes as an eluent) to give 1-(3,4-dimethoxy-5-trifluoromethylthiobenzoyl)₄R-methoxypyrrolidine-2R-carboxylic acid methyl ester in 83% yield.

Step 5: 1-(3,4-Dimethoxy-5-trifluoromethylthiobenzoyl)₄R-methoxypyrrolidine-2R-carboxylic acid hydroxyamide was prepared from 1-(3,4-dimethoxy-5-trifluoromethylthiobenzoyl)-4R-methoxypyrrolidine-2R-carboxylic acid methyl ester following Method B in 24 h. ESMS: m/z 423.5 [M−H]. ¹H NMR (300 MHz, CD₃OD): 7.53 (s, 1H), 7.48 (s, 1H), 4.55 (t, J=7.2 Hz, 1H), 4.01-3.94 (m, 1H), 3.93 (s, 3H), 3.91 (s, 3H), 3.76-3.67 (m, 1H), 3.64-3.56 (m, 1H), 3.28 (s, 3H), 2.52-2.41 (m, 1H), 2.36-2.25 (m, 1H).

Example 93

Preparation of 1-(3,4-dimethoxy-5-trifluoromethylthiobenzoyl)₄S-hydroxypyrrolidine-2R-carboxylic acid hydroxyamide

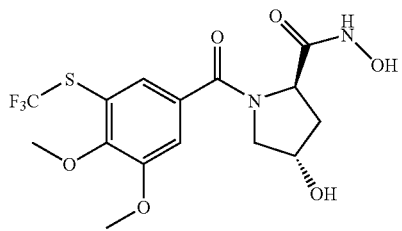

Step 1: To a suspension of 4R-hydroxypyrrolidine-2R-carboxylic acid methyl ester hydrochloride salt (7.94 g, 38.2 mmol, 1 eq.; Product from Step 1 of Example 90) in CHCl₃ (100 mL) at 23° C. was added Et₃N (16.0 mL, 115 mmol, 3 eq.) followed by trityl chloride (11.2 g, 40.1 mmol, 1.05 eq.). After 15 min THF (15 mL) was added. The resulting mixture was stirred for 3 h, then partitioned between H₂O (300 mL) and Et₂O (400 mL). The layers were separated and the organic layer washed with 1.0 N HCl (300 mL), brine (200 mL), dried MgSO₄ and concentrated in vacuo. The product was purified via flash column chromatography on silica gel (40% EtOAc/hexanes as eluent) to give 4R-hydroxy-1-tritylpyrrolidine-2R-carboxylic acid methyl ester (7.37 g, 19.0 mmol, 50% yield).

Step 2: To a solution of 4R-hydroxy-1-tritylpyrrolidine-2R-carboxylic acid methyl ester (7.37 g, 19.0 mmol, 1 eq.), PhCO₂H (4.64 g, 38.0 mmol, 2 eq.) and PPh₃ (9.96 g, 38.0 mmol, 2 eq.) in toluene (200 mL) at 0° C. was added DIAD (7.47 mL, 38.0 mmol, 2 eq.). The reaction bath was slowly allowed to warm to 23° C. After 16 h the reaction mixture was partitioned between H₂O (300 mL) and EtOAc (300 mL). The layers were separated, the organic layer washed with saturated aqueous NaHCO₃ (300 mL), brine (300 mL), dried MgSO₄ and concentrated in vacuo. The product was purified via flash column chromatography on silica gel (18% EtOAc/hexanes as eluent) to give 4S-benzoyloxy-1-tritylpyrrolidine-2R-carboxylic acid methyl ester (8.06 g, 16.4 mmol, 86%).

Step 3: To a solution of 4S-benzoyloxy-1-tritylpyrrolidine-2R-carboxylic acid methyl ester (8.06 g, 16.4 mmol, 1 eq.) in THF (100 mL) at 0° C. was added 0.5 M MeONa in MeOH (39.4 mL, 19.7 mmol, 1.2 eq.). The resulting solution was stirred at 0° C. for 20 min, then at 23° C. for 1 h. The mixture was partitioned between brine: 1.0 N HCl (1:1, 300 mL) and EtOAc (300 mL). The layers were separated and the organic layer washed with brine (100 mL), dried MgSO₄ and concentrated in vacuo. The product was purified via flash column chromatography on silica gel (50% EtOAc/hexanes as an eluenteluent) to give 4S-hydroxyoxy-1-tritylpyrrolidine-2R-carboxylic acid methyl ester (3.37 g, 8.71 mmol, 53% yield).

Step 4: 4S-Hydroxyoxy-1-tritylpyrrolidine-2R-carboxylic acid methyl ester (510 mg, 1.32 mmol, 1 eq.) was treated with anhydrous 4.0 M HCl in dioxane (20 mL, excess). The resulting mixture was stirred vigorously at 23° C. for 3 h, then concentrated to give 4S-hydroxyoxy-1-pyrrolidine-2R-carboxylic acid methyl ester hydrochloride salt.

Step 5: 1-(3,4-dimethoxy-5-trifluoromethylthiobenzoyl)4S-hydroxypyrrolidine-2R-carboxylic acid methyl ester was prepared by reacting 4S-hydroxyoxy-1-pyrrolidine-2R-carboxylic acid methyl ester hydrochloride salt with 3,4-dimethoxy-5-trifluoromethylthiobenzoyl chloride according to Method W in 16 h. The resulting product was purified by silica gel column chromatography using EtOAc as an eluent to furnish 1-(3,4-dimethoxy-5-trifluoromethylthiobenzoyl)4S-hydroxypyrrolidine-2R-carboxylic acid methyl ester in 66% yield. ESMS: m/z 410.5 [M+H]

Step 6: 1-(3,4-dimethoxy-5-trifluoromethylthiobenzoyl)-4S-hydroxypyrrolidine-2R-carboxylic acid hydroxyamide was prepared from 1-(3,4-dimethoxy-5-trifluoromethylthiobenzoyl)-4S-hydroxypyrrolidine-2R-carboxylic acid methyl ester following Method B in 24 h. ESMS: m/z 409.4 [M–H]. $^1$H NMR (300 MHz, CD$_3$OD): 7.50 (s, 1H), 7.46 (d, J=1.8 Hz, 1H), 4.58 (dd, J=7.5, 9.9 Hz, 1H), 4.40 (br s, 1H), 3.92 (s, 3H), 3.90 (s, 3H), 3.89-3.83 (m, 1H), 3.41 (d, J=11.1 Hz, 1H), 2.29-2.20 (m, 1H), 2.17-2.06 (m, 1H).

Example 94

Preparation of 1-(3,4-dimethoxy-5-trifluoromethylthiobenzoyl)-4-ethynyl-2,5-dihydro-1H-pyrrole-2R-carboxylic acid hydroxyamide

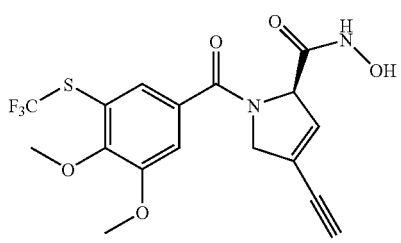

Step 1: To a stirred solution of 4R-hydroxypyrrolidine-1,2R-dicarboxylic acid 1-tert-butyl ester 2-methyl ester (30.4 g, 0.124 mol, 1.0 eq.; product from Step 2 of Example 90) in CH$_2$Cl$_2$ (800 mL) at 23° C., was added NaHCO$_3$ (103 g, 1.23 mol, 10.0 eq.), followed by Dess-Martin periodinane (61 g, 0.144 mol, 1.16 eq.). After being stirred at 23° C. for 1 h, another batch of Dess-Martin periodinane (14 g, 0.033 mol, 0.27 eq.) was added. After 3 h, the reaction mixture was quenched by addition of aqueous solution of Na$_2$S$_2$O$_3$ and extracted with CH$_2$Cl$_2$ (3×300 mL). The combined organic layer was washed with brine, dried (Na$_2$SO$_4$) and concentrated in vacuo. The residue was chromatographed on silica gel (EtOAc/Hexane: 0%-40%) to afford 4-oxopyrrolidine-1,2R-dicarboxylic acid 1-tert-butyl ester 2-methyl ester (14.3 g, 48%).

Step 2: To a stirred solution of 4-oxopyrrolidine-1,2R-dicarboxylic acid 1-tert-butyl ester 2-methyl ester (14.3 g, 58.8 mmol, 1.0 eq.) in ThF (120 mL) at −78° C., was added NaHMDS (65 mL, 65 mmol, 1.1 eq., 1.0 M solution in THF) dropwise over 10 min. After 20 min, a cold (0° C.) solution of N-phenyl trifluoromethane sulfonimide (22.7 g, 63.5 mmol, 1.1 eq.) in THF (120 mL) was added and the reaction mixture was warmed to 4° C. and stirred for 17 hours. The reaction mixture was concentrated in vacuo and chromatographed on silica gel (EtOAc/Hexane: 0%-10%) to afford 4-trifluoromethanesulfonyloxy-2,5-dihydropyrrole-1,2R-dicarboxylic acid 1-tert-butyl ester 2-methyl ester (11.5 g, 52%) along with benzenesulfonamide (1:1 ratio according to $^1$H NMR). This was used without further purification.

Step 3: To a stirred solution of 4-trifluoromethanesulfonyloxy-2,5-dihydropyrrole-1,2R-dicarboxylic acid 1-tert-butyl ester 2-methyl ester (1.5 g, 4.0 mmol, 1 eq.) in Et$_3$N (10 mL) and benzene (10 mL) at 23° C. was added CuI (76 mg, 0.4 mmol, 0.1 eq.), Pd(PPh$_3$)$_4$ (90 mg, 0.08 mmol, 0.02 eq.) and (trimethylsilyl)acetylene (1.13 mL, 8 mmol, 2 eq.). After stirring for 20 h at 23° C., the solvent was removed and the residue was chromatographed on silica gel (EtOAc/Hexane: 00%-10%) to afford 4-(trimethylsilanylethynyl)-2,5-dihydropyrrole-1,2R-dicarboxylic acid 1-tert-butyl ester 2-methyl ester (1.8 g, 100%).

Step 4: To a stirred solution of 4-(trimethylsilanylethynyl)-2,5-dihydropyrrole-1,2R-dicarboxylic acid 1-tert-butyl ester 2-methyl ester (1.8 g, 5.56 mmol, 1.0 eq.) in THF (32 mL) at 0° C. was added TBAF (1.0 M solution in THF, 8.5 mL, 8.5 mmol, 1.53 eq.). The resulting solution was stirred at 0° C. for 60 min, then the reaction mixture was diluted with 1.0M HCl solution (200 mL), and extracted with EtOAc (3×70 mL). The combined organic layer was washed with brine (100 mL), dried (Na$_2$SO$_4$), concentrated in vacuo and the residue was chromatographed on silica gel (EtOAc/Hexane: 0%-40%) to afford 4-ethynyl-2,5-dihydropyrrole-1,2-dicarboxylic acid 1-tert-butyl ester 2-methyl ester (0.15 g, 11%).

Step 5: 4-Ethynyl-2,5-dihydropyrrole-1,2R-dicarboxylic acid 1-tert-butyl ester 2-methyl ester (0.151 g, 0.6 mmol, 1.0 eq.) was dissolved in anhydrous 4.0 M HCl/dioxane solution (3.0 mL) at 23° C. and stirred for 2 h. The solvent was removed in vacuo and the product was used without further purification.

Step 6: 1-(3,4-Dimethoxy-5-trifluoromethylthiobenzoyl)-4-ethynyl-2,5-dihydro-1H-pyrrole-2R-carboxylic acid methyl ester was prepared by reacting 4-ethynyl-2,5-dihydropyrrole-2R-carboxylic acid methyl ester hydrochloride salt with 3,4-dimethoxy-5-trifluoromethylthiobenzoyl chloride (Product from Step 1 of Example 88) following Method W in 14 h. The residue was chromatographed on silica gel (EtOAc/Hexane: 0%40%) to afford 1-(3,4-dimethoxy-5-trifluoromethylthiobenzoyl)-4-ethynyl-2,5-dihydro-1H-pyrrole-2R-carboxylic acid methyl ester 60% yield.

Step 7: 1-(3,4-Dimethoxy-5-trifluoromethylthiobenzoyl)-4-ethynyl-2,5-dihydro-1H-pyrrole-2R-carboxylic acid hydroxyamide was prepared from 1-(3,4-dimethoxy-5-trifluoromethylthiobenzoyl)-4-ethynyl-2,5-dihydro-1H-pyrrole-2R-carboxylic acid methyl ester following Method B in 17 h. ESMS: m/z 415.4 [M–H]. $^1$H NMR (300 MHz, CD$_3$OD): 7.43 (s, 1H), 7.39 (s, 1H), 7.16 (d, 1H), 6.01 (m, 1H), 5.22 (m, 1H), 4.44 (m, 1H), 4.10 (d, 1H), 3.84 (s, 3H), 3.82 (s, 3H), 3.57 (s, 1H).

Example 95

Preparation of 1-(3,4-dimethoxy-5-trifluoromethylthiobenzoyl)-2,5-dihydro-1H-pyrrole-2R-carboxylic acid hydroxyamide

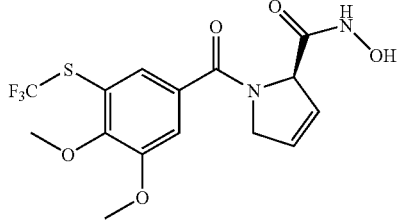

Step 1: To a mixture of 4-trifluoromethanesulfonyloxy-2,5-dihydropyrrole-1,2R-dicarboxylic acid 1-tert-butyl ester 2-methyl ester (1.0 g, 2.7 mmol, 1.0 eq.), Pd(PPh$_3$)$_2$(OAc$_2$ (100 mg, 0.133 mmol, 0.05 eq.) was added DMF (10 mL), Bu$_3$N (1.9 mL, 7.97 mmol, 2.95 eq.), and formic acid (0.2 mL, 5.3 mmol, 2.0 eq.). The resulting reaction mixture was stirred at 60° C. for 15 h and cooled to room temperature. This was quenched by addition of aqueous HCl (1.0 M) and extracted with EtOAc (3×70 mL). The combined organic layer was washed with brine (200 mL), dried (Na$_2$SO$_4$), and concentrated in vacuo. The residue was chromatographed on silica gel (EtOAc/hexane: 0%-20%) to afford 2,5-dihydropyrrole-1,2R-dicarboxylic acid 1-tert-butyl ester 2-methyl ester (0.5 g, 83%).

Step 2: 2,5-Dihydropyrrole-1,2R-dicarboxylic acid 1-tert-butyl ester 2-methyl ester (0.161 g, 0.71 mmol, 1.0 eq.) was dissolved in anhydrous 4.0 M HCl in dioxane (4.0 mL) at 23° C. and stirred for 3 h. Dioxane was removed in vacuo and the product was used without further purification.

Step 3: 1-(3,4-Dimethoxy-5-trifluoromethylthiobenzoyl)-2,5-dihydro-1H-pyrrole-2R-carboxylic acid methyl ester was prepared by reacting 2,5-dihydro-1H-pyrrole-2R-dicarboxylic acid methyl ester hydrochloride salt with 3,4-dimethoxy-5-trifluoromethylthiobenzoyl chloride (Product from Step 1 of Example 88) according to Method W in 19 h. The residue was chromatographed on silica gel (EtOAc/Hexane: 0%-40%) to afford 1-(3,4-dimethoxy-5-trifluoromethylthiobenzoyl)-2,5-dihydro-1H-pyrrole-2R-carboxylic acid methyl ester in 69% yield Step 4: 1-(3,4-Dimethoxy-5-trifluoromethylthiobenzoyl)-2,5-dihydro-1H-pyrrole-2R-carboxylic acid hydroxyamide was prepared from 1-(3,4-dimethoxy-5-trifluoromethylthiobenzoyl)-2,5-dihydro-1H-pyrrole-2R-carboxylic acid methyl ester according to Method B 17 h. ESMS: m/z 391.4 [M−H]. $^1$H NMR (300 MHz, CD$_3$OD): 7.50 (m, 2H), 7.22 (d, 1H), 6.01 (m, 1H), 5.82 (m, 1H), 5.24 (m, 1H), 4.54 (m, 1H), 4.20 (m, 1H), 3.92 (s, 3H), 3.90 (s, 3H).

Example 96

Preparation of 1-(3,4-dimethoxy-5-trifluoromethylthiobenzoyl)-2,5-dihydro-1H-pyrrole-2R-carboxylic acid hydroxyamide

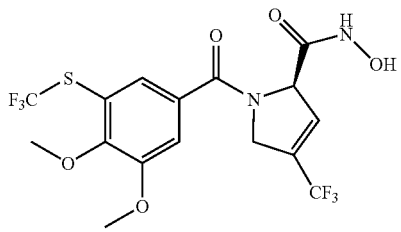

Step 1: To a stirred solution of 4-oxopyrrolidine-1,2R-dicarboxylic acid 1-tert-butyl ester 2-methyl ester (1.5 g, 6.18 mmol; product from Step 1 of Example 94) in THF (30 mL) at 0° C. was added CF$_3$Si(CH$_3$)$_3$ (1.05 mL, 6.55 mmol, 1.06 eq.) and TBAF (218 µL). The mixture was warmed to room temperature and stirred overnight. Saturated aqueous NH$_4$Cl (11 mL) was added and the mixture was stirred for 15 min, then TBAF (10 mL, 1.0 M in THF) was added and the mixture was stirred for 1 h. The organic layer was separated and the aqueous layer was extracted with Et$_2$O (3×100 mL). The combined organic layer was washed with water, brine, dried over Na$_2$SO$_4$ and concentrated in vacuo. The residue was purified by flash chromatography (1:1 EtOAc:hexanes as an eluent) to yield 4R-hydroxy-4-trifluoromethylpyrrolidine-1,2R-dicarboxlic acid tert-butyl ester 2-methyl ester (1.54 g, 80%).

Step 2: A mixture of 4R-hydroxy-4-trifluoromethylpyrrolidine-1,2R-dicarboxlic acid tert-butyl ester 2-methyl ester (385 mg, 1.23 mmol, 1 eq.), pyridine (15 mL), and SOCl$_2$ (1.15 mL) was heated to reflux under nitrogen for 30 min. After cooling to room temperature, H$_2$O (4 mL) was added to quench the reaction. The reaction mixture was passed through a pad of celite and the filtrate was extracted with EtOAc (3×100 mL). The organic layer was washed with 1.0 N HCl (150 mL), saturated aqueous sodium bicarbonate solution (150 mL), H$_2$O (150 mL), brine (150 mL) dried MgSO$_4$ and concentrated in vacuo to yield 4-trifluoromethyl-2,5-dihydropyrrole-1,2R-dicarboxlic acid tert-butyl ester 2-methyl ester (249 mg, 69%).

Step 3: To 4-trifluoromethyl-2,5-dihydropyrrole-1,2R-dicarboxlic acid tert-butyl ester 2-methyl ester (120 mg, 0.41 mmol) at 0° C. was added anhydrous 4.0 M HCl in dioxane (3.0 mL), and the reaction mixture was stirred for 30 min then at room temperature for 3 h. The solvent removed in vacuo and the residue was used without further purification.

Step 4: 1-(3,4-Dimethoxy-5-trifluoromethylthiobenzoyl)-2,5-dihydro-1H-pyrrole-2R-carboxylic acid methyl ester was prepared by reacting 4-trifluoromethyl-2,5-dihydropyrrole-2R-carboxylic acid methyl ester hydrochloride salt with 3,4-dimethoxy-5-trifluoromethylthiobenzoyl chloride (Product from Step 1 of Example 88) according to Method W. The residue was used without further purification. ESMS: 460.5 [M+H].

Step 5: 1-(3,4-Dimethoxy-5-trifluoromethylthiobenzoyl)-2,5-dihydro-1H-pyrrole-2R-carboxylic acid hydroxyamide was prepared from 1-(3,4-dimethoxy-5-trifluoromethylthiobenzoyl)-2,5-dihydro-1H-pyrrole-2R-carboxylic acid methyl ester according to Method B in 4 h. ESMS: m/z 459.5 [M−H]. $^1$H NMR (300 MHz, CD$_3$OD): 7.46 (s, 1H), 7.40 (s, 1H), 6.43-6.40 (m, 1H), 5.38-5.30 (m, 1H), 4.67-4.53 (m, 2H) 4.33-4.27 (m, 1H), 3.84 (s, 3H), 3.82 (s, 3H).

Example 97

Preparation of 1-(3,4-dimethoxy-5-trifluoromethylthiobenzoyl)-4R-trifluoromethylpyrrolidine-2R-carboxylic acid hydroxyamide

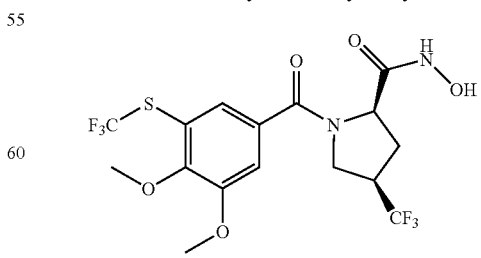

Step 1: To a solution of 4-trifluoromethyl-2,5-dihydropyrrole-1,2R-dicarboxlic acid tert-butyl ester 2-methyl ester (100 mg, 0.34 mmol; Product from Step 2 of Example 96) in MeOH (10 mL) was added Pd/C (70 mg, 70 wt. %). This was subjected to catalytic hydrogenation using a balloon pressure of hydrogen at room temperature for overnight. The catalyst was filtered through a pad of Celite and the filtrate was concentrated in vacuo to furnish 4R-trifluoromethylpyrrolidine-1,2R-dicarboxylic acid 1-tert-butyl ester 2-methyl ester (55 mg, 54%).

Step 2: To a solution of 4R-trifluoromethylpyrrolidine-1,2R-dicarboxylic acid 1-tert-butyl ester 2-methyl ester (55 mg, 0.18 mmol) at 0° C. was added anhydrous 4.0 M HCl in dioxane (2.0 mL), and stirred for 30 min. The reaction mixture was warmed to room temperature and stirred for another 3 h. Removal of the solvent in vacuo gave the product and used without further purification.

Step 3: 1-(3,4-Dimethoxy-5-trifluoromethylthiobenzoyl)-4R-trifluoromethylpyrrolidine-2R-carboxylic acid methyl ester was prepared by reacting 4R-trifluoromethylpyrrolidine-2R-carboxylic acid methyl ester hydrochloride salt with 3,4-dimethoxy-5-trifluoromethylthiobenzoyl chloride (Product from Step 1 of Example 88) according to Method W. The product obtained was used without further purification. ESMS: m/z 462.5 [M+H].

Step 4: To a solution of 1-(3,4-Dimethoxy-5-trifluoromethylthiobenzoyl)-4R-trifluoromethylpyrrolidine-2R-carboxylic acid methyl ester (80 mg, 0.17 mmol, 1 eq.) in methanol (5 mL) at 23° C. was added NaOMe (0.5 M in MeOH, 1.04 mL, 0.52 mmol, 3 eq.), followed by hydroxylamine hydrochloride (24 mg, 0.34 mmol, 2 eq.), and the reaction mixture was stirred at room temperature for 24 h. The reaction mixture was concentrated and the crude product was purified by preparative HPLC($H_2O$/Acetonitrile in 0.1% TFA) to furnish 1-(3,4-dimethoxy-5-trifluoromethylthiobenzoyl)-4R-trifluoromethylpyrrolidine-2R-carboxylic acid hydroxyamide. ESMS: m/z 461.5 [M–H]. $^1$H NMR (300 MHz, $CD_3OD$): 7.42 (s, 1H), 7.38 (s, 1H), 4.47-4.42 (m, 1H), 3.83 (s, 3H), 3.81 (s, 3H), 3.74-3.65 (m, 2H), 3.15-3.05 (m, 1H), 2.53-2.43 (m, 1H), 2.13-2.03 (m, 1H).

Example 98

Preparation of 1-(3,4-dimethoxy-5-trifluoromethylthiobenzoyl)-4S-(naphthalene-2-yloxy)pyrrolidine-2R-carboxylic acid hydroxyamide

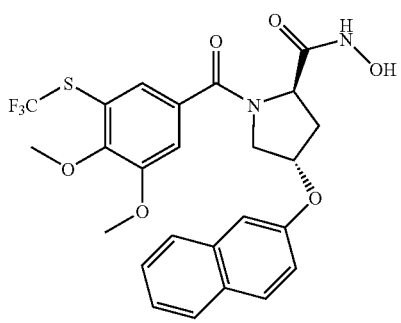

Step 1: To a stirred mixture of 4R-hydroxypyrrolidine-1,2R-dicarboxylic acid 1-tert-butyl ester 2-methyl ester (1.0 g, 4.07 mmol, 1 eq.; Product from Step 2 of Example 90), 2-naphthol (1.19 g, 8.15 mmol, 2 eq.), and $Ph_3P$ (2.38 g, 8.97 mmol, 2.20 eq.) in dry THF (50 mL) at 0° C. was added DIAD (1.86 mL, 8.97 mmol, 2.20 eq.) dropwise. The reaction was allowed to warm to room temperature and stirred for 8 h. The solvent was removed in vacuo and the residue was pre-adsorbed in silica gel and chromatographed using 30% EtOAc in hexanes as an eluent to afford 4S-(naphthalen-2-yloxy) pyrrolidine-1,2R-dicarboxylic acid 1-tert-butyl ester 2-methyl ester in 79% yield. ESMS: m/z 394.5 [M+Na].

Step 2: To 4S-(naphthalen-2-yloxy)pyrrolidine-1,2R-dicarboxylic acid 1-tert-butyl ester 2-methyl ester (180 mg, 0.48 mmol, 1 eq.) was added 4 M HCl in dioxane (2.5 mL) at 0° C. and then warmed the reaction to room temperature for 3 h. The dioxane was removed in vacuo to afford the residue, which was used without further purification.

Step 3: 1-(3,4-dimethoxy-5-trifluoromethylthiobenzoyl)4S-(naphthalene-2-yloxy)-pyrrolidine-2R-carboxylic acid methyl ester was prepared by reacting 4S-(naphthalen-2-yloxy)pyrrolidine-2R-carboxylic acid methyl ester hydrochloride salt with 3,4-dimethoxy-5-trifluoromethylthiobenzoyl chloride (Product from Step 1 of Example 88) according to Method W. The product was used without further purification. ESMS: m/z 536.7 [M+H].

Step 4: 1-(3,4-Dimethoxy-5-trifluoromethylthiobenzoyl)-4S-(naphthalene-2-yloxy)pyrrolidine-2R-carboxylic acid hydroxyamide was prepared from 1-(3,4-dimethoxy-5-trifluoromethylthiobenzoyl)-4S-(naphthalene-2-yloxy)pyrrolidine-2R-carboxylic acid methyl ester according to Method B in 8 h. ESMS: m/z 535.7 [M–H] $^1$H NMR (300 MHz, $CD_3OD$): 7.62 (m, 3H), 7.26 (m, 4H), 7.09 (m, 1H), 6.98 (m, 1H), 5.10 (m, 1H), 4.59 (m, 1H), 3.97 (m, 1H), 3.73 (s, 6H), 3.70 (m, 1H), 2.52 (m, 1H), 2.31 (m, 1H).

Example 99

Preparation of 4S-(biphenyl-4-yloxy)-1-(3,4-dimethoxy-5-trifluoromethylthiobenzoyl)-pyrrolidine-2R-carboxylic acid hydroxyamide

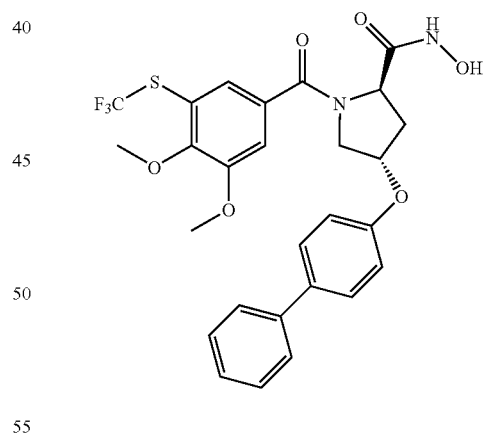

Step 1: To a stirred mixture of 4R-hydroxypyrrolidine-1,2R-dicarboxylic acid 1-tert-butyl ester 2-methyl ester (1.0 g, 4.07 mmol, 1 eq.; Product from Step 2 of Example 90), biphenyl-4-ol (1.43 g, 8.15 mmol, 2 eq.), and $Ph_3P$ (2.38 g, 8.97 mmol, 2.20 eq.) in dry THF (50 mL) at 0° C. was added DIAD (1.86 mL, 8.97 mmol, 2.20 eq.) dropwise. The reaction was allowed to warm to room temperature and stirred for 8 h. The solvent was removed in vacuo and the residue was pre-adsorbed on to silica gel and chromatographed on silica gel using 30% EtOAc/hexanes as an eluent to afford 4S-(biphenyl-4-yloxy)pyrrolidine-1,2R-dicarboxylic acid 1-tert-butyl ester 2-methyl ester in 47% yield. ESMS: m/z 420.6 [M+Na].

Step 2: To 4S-(biphenyl-4-yloxy)pyrrolidine-1,2R-dicarboxylic acid 1-tert-butyl ester 2-methyl ester (210 mg, 0.53 mmol, 1 eq.) was added anhydrous 4 M HCl in dioxane (2.5 mL) at 0° C. and then warmed the reaction to rt for 3 h. The dioxane was removed in vacuo and the residue was used without further purification.

Step 3: 4S-(Biphenyl-4-yloxy)-1-(3,4-dimethoxy-5-trifluoromethylthiobenzoyl)-pyrrolidine-2R-carboxylic acid methyl ester was prepared by reacting 4S-(biphenyl-4-yloxy) pyrrolidine-2R-carboxylic acid methyl ester hydrochloride salt with 3,4-dimethoxy-5-trifluoromethylthiobenzoyl chloride (Product from Step 1 of Example 88) according to Method W. The product was used without further purification. ESMS: m/z 562.7 [M+H].

Step 4: 4S-(Biphenyl-4-yloxy)-1-(3,4-dimethoxy-5-trifluoromethylthiobenzoyl)-pyrrolidine-2R-carboxylic acid hydroxyamide was prepared from 4S-(biphenyl-4-yloxy)-1-(3,4-dimethoxy-5-trifluoromethylthiobenzoyl)pyrrolidine-2R-carboxylic acid methyl ester according to Method B in 8 h. ESMS: m/z 561.5 [M–H]. $^1$H NMR (300 MHz, CD$_3$OD): 7.42 (m, 6H), 7.26 (m, 2H), 7.16 (m, 1H), 6.83 (d, 2H), 4.99 (m, 1H), 4.57 (m, 1H), 3.93 (m, 1H), 3.76 (s, 6H), 3.63 (m, 1H), 2.48 (m, 1H), 2.27 (m, 1H).

Example 100

Preparation of 4R-(biphenyl-4-yloxy)-1-(3,4-dimethoxy-5-trifluoromethylthiobenzoyl)-pyrrolidine-2R-carboxylic acid hydroxyamide

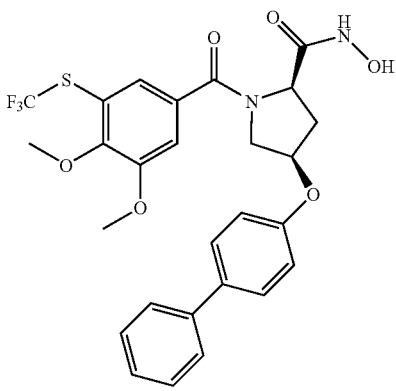

Step 1: To a mixture of 4S-hydroxypyrrolidine-1,2R-dicarboxylic acid 1-tert-butyl ester 2-methyl ester (1.0 g, 4.08 mmol, 1 eq.; Product from Step 2 of Example 91), biphenyl-4-ol (860 mg, 4.89 mmol, 1.2 eq.), and Ph$_3$P (1.64 g, 6.12 mmol, 1.5 eq.) in dry THF (50 mL) at 0° C. was added DIAD (1.27 mL, 6.12 mmol, 1.5 eq.) dropwise. The reaction was allowed to warm to rt and stirred for 8 h. The solvent was removed in vacuo and the residue was pre-adsorbed on to silica gel and chromatographed on silica gel using in 30% EtOAc/hexanes as an eluent to afford 4R-(biphenyl-4-yloxy)pyrrolidine-1,2-dicarboxylic acid 1-tert-butyl ester 2-methyl ester.

Step 2: To 4R-(biphenyl-4-yloxy)pyrrolidine-1,2R-dicarboxylic acid 1-tert-butyl ester 2-methyl ester (155 mg, 0.39 mmol, 1 eq.) was added anhydrous 4 M HCl in dioxane (2.5 mL) at 0° C. and then warmed the reaction to rt for 3 h. The dioxane was removed in vacuo and the residue was used without further purification.

Step 3: 4R-(Biphenyl-4-yloxy)-1-(3,4-dimethoxy-5-trifluoromethylthiobenzoyl)-pyrrolidine-2R-carboxylic acid methyl ester was prepared by reacting 4R-(biphenyl-4-yloxy) pyrrolidine-2R-carboxylic acid methyl ester hydrochloride salt with 3,4-dimethoxy-5-trifluoromethylthiobenzoyl chloride (Product from Step 1 of Example 88) according to Method W. The product was used without further purification. ESMS: m/z 562.7 [M+H].

Step 4: 4R-(Biphenyl-4-yloxy)-1-(3,4-dimethoxy-5-trifluoromethylthiobenzoyl)-pyrrolidine-2R-carboxylic acid hydroxyamide was prepared from 4R-(biphenyl-4-yloxy)-1-(3,4-dimethoxy-5-trifluoromethylthiobenzoyl)-pyrrolidine-2R-carboxylic acid methyl ester according to Method B in 8 h. ESMS: m/z 561.5 [M–H]. $^1$H NMR (300 MHz, CD$_3$OD): 7.42 (m, 6H), 7.25 (m, 2H), 7.16 (m, 1H), 6.90 (d, 2H), 4.97 (m, 1H), 4.64 (m, 1H), 3.81 (s, 6H), 3.78 (m, 2H), 2.55 (m, 1H), 2.40 (m, 1H).

Example 101

Preparation of 1-(3,4-dimethoxy-5-trifluoromethylthiobenzoyl)-4,4-difluoropyrrolidine-2R-carboxylic acid hydroxyamide

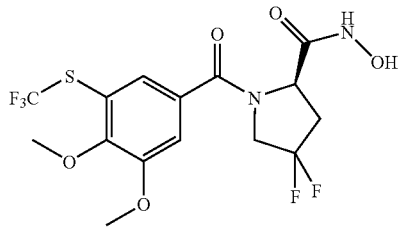

Step 1: To a portion of 4-oxopyrrolidine-1,2R-dicarboxylic acid 1-tert-butyl ester 2-methyl ester (650 mg, 2.67 mmol, 1 eq.; Product from Step 1 of Example 94) in dichloromethane (12 mL) at –78° C. was added DAST (0.4 mL), and the reaction mixture was stirred for 30 min. A second eq. of DAST (0.4 mL) was added and the reaction mixture was stirred for a further 1 h. The reaction mixture was warmed to –5° C. and quenched by adding saturated aqueous sodium bicarbonate (30 mL). The quenched reaction mixture was diluted with CH$_2$Cl$_2$ (100 mL), the organic layer was separated, washed with brine (100 mL), dried MgSO$_4$ and concentrated in vacuo. Column chromatography (1:1 EtOAc:hexane as an eluent) furnished 4,4-difluoropyrrolidine-1,2R-dicarboxylic acid 1-tert-butyl ester 2-methyl ester as a clear oil (391 mg, 55%).

Step 2: To 4,4-difluoropyrrolidine-1,2R-dicarboxylic acid 1-tert-butyl ester 2-methyl ester (391 mg, 1.47 mmol) at 0° C. was added anhydrous 4.0 M HCl in dioxane (7.0 mL), and the reaction mixture was stirred for 30 min. The reaction mixture was warmed to room temperature and stirred for another 3 h. The reaction mixture was concentrated in vacuo to yield 4,4-difluoropyrrolidine-2R-dicarboxylic acid methyl ester hydrochloride salt as a white solid (242 mg, 100%).

Step 3: 1-(3,4-Dimethoxy-5-trifluoromethylthiobenzoyl)-4,4-difluoropyrrolidine-2R-carboxylic acid methyl ester was prepared by coupling 4,4-difluoropyrrolidine-2R-dicarboxylic acid methyl ester hydrochloride salt with 3,4-dimethoxy-5-trifluoromethylthiobenzoyl chloride (Product from Step 1 of Example 88) according to Method W in 14 h. The resulting product was used without further purification. ESMS: 430.5 [M+H].

Step 4: 1-(3,4-Dimethoxy-5-trifluoromethylthiobenzoyl)-4,4-difluoropyrrolidine-2R-carboxylic acid hydroxyamide was prepared from 1-(3,4-dimethoxy-5-trifluoromethylthiobenzoyl)-4,4-difluoropyrrolidine-2R-carboxylic acid methyl ester following Method B in 1 h. ESMS: 429.5 [M–H]. $^1$H NMR (300 MHz, CD$_3$OD): 7.48 (s, 1H), 7.45 (s, 1H), 4.69 (t, J=9.9 Hz, 1H), 4.25-4.06 (m, 1H), 3.93 (s, 3H), 3.92 (s, 3H), 3.90-3.78 (m, 1H), 2.85-2.68 (m, 1H), 2.65-2.44 (m, 1H).

The following Methods may be used to test compounds of this invention.

Example A

Susceptibility Testing

Compounds were tested following the microdilution method of NCCLS (National Committee for Clinical Laboratory Standards. Methods for dilution antimicrobial susceptibility tests for bacteria that grow aerobically; Approved standard—fifth edition. NCCLS document M7-A5, NCCLS, Wayne, Pa. 2000). Assays were performed in sterile plastic 96-well microtiter trays with round bottom wells (Greiner).

Compound Preparation

Stock solutions of test compounds and control antibiotics are prepared at 10 mg/ml in DMSO. Serial 2-fold dilutions of each drug are performed in a microtiter plate across each row using DMSO as solvent at 100-fold the desired final concentration. Wells in columns #1-11 contain drug and column #12 was kept as a growth control for the organism with no drug. Each well in the mother plate is diluted with sterile deionized water and DMSO, mixed, and volumes of 10 µl distributed to each well in the resulting assay plates.

Preparation of Inoculum

Stock cultures were prepared using the Microbank™ method (Pro-Lab Diagnostics) and stored at −80° C. To propagate each strain, one bead was removed from the frozen vial and aseptically streaked onto Trypticase Soy Agar (Difco) which were incubated at 35° C. Standardized inocula were prepared using the direct colony suspension method according to NCCLS guidelines (National Committee for Clinical Laboratory Standards. Methods for dilution antimicrobial susceptibility tests for bacteria that grow aerobically; Approved standard—fifth edition. NCCLS document M7-A5, NCCLS, Wayne, Pa., 2000). Isolated colonies were selected from an 18-24 hr agar plate and resuspended in 0.9% sterile saline to match a 0.5 McFarland turbidity standard. The suspension was used within 15 minutes of preparation.

| | |
|---|---|
| Escherichia coli VECO1003 | Escherichia coli ATCC 25922 |
| Escherichia coli VECO2096 | Escherichia coli MG1655 |
| Escherichia coli VECO2526 tolC | Escherichia coli MG1655 tolC |
| Enterobacter cloacae VECL1001 | Enterobacter cloacae ATCC 35030 |
| Klebsiella pneumoniae VKPN1001 | Klebsiella pneumoniae ATCC 10031 |
| Morganella morganii VMMO1001 | Morganella morganii ATCC 25830 |
| Pseudomonas aeruginosa VPAE1003 | Pseudomonas aeruginosa ATCC 35032 |
| Pseudomonas aeruginosa VPAE1004 | Pseudomonas aeruginosa ATCC 27853 |
| Pseudomonas aeruginosa VPAE1010 | Pseudomonas aeruginosa K799 |
| Pseudomonas aeruginosa VPAE1010 | Pseudomonas aeruginosa K799/61 |
| Staphylococcus aureus VSAU1003 | Staphylococcus aureus ATCC 25923 |

Preparation of Assay Plates for MICs

Mueller-Hinton Broth MHB (Difco) was prepared at a 1.1× concentration and supplemented with Ca$^{++}$ and Mg$^{++}$ as recommended by NCCLS. For each organism, the standardized suspension was diluted 1:180 into appropriate growth medium in a sterile reservoir. After mixing, wells in the drug-containing assay plates were inoculated with a volume of 90 µl. Thus, for each MIC determination, each well contains a final volume of 100 µl with an inoculum size of approximately 5×10$^5$ cfu/ml and no more than 5% DMSO.

Interpretation of MIC

The completed microtiter plates were incubated 16-20 h at 35° C. in ambient air. Optical density of each well was determined at 600 nm using a VersaMax Microplate reader (Molecular Devices, Sunnyvale, Calif.). The MIC was defined as the lowest drug concentration causing complete suppression of visible bacterial growth.

Example B

Efficacy in Murine *E. coli* Septicemia

Efficacy studies were performed in an *E. coli* murine septicemia model according to models published elsewhere (Goldstein, B. P., G. Candiani, T. M. Arain, G. Romano, I. Ciciliato, M. Berti, M. Abbondi, R. Scotti, M. Mainini, F. Ripamonti, and et al. 1995. Antimicrobial activity of MDL 63,246, a new semisynthetic glycopeptide antibiotic Antimicrob Agents Chemother. 39:1580-1588; Misiek, M., T. A. Pursiano, F. Leitner, and K. E. Price 1973. Microbiological properties of a new cephalosporin, BL-S 339: 7-(phenylacetimidoyl-aminoacetamido)-3-(2-methyl-1,3,4-thiadiazol-5-ylthio methyl)ceph-3-em-4-carboxylic acid Antimicrob Agents Chemother. 3:40-48).

Compound Preparation

The compound was dissolved in 10% DMSO, 0.1% Tween 80, 0.9% NaCl solution and administered intravenously at 10 ml/kg at 1 hour after bacterial inoculation. The compound was administered at 80, 40, 20, 5, 2.5, and 1.25 mg/kg. A control with ampicillin was included in the evaluation.

Efficacy Model

Male or female ICR mice weighing 22±2 g from MDS Pharma Services were used for the evaluation. Food and water was given ad libitum. Groups of 6 mice weighing 22+g were used for the experiment. Mice were inoculated intraperitoneally with *Escherichia coli* ATCC 25922 at 4×10$^4$ CFU in 0.5 ml of Brain Heart Infusion Broth (Difco) containing 5% mucin (Sigma). Mortality was recorded once daily for 7 days following bacterial inoculation. The ED50 was determined by non-linear regression and is 28.3 for the compound and 14.1 for ampicillin.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

Example C

Efficacy in Murine *Proteus vulgaris* Septicemia

Efficacy studies were performed in an *P. vulgaris* murine septicemia model according to models published elsewhere (Goldstein, B. P., G. Candiani, T. M. Arain, G. Romano, I. Ciciliato, M. Berti, M. Abbondi, R. Scotti, M. Mainini, F. Ripamonti, and et al. 1995. Antimicrobial activity of MDL 63,246, a new semisynthetic glycopeptide antibiotic Antimicrob Agents Chemother. 39:1580-1588; Misiek, M., T. A. Pursiano, F. Leitner, and K. E. Price 1973. Microbiological properties of a new cephalosporin, BL-S 339: 7-(phenylacetimidoyl-aminoacetamido)-3-(2-methyl-1,3,4-thiadiazol-5-ylthio methyl)ceph-3-em-4-carboxylic acid Antimicrob Agents Chemother. 3:40-48).

Compound Preparation

The compound was dissolved in 10% DMSO, 0.1% Tween 80, 0.9% NaCl solution and administered intravenously at 10 ml/kg at 1 hour after bacterial inoculation. The compound was administered at 20, 10, 5, 2.5, and 1.25 mg/kg. A control with ampicillin was included in the evaluation.

Efficacy Model

Male or female ICR mice weighing 24±2 g from MDS Pharma Services were used for the evaluation. Food and water was given ad libitum. Groups of 6 mice weighing 24±g were used for the experiment. Mice were inoculated intraperitoneally with *Proteus vulgaris* ATCC 13315 at 1×10$^8$ CFU in 0.5 ml of Brain Heart Infusion Broth (Difco) containing 5% mucin (Sigma). Mortality was recorded once daily for 7 days following bacterial inoculation. The ED50 was determined by non-linear regression and is 11.7 for the compound and 29.7 for ampicillin.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

Example D

Efficacy in Murine *Klebsiella pneumoniae* Septicemia

Efficacy studies were performed in an *K. pneumoniae* murine septicemia model according to models published elsewhere (Goldstein, B. P., G. Candiani, T. M. Arain, G. Romano, I. Ciciliato, M. Berti, M. Abbondi, R. Scotti, M. Mainini, F. Ripamonti, and et al. 1995. Antimicrobial activity of MDL 63,246, a new semisynthetic glycopeptide antibiotic Antimicrob Agents Chemother. 39:1580-1588; Misiek, M., T. A. Pursiano, F. Leitner, and K. E. Price 1973. Microbiological properties of a new cephalosporin, BL-S 339: 7-(phenylacetimidoyl-aminoacetamido)-3-(2-methyl-1,3,4-thiadiazol-5-ylthio methyl)ceph-3-em-4-carboxylic acid Antimicrob Agents Chemother. 3:40-48).

Compound Preparation

The compound was dissolved in 10% DMSO, 0.1% Tween 80, 0.9% NaCl solution and administered intravenously at 10 ml/kg at 1 hour after bacterial inoculation. The compound was administered at 20, 10, 5, 2.5, and 1.25 mg/kg. A control with ampicillin was included in the evaluation.

Efficacy Model

Male or female ICR mice weighing 24±2 g from MDS Pharma Services were used for the evaluation. Food and water was given ad libitum. Groups of 6 mice weighing 24±g were used for the experiment. Mice were inoculated intraperitoneally with *Klebsiella pneumoniae* ATCC 10031 at 3×10$^7$ CFU in 0.5 ml of Brain Heart Infusion Broth (Difco) containing 5% mucin (Sigma). Mortality was recorded once daily for 7 days following bacterial inoculation. The ED50 was determined by non-linear regression and is 10.1 for the compound and 6.8 for ampicillin.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. The compound of formula I:

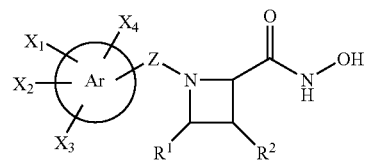

wherein

Ar is phenyl or 2,5-dihydro-benzo[b]oxepine;

$X_1$, $X_2$, $X_3$, and $X_4$ are independently selected from the group consisting of hydrogen, alkyl, haloalkyl, alkylthio, alkylsulfinyl, alkylsulfonyl, hydroxyalkyl, alkoxy, alkoxyalkyl, haloalkoxy, alkenyl, alkenoxy, alkenoxyalkyl, alkynyl, alkynyloxy, nitro, halo, hydroxy, cycloalkyl, haloalkylthio, haloalkylsulfinyl, haloalkylsulfonyl, alkylsilylalkynyl, alkynyloxy, anaminocarbonylalkyl, carboxylate, carboxyl, carboxamide;

$R^1$ and $R^3$ are independently selected from the group consisting of hydrogen and alkyl;

$R^2$ is selected from the group consisting of hydrogen and alkyl;

Z is —CH$_2$— or C(O):

or pharmaceutically acceptable salts thereof, tautomers thereof, or prodrugs thereof; and provided that the compounds of Formula I have a minimum inhibition concentration of 128 µ/ml or less against at least one of the organisms selected from the group consisting of *Acinetobacter baumannil, Acinetobacter haemolyticus, Actinobacillus actinomycetemcomitans, Aeromonas hydrophila, Bacteroides fragilis, Bacteroides theataioatamicron, Bacteroides distasonis, Bacteroides ovatus, Bacteroides vulgatus, Bordetella pertussis, Brucella melitensis, Burkholderia cepacia, Burkholderia pseudomallei, Burkholderia mallei Fusobacterium, Prevotella corporis, Prevotella intermedia, Prevotella endodontalis, Porphyromonas asaccharolytica, Campylobacter jejuni, Campylobacter fetus, Citrobacter freundii, Citrobacter koseri, Edwarsiella tarda, Eikenella corrodens, Enterobacter cloacae, Enterobacter aerogenes, Enterobacter agglomerans, Escherichia coli, Francisella tularensis, Haemophilus influenzae, Haemophilus ducreyi, Helicobacter pylori, Kingella kingae, Klebsiella pneumoniae, Klebsiella oxytoca, Klebsiella rhinoscieromatis, Klebsiella ozaenae, Legionella penumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens,*

Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydia pneumoniae, Chlamydia trachomatis, Ricketsia prowazekii, Coxiella burnetii, Ehrlichia chafeensis, and Bartonella hensenae.

2. The compound according to claim 1, wherein said compound has the formula IV:

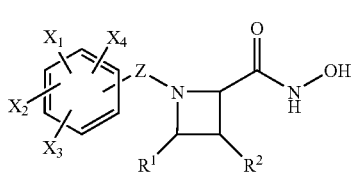

IV wherein
$X_1$, $X_2$, $X_3$, and $X_4$ are independently selected from the group consisting of hydrogen, alkyl, haloalkyl, alkylthio, alkylsulfinyl, alkylsulfonyl, hydroxyalkyl, alkoxy, alkoxyalkyl, haloalkoxy, alkenyl, alkenoxy, alkenoxyalkyl, alkynyl, alkynyloxy, nitro, halo, hydroxy, cycloalkyl, haloalkylthio, haloalkylsulfinyl, haloalkylsulfonyl, alkylsilylalkynyl, alkynyloxy. anaminocarbonylalkyl, carboxylate, carboxyl, carboxamide;

$R^1$ and $R^3$ are independently selected from the group consisting of hydrogen and alkyl;

$R^2$ is selected from the group consisting of hydrogen and alkyl;

Z is —$CH_2$— or C(O):

or pharmaceutically acceptable salts thereof, tautomers thereof, or prodrugs thereof; and provided that the compounds of Formula IV have a minimum inhibition concentration of 128 µ/ml or less against at least one of the organisms selected from the group consisting of Acinetobacter baumannii, Acinetobacter haemolyticus, Actinobacillus actinomycetemcomitans, Aeromonas hydrophila, Bacteroides fragilis, Bacteroides theataioatamicron, Bacteroides distasonis, Bacteroides ovatus, Bacteroides vulgatus, Bordetella pertussis, Brucella melitensis, Burkholderia cepacia, Burkholderia pseudomallei, Burkholderia mallei Fusobacterium, Prevotella corporis, Prevotella intermedia, Prevotella endodontalis, Porphyromonas asaccharolytica, Campylobacter jejuni, Campylobacter fetus, Citrobacter freundii, Citrobacter koseri, Edwarsiella tarda, Eikenella corrodens, Enterobacter cloacae, Enterobacter aerogenes, Enterobacter agglomerans, Escherichia coli, Francisella tularensis, Haemophilus influenzae, Haemophilus ducreyi, Helicobacter pylon, Kingella kingae, Klebsiella pneumoniae, Klebsiella oxytoca, Klebsiella rhinoscieromatis, Klebsiella ozaenae, Legionella penumophila, Moraxella catarrhalis, Morganella morganii, Neisseria gonorrhoeae, Neisseria meningitidis, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonas fluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydia pneumoniae, Chlamydia trachomatis, Ricketsia prowazekii, Coxiella burnetii, Ehrlichia chafeensis, and Bartonella hensenae.

3. The compound according to claim 1, wherein ($X_1$—)($X_2$—)($X_3$—)($X_4$—)—Ar— is selected from the group consisting of:

3,4-dimethoxy-5-propylphenyl;
9-methoxy-2,5-dihydro-benzo[b]oxepine;
3-allyl-4-allyloxy-5-methoxyphenyl;
3,4,5-triethoxyphenyl;
3,4,5-trimethoxyphenyl;
3,5-dimethyl-4-nitrophenyl;
3,5-dimethoxy-4-methylphenyl;
3-(3-hydroxypropyl)-4,5-dimethoxyphenyl;
3-trifluoromethoxyphenyl;
3,5-dibromo-4-methylphenyl;
3-methoxy-4-methylphenyl;
3,5-dimethylphenyl;
4-hydroxy-3-methoxy-5-propylphenyl;
3-(3-allyloxypropyl)-4,5-dimethoxyphenyl;
3-(3-benzyloxypropyl)-4,5-dimethoxyphenyl;
3,4-dimethoxy-5-(3-propoxypropyl)phenyl;
3-cyclopropylmethyl-4,5-dimethoxyphenyl;
3-hexyl-4,5-dimethoxyphenyl;
3,4-dimethoxy-5-pentylphenyl;
3-allyl-4-hydroxy-5-methoxyphenyl;
4-methoxy-34trifluoromethoxyphenyl;
3-propylphenyl;
3-allylphenyl;
4-allyloxy-3-trifluoromethoxyphenyl;
3-trifluoromethylphenyl;
3,4-dimethoxy-5-(3-methoxypropyl)phenyl;
3-(3-ethoxypropyl)-4,5-dimethoxyphenyl;
3-allyl-4,5-dimethoxyphenyl;
3-butyl-4,5-dimethoxyphenyl;
3,4-dimethoxy-5-(3,3,3-trifluoropropyl)phenyl;
3-dimethylcarbamoylmethyl-4,5-dimethoxyphenyl;
3,5-dibromo-4-methoxyphenyl;
3-iodo-4,5-dimethoxyphenyl;
3-(3-fluoropropyl)-4,5-dimethoxyphenyl;
3-trifluoromethylthiophenyl;
4-trifluoromethylthiophenyl;
3-trifluoromethylsulfinylphenyl;
3-(1-fluoropropyl)-4,5-dimethoxyphenyl;
3-ethynyl-4,5-dimethoxyphenyl;
4-methylthio-3-trifluoromethoxyphenyl;
4-methoxy-3-propylphenyl;
3-(2,2,2-trifluoroethylthio)phenyl;
3-pentafluoroethylthiophenyl;
3,5-diallyl-4-methoxyphenyl;
3-trifluoromethoxy-4-methoxy-5-propylphenyl;
3-bromo-4,5-dimethoxyphenyl;
3,4-dimethoxy-5-prop-1-ynylphenyl;
3,4-dimethoxy-5(2,2,2-trifluoroethoxy)phenyl;
4-methoxy-3,5-dipropylphenyl;
3-methoxy-5-propylphenyl;
4-methoxy-3-trifluoromethylthiophenyl;
3-(1,2,2,2-tetrafluoro-1-trifluoromethyl)ethylethiophenyl;
3,5-bis-trifluoromethylthiophenyl;
3-methoxy-5-trifluoromethylthiophenyl;
4-methoxy-3-propyl-5-trifluoromethylthiophenyl;
3,4-dimethoxy-5-trifluoromethylthiophenyl;
4-alloxy-3-trifluoromethylthiophenyl;

4-n-propoxy-3-trifluoromethylthiophenyl;
4-n-but-3-enyloxy-3-trifluoromethylthiophenyl;
4-n-butoxy-3-trifluoromethylthiophenyl;
4-(3-methylbut-2-enyloxy-3-trifluoromethylthiophenyl;
4-(3-fluorophenethyl)-3-trifluoromethylthiophenyl;
4-n-pentyl-3-trifluoromethylthiophenyl;
3-trifluoromethylthio-4-(trimethylsilanylethynyl)phenyl;
4-ethynyl-3-trifluoromethylthiophenyl;
4-allyl-3-trifluoromethylthiophenyl;
4-n-propyl-3-trifluoromethylthiophenyl;
3-trifluoromethylthio-4-vinylphenyl;
4-ethyl-3-trifluoromethylthiophenyl;
4-propargyloxy-3-trifluoromethylthiophenyl;
3-trifluoromethoxy-4-trifluoromethylthiophenyl;
4-ethoxy-3-trifluoromethylthio-phenyl;
4-(2,2,2-trifluoroeth-1-yloxy)-3-trifluoromethylthiophenyl;
3,4-dimethoxy-5-phenylphenyl;
3-trifluoromethoxy-4-vinylphenyl;
4-benzyloxy-3-trifluoromethylthiophenyl;
3-(3-fluorophenylethynyl)4,5-dimethoxyphenyl; and
4-ethyl-3-trifluoromethoxyphenyl.

4. The compound according to claim 1, wherein $R^2$ is selected from the group consisting of hydrogen, alkyl, alkoxy, haloalkyl, hydroxyl, aryl, substituted aryl, and alkynyl.

5. A compound selected from the group consisting of:
1-(3,4-dimethoxy-5-propylbenzoyl)azetidine-2R-carboxylic acid hydroxyamide;
1-(9-methoxy-2,5dihydro-benzo[b]oxepine-7-carbonyl)azetidine-2R-carboxylic acid hydroxyamide;
1-(3-allyl-4-allyloxy-5-methoxybenzoyl)azetidine-2R-carboxylic acid hydroxyamide;
1-(3,4,5-trimethoxybenzoyl)azetidine-2R-carboxylic acid hydroxyamide;
1-(3,4,5-trimethoxybenzoyl)azetidine-2R-carboxylic acid hydroxyamide;
1-(3,4-dimethoxy-5-propylbenzyl)azetidine-2R-carboxylic acid hydroxyamide;
1-(3,5-dimethyl-4-nitrobenzoyl)azetidine-2R-carboxylic acid hydroxyamide;
1-(3,5-dimethoxy-4-methylbenzoyl)azetidine-2R-carboxylic acid hydroxyamide;
1-[3-(3-hydroxypropyl)-4,5-dimethoxybenzoyl]azetidine-2R-carboxylic acid hydroxyamide;
1-(3-trifluoromethoxybenzoyl)azetidine-2R-carboxylic acid hydroxyamide;
1-(3,5-dibromo-4-methylbenzoyl)azetidine-2R-carboxylic acid hydroxyamide;
1-(3-methoxy-4-methylbenzoyl)azetidine-2R-carboxylic acid hydroxyamide;
1-(3,5-dimethylbenzoyl)azetidine-2R-carboxylic acid hydroxyamide;
1-(4-hydroxy-3-methoxy-5-propylbenzoyl)azetidine-2R-carboxylic acid hydroxyamide;
1-[3-(3-allyloxy-propyl)-4,5-dimethoxybenzoyl]azetidine-2R-carboxylic acid hydroxyamide;
1-[3-(3-benzyloxy-propyl)4,5-dirnethoxybenzoyl]azetidine-2R-carboxylic acid hydroxyamide;
1-[3,4-dimethoxy-5-(3-propoxypropyl)benzoyl]azetidine-2R-carboxylic acid hydroxyamide;
1-(3-cyclopropylmethyl-4,5-dimethoxybenzoyl)azetidine-2R-carboxylic acid hydroxyamide;
1-(3-hexyl-4,5-dimethoxybenzoyl)azetidine-2R-carboxylic acid hydroxyamide;
1-(3,4-dimethoxy-5-pentylbenzoyl)azetidine-2R-carboxylic acid hydroxyamide;
1-(4-methoxy-3-trifluoromethoxybenzoyl)azetidine-2R-carboxylic acid hydroxyamide;
1-(3-propylbenzoyl)azetidine-2R-carboxylic acid hydroxyamide;
1-(3-allylbenzoyl)azetidine-2R-carboxylic acid hydroxyamide;
1-(4-allyloxy-3-trifluoromethoxybenzoyl)azetidine-2R-carboxylic acid hydroxyamide;
1-(3-trifluoromethylbenzoyl)azetidine-2R-carboxylic acid hydroxyamide;
1-[3,4-dimethoxy-5-(3-methoxypropyl)benzoy]azetidine2R-carboxylic acid hydroxyamide;
1-[3(3-ethoxypropyl)-4,5-dimethoxybenzoyl]azetidine2R-carboxylic acid hydroxyamide;
1-(3-allyl-4,5-dimethoxybenzoyl)azetidine-2R-carboxylic acid hydroxyamide;
1-(3-butyl-4,5-dimethoxybenzoyl)azetidine-2R-carboxylic acid hydroxyamide;
1-[34-dimethoxy-5-(3,3,3-trifluoropropyl)benzoy]azetidine-2R-carboxylic acid hydroxyamide;
1-(3-dimethylcarbamoylmethyl-4,5-dimethoxybenzoyl)azetidine-2R-carboxylic acid hydroxyamide;
1-(3,5-dibromo-4-methoxybenzoyl)azetidine-2R-carboxylic acid hydroxyamide;
1-(3-iodo-4,5-dimethoxybenzoyl)azetidine-2R-carboxylic acid hydroxyamide;
1-[3-(3-fluoropropyl)4,5-dimethoxybenzoyl]azetidine2R-carboxylic acid hydroxyamide;
1-(3-trifluoromethylthiobenzoyl)azetidine-2R-carboxylic acid hydroxyamide;
1-(4-trifluoromethylthiobenzoyl)azetidine-2R-carboxylic acid hydroxyamide;
1-(3-trifluoromethanesulfinylbenzoyl )azetidine-2R-carboxylic acid hydroxyamide;
1-[3-(1-fluoropropyl)-4,5-dimethoxybenzoyl]azetidine-2R-carboxylic acid hydroxyamide;
1-(3-ethynyl-4,5dimethoxybenzoyl)azetidine-2R-carboxylic acid hydroxyamide;
1-(4-methylthio-3trifluoromethoxybenzoyl)azetidine2R-carboxylic add hydroxyamide;
1-(4methoxy-3propylbenzoyl)azetidine-2R-carboxylic acid hydroxyamide;
1-[3-(2,2,2-trifluoroethylthio)benzoyl]azetidine-2carboxylic acid hydroxyamide;
1-(3-pentafluoroethylthiobenzoyl)azetidine-2R-carboxylic acid hydroxyamide;
1-(3,5-diallyl-4-methoxybenzoyl)azetidine-2R-carboxylic acid hydroxyamide;
1-(3-trifluoromethoxy-4-methoxy-5-propylbenzoyl)azetidine-2R-carboxylic acid hydroxyamide;
1-(3-bromo-4,5-dimethoxybenzoyl)azetidine-2R-carboxylic acid hydroxyamide;
1-(3,4-dimethoxy-5-prop-1-ynylbenzoyl)azetidine-2R-carboxylic acid hydroxyamide;
1-[3,4-dimethoxy-5-(2,2,2-trifluoroethoxy)benzoyl]azetidine-2R-carboxylic acid hydroxyamide;
1-(4-methoxy-3,5-dipropylbenzoyl)azetidine-2R-carboxylic acid hydroxyamide;
1-(3-methoxy-5-propylbenzoyl)azetidine-2R-carboxylic acid hydroxyamide;
1-(4methoxy-3-R-carboxylic acid hydroxyamide;
1-[3-(1,2,2,2-tetrafluoro-1-trifluoromethylthiobenzoyl-]azetidine-2R-carboxylic acid hydroxyamide;
1-(3,5-bis-trifluoromethylthiobenzoyl)azetidine-2R-carboxylic acid hydroxyamide;
1-(3-methoxy-5trifluoromethylthiobenzoyl)azetidine-2R-carboxylic acid hydroxyamide;

1-(4-methoxy-3-propyl-5-trifluromethylthiobenzoyl)azetidine-2R-carboxylic acid hydroxyamide;
1-(3,4-dimethoxy-5-trifluoromethylthiobenzoyl)azetidine-2R-carboxylic acid hydroxyamide;
1-(4-allyloxy-3-trifluoromethylthiobenzoyl)azetidine-2R-carboxylic acid hydroxyamide;
1-(4-propoxy-3-trifluoromethylthiobenzyl)azetidine-2R-carboxylic acid hydroxyamide;
1-(4-but-3-enyloxy-3-trifluoromethylthiobenzoyl)azetidine-2R-carboxylic acid hydroxyamide;
1-(4-butoxy-3-trifluoromethylthiobenzoyl)azetidine2R-carboxylic acid hydroxyamide;
1-[4-(3-methyl-but-2-enyloxy)-3-trifluoromethylthiobenzoyl 1]azetidine-2R-carboxylic acid hydroxyamide;
1-{4-[2-(3-fluorophenyl)ethyl]-3-trifluoromethylthiobenzoyl}azetidine-2R-carboxylic acid hydroxyamide;
1-(4-pentyl-3-trifluoromethylthiobenzoyl)azetidine-2R-carboxylic acid hydroxyamide;
1-[3-trifluoromethylthio-4-(trimethylsilanylethynyl)benzoyl]azetidine-2R-carboxylic acid hydroxyamide;
1-(4-ethynyl-3-trifluoromethylthiobenzoyl)azetidine-2R-carboxylic acid hydroxyamide;
1-(4-allyl-3-trifluommethylthiobenzoy!)azetidine-2R-carboxylic acid hydroxyamide;
1-(4-propyl-3-trifluoromethylthiobenzoyl)azetidine-2R-carboxylic acid hydroxyamide;
1-(4-methoxy-3-trifluoromethylthiobenzoyl)azetidine-2R-carboxylic acid hydroxyamide;
1-(3,4-dimethoxy-5-trifluoroethylthiobenzyl)azetidine-2R-carboxylic acid hydroxyamide;
1-(3-trifluoromethylthiobenzyl)azetidine-2R-carboxylic acid hydroxyamide;
1-(3-trifluoromethylthio-4-vinylbenzoyl)azetidine-2R-carboxylic acid hydroxyamide;
1-(4-ethyl-3-trifluoromethylthiobenzoyl)azetidine-2R-carboxylic acid hydroxyamide;
1-(4-prop-2-ynyloxy-3-trifluoromethylthiobenzoyl)azetidine-2R-carboxylic acid hydroxyamide;
1-(3-trifluoromethoxy-4-trifluoromethylthiobenzoyl)azetidine-2R-carboxylic acid hydroxyamide;
1-(4-ethoxy-3-trifluoromethylthiobenzoyl)azetidine-2R-carboxylic acid hydroxyamide;
1-[4-(2,2,2-trifluoroethoxy)-3-trifluoromethylthiobenzoyl]-azetidine-2R-carboxylic acid hydroxyamide;
(+)-trans-1-(3,4-dimethoxy-5-propylbenzoyl)-3-ethylazetidine-2-carboxylic acid hydroxyamide;
1-(5,6-dimethoxybiphenyl-3-carbonyl)azetidine-2R-carboxylic acid hydroxyamide;
1-[3-(3-fluorophenylethynyl)-4,5-dimethoxybenzoyl]azetidine-2R-carboxylic acid hydroxyamide;
1-(3-trifluoromethoxy-4-vinylbenzoyl)azetidine-2R-carboxylic acid hydroxyamide;
1-(4-ethyl-3-trifluoromethoxybenzoyl)azetidine-2R-carboxylic acid hydroxyamide; and
1-(4-benzyloxy-3-trifluoromethylthiobenzoyl)-azetidine-2R-carboxylic acid hydroxyamide;
or pharmaceutically acceptable salts thereof or tautomers thereof.

6. A pharmaceutical composition comprising a pharmaceutically acceptable carrier and a therapeutically effective amount of one or more of a compound of claim 1.

7. A pharmaceutical composition comprising a pharmaceutically acceptable carrier and a therapeutically effective amount of one or more of a compound of claim 2.

8. The pharmaceutical composition according to claim 6 further comprising one or more additional antibacterial agents.

9. The pharmaceutical composition according to claim 7 further comprising one or more additional antibacterial agents.

10. The pharmaceutical composition according to claims 8 or 9 wherein said antibacterial agent is active against gram negative bacteria.

11. The pharmaceutical composition according to claims 8 or 9 wherein said antibacterial agent is active against gram positive bacteria.

12. A method for the treatment of a microbial infection in a mammal, comprising administering to said mammal a therapeutically effective amount of one or more of a compound of claim 1.

13. A method for the treatment of a microbial infection in a mammal, comprising administering to said mammal a therapeutically effective amount of one or more of a compound of claim 2.

14. A method for the treatment of a microbial infection in a mammal comprising administering to said mammal, a pharmaceutical composition of claim 6.

15. A method for the treatment of a microbial infection in a mammal comprising administering to said mammal, a pharmaceutical composition of claim 7.

16. The method according to claims 14 or 15, wherein said composition is administered in combination with one or more additional antibacterial agents.

17. The method according to claim 16, wherein said infection is a gram negative infection.

18. The method according to claim 17, wherein said antibacterial agent is active against gram negative bacteria.

19. The method according to claim 16, wherein said infection is a gram positive infection.

20. The method according to claim 19, wherein said antibacterial agent is active against gram positive bacteria.

21. The method according to claims 14 or 15, wherein said compound is administered to the mammal orally, parenterally, transdermally, topically, rectally, or intranasally.

22. The method according to claims 14 or 15, wherein said composition is administered in an amount of from, about 0.1 to about 100 mg/kg of body weight/day.

23. A compound of formula (I):

wherein:
Ar is phenyl or 2,5-dihydro-benzo[b]oxepine;
X is selected from the group consisting of alkyl, haloalkyl, alkylthio, hydroxyalkyl, alkoxy, alkoxyalkyl, haloalkoxy, alkenyl, alkenoxy, alkenoxyalkyl, alkynyl, nitro, halo, hydroxyl, cycloalkyl, haloalkylthio, haloalkyl-sulfinyl, and aminocarboxyalkyl;
$R^1$ is selected from the group consisting of hydrogen and alkyl;
$R^2$ is selected from the group consisting of hydrogen and alkyl;
n is an integer from 1 to 4;
Z is —$CH_2$— or C(O);

m is an integer from 1 to 2;

and pharmaceutically acceptable salts thereof;

provided that when m is 2, then $R^2$ is H; and provided that the compound of formula I has a minimum inhibition concentration of 128 μ/ml or less against at least one of the organisms selected from the group consisting of *Acinetobacter baumannii, Acinetobacter haemolyticus, Actinobacillus actinomycetemcomitans, Aeromonas hydrophila, Bacteroides fragilis, Bacteroides theataioatamicron, Bacteroides distasonis, Bacteroides ovatus, Bacteroides vulgatus, Bordetella pertussis, Brucella melitensis, Burkholderia cepacia, Burkholderia pseudomallei, Burkholderia mallei Fusobacterium, Prevotella corporis, Prevotella intermedia, Prevotella endodontalis, Porphyromonas asaccharolytica, Campylobacter jejuni, Campylobacter fetus, Citrobacter freundii, Citrobacter koseri, Edwarsiella tarda, Eikenella corrondens, Enterobacter cloacae, Enterobacter aerogenes, Enterobacter agglomerans, Escherichia coil, Francisella tularensis, Haemophilus influenzae, Haemophilus ducreyi, Helicobacter pylon, Kingella kingae, Klebsiella pneumoniae, Klebsiella oxytoca, Klebsiella rhinoscieromatis, Klebsiella ozaenae, Legionella penumophila, Moraxella catarrhalis, Morganella morganii, Neisseria gonorrhoeae, Neisseria meningitides, Pasteurella multocida, Plesiomonas shigelloides, Proteus mirabilis, Proteus vulgaris, Proteus penneri, Proteus myxofaciens, Providencia stuartii, Providencia rettgeri, Providencia alcalifaciens, Pseudomonas aeruginosa, Pseudomonasfluorescens, Salmonella typhi, Salmonella paratyphi, Serratia marcescens, Shigella flexneri, Shigella boydii, Shigella sonnei, Shigella dysenteriae, Stenotrophomonas maltophilia, Streptobacillus moniliformis, Vibrio cholerae, Vibrio parahaemolyticus, Vibrio vulnificus, Vibrio alginolyticus, Yersinia enterocolitica, Yersinia pestis, Yersinia pseudotuberculosis, Chlamydia pneumoiae, Chlamydia trachomatis, Ricketsia prowazekii, Coxiella burnetii, Ehrlichia chafeenis*, and *Bartonella hensenae.*

\* \* \* \* \*